(12) United States Patent
Schmees et al.

(10) Patent No.: US 9,663,523 B2
(45) Date of Patent: May 30, 2017

(54) BET PROTEIN-INHIBITING 5-ARYLTRIAZOLEAZEPINES

(71) Applicants: BAYER PHARMA AKTIENGESELLSCHAFT, Berlin (DE); Helga Künzer, Reinsfeld (DE); Klara Muno, Reinsfeld (DE); Erich Künzer, Reinsfeld (DE); Martin Künzer, Aachen (DE); Christel Bernsdorf, Sylt (DE)

(72) Inventors: Norbert Schmees, Berlin (DE); Joachim Kuhnke, Potsdam (DE); Bernard Haendler, Berlin (DE); Roland Neuhaus, Berlin (DE); Pascale Lejeune, Berlin (DE); Stephan Siegel, Berlin (DE); Martin Krüger, Berlin (DE); Amaury Ernesto Fernandez-Montalvan, Berlin (DE); Hermann Künzer, Berlin (DE); Daniel Gallenkamp, Wuppertal (DE)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 0 days.

(21) Appl. No.: 14/432,158

(22) PCT Filed: Sep. 25, 2013

(86) PCT No.: PCT/EP2013/069902
§ 371 (c)(1),
(2) Date: Mar. 27, 2015

(87) PCT Pub. No.: WO2014/048945
PCT Pub. Date: Apr. 3, 2014

(65) Prior Publication Data
US 2015/0299201 A1  Oct. 22, 2015

(30) Foreign Application Priority Data
Sep. 28, 2012 (EP) ...................... 12186658

(51) Int. Cl.
*A61K 31/55* (2006.01)
*C07D 487/04* (2006.01)
*C07D 519/00* (2006.01)

(52) U.S. Cl.
CPC ............ *C07D 487/04* (2013.01); *A61K 31/55* (2013.01); *C07D 519/00* (2013.01)

(58) Field of Classification Search
CPC .......................... A61K 31/55; C07D 487/04
USPC .................... 514/214.02; 540/578
See application file for complete search history.

(56) References Cited

U.S. PATENT DOCUMENTS 5,712,274 A  1/1998  Sueoka

FOREIGN PATENT DOCUMENTS

| CN | 1227555 | 9/1999 |
|---|---|---|
| EP | 0638560 A1 | 2/1995 |
| EP | 0934940 | 8/1999 |
| EP | 0934940 A1 | 8/1999 |
| EP | 0989131 A1 | 3/2000 |
| EP | 1887008 A1 | 2/2008 |
| EP | 2239264 A1 | 10/2010 |
| WO | 94/26718 A1 | 11/1994 |
| WO | 2009/084693 A1 | 7/2009 |
| WO | 2011/054553 A1 | 5/2011 |
| WO | 2011/054843 A1 | 5/2011 |
| WO | 2011/054844 A1 | 5/2011 |
| WO | 2011/054845 A1 | 5/2011 |
| WO | 2012/075456 A1 | 6/2011 |
| WO | 2011/143669 A2 | 11/2011 |
| WO | 2012/075383 A2 | 6/2012 |

OTHER PUBLICATIONS

P. Filippakopoulos et al., Nature 2010, vol. 468, 1067-1073.
Wu and Chiang, J. Biol. Chem., 2007, 282:13141-13145.
Kuo and Allis, Bioessays, 1998, 20:615-626.
Huang et al., Mol. Cell. Biol., 2009, 29:1375-1387.
Rahman et al., Mol. Cell. Biol., 2011, 31:2641-2652.
Dey et al., Mol. Biol. Cell, 2009, 20:4899-4909.
(Continued)

*Primary Examiner* — Brenda Coleman
(74) *Attorney, Agent, or Firm* — Nixon & Vanderhye P.C.

(57) ABSTRACT

The present invention relates to BET-protein-inhibitory, in particular BRD4-inhibitory 5-aryltriazoloazepines of the general formula (I)

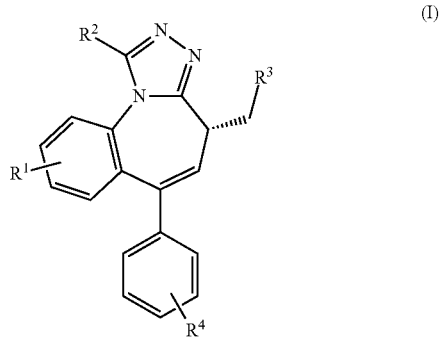

in which $R^1$, $R^2$, $R^3$ and $R^4$ have the meanings given for the general formula (I),
to pharmaceutical compositions comprising the compounds according to the invention, and to the prophylactic and therapeutic use thereof for hyperproliferative disorders, especially for neoplastic disorders. The present invention further relates to the use of BET protein inhibitors in viral infections, in neurodegenerative disorders, in inflammatory diseases, in atherosclerotic disorders and in male fertility control.

10 Claims, No Drawings

(56) References Cited

OTHER PUBLICATIONS

Yang et al., Mol. Cell. Biol., 2008, 28:967-976.
Yang et al., Mol. Cell, 2005, 19:535-545.
You et al., Mol. Cell. Biol., 2009, 29:5094-5103.
Zuber et al., Nature, 2011, doi:10.1038.
LeRoy et al., Mol. Cell, 2008, 30:51-60.
Mochizuki et al., J. Biol. Chem., 2008, 283:9040-9048.
Nicodeme et al., Nature, 2010, 468:1119-1123.
Gyuris et al., Biochim. Biophys. Acta, 2009, 1789:413-421.
Houzelstein et al., Mol. Cell. Biol., 2002, 22:3794-3802.
French, Cancer Genet. Cytogenet., 2010, 203:16-20.
Yan et al., J. Biol. Chem., 2011, 286:27663-27675.
Kadota et al., Cancer Res, 2009, 69:7357-7365.
Greenwall et al., Blood, 2005, 103:1475-1484.
Wu et al., Genes Dev., 2006, 20:2383-2396.
Viejo-Borbolla et aL, J. Virol., 2005, 79:13618-13629.
You et al., J. Virol., 2006, 80:8909-8919.
Bisgrove et al., Proc. Natl Acad. Sci. USA, 2007, 104:13690-13695.
Wang et al., Biochem. J., 2009, 425:71-83.
Co-pending U.S. Appl. No. 14/342,519, filed Mar. 3, 2014.
Co-pending U.S. Appl. No. 14/421,994, filed Feb. 16, 2015.
Co-pending U.S. Appl. No. 14/769,921, filed Aug. 24, 2015.
Co-pending U.S. Appl. No. 14/770,000, filed Aug. 24, 2015.
Mirguet et al., Bioorg. Med. Chem. Lett., 2012, 22:2963-2967.
Smith, Arterioscler. Thromb. Vasc. Biol., 2010, 30:151-155.
Shang et al., Development, 2007, 134:3507-3515.
Matzuk et al., Cell, 2012, 150:673-684.
Dhar et al., J. Biol. Chem., 2012, 287:6387-6405.
Chun-Wa Chung et al., Progress in Medicinal Chemistry 2012, 51, 1-55.
Chun-Wa Chung J. Med. Chem. 2011, 54, 3827-3838.
First Office Action for CN 201380050956.6 from Chinese State Intellectual Property Office, dated Aug. 1, 2016 (Original in Chinese and English translation attached).

BET PROTEIN-INHIBITING 5-ARYLTRIAZOLEAZEPINES

The present invention relates to BET protein-inhibitory, especially BRD4-inhibitory, 5-aryltriazoloazepines, to pharmaceutical compositions comprising the compounds according to the invention, and to the prophylactic and therapeutic use thereof for hyperproliferative disorders, especially for neoplastic disorders. This invention further relates to the use of BET protein inhibitors in viral infections, in neurodegenerative disorders, in inflammation diseases, in atherosclerotic disorders and in male fertility control.

The human BET family (bromo domain and extra C-terminal domain family) has four members (BRD2, BRD3, BRD4 and BRDT) containing two related bromo domains and one extraterminal domain (Wu and Chiang, J. Biol. Chem., 2007, 282:13141-13145). The bromo domains are protein regions which recognize acetylated lysine residues. Such acetylated lysines are often found at the N-terminal end of histones (e.g. histone 3 or histone 4) and are features of an open chromatin structure and active gene transcription (Kuo and Allis, Bioessays, 1998, 20:615-626). In addition, bromo domains may recognize further acetylated proteins. For example, BRD4 binds to RelA, which leads to stimulation of NF-κB and transcriptional activity of inflammatory genes (Huang et al., Mol. Cell. Biol., 2009, 29:1375-1387). The extraterminal domain of BRD2, BRD3 and BRD4 interacts with several proteins involved in chromatin modulation and the regulation of gene expression (Rahman et al., Mol. Cell. Biol., 2011, 31:2641-2652).

In mechanistic terms, BET proteins play an important role in cell growth and in the cell cycle. They are associated with mitotic chromosomes, suggesting a role in epigenetic memory (Dey et al., Mol. Biol. Cell, 2009, 20:4899-4909; Yang et al., Mol. Cell. Biol., 2008, 28:967-976). BRD4 is essential for transcription elongation and recruits the elongation complex P-TEFb consisting of CDK9 and cyclin T1, which leads to activation of RNA polymerase II (Yang et al., Mol. Cell, 2005, 19:535-545). Consequently, the expression of genes involved in cell proliferation is stimulated, for example of c-Myc and aurora B (You et al., Mol. Cell. Biol., 2009, 29:5094-5103; Zuber et al., Nature, 2011, doi: 10.1038). BRD2 and BRD3 bind to transcribed genes in hyperacetylated chromatin regions and promote transcription by RNA polymerase II (LeRoy et al., Mol. Cell, 2008, 30:51-60).

The knock-down of BRD4 in various cell lines leads to a G1 arrest (Mochizuki et al., J. Biol. Chem., 2008, 283:9040-9048). It has also been shown that BRD4 binds to promoter regions of several genes which are activated in the G1 phase, for example cyclin D1 and D2 (Mochizuki et al., J. Biol. Chem., 2008, 283:9040-9048).

BRD2 and BRD4 knockout mice die early in embryogenesis (Gyuris et al., Biochim Biophys. Acta, 2009, 1789:413-421; Houzelstein et al., Mol. Cell. Biol., 2002, 22:3794-3802). Heterozygotic BRD4 mice have various growth defects attributable to reduced cell proliferation (Houzelstein et al., Mol. Cell. Biol., 2002, 22:3794-3802).

BET proteins play an important role in various tumour types. Fusion between the BET proteins BRD3 or BRD4 and NUT, a protein which is normally expressed only in the testes, leads to an aggressive form of squamous cell carcinoma, called NUT midline carcinoma (French, Cancer Genet. Cytogenet., 2010, 203:16-20). The fusion protein prevents cell differentiation and promotes proliferation (Yan et al., J. Biol. Chem., 2011, 286:27663-27675). The growth of in vivo models derived therefrom is inhibited by a BRD4 inhibitor (Filippakopoulos et al., Nature, 2010, 468:1067-1073). Screening for therapeutic targets in an acute myeloid leukaemia cell line (AML) showed that BRD4 plays an important role in this tumour (Zuber et al., Nature, 2011, doi:10.1038). Reduction in BRD4 expression leads to a selective arrest of the cell cycle and to apoptosis. Treatment with a BRD4 inhibitor prevents the proliferation of an AML xenograft in vivo. Amplification of the DNA region containing the BRD4 gene was detected in primary breast tumours (Kadota et al., Cancer Res, 2009, 69:7357-7365). For BRD2 too, there are data relating to a role in tumours. A transgenic mouse which overexpresses BRD2 selectively in B cells develops B cell lymphoma and leukaemias (Greenwall et al., Blood, 2005, 103:1475-1484).

BET proteins are also involved in viral infections. BRD4 binds to the E2 protein of various papillomaviruses and is important for the survival of the viruses in latently infected cells (Wu et al., Genes Dev., 2006, 20:2383-2396). The herpes virus, which is responsible for Kaposi's sarcoma, also interacts with various BET proteins, which is important for disease survival (Viejo-Borbolla et al., J. Virol., 2005, 79:13618-13629; You et al., J. Virol., 2006, 80:8909-8919). Through binding to P-TEFb, BRD4 also plays an important role in the replication of HIV (Bisgrove et al., Proc. Natl. Acad. Sci. USA, 2007, 104:13690-13695).

BET proteins are additionally involved in inflammation processes. BRD2-hypomorphic mice show reduced inflammation in adipose tissue (Wang et al., Biochem. J., 2009, 425:71-83). Infiltration of macrophages in white adipose tissue is also reduced in BRD2-deficient mice (Wang et al., Biochem. J., 2009, 425:71-83). It has also been shown that BRD4 regulates a number of genes involved in inflammation. In LPS-stimulated macrophages, a BRD4 inhibitor prevents the expression of inflammatory genes, for example IL-1 or IL-6 (Nicodeme et al., Nature, 2010, 468:1119-1123). BET proteins are also involved in the regulation of the ApoA1 gene (Mirguet et al., Bioorg. Med. Chem. Lett., 2012, 22:2963-2967). The corresponding protein is part of high-density lipoprotein (HDL), which plays an important role in atherosclerosis (Smith, Arterioscler. Thromb. Vasc. Biol., 2010, 30:151-155). Through the stimulation of ApoA1 expression, BET protein inhibitors can increase the concentrations of cholesterol HDL and hence may potentially be useful for the treatment of atherosclerosis (Mirguet et al., Bioorg. Med. Chem. Lett., 2012, 22:2963-2967).

The BET protein BRDT plays an essential role in spermatogenesis through the regulation of the expression of several genes important during and after meiosis (Shang et al., Development, 2007, 134:3507-3515; Matzuk et al., Cell, 2012, 150:673-684). In addition, BRDT is involved in the post-meiotic organization of chromatin (Dhar et al., J. Biol. Chem., 2012, 287:6387-6405). In vivo experiments in mice show that treatment with a BET inhibitor which also inhibits BRDT leads to a decrease in sperm production and infertility (Matzuk et al., Cell, 2012, 150:673-684).

All these studies show that the BET proteins play an essential role in various pathologies, and also in male fertility. It would therefore be desirable to find potent and selective inhibitors which prevent the interaction between the BET proteins and acetylated proteins. These novel inhibitors should also have suitable pharmacokinetic properties which allow inhibition of these interactions in vivo, i.e. in patients.

It has now been found that substituted 4-alkyl-6-aryl-4H-[1,2,4]triazolo[4,3-a][1]benzazepines have the desired properties, i.e. show BRD4-inhibitory action.

PRIOR ART

The nomenclature employed in the assessment of the structural prior art is illustrated by the following figure:

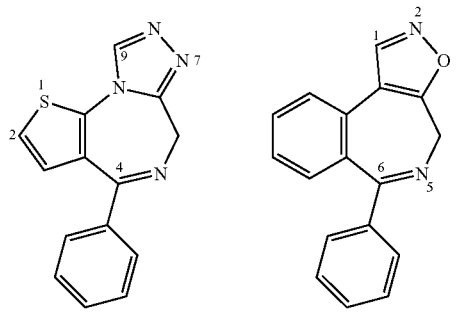

4-Phenyl-6H-thieno[3,2-f][1,2,4]triazolo[4,3-a][1,4]diazepine

6-Phenyl-4H-isoxazolo[5,4-d][2]benzazepine

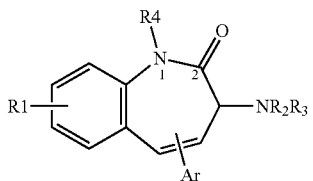

substituted 3-amino-2,3-dihydro-1H-1-benzazepin-2-ones

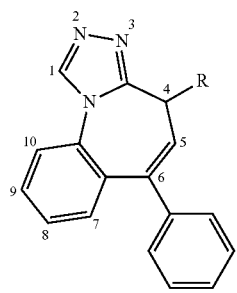

substituted 4-alkyl-6-aryl-4H-[1,2,4]triazolo[4,3-a][1]benzazepines

Based on the chemical structure, only very few types of BRD4 inhibitors have been described to date (Chun-Wa Chung et al., Progress in Medicinal Chemistry 2012, 51, 1-55).

The first published BRD4 inhibitors were diazepines. For example, phenylthienotriazolo-1,4-diazepines (4-phenyl-6H-thieno[3,2-f][1,2,4]triazolo[4,3-a][1,4]diazepines) are described in WO2009/084693 (Mitsubishi Tanabe Pharma Corporation) and as compound JQ1 in WO2011/143669 (Dana Farber Cancer Institute). Replacement of the thieno moiety by a benzo moiety also led to active inhibitors (J. Med. Chem. 2011, 54, 3827-3838; E. Nicodeme et al., Nature 2010, 468, 1119). Further 4-phenyl-6H-thieno[3,2-f][1,2,4]triazolo[4,3-a][1,4]diazepines and related compounds having alternative rings as a fusion partner rather than the benzo unit have been addressed generically or described directly in WO2012/075456 (Constellation Pharmaceuticals).

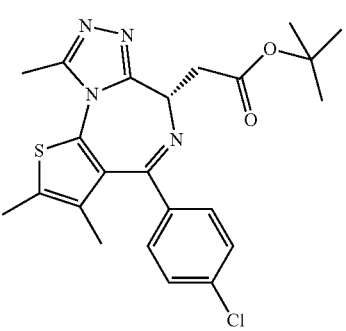

JQ1

Azepines as BRD-4 inhibitors have recently been described in WO2012/075383 (Constellation Pharmaceuticals). This application encompasses 6-substituted 4H-isoxazolo[5,4-d][2]benzazepines and 4H-isoxazolo[3,4-d][2]benzazepines, including those compounds which have optionally substituted phenyl at position 6, and also analogues with alternative heterocyclic fusion partners rather than the benzo unit, for example thieno- or pyridoazepines. In contrast, the compounds according to the invention are substituted 4-alkyl-6-aryl-4H-[1,2,4]triazolo[4,3-a][1]benzazepines, which, in contrast to the 4H-isoxazolo[5,4-d][2]benzazepines mentioned further up, have the ring nitrogen at an entirely different position, namely at position 10b. Because of the significant structural differences, it could not have been assumed that the compounds claimed here also have BRD4-inhibitory action. It is therefore surprising that the compounds according to the invention have good inhibitory action in spite of the structural differences. Another structural class of BRD4 inhibitors described is that of 7-isoxazoloquinolines and related quinolone derivatives (Bioorganic & Medicinal Chemistry Letters 22 (2012) 2963-2967). WO2011/054845 (GlaxoSmithKline) describes further benzodiazepines as BRD4 inhibitors. Some documents include compounds which are structurally similar but are aimed at completely different targets or indications. For instance, WO94/26718/EP0703222A1 (Yoshitomi Pharmaceutical Industries) describes substituted 3-amino-2,3-dihydro-1H-1-benzazepin-2-ones or the corresponding 2-thiones and analogues in which the benzo unit has been replaced by alternative monocyclic systems, and in which the 2-ketone or the 2-thione together with the substituted nitrogen atom in the azepine ring may form a heterocycle, as CCK and gastrin antagonists for the treatment of CNS disorders, such as states of anxiety and depression, and of pancreatic disorders and of gastrointestinal ulcers. However, these compounds differ from the compounds according to the invention by the obligatory 2-oxo group and the nitrogen group at position 4 rather than an alkyl group.

WO2012/075456A1/EP1939205A1 (Daiichi Sankyo) describes substituted 4-alkyl-6-aryl-5,6-dihydro-4H-[1,2,4]triazolo[4,3-a][1]benzazepines for the indications of hypercholesterolaemia, hyperlipidaemia and atherosclerosis. In contrast to the compounds according to the invention, these compounds lack the 5,6 double bond in the azepine ring.

Nevertheless, there is still a great need for selective active compounds for prophylaxis and treatment of cancers and especially neoplastic disorders.

It has now been found that compounds of the general formula (I)

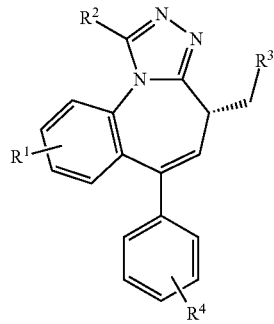

(I)

in which
R¹ represents hydrogen, hydroxy, $C_1$-$C_6$-alkyl, halo-$C_1$-$C_6$-alkyl, $C_1$-$C_6$-alkoxy, halo-$C_1$-$C_6$-alkoxy, halogen or cyano, or represents $C_3$-$C_8$-cycloalkyl, $C_3$-$C_8$-cycloalkoxy, $C_3$-$C_8$-heterocycloalkyl, aryl or heteroaryl having 5 or 6 ring atoms which may optionally be mono- or polysubstituted by identical or different substituents from the group consisting of $C_1$-$C_6$-alkyl, halo-$C_1$-$C_6$-alkyl, $C_1$-$C_6$-alkoxy, halo-$C_1$-$C_6$-alkoxy, hydroxy, oxo, halogen, cyano, heteroaryl and aryl, or represents —C(=O)—OR⁸, —C(=O)—NR¹²R¹³, —C(=O)—R¹⁴, —S(=O)₂—$C_1$-$C_6$-alkyl, —S(=O)₂—OR⁸ or —S(=O)₂—NR¹²R¹³, R² represents hydrogen, $C_1$-$C_6$-alkyl or —NR⁶R⁷, R³ represents cyano, —C(=O)—OR⁸, —C(=O)—R⁹ or —C(=O)—NR⁶R⁷, or represents a 5- or 6-membered ring system which contains 0, 1, 2, 3 or 4 heteroatoms independently of one another selected from the group consisting of O, N and S, which may optionally be aromatic or else non-aromatic and which may optionally be mono- or polysubstituted by identical or different radicals R⁵, R⁴ represents hydrogen, fluorine, chlorine, bromine or cyano, R⁵ represents hydrogen, $C_1$-$C_6$-alkyl, $C_3$-$C_8$-cycloalkyl, $C_3$-$C_8$-heterocycloalkyl, halo-$C_1$-$C_6$-alkyl, aryl, heteroaryl, hydroxy, $C_1$-$C_6$-alkoxy, $C_1$-$C_3$-alkoxy-$C_1$-$C_3$-alkyl, aryloxy-$C_1$-$C_3$-alkyl, aryl-$C_1$-$C_3$-alkoxy-$C_1$-$C_3$-alkyl, halo-$C_1$-$C_6$-alkoxy, halogen, cyano or oxo, R⁶ and R⁷ independently of one another
represent hydrogen or —NH—C(=O)—R¹⁵, or represent $C_1$-$C_6$-alkyl, $C_1$-$C_6$-alkoxy, $C_3$-$C_8$-heterocycloalkyl, aryl, heteroaryl, $C_3$-$C_8$-cycloalkyl, $C_6$-$C_{12}$-bicycloalkyl, $C_5$-$C_{11}$-spirocycloalkyl, $C_6$-$C_{12}$-heterobicycloalkyl or $C_5$-$C_{11}$-heterospirocycloalkyl which may optionally be mono- or polysubstituted by identical or different substituents from the group consisting of $C_1$-$C_6$-alkyl, halo-$C_1$-$C_6$-alkyl, $C_1$-$C_6$-alkoxy, halo-$C_1$-$C_6$-alkoxy, phenoxy, hydroxy, oxo, halogen, cyano, $C_3$-$C_8$-cycloalkyl, $C_3$-$C_8$-heterocycloalkyl, heteroaryl and aryl, or represent the group

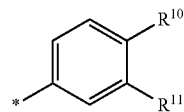

in which
R¹⁰ and R¹¹ together represent $C_3$-$C_6$-alkylene or $C_3$-$C_6$-heteroalkylene which may optionally be mono- or polysubstituted by identical or different substituents from the group consisting of halogen, oxo, hydroxy, cyano, nitro, $C_1$-$C_3$-alkyl, halo-$C_1$-$C_6$-alkyl, $C_1$-$C_6$-alkoxy, halo-$C_1$-$C_6$-alkoxy, $C_1$-$C_6$-alkoxy-$C_1$-$C_6$-alkyl, $C_1$-$C_6$-alkylcarbonyl, and in which "*" denotes the point of attachment to the remainder of the molecule, R⁸ represents hydrogen, $C_1$-$C_6$-alkyl, $C_3$-$C_8$-cycloalkyl, $C_3$-$C_8$-heterocycloalkyl, aryl or heteroaryl which may optionally be mono- or polysubstituted by identical or different substituents from the group consisting of $C_1$-$C_6$-alkyl, halo-$C_1$-$C_6$-alkyl, $C_1$-$C_6$-alkoxy, halo-$C_1$-$C_6$-alkoxy, hydroxy, oxo, halogen, cyano, nitro, heteroaryl and aryl, R⁹ represents $C_3$-$C_8$-heterocycloalkyl, $C_5$-$C_{11}$-spiroheterocycloalkyl, $C_6$-$C_{12}$-heterobicycloalkyl or represents a bridged heterocycle consisting of 7 to 15 ring atoms which may optionally be mono- or polysubstituted by identical or different substituents from the group consisting of $C_1$-$C_4$-alkyl, $C_3$-$C_8$-cycloalkyl, $C_3$-$C_8$-heterocycloalkyl, halo-$C_1$-$C_6$-alkyl, aryl, aryloxy, aryl-$C_1$-$C_2$-alkyl, —C(=O)—O—$C_1$-$C_6$-alkyl, heteroaryl, hydroxy, $C_1$-$C_6$-alkoxy, halo-$C_1$-$C_6$-alkoxy, halogen, cyano and oxo, R¹² and R¹³ independently of one another represent hydrogen, $C_1$-$C_6$-alkyl, R¹⁴ represents hydrogen, $C_1$-$C_6$-alkyl, amino, $C_1$-$C_6$-alkoxy, $C_3$-$C_8$-cycloalkyl, $C_3$-$C_8$-heterocycloalkyl, aryl or heteroaryl which may optionally be mono- or polysubstituted by identical or different substituents from the group consisting of $C_1$-$C_6$-alkyl, halo-$C_1$-$C_6$-alkyl, $C_1$-$C_6$-alkoxy, halo-$C_1$-$C_6$-alkoxy, hydroxy, oxo, halogen, cyano, nitro, heteroaryl and aryl, and R¹⁵ represents hydrogen, $C_1$-$C_6$-alkyl, halo-$C_1$-$C_6$-alkyl, aryl or aryl-$C_1$-$C_2$-alkyl, where the aryl and the aryl present in aryl-$C_1$-$C_2$-alkyl for their part may optionally be mono- or polysubstituted by identical or different substituents from the group consisting of halogen, cyano, $C_1$-$C_3$-alkyl, $C_1$-$C_3$-alkoxy and trifluoromethyl, and the diastereomers, racemates, tautomers, polymorphs, solvates and physiologically acceptable salts thereof, are suitable for prophylaxis and treatment of hyperproliferative disorders and in particular of tumour disorders.

Thus, surprisingly, the compounds according to the invention prevent the interaction between BET proteins, in particular BRD4, and an acetylated histone 4 peptide and hence inhibit the growth of cancer and tumour cells.

Preference is given to those compounds of the general formula (I) in which
R¹ represents hydrogen, hydroxy, $C_1$-$C_6$-alkyl, fluoro-$C_1$-$C_6$-alkyl, $C_1$-$C_6$-alkoxy, fluoro-$C_1$-$C_6$-alkoxy, halogen or cyano, or represents $C_3$-$C_8$-cycloalkyl, $C_3$-$C_8$-cycloalkoxy, $C_3$-$C_8$-heterocycloalkyl, aryl or heteroaryl having 5 or 6 ring atoms which may optionally be mono- or polysubstituted by identical or different substituents from the group consisting of $C_1$-$C_6$-alkyl, fluoro-$C_1$-$C_6$-alkyl, $C_1$-$C_6$-alkoxy, fluoro-$C_1$-$C_6$-alkoxy, hydroxy, oxo, halogen, cyano, heteroaryl and aryl, $R^2$ represents methyl or methylamino, $R^3$ represents cyano, —C(=O)—$OR^8$, —C(=O)—$R^9$ or —C(=O)—$NR^6R^7$, or represents a 5- or 6-membered ring system which contains 0, 1, 2 or 3 heteroatoms independently of one another selected from the group consisting of O, N and S, which may optionally be aromatic or else non-aromatic and which may optionally be mono- or polysubstituted by identical or different radicals $R^5$, $R^4$ represents hydrogen, fluorine, chlorine, bromine or cyano, $R^5$ represents hydrogen, $C_1$-$C_6$-alkyl, $C_3$-$C_8$-cycloalkyl, $C_3$-$C_8$-heterocycloalkyl, fluoro-$C_1$-$C_6$-alkyl, aryl, heteroaryl, hydroxy, $C_1$-$C_6$-alkoxy, $C_1$-$C_3$-alkoxy-$C_1$-$C_3$-alkyl, aryloxy-$C_1$-$C_3$-alkyl, aryl-$C_1$-$C_3$-alkoxy-$C_1$-$C_3$-alkyl, fluoro-$C_1$-$C_6$-alkoxy, halogen, cyano or oxo, $R^6$ and $R^7$ independently of one another represent hydrogen or —NH—C(=O)—$R^{15}$, or represent $C_1$-$C_6$-alkyl, $C_1$-$C_6$-alkoxy, $C_3$-$C_8$-heterocycloalkyl, aryl, heteroaryl, $C_3$-$C_8$-cycloalkyl, $C_6$-$C_{12}$-bicycloalkyl, $C_5$-$C_{11}$-spirocycloalkyl, $C_6$-$C_{12}$-heterobicycloalkyl or $C_5$-$C_{11}$-heterospirocycloalkyl which may optionally be mono- or polysubstituted by identical or different substituents from the group consisting of $C_1$-$C_3$-alkyl, fluoro-$C_1$-$C_3$-alkyl, $C_1$-$C_3$-alkoxy, fluoro-$C_1$-$C_3$-alkoxy, phenoxy, hydroxy, oxo, halogen, cyano, $C_3$-$C_8$-cycloalkyl, $C_3$-$C_8$-heterocycloalkyl, heteroaryl and aryl, or represent the group

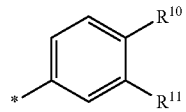

in which $R^{10}$ and $R^{11}$ together represent $C_3$-$C_6$-alkylene or $C_3$-$C_6$-heteroalkylene which may optionally be mono- or polysubstituted by identical or different substituents from the group consisting of halogen, oxo, hydroxy, cyano, nitro, $C_1$-$C_3$-alkyl, fluoro-$C_1$-$C_3$-alkyl, $C_1$-$C_3$-alkoxy, fluoro-$C_1$-$C_3$-alkoxy, $C_1$-$C_3$-alkoxy-$C_1$-$C_3$-alkyl, $C_1$-$C_3$-alkylcarbonyl, and in which "*" denotes the point of attachment to the remainder of the molecule, $R^8$ represents hydrogen, $C_1$-$C_6$-alkyl, $C_3$-$C_8$-cycloalkyl, aryl or heteroaryl which may optionally be mono- or polysubstituted by identical or different substituents from the group consisting of $C_1$-$C_6$-alkyl, fluoro-$C_1$-$C_6$-alkyl, $C_1$-$C_6$-alkoxy, fluoro-$C_1$-$C_6$-alkoxy, hydroxy, oxo, halogen, cyano, nitro, heteroaryl and aryl, $R^9$ represents $C_3$-$C_8$-heterocycloalkyl, $C_5$-$C_{11}$-spiroheterocycloalkyl, $C_6$-$C_{12}$-heterobicycloalkyl or represents a bridged heterocycle consisting of 7 to 15 ring atoms which may optionally be mono- or polysubstituted by identical or different substituents from the group consisting of $C_1$-$C_4$-alkyl, $C_3$-$C_8$-cycloalkyl, $C_3$-$C_8$-heterocycloalkyl, fluoro-$C_1$-$C_6$-alkyl, aryl, aryloxy, aryl-$C_1$-$C_2$-alkyl, —C(=O)—O—$C_1$-$C_6$-alkyl, heteroaryl, hydroxy, $C_1$-$C_6$-alkoxy, fluoro-$C_1$-$C_6$-alkoxy, halogen, cyano and oxo, and $R^{15}$ represents $C_1$-$C_6$-alkyl, fluoro-$C_1$-$C_3$-alkyl, phenyl or phenyl-$C_1$-$C_2$-alkyl, where the phenyl and the phenyl present in phenyl-$C_1$-$C_2$-alkyl for their part may optionally be mono- or polysubstituted by identical or different substituents from the group consisting of halogen, cyano, $C_1$-$C_3$-alkyl, $C_1$-$C_3$-alkoxy and trifluoromethyl, and the diastereomers, racemates, tautomers, polymorphs, solvates and physiologically acceptable salts thereof.

Particular preference is given to those compounds of the general formula (I) in which $R^1$ represents hydrogen, hydroxy, $C_1$-$C_3$-alkyl, fluoro-$C_1$-$C_3$-alkyl, $C_1$-$C_3$-alkoxy or fluoro-$C_1$-$C_3$-alkoxy, or represents heteroaryl having 5 or 6 ring atoms which may optionally be mono- or polysubstituted by identical or different substituents from the group consisting of $C_1$-$C_3$-alkyl, fluoro-$C_1$-$C_3$-alkyl, $C_1$-$C_3$-alkoxy, fluoro-$C_1$-$C_3$-alkoxy, halogen and cyano, $R^2$ represents methyl, $R^3$ represents —C(=O)—$OR^8$, —C(=O)—$R^9$ or —C(=O)—$NR^6R^7$, or represents a 5-membered aromatic ring system which contains 1, 2 or 3 heteroatoms independently of one another selected from the group consisting of O, N and S, which may optionally be mono- or polysubstituted by identical or different radicals $R^5$, $R^4$ represents chlorine, $R^5$ represents hydrogen, $C_1$-$C_3$-alkyl, $C_3$-$C_6$-cycloalkyl, $C_3$-$C_6$-heterocycloalkyl, fluoro-$C_1$-$C_3$-alkyl, aryl, heteroaryl, hydroxy, $C_1$-$C_3$-alkoxy, $C_1$-$C_3$-alkoxy-$C_1$-$C_3$-alkyl, aryloxy-$C_1$-$C_3$-alkyl, aryl-$C_1$-$C_3$-alkoxy-$C_1$-$C_3$-alkyl, fluoro-$C_1$-$C_3$-alkoxy, halogen or cyano, $R^6$ and $R^7$ independently of one another represent hydrogen or —NH—C(=O)—$R^{15}$, or represent $C_1$-$C_6$-alkyl, $C_1$-$C_6$-alkoxy, $C_3$-$C_8$-heterocycloalkyl, aryl, heteroaryl, $C_3$-$C_8$-cycloalkyl, $C_6$-$C_{12}$-bicycloalkyl, $C_5$-$C_{11}$-spirocycloalkyl, $C_6$-$C_{12}$-heterobicycloalkyl or $C_5$-$C_{11}$-heterospirocycloalkyl which may optionally be mono- or polysubstituted by identical or different substituents from the group consisting of $C_1$-$C_3$-alkyl, fluoro-$C_1$-$C_3$-alkyl, $C_1$-$C_3$-alkoxy, fluoro-$C_1$-$C_3$-alkoxy, phenoxy, hydroxy, oxo, halogen, cyano, $C_3$-$C_8$-cycloalkyl, $C_3$-$C_8$-heterocycloalkyl, heteroaryl and aryl, or represent the group

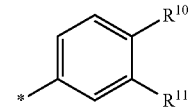

in which $R^{10}$ and $R^{11}$ together represent $C_3$-$C_6$-alkylene or $C_3$-$C_6$-heteroalkylene which may optionally be mono- or polysubstituted by identical or different substituents from the group consisting of halogen, oxo, hydroxy, cyano, nitro, $C_1$-$C_3$-alkyl, fluoro-$C_1$-$C_3$-alkyl, $C_1$-$C_3$-alkoxy, fluoro-$C_1$-$C_3$-alkoxy, $C_1$-$C_3$-alkoxy-$C_1$-$C_3$-alkyl, $C_1$-$C_3$-alkylcarbonyl, and in which "*" denotes the point of attachment to the remainder of the molecule, $R^8$ represents $C_1$-$C_6$-alkyl, $R^9$ represents one of the groups below

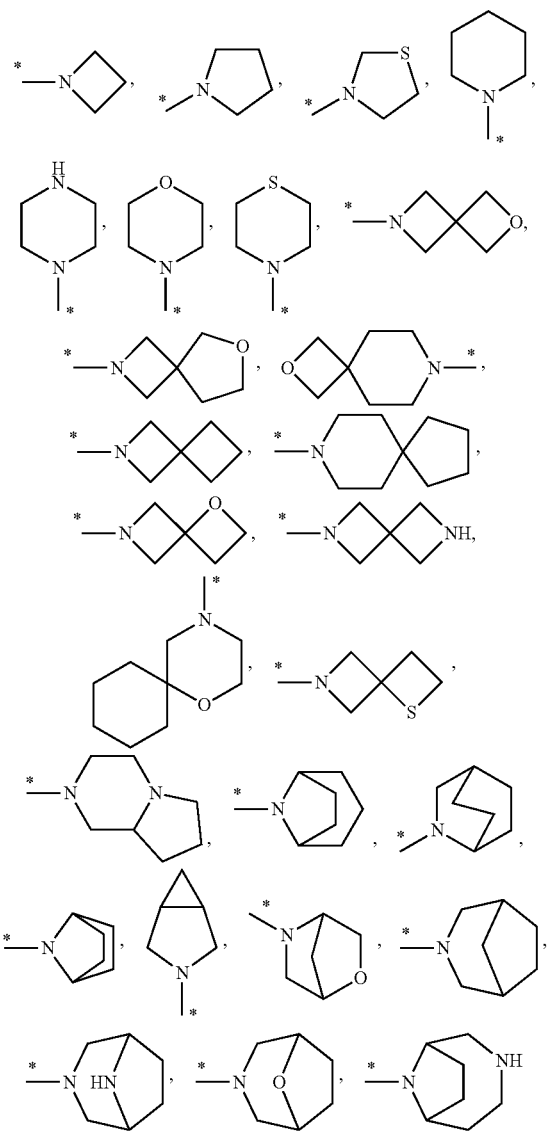

which may optionally be mono- or polysubstituted by identical or different substituents from the group consisting of $C_1$-$C_4$-alkyl, $C_3$-$C_8$-cycloalkyl, $C_3$-$C_8$-heterocycloalkyl, fluoro-$C_1$-$C_6$-alkyl, aryl, aryloxy, aryl-$C_1$-$C_2$-alkyl, —C(=O)—O—$C_1$-$C_6$-alkyl, heteroaryl, hydroxy, $C_1$-$C_6$-alkoxy, fluoro-$C_1$-$C_6$-alkoxy, halogen, cyano and oxo, and in which "*" denotes the point of attachment to the remainder of the molecule, and $R^{15}$ represents $C_1$-$C_3$-alkyl, trifluoromethyl, phenyl or benzyl, in which the phenyl and the phenyl present in benzyl for their part may optionally be mono- or polysubstituted by identical or different substituents from the group consisting of fluorine, chlorine, bromine, methyl and methoxy, and the diastereomers, racemates, tautomers, polymorphs, solvates and physiologically acceptable salts thereof.

Very particular preference is given to those compounds of the general formula (I) in which $R^1$ represents hydrogen, hydroxy, $C_1$-$C_3$-alkyl, fluoro-$C_1$-$C_3$-alkyl, $C_1$-$C_3$-alkoxy or fluoro-$C_1$-$C_3$-alkoxy, or represents heteroaryl having 5 ring atoms which may optionally be mono- or polysubstituted by identical or different substituents from the group consisting of $C_1$-$C_3$-alkyl and $C_1$-$C_3$-alkoxy, $R^2$ represents methyl, $R^3$ represents —C(=O)—$OR^8$, —C(=O)—$R^9$ or —C(=O)—$NR^6R^7$, or represents one of the ring systems below

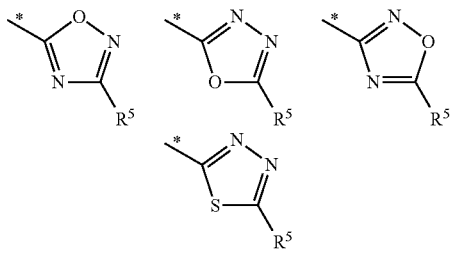

in which "*" denotes the point of attachment to the remainder of the molecule, $R^4$ represents chlorine, $R^5$ represents hydrogen, $C_1$-$C_3$-alkyl, $C_3$-$C_6$-cycloalkyl, $C_3$-$C_6$-heterocycloalkyl, phenyl, 5- or 6-membered heteroaryl, $C_1$-$C_3$-alkoxy-$C_1$-$C_3$-alkyl, phenoxy-$C_1$-$C_3$-alkyl or benzyloxy-$C_1$-$C_3$-alkyl, $R^6$ and $R^7$ independently of one another represent hydrogen or —NH—C(=O)—$R^{15}$, or represent $C_1$-$C_6$-alkyl, $C_3$-$C_8$-heterocycloalkyl, phenyl, heteroaryl having 5 or 6 ring atoms or $C_3$-$C_8$-cycloalkyl which may optionally be mono- or polysubstituted by identical or different substituents from the group consisting of $C_1$-$C_3$-alkyl, fluoro-$C_1$-$C_3$-alkyl, $C_1$-$C_3$-alkoxy, phenoxy, hydroxy, oxo, halogen, cyano, $C_3$-$C_8$-cycloalkyl, $C_3$-$C_8$-heterocycloalkyl, 5- or 6-membered heteroaryl and phenyl, or represent the group

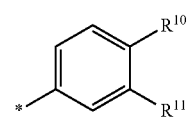

in which $R^{10}$ and $R^{11}$ together represent $C_3$-$C_4$-alkylene or $C_3$-$C_4$-heteroalkylene which may optionally be mono- or polysubstituted by identical or different substituents from the group consisting of halogen, oxo, hydroxy, $C_1$-$C_3$-alkyl, $C_1$-$C_3$-alkoxy, $C_1$-$C_3$-alkylcarbonyl, and in which "*" denotes the point of attachment to the remainder of the molecule, $R^8$ represents $C_1$-$C_4$-alkyl, $R^9$ represents one of the groups below

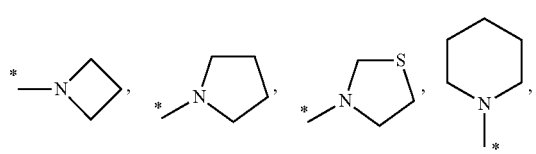

-continued

[ring system structures]

which may optionally be mono- or polysubstituted by identical or different substituents from the group consisting of $C_1$-$C_4$-alkyl, phenyl, phenoxy, benzyl, —C(=O)—O—$C_1$-$C_4$-alkyl, 5- or 6-membered heteroaryl, hydroxy, $C_1$-$C_4$-alkoxy, fluorine, cyano and oxo, and in which "*" denotes the point of attachment to the remainder of the molecule, and $R^{15}$ represents $C_1$-$C_3$-alkyl, and the diastereomers, racemates, tautomers, polymorphs, solvates and physiologically acceptable salts thereof.

Even more preference is given to those compounds of the general formula (I) in which $R^1$ represents hydrogen, $C_1$-$C_3$-alkoxy or fluoro-$C_1$-$C_3$-alkoxy, or represents oxazolyl or isoxazolyl which may optionally be mono- or polysubstituted by identical or different substituents from the group consisting of $C_1$-$C_3$-alkyl and $C_1$-$C_3$-alkoxy, $R^2$ represents methyl, $R^3$ represents —C(=O)—$OR^8$, —C(=O)—$R^9$ or —C(=O)—$NR^6R^7$, or represents one of the ring systems below

[ring system structures with $R^5$]

in which "*" denotes the point of attachment to the remainder of the molecule, $R^4$ represents chlorine, $R^5$ represents hydrogen, $C_1$-$C_3$-alkyl-, $C_3$-$C_6$-cycloalkyl, pyridinyl or benzyloxy-$C_1$-$C_3$-alkyl, $R^6$ and $R^7$ independently of one another represent hydrogen or —NH—C(=O)—$R^{15}$, or represent $C_1$-$C_6$-alkyl which may optionally be mono- or polysubstituted by identical or different substituents from the group consisting of $C_3$-$C_8$-heterocycloalkyl, or represent the group

[indolin-2-one structure]

in which "*" denotes the point of attachment to the remainder of the molecule, $R^8$ represents ethyl or tert-butyl, $R^9$ represents one of the groups below

[ring system structures]

which may optionally be mono- or polysubstituted by identical or different substituents from the group consisting of $C_1$-$C_4$-alkyl, phenoxy, benzyl, —C(=O)—O—$C_1$-$C_4$-alkyl, fluorine and oxo, and in which "*" denotes the point of attachment to the remainder of the molecule, and $R^{15}$ represents $C_1$-$C_3$-alkyl, and the diastereomers, racemates, tautomers, polymorphs, solvates and physiologically acceptable salts thereof.

Exceptional preference is given to those compounds of the general formula (I) in which $R^1$ represents hydrogen, methoxy, trifluoromethoxy or represents 3,5-dimethylisoxazol-4-yl,
$R^2$ represents methyl,
$R^3$ represents —C(=O)—OR$^8$, —C(=O)—R$^9$ or —C(=O)—NR$^6$R$^7$,
or
represents one of the ring systems below

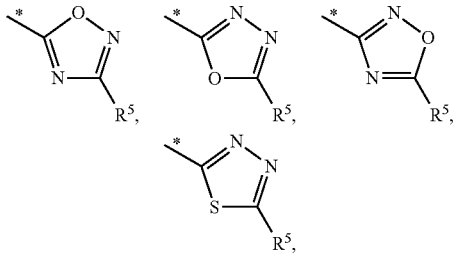

in which "*" denotes the point of attachment to the remainder of the molecule,
$R^4$ represents chlorine,
$R^5$ represents methyl, isopropyl, cyclopropyl, pyridin-3-yl or benzyloxymethyl,
$R^6$ and $R^7$ independently of one another
represent hydrogen or —NH—C(=O)—R$^{15}$,
or
represent ethyl which may optionally be monosubstituted by morpholinyl, or represent the group

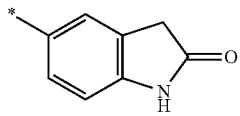 [SMILES: *c1ccc2c(c1)CC(=O)N2]

in which "*" denotes the point of attachment to the remainder of the molecule,
$R^8$ represents ethyl or tert-butyl,
$R^9$ represents one of the groups below

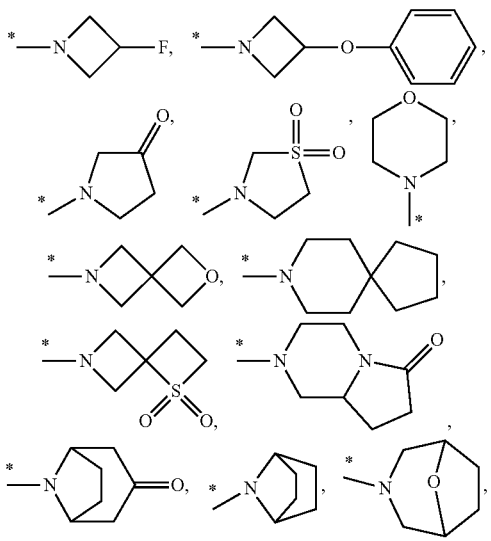

in which "*" denotes the point of attachment to the remainder of the molecule, and $R^{15}$ represents methyl,
and the diastereomers, racemates, tautomers, polymorphs, solvates and physiologically acceptable salts thereof.

Furthermore of interest are those compounds of the general formula I in which
$R^1$ represents hydrogen, hydroxy, $C_1$-$C_6$-alkyl, halo-$C_1$-$C_6$-alkyl, $C_1$-$C_6$-alkoxy, halo-$C_1$-$C_6$-alkoxy, halogen, cyano, or represents aryl which may be mono- or polysubstituted by identical or different substituents from the group consisting of $C_1$-$C_6$-alkyl, halo-$C_1$-$C_6$-alkyl, $C_1$-$C_6$-alkoxy, halo-$C_1$-$C_6$-alkoxy, hydroxy, oxo, halogen, cyano, heteroaryl and aryl, or represents $C_3$-$C_8$-cycloalkyl, $C_3$-$C_8$-cycloalkoxy, $C_3$-$C_8$-heterocycloalkyl, aryl or heteroaryl having 5-6 ring atoms and 1-3 heteroatoms from the group consisting of N, O and S, which may be mono- or polysubstituted by identical or different substituents from the group consisting of $C_1$-$C_6$-alkyl, halo-$C_1$-$C_6$-alkyl, $C_1$-$C_6$-alkoxy, halo-$C_1$-$C_6$-alkoxy, hydroxy, oxo, halogen, cyano, heteroaryl and aryl, or represents the group —C(O)OR$^8$, —C(O)NR$^6$R$^7$, —C(O)R$^{14}$, —S(O)$_2$C$_1$-C$_6$-alkyl, —S(O)$_2$ OR$^8$ or —S(O)$_2$NR$^6$R$^7$,
$R^2$ represents hydrogen, a $C_1$-$C_6$-alkyl group or —NR$^6$R$^7$,
$R^3$ represents a —C(O)OR$^8$, —C(O)R$^9$, —C(O)NR$^6$R$^7$ group, or represents cyano, or represents a 5-6-membered ring system containing 0-4 heteroatoms selected from the group consisting of O, N and S, which may optionally be aromatic or else non-aromatic and may carry further $R^5$ radicals,
$R^4$ represents hydrogen, fluorine, chlorine, bromine or cyano,
$R^5$ represents hydrogen, $C_1$-$C_6$-alkyl, $C_3$-$C_8$-cycloalkyl, $C_3$-$C_8$-heterocycloalkyl, halo-$C_1$-$C_6$-alkyl, aryl, heteroaryl, hydroxy, $C_1$-$C_6$-alkoxy, halo-$C_1$-$C_6$-alkoxy, halogen, cyano or oxo,
$R^6$ and $R^7$ independently of one another represent hydrogen, $C_1$-$C_6$-alkyl, $C_1$-$C_6$-alkoxy, $C_3$-$C_8$-heterocycloalkyl, aryl, heteroaryl, $C_3$-$C_8$-cycloalkyl, $C_6$-$C_{12}$-bicycloalkyl, $C_5$-$C_{11}$-spirocycloalkyl, $C_6$-$C_{12}$-heterobicycloalkyl or $C_5$-$C_{11}$-heterospirocycloalkyl, which may carry further substituents from the group consisting of $C_1$-$C_6$-alkyl, halo-$C_1$-$C_6$-alkyl, $C_1$-$C_6$-alkoxy, halo-$C_1$-$C_6$-alkoxy, phenoxy, hydroxy, oxo, halogen, cyano, $C_3$-$C_8$-cycloalkyl, $C_3$-$C_8$-heterocycloalkyl, heteroaryl and aryl, or represent the group

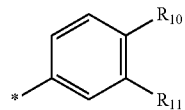

in which
$R^{10}$ and $R^{11}$ together form a 5- to 8-membered cycloalkyl or 5- to 8-membered heterocycloalkyl ring having 1-3 heteroatoms from the group consisting of N, O and S, which may optionally be mono- or polysubstituted by identical or different substituents from the group consisting of halogen, hydroxy, cyano, nitro and/or by a $C_1$-$C_3$-alkyl, halo-$C_1$-$C_6$-alkyl, $C_1$-$C_6$-alkoxy, halo-$C_1$-$C_6$-alkoxy, $C_1$-$C_6$-alkoxy-$C_1$-$C_6$-alkyl and/or $C_1$-$C_6$-alkylcarbonyl radical, and may carry a —C(O)— or —S(O)$_2$— group in the ring,
$R^8$ represents hydrogen, $C_1$-$C_6$-alkyl, $C_3$-$C_8$-cycloalkyl, $C_3$-$C_8$-heterocycloalkyl, aryl or heteroaryl, which may be mono- or polysubstituted by identical or different substituents from the group consisting of $C_1$-$C_6$-alkyl, halo-$C_1$-$C_6$-alkyl, $C_1$-$C_6$-alkoxy, halo-$C_1$-$C_6$-alkoxy, hydroxy, oxo, halogen, cyano, nitro, heteroaryl and aryl, $R^9$ represents the group of a mono- or bicyclic heterocycle having 3-14 ring atoms, a spiroheterocycle consisting of 5-12 ring atoms or a bridged heterocycle consisting of 7-15 ring atoms, each of which may include 0, 1, 2, 3, 4 or 5 further heteroatoms from the group consisting of N, O and S and which may optionally be mono- or polysubstituted by $C_1$-$C_4$-alkyl, $C_3$-$C_8$-cycloalkyl, $C_3$-$C_8$-heterocycloalkyl, halo-$C_1$-$C_6$-alkyl, aryl, aryloxy, $C_1$-$C_2$-alkylaryl, —C(O)—O—$C_1$-$C_6$-alkyl, heteroaryl, hydroxy, $C_1$-$C_6$-alkoxy, halo-$C_1$-$C_6$-alkoxy, halogen, cyano or oxo, and $R^{12}$ and $R^{13}$ independently of one another represent hydrogen, $C_1$-$C_6$-alkyl, $R^{14}$ represents hydrogen, $C_1$-$C_6$-alkyl, amino, $C_1$-$C_6$-alkoxy, $C_3$-$C_8$-cycloalkyl, $C_3$-$C_8$-heterocyclyl, aryl or heteroaryl, which may be mono- or polysubstituted by identical or different substituents from the group consisting of $C_1$-$C_6$-alkyl, halo-$C_1$-$C_6$-alkyl, $C_1$-$C_6$-alkoxy, halo-$C_1$-$C_6$-alkoxy, hydroxy, oxo, halogen, cyano, nitro, heteroaryl and aryl, and the diastereomers, racemates, metabolites and physiologically acceptable salts thereof.

Also of interest are those compounds of the general formula I in which $R^1$ represents hydrogen, hydroxy, $C_1$-$C_6$-alkyl, halo-$C_1$-$C_6$-alkyl, $C_1$-$C_6$-alkoxy, halo-$C_1$-$C_6$-alkoxy, halogen or cyano, or represents aryl which may be mono- or polysubstituted by identical or different substituents from the group consisting of $C_1$-$C_6$-alkyl, halo-$C_1$-$C_6$-alkyl, $C_1$-$C_6$-alkoxy, halo-$C_1$-$C_6$-alkoxy, hydroxy, oxo, halogen, cyano, heteroaryl and aryl, or represents $C_3$-$C_8$-cycloalkyl, $C_3$-$C_8$-cycloalkoxy, heterocycloalkyl, aryl or heteroaryl having 1-3 heteroatoms from the group of N, O and S, which may be mono- or polysubstituted by identical or different substituents from the group consisting of $C_1$-$C_6$-alkyl, halo-$C_1$-$C_6$-alkyl, $C_1$-$C_6$-alkoxy, halo-$C_1$-$C_6$-alkoxy, hydroxy, oxo, halogen and cyano, $R^2$ represents methyl or methylamino, $R^3$ represents a —C(O)O$R^8$, —C(O)$R^9$, —C(O)N$R^6R^7$ group, or represents cyano, or represents a 5- to 6-membered ring system containing 0-3 heteroatoms selected from the group consisting of O, N and S, which may optionally be aromatic or else non-aromatic and may carry further $R^5$ radicals, $R^4$ represent hydrogen, fluorine, chlorine, bromine or cyano, $R^5$ represents hydrogen, $C_1$-$C_6$-alkyl, $C_3$-$C_8$-cycloalkyl, $C_3$-$C_8$-heterocycloalkyl, halo-$C_1$-$C_6$-alkyl, aryl, heteroaryl, hydroxy, $C_1$-$C_6$-alkoxy, halo-$C_1$-$C_6$-alkoxy, halogen, cyano or oxo, $R^6$ and $R^7$ independently of one another represent hydrogen, $C_1$-$C_3$-alkyl, $C_1$-$C_3$-alkoxy, $C_3$-$C_8$-heterocycloalkyl, aryl, heteroaryl, $C_3$-$C_8$-cycloalkyl, $C_6$-$C_{12}$-bicycloalkyl, $C_5$-$C_{11}$-spirocycloalkyl, $C_6$-$C_{12}$-heterobicycloalkyl or $C_5$-$C_{11}$-heterospirocycloalkyl, which may carry further substituents from the group consisting of $C_1$-$C_3$-alkyl, halo-$C_1$-$C_3$-alkyl, $C_1$-$C_3$-alkoxy, halo-$C_1$-$C_3$-alkoxy, phenoxy, hydroxy, oxo, halogen, cyano, $C_3$-$C_8$-cycloalkyl, $C_3$-$C_8$-heterocycloalkyl, heteroaryl and aryl, or represent the group

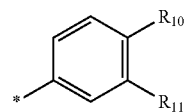

in which $R^{10}$ and $R^{11}$ together form a 5- to 8-membered cycloalkyl or 5- to 8-membered heterocycloalkyl ring having 1-3 heteroatoms from the group consisting of N, O and S, which may optionally be mono- or polysubstituted by identical or different substituents from the group consisting of halogen, hydroxy, cyano, oxo, nitro and/or by a $C_1$-$C_3$-alkyl, halo-$C_1$-$C_6$-alkyl, $C_1$-$C_6$-alkoxy, halo-$C_1$-$C_6$-alkoxy, $C_1$-$C_6$-alkoxy-$C_1$-$C_6$-alkyl and/or $C_1$-$C_6$-alkylcarbonyl radical, and may carry a —C(O)— or —S(O)$_2$— group in the ring, $R^8$ represents hydrogen, $C_1$-$C_6$-alkyl, $C_3$-$C_8$-cycloalkyl, aryl or heteroaryl, which may be mono- or polysubstituted by identical or different substituents from the group consisting of $C_1$-$C_6$-alkyl, halo-$C_1$-$C_6$-alkyl, $C_1$-$C_6$-alkoxy, halo-$C_1$-$C_6$-alkoxy, hydroxy, oxo, halogen, cyano, nitro, heteroaryl and aryl, $R^9$ represents a mono- or bicyclic heterocycle, a spiroheterocycle or a bridged heterocycle of the group

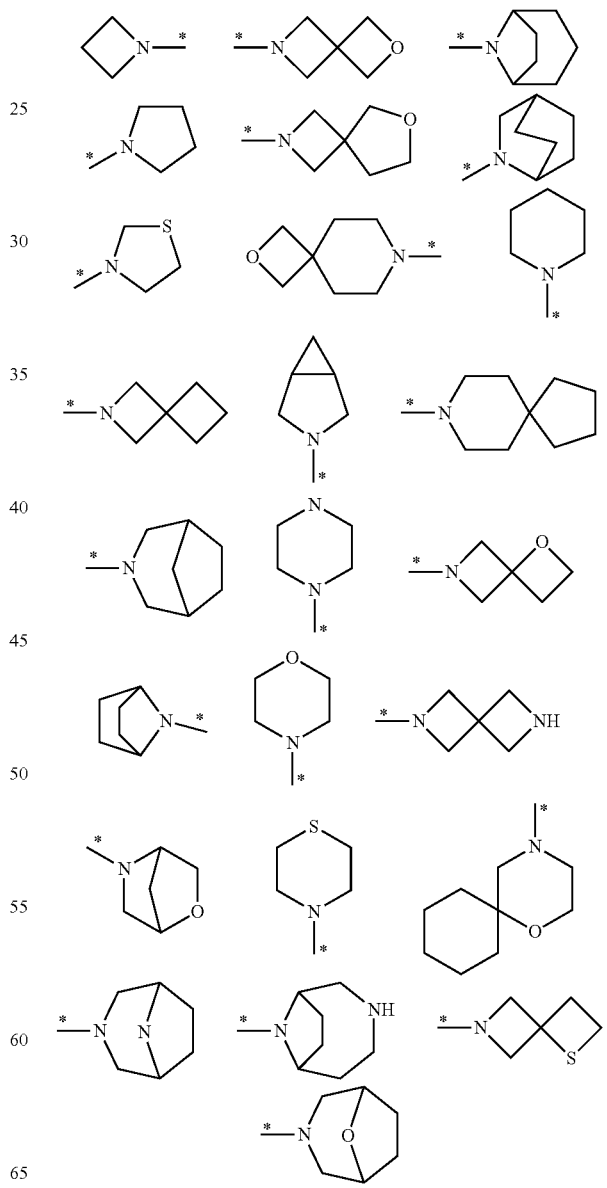

and which may optionally be mono- or polysubstituted by C$_1$-C$_4$-alkyl, C$_3$-C$_8$-cycloalkyl, C$_3$-C$_8$-heterocycloalkyl, halo-C$_1$-C$_6$-alkyl, aryl, aryloxy, C$_1$-C$_2$-alkylaryl, —C(O)—O—C$_1$-C$_6$-alkyl, heteroaryl, hydroxy, C$_1$-C$_6$-alkoxy, halo-C$_1$-C$_6$-alkoxy, halogen, cyano or oxo, and the diastereomers, racemates, metabolites and physiologically acceptable salts thereof.

Also of particular interest are those compounds of the general formula I in which R$^1$ represents hydrogen, R$^2$ represents methyl, R$^3$ represents a —C(O)OR$^8$, —C(O)R$^9$ or —C(O)NR$^6$R$^7$ group, or represents a 5-membered aromatic ring system which contains 1-3 heteroatoms selected from the group consisting of O, N and S and which may optionally carry further R$^5$ radicals, R$^4$ represents chlorine, R$^5$ represents hydrogen, C$_1$-C$_6$-alkyl, C$_3$-C$_8$-cycloalkyl, C$_3$-C$_8$-heterocycloalkyl, halo-C$_1$-C$_6$-alkyl, aryl, heteroaryl, hydroxy, C$_1$-C$_6$-alkoxy, halo-C$_1$-C$_6$-alkoxy, halogen, cyano or oxo, R$^6$ and R$^7$ independently of one another represent hydrogen, C$_1$-C$_3$-alkyl, C$_1$-C$_3$-alkoxy, C$_3$-C$_8$-heterocycloalkyl, aryl, heteroaryl, C$_3$-C$_8$-cycloalkyl, C$_6$-C$_{12}$-bicycloalkyl or C$_5$-C$_{11}$-spirocycloalkyl, which may bear further substituents from the group of C$_1$-C$_3$-alkyl, halo-C$_1$-C$_3$-alkyl, C$_1$-C$_3$-alkoxy, halo-C$_1$-C$_3$-alkoxy, phenoxy, hydroxy, oxo, halogen, cyano, C$_3$-C$_8$-cycloalkyl, C$_3$-C$_8$-heterocycloalkyl, heteroaryl and aryl, or represent the group

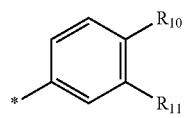

in which

R$^{10}$ and R$^{11}$ together form a 5- to 6-membered cycloalkyl or 5- to 6-membered heterocycloalkyl ring having 1-3 heteroatoms from the group of N, O and S, which may optionally be mono- or polysubstituted identically or differently by halogen, hydroxy, cyano, oxo, nitro and/or by a C$_1$-C$_3$-alkyl, halo-C$_1$-C$_6$-alkyl, C$_1$-C$_6$-alkoxy, halo-C$_1$-C$_6$-alkoxy, C$_1$-C$_6$-alkoxy-C$_1$-C$_6$-alkyl and/or C$_1$-C$_6$-alkylcarbonyl radical, and may carry a —C(O)— or —S(O)$_2$— group in the ring, R$^8$ represents ethyl or tert-butyl, R$^9$ represents a mono- or bicyclic heterocycle, a spiroheterocycle or a bridged heterocycle of the group

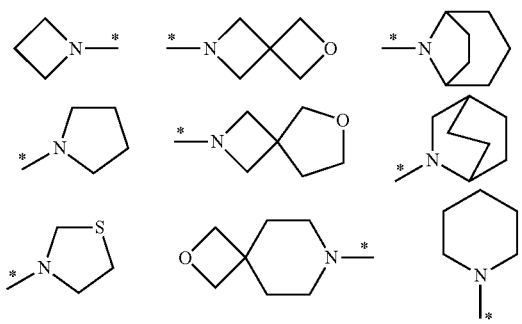

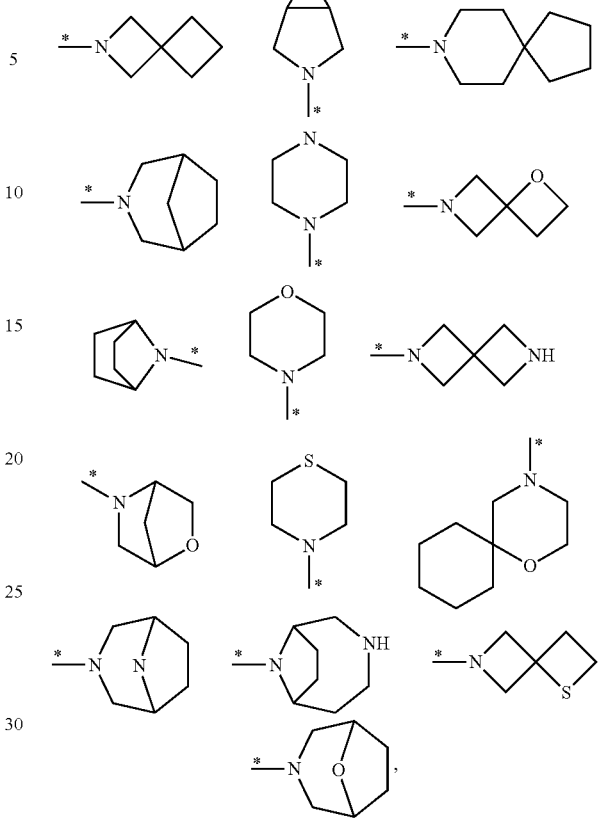

and which may optionally be mono- or polysubstituted by C$_1$-C$_4$-alkyl, C$_3$-C$_8$-cycloalkyl, C$_3$-C$_8$-heterocycloalkyl, halo-C$_1$-C$_6$-alkyl, aryl, aryloxy, C$_1$-C$_2$-alkylaryl, —C(O)—O—C$_1$-C$_6$-alkyl, heteroaryl, hydroxy, C$_1$-C$_6$-alkoxy, halo-C$_1$-C$_6$-alkoxy, halogen, cyano or oxo, and the diastereomers, racemates, metabolites and physiologically acceptable salts thereof.

More interesting are those compounds of the general formula I in which

R$^1$ represents hydrogen,

R$^2$ represents methyl,

R$^3$ represents a —C(O)OR$^8$, —C(O)R$^9$ or —C(O)NR$^6$R$^7$ group, or represents a 5-membered aromatic ring system which contains 1-3 heteroatoms selected from the group consisting of O, N and S and which may optionally carry further R$^5$ radicals, R$^4$ represents chlorine, R$^5$ represents hydrogen, C$_1$-C$_6$-alkyl, C$_3$-C$_8$-cycloalkyl, C$_3$-C$_8$-heterocycloalkyl, halo-C$_1$-C$_6$-alkyl, aryl, heteroaryl, hydroxy, C$_1$-C$_6$-alkoxy, halo-C$_1$-C$_6$-alkoxy, halogen, cyano or oxo, R$^6$ and R$^7$ independently of one another represent hydrogen, ethyl or the group

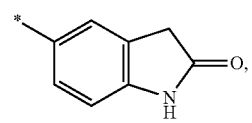 [SMILES: *c1ccc2c(c1)CC(=O)N2]

$R^8$ represents ethyl or tert-butyl, $R^9$ represents a mono- or bicyclic heterocycle, a spiroheterocycle or a bridged heterocycle of the group

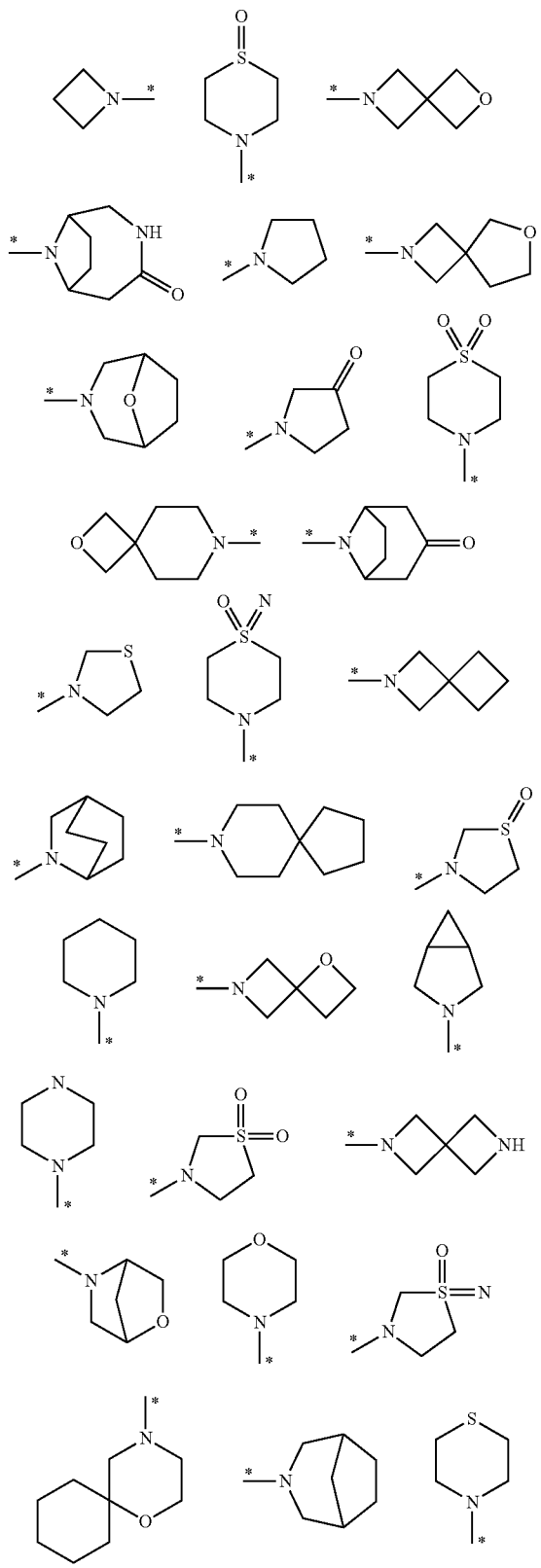
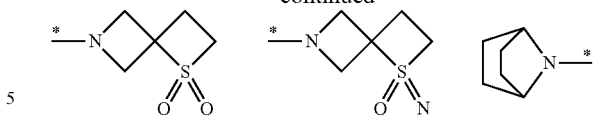

and which may optionally be mono- or polysubstituted by $C_1$-$C_4$-alkyl, $C_3$-$C_8$-cycloalkyl, $C_3$-$C_8$-heterocycloalkyl, halo-$C_1$-$C_6$-alkyl, aryl, phenoxy, $C_1$-$C_2$-alkylaryl, —C(O)—O—$C_1$-$C_6$-alkyl, heteroaryl, hydroxy, $C_1$-$C_6$-alkoxy, halo-$C_1$-$C_6$-alkoxy, halogen, cyano or oxo, and the diastereomers, racemates, metabolites and physiologically acceptable salts thereof.

Also of particular interest are those compounds of the general formula I in which $R^1$ represents hydrogen, $R^2$ represents methyl, $R^3$ represents a —C(O)OR$^8$, —C(O)R$^9$ or —C(O)NR$^6$R$^7$ group, or represents a 5-membered ring system containing 2-3 heteroatoms and a further $R^5$ radical of the structure

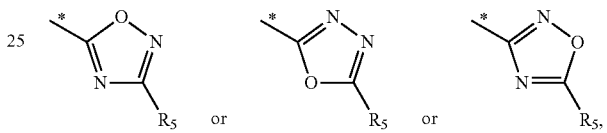

$R^4$ represents chlorine, $R^5$ represents hydrogen, methyl, ethyl, propyl, isopropyl, cyclopropyl or tert-butyl, $R^6$ and $R^7$ independently of one another represent hydrogen, ethyl or the group

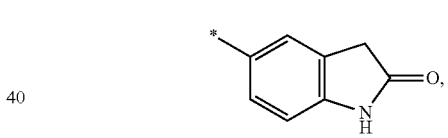

$R^8$ represents ethyl or tert-butyl, $R^9$ represents the group

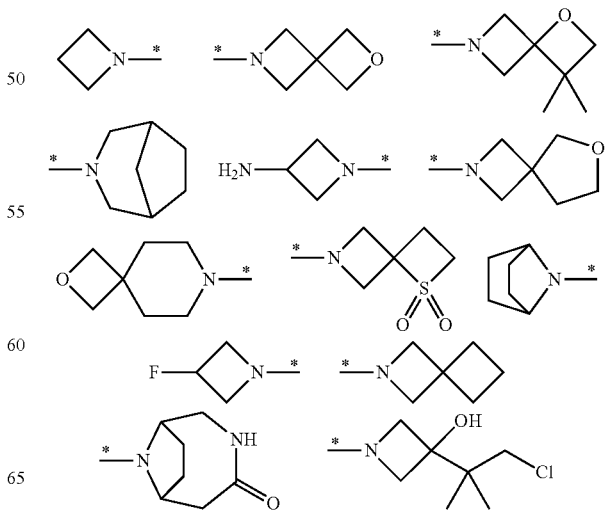

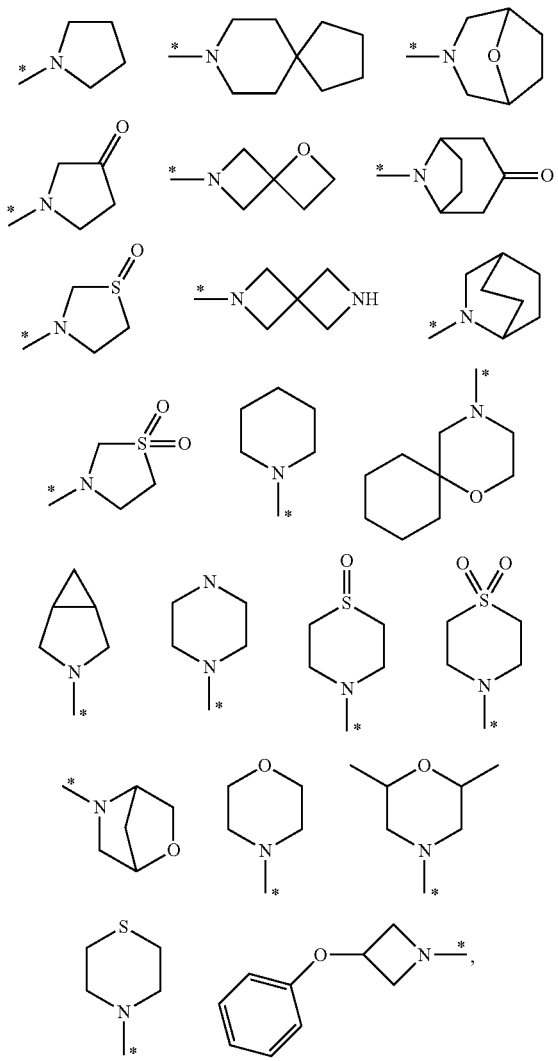

and the diastereomers, racemates, metabolites and physiologically acceptable salts thereof.

Of particular interest are those compounds of the general formula I in which $R^1$ represents hydrogen, $R^2$ represents methyl, $R^3$ represents a —C(O)OR$^8$, —C(O)R$^9$ or —C(O)NR$^6$R$^7$ group, or represents a 5-membered ring system having 3 heteroatoms and a further $R^5$ radical of the structure

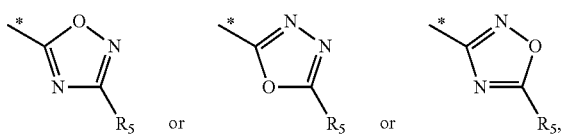

$R^4$ represents chlorine.

$R^5$ represents methyl, isopropyl or cyclopropyl, $R^6$ and $R^7$ independently of one another represent hydrogen, ethyl or the group

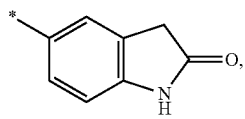 [SMILES: *c1ccc2c(c1)CC(=O)N2]

$R^8$ represents ethyl or tert-butyl, $R^9$ represents the group and the diastereomers, racemates, metabolites and physiologically acceptable salts thereof.

In the general formula (I), $R^1$ may represent hydrogen, hydroxy, $C_1$-$C_6$-alkyl, halo-$C_1$-$C_6$-alkyl, $C_1$-$C_6$-alkoxy, halo-$C_1$-$C_6$-alkoxy, halogen or cyano, or may represent $C_3$-$C_8$-cycloalkyl, $C_3$-$C_8$-cycloalkoxy, $C_3$-$C_8$-heterocycloalkyl, aryl or heteroaryl having 5 or 6 ring atoms which may optionally be mono- or polysubstituted by identical or different substituents from the group consisting of $C_1$-$C_6$-alkyl, halo-$C_1$-$C_6$-alkyl, $C_1$-$C_6$-alkoxy, halo-$C_1$-$C_6$-alkoxy, hydroxy, oxo, halogen, cyano, heteroaryl and aryl, or may represent —C(=O)—OR$^8$, —C(=O)—NR$^{12}$R$^{13}$, —C(=O)—R$^{14}$, —S(=O)$_2$—$C_1$-$C_6$-alkyl, —S(=O)$^2$—OR$^8$ or —S(=O)$_2$—NR$^{12}$R$^{13}$.

In the general formula (I), $R^1$ preferably represents hydrogen, hydroxy, $C_1$-$C_6$-alkyl, fluoro-$C_1$-$C_6$-alkyl, $C_1$-$C_6$-alkoxy, fluoro-$C_1$-$C_6$-alkoxy, halogen or cyano, or represents $C_3$-$C_8$-cycloalkyl, $C_3$-$C_8$-cycloalkoxy, $C_3$-$C_8$-heterocycloalkyl, aryl or heteroaryl having 5 or 6 ring atoms which may optionally be mono- or polysubstituted by identical or different substituents from the group consisting of $C_1$-$C_6$-alkyl, fluoro-$C_1$-$C_6$-alkyl, $C_1$-$C_6$-alkoxy, fluoro-$C_1$-$C_6$-alkoxy, hydroxy, oxo, halogen, cyano, heteroaryl and aryl.

In the general formula (I), $R^1$ particularly preferably represents hydrogen, hydroxy, $C_1$-$C_3$-alkyl, fluoro-$C_1$-$C_3$-alkyl, $C_1$-$C_3$-alkoxy or fluoro-$C_1$-$C_3$-alkoxy, or represents heteroaryl having 5 or 6 ring atoms which may optionally be mono- or polysubstituted by identical or different substituents from the group consisting of $C_1$-$C_3$-alkyl, fluoro-$C_1$-$C_3$-alkyl, $C_1$-$C_3$-alkoxy, fluoro-$C_1$-$C_3$-alkoxy, halogen and cyano.

In the general formula (I), $R^1$ very particularly preferably represents hydrogen, hydroxy, $C_1$-$C_3$-alkyl, fluoro-$C_1$-$C_3$-alkyl, $C_1$-$C_3$-alkoxy or fluoro-$C_1$-$C_3$-alkoxy, or represents heteroaryl having 5 ring atoms which may optionally be mono- or polysubstituted by identical or different substituents from the group consisting of $C_1$-$C_3$-alkyl and $C_1$-$C_3$-alkoxy.

In the general formula (I), $R^1$ even more preferably represents hydrogen, $C_1$-$C_3$-alkoxy or fluoro-$C_1$-$C_3$-alkoxy, or represents oxazolyl or isoxazolyl which may optionally be mono- or polysubstituted by identical or different substituents from the group consisting of $C_1$-$C_3$-alkyl and $C_1$-$C_3$-alkoxy.

In the general formula (I), $R^1$ most preferably represents hydrogen, methoxy, trifluoromethoxy or 3,5-dimethylisoxazol-4-yl.

In the general formula (I), $R^1$ furthermore most preferably represents hydrogen.

In the general formula (I), $R^1$ furthermore most preferably represents methoxy.

In the general formula (I), $R^1$ furthermore most preferably represents trifluoromethoxy.

In the general formula (I), $R^1$ furthermore most preferably represents 3,5-dimethylisoxazol-4-yl.

In the general formula (I), $R^2$ may represent hydrogen, $C_1$-$C_6$-alkyl or —$NR^6R^7$.

In the general formula (I), $R^2$ also represents $C_1$-$C_3$-alkyl or $C_1$-$C_3$-alkylamino.

In the general formula (I), $R^2$ also represents $C_1$-$C_3$-alkyl.

In the general formula (I), $R^2$ preferably represents methyl or methylamino.

In the general formula (I), $R^2$ particularly preferably represents methyl.

In the general formula (I), $R^3$ may represent cyano, —C(=O)—$OR^8$, —C(=O)—$R^9$ or —C(=O)—$NR^6R^7$, or a 5- or 6-membered ring system which contains 0, 1, 2, 3 or 4 heteroatoms independently of one another selected from the group consisting of O, N and S, which may optionally be aromatic or else non-aromatic and which may optionally be mono- or polysubstituted by identical or different radicals $R^5$.

In the general formula (I), $R^3$ preferably represents cyano, —C(=O)—$OR^8$, —C(=O)—$R^9$ or —C(=O)—$NR^6R^7$, or a 5- or 6-membered ring system which contains 0, 1, 2 or 3 heteroatoms independently of one another selected from the group consisting of O, N and S, which may optionally be aromatic or else non-aromatic and which may optionally be mono- or polysubstituted by identical or different radicals $R^5$.

In the general formula (I), $R^3$ particularly preferably represents —C(=O)—$OR^8$, —C(=O)—$R^9$ or —C(=O)—$NR^6R^7$, or a 5-membered aromatic ring system which contains 1, 2 or 3 heteroatoms independently of one another selected from the group consisting of O, N and S and which may optionally be mono- or polysubstituted by identical or different radicals $R^5$.

In the general formula (I), $R^3$ very particularly preferably represents —C(=O)—$OR^8$, —C(=O)—$R^9$ or —C(=O)—$NR^6R^7$, or one of the ring systems below

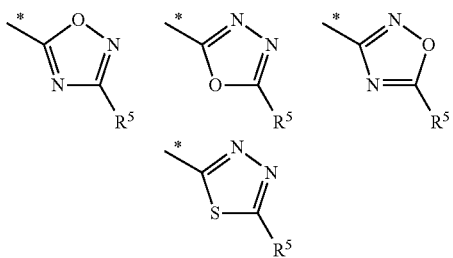

in which "*" denotes the point of attachment to the remainder of the molecule.

In the general formula (I), $R^3$ very particularly preferably represents —C(=O)—$OR^8$, —C(=O)—$R^9$ or —C(=O)—$NR^6R^7$.

In the general formula (I), $R^3$ very particularly preferably represents —C(=O)—$OR^8$.

In the general formula (I), $R^3$ very particularly preferably represents —C(=O)—$R^9$.

In the general formula (I), $R^3$ very particularly preferably represents —C(=O)—$NR^6R^7$.

In the general formula (I), $R^3$ very particularly preferably represents one of the ring systems below

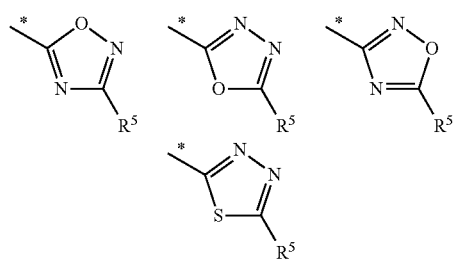

in which "*" denotes the point of attachment to the remainder of the molecule.

In the general formula (I), $R^3$ very particularly preferably represents one of the ring systems below

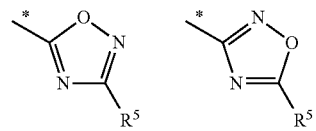

in which "*" denotes the point of attachment to the remainder of the molecule.

In the general formula (I), $R^3$ very particularly preferably represents one of the ring systems below

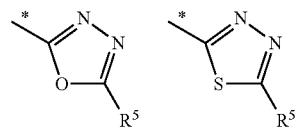

in which "*" denotes the point of attachment to the remainder of the molecule.

In the general formula (I), $R^4$ may represent hydrogen, fluorine, chlorine, bromine or cyano.

In the general formula (I), $R^4$ may also represent hydrogen, fluorine or chlorine.

In the general formula (I), $R^4$ particularly preferably represents chlorine.

In the general formula (I), $R^5$ may represent hydrogen, $C_1$-$C_6$-alkyl, $C_3$-$C_8$-cycloalkyl, $C_3$-$C_8$-heterocycloalkyl, halo-$C_1$-$C_6$-alkyl, aryl, heteroaryl, hydroxy, $C_1$-$C_6$-alkoxy, $C_1$-$C_3$-alkoxy-$C_1$-$C_3$-alkyl, aryloxy-$C_1$-$C_3$-alkyl, aryl-$C_1$-$C_3$-alkoxy-$C_1$-$C_3$-alkyl, halo-$C_1$-$C_6$-alkoxy, halogen, cyano or oxo.

In the general formula (I), $R^5$ preferably represents hydrogen, $C_1$-$C_6$-alkyl, $C_3$-$C_8$-cycloalkyl, $C_3$-$C_8$-heterocycloalkyl, fluoro-$C_1$-$C_6$-alkyl, aryl, heteroaryl, hydroxy, $C_1$-$C_6$-alkoxy, $C_1$-$C_3$-alkoxy-$C_1$-$C_3$-alkyl, aryloxy-$C_1$-$C_3$-alkyl, aryl-$C_1$-$C_3$-alkoxy-$C_1$-$C_3$-alkyl, fluoro-$C_1$-$C_6$-alkoxy, halogen, cyano or oxo.

In the general formula (I), $R^5$ particularly preferably represents hydrogen, $C_1$-$C_3$-alkyl, $C_3$-$C_6$-cycloalkyl, $C_3$-$C_6$-heterocycloalkyl, fluoro-$C_1$-$C_3$-alkyl, aryl, heteroaryl, hydroxy, $C_1$-$C_3$-alkoxy, $C_1$-$C_3$-alkoxy-$C_1$-$C_3$-alkyl, aryloxy-$C_1$-$C_3$-alkyl, aryl-$C_1$-$C_3$-alkoxy-$C_1$-$C_3$-alkyl, fluoro-$C_1$-$C_3$-alkoxy, halogen or cyano.

In the general formula (I), $R^5$ very particularly preferably represents hydrogen, $C_1$-$C_3$-alkyl, $C_3$-$C_6$-cycloalkyl, $C_3$-$C_6$-heterocycloalkyl, phenyl, 5- or 6-membered heteroaryl, $C_1$-$C_3$-alkoxy-$C_1$-$C_3$-alkyl, phenoxy-$C_1$-$C_3$-alkyl or benzyloxy-$C_1$-$C_3$-alkyl.

In the general formula (I), $R^5$ even more preferably represents hydrogen, $C_1$-$C_3$-alkyl, $C_3$-$C_6$-cycloalkyl, pyridinyl or benzyloxy-$C_1$-$C_3$-alkyl.

In the general formula (I), $R^5$ even more preferably represents $C_1$-$C_3$-alkyl.

In the general formula (I), $R^5$ most preferably represents methyl, isopropyl, cyclopropyl, pyridin-3-yl or benzyloxymethyl.

In the general formula (I), $R^6$ and $R^7$ independently of one another may represent hydrogen or may represent —NH—C(=O)—$R^{15}$, or may represent $C_1$-$C_6$-alkyl, $C_1$-$C_6$-alkoxy, $C_3$-$C_8$-heterocycloalkyl, aryl, heteroaryl, $C_3$-$C_8$-cycloalkyl, $C_6$-$C_{12}$-bicycloalkyl, $C_5$-$C_{11}$-spirocycloalkyl, $C_6$-$C_{12}$-heterobicycloalkyl or $C_5$-$C_{11}$-heterospirocycloalkyl which may optionally be mono- or polysubstituted by identical or different substituents from the group consisting of $C_1$-$C_6$-alkyl, halo-$C_1$-$C_6$-alkyl, $C_1$-$C_6$-alkoxy, halo-$C_1$-$C_6$-alkoxy, phenoxy, hydroxy, oxo, halogen, cyano, $C_3$-$C_8$-cycloalkyl, $C_3$-$C_8$-heterocycloalkyl, heteroaryl and aryl, or may represent the group

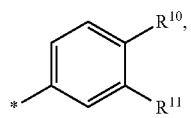

in which $R^{10}$ and $R^{11}$ together represent $C_3$-$C_6$-alkylene or $C_3$-$C_6$-heteroalkylene which may optionally be mono- or polysubstituted by identical or different substituents from the group consisting of halogen, oxo, hydroxy, cyano, nitro, $C_1$-$C_3$-alkyl, halo-$C_1$-$C_6$-alkyl, $C_1$-$C_6$-alkoxy, halo-$C_1$-$C_6$-alkoxy, $C_1$-$C_6$-alkoxy-$C_1$-$C_6$-alkyl, $C_1$-$C_6$-alkylcarbonyl,
and in which "*" denotes the point of attachment to the remainder of the molecule.

In the general formula (I), $R^6$ and $R^7$ preferably and independently of one another represent hydrogen or represent —NH—C(=O)—$R^{15}$, or represent $C_1$-$C_6$-alkyl, $C_1$-$C_6$-alkoxy, $C_3$-$C_8$-heterocycloalkyl, aryl, heteroaryl, $C_3$-$C_8$-cycloalkyl, $C_6$-$C_{12}$-bicycloalkyl, $C_5$-$C_{11}$-spirocycloalkyl, $C_6$-$C_{12}$-heterobicycloalkyl or $C_5$-$C_{11}$-heterospirocycloalkyl which may optionally be mono- or polysubstituted by identical or different substituents from the group consisting of $C_1$-$C_3$-alkyl, fluoro-$C_1$-$C_3$-alkyl, $C_1$-$C_3$-alkoxy, fluoro-$C_1$-$C_3$-alkoxy, phenoxy, hydroxy, oxo, halogen, cyano, $C_3$-$C_8$-cycloalkyl, $C_3$-$C_8$-heterocycloalkyl, heteroaryl and aryl,
or represent the group

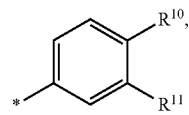

in which $R^{10}$ and $R^{11}$ together represent $C_3$-$C_6$-alkylene or $C_3$-$C_6$-heteroalkylene which may optionally be mono- or polysubstituted by identical or different substituents from the group consisting of halogen, oxo, hydroxy, cyano, nitro, $C_1$-$C_3$-alkyl, fluoro-$C_1$-$C_3$-alkyl, $C_1$-$C_3$-alkoxy, fluoro-$C_1$-$C_3$-alkoxy, $C_1$-$C_3$-alkoxy-$C_1$-$C_3$-alkyl, $C_1$-$C_3$-alkylcarbonyl,
and in which "*" denotes the point of attachment to the remainder of the molecule.

In the general formula (I), $R^6$ and $R^7$ very particularly preferably and independently of one another represent hydrogen or represent —NH—C(=O)—$R^{15}$, or represent $C_1$-$C_6$-alkyl, $C_3$-$C_8$-heterocycloalkyl, phenyl, heteroaryl having 5 or 6 ring atoms or $C_3$-$C_8$-cycloalkyl which may optionally be mono- or polysubstituted by identical or different substituents from the group consisting of $C_1$-$C_3$-alkyl, fluoro-$C_1$-$C_3$-alkyl, $C_1$-$C_3$-alkoxy, phenoxy, hydroxy, oxo, halogen, cyano, $C_3$-$C_8$-cycloalkyl, $C_3$-$C_8$-heterocycloalkyl, 5- or 6-membered heteroaryl and phenyl,
or represent the group

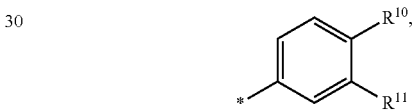

in which $R^{10}$ and $R^{11}$ together represent $C_3$-$C_4$-alkylene or $C_3$-$C_4$-heteroalkylene which may optionally be mono- or polysubstituted by identical or different substituents from the group consisting of halogen, oxo, hydroxy, $C_1$-$C_3$-alkyl, $C_1$-$C_3$-alkoxy, $C_1$-$C_3$-alkylcarbonyl,
and in which "*" denotes the point of attachment to the remainder of the molecule.

In the general formula (I), $R^7$ furthermore very particularly preferably represents hydrogen, and $R^6$ very particularly preferably represents $C_1$-$C_6$-alkyl, $C_3$-$C_8$-heterocycloalkyl, phenyl, heteroaryl having 5 or 6 ring atoms or represents $C_3$-$C_8$-cycloalkyl which may optionally be mono- or polysubstituted by identical or different substituents from the group consisting of $C_1$-$C_3$-alkyl, fluoro-$C_1$-$C_3$-alkyl, $C_1$-$C_3$-alkoxy, phenoxy, hydroxy, oxo, halogen, cyano, $C_3$-$C_8$-cycloalkyl, $C_3$-$C_8$-heterocycloalkyl, 5- or 6-membered heteroaryl and phenyl,
or represent the group

in which $R^{10}$ and $R^{11}$ together represent $C_3$-$C_4$-alkylene or $C_3$-$C_4$-heteroalkylene which may optionally be mono- or polysubstituted by identical or different substituents from the group consisting of halogen, oxo, hydroxy, $C_1$-$C_3$-alkyl, $C_1$-$C_3$-alkoxy, $C_1$-$C_3$-alkylcarbonyl,
and in which "*" denotes the point of attachment to the remainder of the molecule.

In the general formula (I), $R^7$ furthermore very particularly preferably represents hydrogen, and $R^6$ very particularly preferably represents $C_1$-$C_6$-alkyl, $C_3$-$C_8$-heterocycloalkyl, phenyl, heteroaryl having 5 or 6 ring atoms or $C_3$-$C_8$-cycloalkyl which may optionally be mono- or polysubstituted by identical or different substituents from the group consisting of $C_1$-$C_3$-alkyl, fluoro-$C_1$-$C_3$-alkyl, $C_1$-$C_3$-alkoxy, phenoxy, hydroxy, oxo, halogen, cyano, $C_3$-$C_8$-cycloalkyl, $C_3$-$C_8$-heterocycloalkyl, 5- or 6-membered heteroaryl and phenyl.

In the general formula (I), $R^7$ furthermore very particularly preferably represents hydrogen, and $R^6$ very particularly preferably represents the group

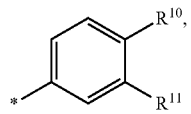

in which $R^{10}$ and $R^{11}$ together represent $C_3$-$C_4$-alkylene or $C_3$-$C_4$-heteroalkylene which may optionally be mono- or polysubstituted by identical or different substituents from the group consisting of halogen, oxo, hydroxy, $C_1$-$C_3$-alkyl, $C_1$-$C_3$-alkoxy, $C_1$-$C_3$-alkylcarbonyl,
and in which "*" denotes the point of attachment to the remainder of the molecule.

In the general formula (I), $R^6$ and $R^7$ even more preferably and independently of one another represent hydrogen or represent —NH—C(=O)—$R^{15}$, or represent $C_1$-$C_6$-alkyl which may optionally be mono- or polysubstituted by identical or different substituents from the group consisting of $C_3$-$C_8$-heterocycloalkyl,
or represent the group

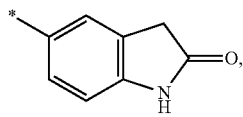

in which "*" denotes the point of attachment to the remainder of the molecule.

In the general formula (I), $R^7$ even more preferably represents hydrogen and $R^6$ even more preferably represents $C_1$-$C_6$-alkyl which may optionally be mono- or polysubstituted by identical or different substituents from the group consisting of $C_3$-$C_8$-heterocycloalkyl,
or represents the group

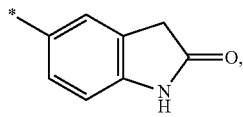

in which "*" denotes the point of attachment to the remainder of the molecule.

In the general formula (I), $R^7$ even more preferably represents hydrogen and $R^6$ even more preferably represents $C_1$-$C_6$-alkyl which may optionally be mono- or polysubstituted by identical or different substituents from the group consisting of $C_3$-$C_8$-heterocycloalkyl.

In the general formula (I), $R^7$ even more preferably represents hydrogen, and $R^6$ even more preferably represents the group

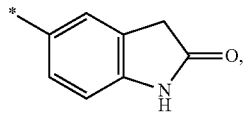

in which "*" denotes the point of attachment to the remainder of the molecule.

In the general formula (I), $R^6$ and $R^7$ most preferably and independently of one another represent hydrogen or represent —NH—C(=O)—$R^{15}$, or ethyl which may optionally be monosubstituted by morpholinyl,
or represent the group

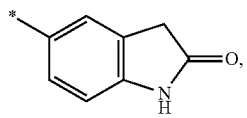

in which "*" denotes the point of attachment to the remainder of the molecule.

In the general formula (I), $R^8$ may represent hydrogen, $C_1$-$C_6$-alkyl, $C_3$-$C_8$-cycloalkyl, $C_3$-$C_8$-heterocycloalkyl, aryl or heteroaryl which may optionally be mono- or polysubstituted by identical or different substituents from the group consisting of $C_1$-$C_6$-alkyl, halo-$C_1$-$C_6$-alkyl, $C_1$-$C_6$-alkoxy, halo-$C_1$-$C_6$-alkoxy, hydroxy, oxo, halogen, cyano, nitro, heteroaryl and aryl.

In the general formula (I), $R^8$ preferably represents hydrogen, $C_1$-$C_6$-alkyl, $C_3$-$C_8$-cycloalkyl, aryl or heteroaryl which may optionally be mono- or polysubstituted by identical or different substituents from the group consisting of $C_1$-$C_6$-alkyl, fluoro-$C_1$-$C_6$-alkyl, $C_1$-$C_6$-alkoxy, fluoro-$C_1$-$C_6$-alkoxy, hydroxy, oxo, cyano, nitro, heteroaryl and aryl.

In the general formula (I), $R^8$ also preferably represents hydrogen or represents $C_1$-$C_6$-alkyl which may optionally be mono- or polysubstituted by identical or different substituents from the group consisting of $C_1$-$C_6$-alkoxy, hydroxy, oxo, fluorine, cyano, nitro, heteroaryl and aryl.

In the general formula (I), $R^8$ particularly preferably represents $C_1$-$C_6$-alkyl.

In the general formula (I), $R^8$ very particularly preferably represents $C_1$-$C_4$-alkyl.

In the general formula (I), $R^8$ even more preferably represents ethyl or tert-butyl.

In the general formula (I), $R^9$ may represent $C_3$-$C_8$-heterocycloalkyl, $C_5$-$C_{11}$-spiroheterocycloalkyl, $C_6$-$C_{12}$-heterobicycloalkyl or may represent a bridged heterocycle consisting of 7 to 15 ring atoms which may optionally be mono- or polysubstituted by identical or different substituents from the group consisting of $C_1$-$C_4$-alkyl, $C_3$-$C_8$-cycloalkyl, $C_3$-$C_8$-heterocycloalkyl, halo-$C_1$-$C_6$-alkyl, aryl, aryloxy, aryl-$C_1$-$C_2$-alkyl, —C(=O)—O—$C_1$-$C_6$-alkyl, heteroaryl, hydroxy, $C_1$-$C_6$-alkoxy, halo-$C_1$-$C_6$-alkoxy, halogen, cyano and oxo.

In the general formula (I), $R^9$ preferably represents $C_3$-$C_8$-heterocycloalkyl, $C_5$-$C_{11}$-spiroheterocycloalkyl, $C_6$-$C_{12}$-heterobicycloalkyl or represents a bridged heterocycle consisting of 7 to 15 ring atoms which may optionally be mono- or polysubstituted by identical or different substituents from the group consisting of $C_1$-$C_4$-alkyl, $C_3$-$C_8$-cycloalkyl, $C_3$-$C_8$-heterocycloalkyl, fluoro-$C_1$-$C_6$-alkyl, aryl, aryloxy, aryl-$C_1$-$C_2$-alkyl, —C(=O)—O—$C_1$-$C_6$-alkyl, heteroaryl, hydroxy, $C_1$-$C_6$-alkoxy, fluoro-$C_1$-$C_6$-alkoxy, halogen, cyano and oxo.

In the general formula (I), $R^9$ particularly preferably represents one of the groups below

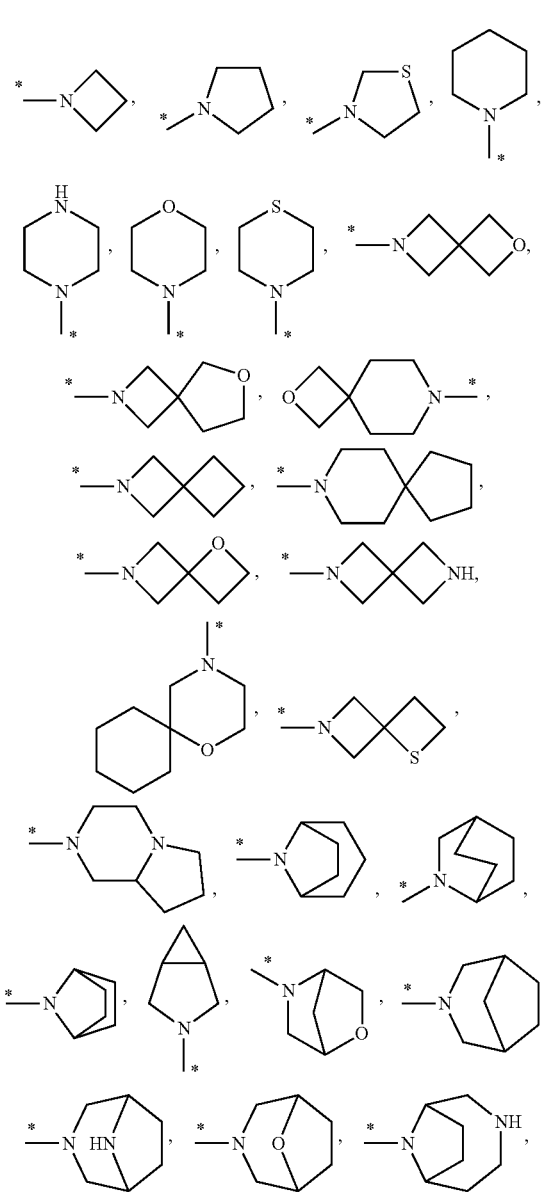

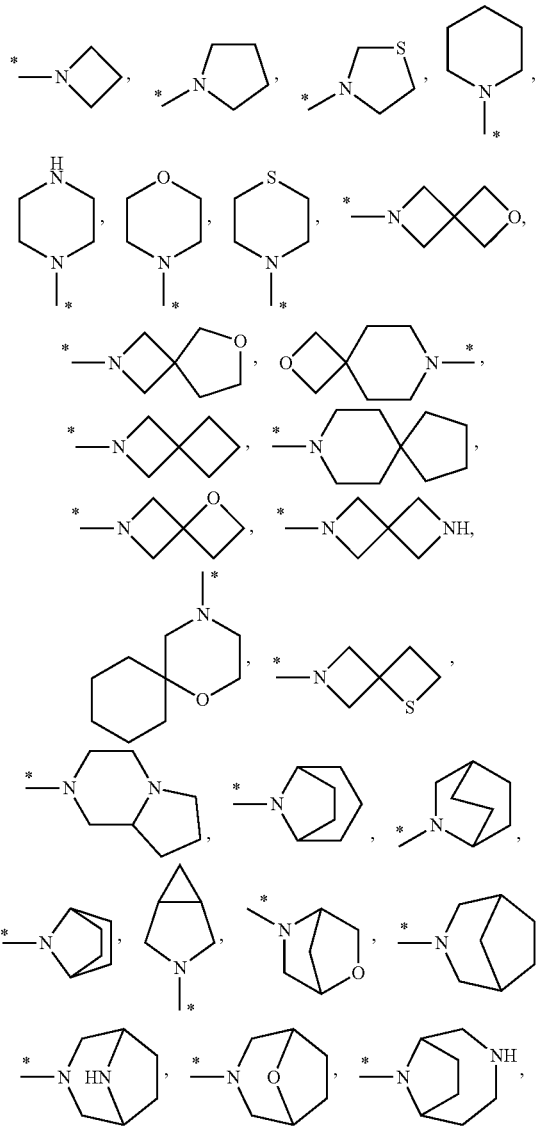

which may optionally be mono- or polysubstituted by identical or different substituents from the group consisting of $C_1$-$C_4$-alkyl, phenyl, phenoxy, benzyl, —C(=O)—O—$C_1$-$C_4$-alkyl, 5- or 6-membered heteroaryl, hydroxy, $C_1$-$C_4$-alkoxy, fluorine, cyano and oxo, and in which "*" denotes the point of attachment to the remainder of the molecule.

In the general formula (I), $R^9$ even more preferably represents one of the groups below

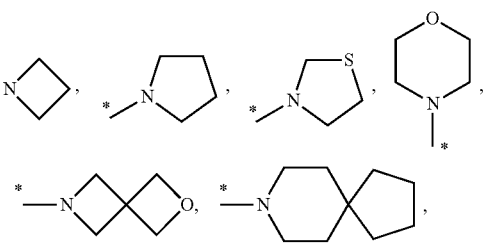

which may optionally be mono- or polysubstituted by identical or different substituents from the group consisting of $C_1$-$C_4$-alkyl, $C_3$-$C_8$-cycloalkyl, $C_3$-$C_8$-heterocycloalkyl, fluoro-$C_1$-$C_6$-alkyl, aryl, aryloxy, aryl-$C_1$-$C_2$-alkyl, —C(=O)—O—$C_1$-$C_6$-alkyl, heteroaryl, hydroxy, $C_1$-$C_6$-alkoxy, fluoro-$C_1$-$C_6$-alkoxy, halogen, cyano and oxo, and in which "*" denotes the point of attachment to the remainder of the molecule.

In the general formula (I), $R^9$ very particularly preferably represents one of the groups below which may optionally be mono- or polysubstituted by identical or different substituents from the group consisting of $C_1$-$C_4$-alkyl, phenoxy, benzyl, —C(=O)—O—$C_1$-$C_4$-alkyl, fluorine and oxo,
and in which "*" denotes the point of attachment to the remainder of the molecule.

In the general formula (I), $R^9$ most preferably represents one of the groups below in which "*" denotes the point of attachment to the remainder of the molecule.

In the general formula (I), $R^{12}$ and $R^{13}$ independently of one another may represent hydrogen or $C_1$-$C_6$-alkyl.

In the general formula (I), $R^{12}$ and $R^{13}$ independently of one another may also represent hydrogen or methyl.

In the general formula (I), $R^{14}$ may represent hydrogen, $C_1$-$C_6$-alkyl, amino, $C_1$-$C_6$-alkoxy, $C_3$-$C_8$-cycloalkyl, $C_3$-$C_8$-heterocycloalkyl, aryl or heteroaryl which may optionally be mono- or polysubstituted by identical or different substituents from the group consisting of $C_1$-$C_6$-alkyl, halo-$C_1$-$C_6$-alkyl, $C_1$-$C_6$-alkoxy, halo-$C_1$-$C_6$-alkoxy, hydroxy, oxo, halogen, cyano, nitro, heteroaryl and aryl.

In the general formula (I), $R^{14}$ may also represent $C_1$-$C_6$-alkyl, $C_3$-$C_8$-cycloalkyl, aryl or heteroaryl which may be mono- or polysubstituted by identical or different substituents from the group consisting of $C_1$-$C_3$-alkyl, fluoro-$C_1$-$C_3$-alkyl, $C_1$-$C_3$-alkoxy, fluoro-$C_1$-$C_3$-alkoxy, hydroxy, oxo, halogen, cyano and nitro.

In the general formula (I), $R^{15}$ may represent hydrogen, $C_1$-$C_6$-alkyl, halo-$C_1$-$C_6$-alkyl, aryl or aryl-$C_1$-$C_2$-alkyl, where the aryl and the aryl present in aryl-$C_1$-$C_2$-alkyl for their part may optionally be mono- or polysubstituted by identical or different substituents from the group consisting of halogen, cyano, $C_1$-$C_3$-alkyl, $C_1$-$C_3$-alkoxy and trifluoromethyl.

In the general formula (I), $R^{15}$ preferably represents $C_1$-$C_6$-alkyl, fluoro-$C_1$-$C_3$-alkyl, phenyl or phenyl-$C_1$-$C_2$-alkyl, where the phenyl and the phenyl present in phenyl-$C_1$-$C_2$-alkyl for their part may optionally be mono- or polysubstituted by identical or different substituents from the group consisting of halogen, cyano, $C_1$-$C_3$-alkyl, $C_1$-$C_3$-alkoxy and trifluoromethyl.

In the general formula (I), $R^{15}$ particularly preferably represents $C_1$-$C_3$-alkyl, trifluoromethyl, phenyl or benzyl, where the phenyl and the phenyl present in benzyl for their part may optionally be mono- or polysubstituted by identical or different substituents from the group consisting of fluorine, chlorine, bromine, methyl and methoxy.

In the general formula (I), $R^{15}$ very particularly preferably represents $C_1$-$C_3$-alkyl.

In the general formula (I), $R^{15}$ most preferably represents methyl.

The specific radical definitions given in the particular combinations or preferred combinations of radicals are, irrespective of the particular combinations of radicals specified, also replaced as desired by radical definitions of other combination.

Very particular preference is given to combinations of two or more of the abovementioned preferred ranges.

Extraordinary preference is given to the following compounds of the general formula (I):
ethyl [6-(4-chlorophenyl)-1-methyl-4H-[1,2,4]triazolo[4,3-a][1]benzazepin-4-yl]acetate;
ethyl (−)-(4R)-[6-(4-chlorophenyl)-1-methyl-4H-[1,2,4]triazolo[4,3-a][1]benzazepin-4-yl]acetate;
2-[6-(4-chlorophenyl)-1-methyl-4H-[1,2,4]triazolo[4,3-a][1]benzazepin-4-yl]-1-(2-oxa-6-azaspiro[3.3]hept-6-yl)ethanone;
(−)-2-[(4R)-6-(4-chlorophenyl)-1-methyl-4H-[1,2,4]triazolo[4,3-a][1]benzazepin-4-yl]-1-(2-oxa-6-azaspiro[3.3]hept-6-yl)ethanone;
1-(7-azabicyclo[2.2.1]hept-7-yl)-2-[6-(4-chlorophenyl)-1-methyl-4H-[1,2,4]triazolo[4,3-a][1]benzazepin-4-yl]ethanone;
(−)-1-(7-azabicyclo[2.2.1]hept-7-yl)-2-[(4R)-6-(4-chlorophenyl)-1-methyl-4H-[1,2,4]triazolo[4,3-a][1]benzazepin-4-yl]ethanone;
ethyl [6-(3-chlorophenyl)-1-methyl-4H-[1,2,4]triazolo[4,3-a][1]benzazepin-4-yl]acetate;
tert-butyl [6-(4-chlorophenyl)-1-methyl-4H-[1,2,4]triazolo[4,3-a][1]benzazepin-4-yl]acetate;
tert-butyl (+)[(4R)-6-(4-chlorophenyl)-1-methyl-4H-[1,2,4]triazolo[4,3-a][1]benzazepin-4-yl]acetate;
2-[6-(3-chlorophenyl)-1-methyl-4H-[1,2,4]triazolo[4,3-a][1]benzazepin-4-yl]-1-(2-oxa-6-azaspiro[3.3]hept-6-yl)ethanone;
(−)-2-[(4R)-6-(3-chlorophenyl)-1-methyl-4H-[1,2,4]triazolo[4,3-a][1]benzazepin-4-yl]-1-(2-oxa-6-azaspiro[3.3]hept-6-yl)ethanone;
2-[6-(4-chlorophenyl)-1-methyl-4H-[1,2,4]triazolo[4,3-a][1]benzazepin-4-yl]-N-ethylacetamide;
(−)-2-[(4R)-6-(4-chlorophenyl)-1-methyl-4H-[1,2,4]triazolo[4,3-a][1]benzazepin-4-yl]-N-ethylacetamide;
2-[6-(4-chlorophenyl)-1-methyl-4H-[1,2,4]triazolo[4,3-a][1]benzazepin-4-yl]-1-(morpholin-4-yl)ethanone;
(−)-2-[(4R)-6-(4-chlorophenyl)-1-methyl-4H-[1,2,4]triazolo[4,3-a][1]benzazepin-4-yl]-1-(morpholin-4-yl)ethanone;

2-[6-(4-chlorophenyl)-1-methyl-4H-[1,2,4]triazolo[4,3-a]
[1]benzazepin-4-yl]-1-(3-fluoroazetidin-1-yl)ethanone;
(−)-2-[(4R)-6-(4-chlorophenyl)-1-methyl-4H-[1,2,4]triazolo[4,3-a][1]benzazepin-4-yl]-1-(3-fluoroazetidin-1-yl)ethanone;
2-[6-(4-chlorophenyl)-1-methyl-4H-[1,2,4]triazolo[4,3-a]
[1]benzazepin-4-yl]-1-(1,1-dioxido-1-thia-6-azaspiro
[3.3]hept-6-yl)ethanone;
(−)-2-[(4R)-6-(4-chlorophenyl)-1-methyl-4H-[1,2,4]triazolo[4,3-a][1]benzazepin-4-yl]-1-(1,1-dioxido-1-thia-6-azaspiro[3.3]hept-6-yl)ethanone;
2-[6-(4-chlorophenyl)-1-methyl-4H-[1,2,4]triazolo[4,3-a]
[1]benzazepin-4-yl]-N-(2-oxo-2,3-dihydro-1H-indol-5-yl)acetamide;
(−)-2-[(4R)-6-(4-chlorophenyl)-1-methyl-4H-[1,2,4]triazolo[4,3-a][1]benzazepin-4-yl]-N-(2-oxo-2,3-dihydro-1H-indol-5-yl)acetamide;
3-{[(6-(4-chlorophenyl)-1-methyl-4H-[1,2,4]triazolo[4,3-a]
[1]benzazepin-4-yl]acetyl}-8-azabicyclo[3.2.1]octan-3-one;
(−)-3-{[(4R)-6-(4-chlorophenyl)-1-methyl-4H-[1,2,4]triazolo[4,3-a][1]benzazepin-4-yl]acetyl}-8-azabicyclo
[3.2.1]octan-3-one;
2-[6-(4-chlorophenyl)-1-methyl-4H-[1,2,4]triazolo[4,3-a]
[1]benzazepin-4-yl]-1-(3-phenoxyazetidin-1-yl)ethanone;
(−)-2-[(4R)-6-(4-chlorophenyl)-1-methyl-4H-[1,2,4]triazolo[4,3-a][1]benzazepin-4-yl]-1-(3-phenoxyazetidin-1-yl)ethanone;
1-{[6-(4-chlorophenyl)-1-methyl-4H-[1,2,4]triazolo[4,3-a]
[1]benzazepin-4-yl]acetyl}pyrrolidin-3-one;
(−)-1-{[(4R)-6-(4-chlorophenyl)-1-methyl-4H-[1,2,4]triazolo[4,3-a][1]benzazepin-4-yl]acetyl}pyrrolidin-3-one;
1-(8-azaspiro[4.5]dec-8-yl)-2-[6-(4-chlorophenyl)-1-methyl-4H-[1,2,4]triazolo[4,3-a][1]benzazepin-4-yl]
ethanone;
(−)-1-(8-azaspiro[4.5]dec-8-yl)-2-[(4R)-6-(4-chlorophenyl)-1-methyl-4H-[1,2,4]triazolo[4,3-a][1]benzazepin-4-yl]ethanone;
2-[6-(4-chlorophenyl)-1-methyl-4H-[1,2,4]triazolo[4,3-a]
[1]benzazepin-4-yl]-1-(1,1-dioxido-1,3-thiazolidin-3-yl)ethanone;
(−)-2-[(4R)-6-(4-chlorophenyl)-1-methyl-4H-[1,2,4]triazolo[4,3-a][1]benzazepin-4-yl]-1-(1,1-dioxido-1,3-thiazolidin-3-yl)ethanone;
2-[6-(4-chlorophenyl)-1-methyl-4H-[1,2,4]triazolo[4,3-a]
[1]benzazepin-4-yl]-1-(8-oxa-3-azabicyclo[3.2.1]oct-3-yl)ethanone;
(−)-2-[(4R)-6-(4-chlorophenyl)-1-methyl-4H-[1,2,4]triazolo[4,3-a][1]benzazepin-4-yl]-1-(8-oxa-3-azabicyclo
[3.2.1]oct-3-yl)ethanone;
6-(4-chlorophenyl)-1-methyl-4-[(3-methyl-1,2,4-oxadiazol-5-yl)methyl]-4H-[1,2,4]triazolo[4,3-a][1]benzazepine;
(−)-6-[(4R)-4-chlorophenyl]-1-methyl-4-[(3-methyl-1,2,4-oxadiazol-5-yl)methyl]-4H-[1,2,4]triazolo[4,3-a][1]benzazepine;
(−)-(4R)-6-(4-chlorophenyl)-1-methyl-4-{[3-(propan-2-yl)-1,2,4-oxadiazol-5-yl]methyl}-4H-[1,2,4]triazolo[4,3-a]
[1]benzazepine;
(−)6-(4R)-(4-chlorophenyl)-4-[(3-cyclopropyl-1,2,4-oxadiazol-5-yl)methyl]-1-methyl-4H-[1,2,4]triazolo[4,3-a][1]
benzazepine;
(−)-(4R)-6-(4-chlorophenyl)-1-methyl-4-[(5-methyl-1,3,4-oxadiazol-2-yl)methyl]-4H-[1,2,4]triazolo[4,3-a][1]benzazepine;
6-(4-chlorophenyl)-1-methyl-4-[(5-methyl-1,3,4-oxadiazol-2-yl)methyl]-4H-[1,2,4]triazolo[4,3-a][1]benzazepine;

N'-acetyl-2-[(4R)-6-(4-chlorophenyl)-1-methyl-4H-[1,2,4]
triazolo[4,3-a][1]benzazepin-4-yl]acetohydrazide;
6-(4-chlorophenyl)-1-methyl-4-[(5-methyl-1,3,4-thiadiazol-2-yl)methyl]-4H-[1,2,4]triazolo[4,3-a][1]benzazepine;
(+)-(4R)-6-(4-chlorophenyl)-1-methyl-4-[(5-methyl-1,3,4-thiadiazol-2-yl)methyl]-4H-[1,2,4]triazolo[4,3-a][1]benzazepine;
6-(4-chlorophenyl)-4-[(5-cyclopropyl-1,3,4-oxadiazol-2-yl)methyl]-1-methyl-4H-[1,2,4]triazolo[4,3-a][1]benzazepine;
6-(4-chlorophenyl)-1-methyl-4-{[5-(pyridin-3-yl)-1,3,4-oxadiazol-2-yl]methyl}-4H-[1,2,4]triazolo[4,3-a][1]benzazepine;
(−)-(4R)-6-(4-chlorophenyl)-1-methyl-4-{[5-(pyridin-3-yl)-1,3,4-oxadiazol-2-yl]methyl}-4H-[1,2,4]triazolo[4,3-a]
[1]benzazepine;
6-(4-chlorophenyl)-1-methyl-4-[(5-methyl-1,2,4-oxadiazol-3-yl)methyl]-4H-[1,2,4]triazolo[4,3-a][1]benzazepine;
6-(4-chlorophenyl)-8-methoxy-1-methyl-4-[(5-methyl-1,3,4-oxadiazol-2-yl)methyl]-4H-[1,2,4]triazolo[4,3-a][1]
benzazepine;
6-(4-chlorophenyl)-8-(3,5-dimethyl-1,2-oxazol-4-yl)-1-methyl-4-[(5-methyl-1,3,4-oxadiazol-2-yl)methyl]-4H-
[1,2,4]triazolo[4,3-a][1]benzazepine;
tert-butyl [6-(4-chlorophenyl)-1-methyl-8-(trifluoromethoxy)-4H-[1,2,4]triazolo[4,3-a][1]benzazepin-4-yl]
acetate;
tert-butyl (−)-[(4R)-6-(4-chlorophenyl)-1-methyl-8-(trifluoromethoxy)-4H-[1,2,4]triazolo[4,3-a][1]benzazepin-4-yl]
acetate;
2-[(4R)-6-(4-chlorophenyl)-1-methyl-8-(trifluoromethoxy)-4H-[1,2,4]triazolo[4,3-a][1,4]benzazepin-4-yl]-1-(2-oxa-6-azaspiro[3.3]hept-6-yl)ethanone;
2-[(4R)-6-(4-chlorophenyl)-1-methyl-8-(trifluoromethoxy)-4H-[1,2,4]triazolo[4,3-a][1]benzazepin-4-yl]-N-ethylacetamide;
2-[(4R)-6-(4-chlorophenyl)-1-methyl-8-(trifluoromethoxy)-4H-[1,2,4]triazolo[4,3-a][1]benzazepin-4-yl]-N-[2-(morpholin-4-yl)ethyl]acetamide;
6-(4-chlorophenyl)-1-methyl-4-[(5-methyl-1,3,4-oxadiazol-2-yl)methyl]-8-(trifluoromethoxy)-4H-[1,2,4]triazolo[4,3-a][1]benzazepine;
(4R)-6-(4-chlorophenyl)-1-methyl-4-[(5-methyl-1,3,4-oxadiazol-2-yl)methyl]-8-(trifluoromethoxy)-4H-[1,2,4]triazolo[4,3-a][1]benzazepine;
2-{[(4R)-6-(4-chlorophenyl)-1-methyl-8-(trifluoromethoxy)-4H-[1,2,4]triazolo[4,3-a][1]benzazepin-4-yl]
acetyl}hexahydropyrrolo[1,2-a]pyrazin-6(2H)one;
(4R)-4-({5-[(benzyloxy)methyl]-1,3,4-oxadiazol-2-yl}methyl)-6-(4-chlorophenyl)-1-methyl-4H-[1,2,4]triazolo[4,3-a][1]benzazepine.

DEFINITIONS

The invention is based on the following definitions:
$C_1$-$C_6$-Alkyl-, or a $C_1$-$C_6$-alkyl group, is understood to mean a linear or branched, saturated monovalent hydrocarbyl radical, for example a methyl, ethyl, propyl, butyl, pentyl, hexyl, isopropyl, isobutyl, sec-butyl, tert-butyl, isopentyl, 2-methylbutyl, 1-methylbutyl, 1-ethylpropyl, 1,2-dimethylpropyl, neopentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl or 1,2-dimethylbutyl radical. Preferably, $C_1$-$C_6$-alkyl, or a $C_1$-$C_6$-alkyl group, is understood to mean a methyl, ethyl, propyl or isopropyl radical.

$C_3$-$C_6$-Alkylene, or a $C_3$-$C_6$-alkylene group, is understood to mean a linear or branched saturated divalent hydrocarbon radical such as, for example, a propylene, butylene, pentylene, hexylene, isopropylene, isobutylene, sec-butylene, tert-butylene, isopentylene, 2-methylbutylene, 1-methylbutylene, 1-ethylpropylene, 1,2-dimethylpropylene, neopentylene, 1,1-dimethylpropylene, 4-methylpentylene, 3-methylpentylene, 2-methylpentylene, 1-methylpentylene, 2-ethylbutylene, 1-ethylbutylene, 3,3-dimethylbutylene, 2,2-dimethylbutylene, 1,1-dimethylbutylene, 2,3-dimethylbutylene, 1,3-dimethylbutylene or 1,2-dimethylbutylene radical.

Preferably, $C_3$-$C_6$-alkylene, or a $C_3$-$C_6$-alkylene group, is understood to mean $C_3$-$C_4$-alkylene, in particular a propylene or butylene radical.

$C_3$-$C_6$-Heteroalkylene is to be understood to mean a $C_3$-$C_6$-alkylene group as defined above in which 1, 2 or 3 carbon atoms, preferably 1 or 2 carbon atoms, are replaced by heteroatoms selected from the group consisting of nitrogen, oxygen and sulphur. Preference is given to $C_3$-$C_4$-heteroalkylene.

$C_1$-$C_6$-Alkoxy, or a $C_1$-$C_6$-alkoxy group, is understood to mean a linear or branched, saturated alkyl ether radical —O-alkyl, for example a methoxy, ethoxy, n-propoxy, isopropoxy, tert-butoxy, n-pentoxy or n-hexoxy radical.

Preferably, $C_1$-$C_6$-alkoxy, or a $C_1$-$C_6$-alkoxy group, is understood to mean a methoxy, ethoxy or tert-butoxy radical.

A heteroatom is understood to mean an oxygen, nitrogen or sulphur atom.

Preference is given to an oxygen or nitrogen atom.

Halogen, or hal, is understood to mean fluorine, chlorine or bromine, which may be in the ortho, meta or para position on the phenyl ring. Preference is given to fluorine or chlorine. The preferred position is the meta or para position.

Oxo, an oxo group or an oxo substituent, is understood to mean a double-bonded oxygen atom =O. Oxo may be bonded to atoms of suitable valency, for example to a saturated carbon atom or to sulphur.

Preference is given to the bond to carbon to form a carbonyl group —(C=O)—.

Preference is furthermore given to the bond of two double-bonded oxygen atoms to a sulphur atom, forming a sulphonyl group —(S=O)$_2$—.

A halo-$C_1$-$C_6$-alkyl radical is understood to mean a $C_1$-$C_6$-alkyl radical having at least one halogen substituent.

Preference is given to fluoroalkyl radicals such as fluoro-$C_1$-$C_6$-alkyl or fluoro-$C_1$-$C_3$-alkyl, for example difluoromethyl, trifluoromethyl, 2,2,2-trifluoroethyl, pentafluoroethyl, 5,5,5,4,4-pentafluoropentyl or 5,5,5,4,4,3,3-heptafluoropentyl.

Particular preference is given to perfluorinated alkyl radicals such as trifluoromethyl or pentafluoroethyl.

A halo-$C_1$-$C_6$-alkoxy radical is understood to mean a $C_1$-$C_6$-alkoxy radical having at least one halogen substituent.

Preference is given to fluoroalkoxy radicals such as fluoro-$C_1$-$C_6$-alkoxy or fluoro-$C_1$-$C_3$-alkoxy, for example difluoroethoxy, trifluoromethoxy or 2,2,2-trifluoroethoxy radicals.

A $C_1$-$C_6$-alkylcarbonyl radical is understood to mean a $C_1$-$C_6$—(O=)C— group. Preference is given here to a $C_1$-$C_4$—(O=)C— group. Particular preference is given here to a $C_1$-$C_3$—(O=)C— group such as, for example, acetyl or propanoyl.

Alkylamino represents an amino radical having one or two alkyl substituents (selected independently of one another having generally 1 to 3 carbon atoms ($C_1$-$C_3$-alkylamino) ($C_1$-$C_3$)-Alkylamino represents, for example, a monoalkylamino radical having 1 to 3 carbon atoms or a dialkylamino radical having 1 to 3 carbon atoms each per alkyl substituent.

The following may be mentioned by way of example: methylamino, ethylamino, n-propylamino, isopropylamino, N,N-dimethylamino, N,N-diethylamino, N-ethyl-N-methylamino and N-methyl-N-n-propylamino.

A $C_1$-$C_6$-alkoxy-$C_1$-$C_6$-alkyl radical is understood to mean a $C_1$-$C_6$-alkoxy-substituted $C_1$-$C_6$-alkyl radical such as, for example, methoxymethyl, methoxyethyl, ethoxymethyl and ethoxyethyl. Preference is given to $C_1$-$C_3$-alkoxy-$C_1$-$C_3$-alkyl.

An aryloxy-$C_1$-$C_3$-alkyl radical is to be understood to mean a $C_1$-$C_3$-alkyl radical substituted by aryloxy as defined below, for example phenoxymethyl, phenoxyethyl and naphthyloxymethyl. Preference is given to phenoxy-$C_1$-$C_3$-alkyl.

An aryl-$C_1$-$C_3$-alkoxy-$C_1$-$C_3$-alkyl radical is to be understood to mean a $C_1$-$C_3$-alkoxy-$C_1$-$C_3$-alkyl radical substituted by aryl as defined below, for example benzyloxymethyl, phenethyloxymethyl or benzyloxypropyl. Preference is given to benzyloxy-$C_1$-$C_3$-alkyl.

An aryl-$C_1$-$C_2$-alkyl radical is to be understood to mean a $C_1$-$C_2$-alkyl radical substituted by aryl as defined below, for example naphthylmethyl, phenethyl, 1-phenylethyl or benzyl. Preference is given to phenyl-$C_1$-$C_2$-alkyl, particular preference to benzyl.

Aryl is understood to mean an unsaturated, fully conjugated system which is formed from carbon atoms and has 3, 5 or 7 conjugated double bonds, for example phenyl, naphthyl or phenanthryl. Preference is given to phenyl.

Aryloxy is understood to mean an alkyl radical as defined above which is attached to the remainder of the molecule via an oxygen atom, for example phenoxy, naphthyloxy or phenanthryloxy. Preference is given to phenoxy.

Heteroaryl is understood to mean ring systems having an aromatically conjugated ring system. These may have 5, 6 or 7 ring atoms, or, in the case of fused ring systems, also a combination of 5- and 6-membered ring systems, 5- and 5-membered ring systems, or else 6- and 6-membered ring systems. They may likewise have 1 to 5 heteroatoms from the group of N, O and S. Examples which may be mentioned are ring systems such as pyrrolyl, pyrazolyl, imidazolyl, triazolyl, tetrazolyl, furyl, thienyl, oxazolyl, thiazolyl, isoxazolyl, oxadiazolyl, thiadiazolyl, pyridinyl, pyrimidinyl, pyrazinyl, triazinyl, oxazinyl, indolyl, benzimidazolyl, indazolyl, benzotriazolyl, benzothiazolyl, benzoxazolyl, benzofuryl, benzothienyl, quinolinyl, isoquinolinyl, cinnolinyl, quinazolinyl, quinoxalinyl, imidazopyridinyl or else benzoxazinyl. Preference is given to heteroaryl having 5 or 6 ring atoms which contains 1, 2 or 3 heteroatoms independently of one another selected from the group consisting of O, N and S.

$C_3$-$C_8$-Cycloalkyl, or a 5- to 8-membered cycloalkyl, is understood to mean a ring system formed from carbon atoms and having 3-8 atoms, or 5 to 8 atoms, for example cyclopropyl, cyclobutyl, cyclopentyl, cyclohexyl, cycloheptyl or cyclooctyl.

$C_3$-$C_8$-Cycloalkoxy is understood to mean a $C_3$-$C_8$-cycloalkyl group as defined above, which is bonded via an oxygen atom to the respectively defined position. For example, cyclopropyloxy, cyclobutyloxy, cyclopentyloxy, cyclohexyloxy, cycloheptyloxy or cyclooctyloxy.

$C_3$-$C_8$-Heterocycloalkyl is understood to mean a 3- to 8-membered monocyclic and saturated ring system in which 1, 2 or 3 carbon atoms are replaced by heteroatoms from the group consisting of N, O and S in any combination. Examples include pyrrolidine, piperidine, tetrahydrofuran, tetrahydropyran, oxetane, azetidine, azepane, morpholine, thiomorpholine or piperazine.

A 5-6-membered ring system is understood to mean an aromatic or else nonaromatic ring system consisting of 5-6 atoms, which may bear 0-4 heteroatoms from the group of N, O or S in any possible combination. Preference is given to aromatic ring systems, particular preference to those having 5 atoms, of which 2-3 are heteroatoms. Particular preference is given to ring systems such as, for example, 1,2,4-oxadiazole, 1,3,4-oxadiazole, 1,3-thiazole and 1,3-oxazole. A non-aromatic ring system is to be understood as meaning both saturated and mono- or polyunsaturated but non-aromatic ring systems.

Heterocycloalkoxy is understood to mean a heterocycloalkyl group as defined above, which is bonded via an oxygen atom to the respectively defined position.

$C_5$-$C_{11}$-Spirocycloalkyl or heterospirocycloalkyl with replacement of 1-4 carbon atoms by nitrogen, oxygen and/or sulphur, including the two oxidized forms thereof, S(=O) and S(=O)$_2$, and the derivatives thereof modified as the sulphoximine, is understood to mean a fusion of two ring systems which share a common atom. Examples are spiro[2.2]pentyl, spiro[2.3]hexyl, azaspiro[2.3]hexyl, spiro[3.3]heptyl, azaspiro[3.3]heptyl, oxazaspiro[3.3]heptyl, thiazaspiro[3.3]heptyl, oxaspiro[3.3]heptyl, oxazaspiro[5.3]nonyl, oxazaspiro[4.3]octyl, oxazaspiro[5.5]undecyl, diazaspiro[3.3]heptyl, thiazaspiro[3.3]heptyl, thiazaspiro[4.3]octyl, azaspiro[5.5]decyl, and the further homologous spiro[3.4], spiro[4.4], spiro[5.5], spiro[6.6], spiro[2.4], spiro[2.5], spiro[2.6], spiro[3.5], spiro[3.6], spiro[4.5], spiro[4.6] and spiro[5.6] systems including the variants modified by heteroatoms as per the definition.

$C_6$-$C_{12}$-Bicycloalkyl or heterobicycloalkyl where 1-4 carbon atoms replaced by nitrogen, oxygen and/or sulphur including its two oxidized forms S(=O) or S(=O)$_2$ and the derivatives thereof modified as the sulfoximine is to be understood as meaning a fusion of two ring systems which jointly share two directly adjacent atoms. Examples are bicyclo[2.2.0]hexyl, bicyclo[3.3.0]octyl, bicyclo[4.4.0]decyl, bicyclo[5.4.0]undecyl, bicyclo[3.2.0]heptyl, bicyclo[4.2.0]octyl, bicyclo[5.2.0]nonyl, bicyclo[6.2.0]decyl, bicyclo[4.3.0]nonyl, bicyclo[5.3.0]decyl, bicyclo[6.3.0]undecyl and bicyclo[5.4.0]undecyl, including the heteroatom-modified variants such as, for example, azabicyclo[3.3.0]octyl, azabicyclo[4.3.0]nonyl, diazabicyclo[4.3.0]nonyl, oxazabicyclo[4.3.0]nonyl, thiazabicyclo[4.3.0]nonyl or azabicyclo[4.4.0]decyl and also the other possible combinations in accordance with the definition.

A bridged ring system is understood to mean a fusion of at least two rings which share 2 atoms that are not directly adjacent to one another. This may give rise either to a bridged cycle or to a bridged heterocycle with replacement of 1-4 carbon atoms by nitrogen, oxygen and/or sulphur, including the two oxidized forms thereof, S(=O) or S(=O)$_2$, and the derivatives thereof modified as the sulphoximine. Examples are bicyclo[2.2.1]heptyl, azabicyclo[2.2.1]heptyl, oxazabicyclo[2.2.1]heptyl, thiazabicyclo[2.2.1]heptyl, diazabicyclo[2.2.1]heptyl, bicyclo[2.2.2]octyl, azabicyclo[2.2.2]octyl, diazabicyclo[2.2.2]octyl, oxazabicyclo[2.2.2]octyl, thiazabicyclo[2.2.2]octyl, bicyclo[3.2.1]octyl, azabicyclo[3.2.1]octyl, diazabicyclo[3.2.1]octyl, oxazabicyclo[3.2.1]octyl, thiazabicyclo[3.2.1]octyl, bicyclo[3.3.1]nonyl, azabicyclo[3.3.1]nonyl, diazabicyclo[3.3.1]nonyl, oxazabicyclo[3.3.1]nonyl, thiazabicyclo[3.3.1]nonyl, bicyclo[4.2.1]nonyl, azabicyclo[4.2.1]nonyl, diazabicyclo[4.2.1]nonyl, oxazabicyclo[4.2.1]nonyl, thiazabicyclo[4.2.1]nonyl, bicyclo[3.3.2]decyl, azabicyclo[3.3.2]decyl, diazabicyclo[3.3.2]decyl, oxazabicyclo[3.3.2]decyl, thiazabicyclo[3.3.2]decyl or azabicyclo[4.2.2]decyl and the further possible combinations according to the definition.

A leaving group is an atom or a group of atoms which, in a chemical reaction, leaves the substrate molecule as a stable species, taking the binding electrons along. Examples of leaving groups are halogen, methanesulphonyloxy, p-toluenesulphonyloxy, trifluoromethanesulphonyloxy, nonafluorobutanesulphonyloxy, (4-bromophenyl)sulphonyloxy, (4-nitrophenyl)sulphonyloxy, (2-nitrophenyl)sulphonyloxy, (4-isopropylphenyl)sulphonyloxy, (2,4,6-triisopropylphenyl)sulphonyloxy, (2,4,6-trimethylphenyl)sulphonyloxy, (4-tert-butylphenyl)sulphonyloxy, phenylsulphonyloxy and (4-methoxyphenyl)sulphonyloxy. Preference is given to halogen, particular preference is given to fluorine, chlorine, bromine.

Compounds according to the invention are the compounds of the general formula (I) and the salts, solvates and solvates of the salts thereof, the compounds, encompassed by the general formula (I), of the formulae specified hereinafter and the salts, solvates and solvates of the salts thereof, and the compounds encompassed by the general formula (I) and specified hereinafter as working examples and the salts, solvates and solvates of the salts thereof, to the extent that the compounds encompassed by the general formula (I) and specified hereinafter are not already salts, solvates and solvates of the salts.

The present invention is likewise considered to encompass the use of the salts of the compounds according to the invention.

Preferred salts in the context of the present invention are physiologically acceptable salts of the compounds according to the invention. The invention also encompasses salts which themselves are unsuitable for pharmaceutical applications but which can be used, for example, for the isolation or purification of the compounds according to the invention.

Physiologically acceptable salts of the compounds according to the invention include acid addition salts of mineral acids, carboxylic acids and sulphonic acids, for example salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, trifluoroacetic acid, propionic acid, lactic acid, tartaric acid, malic acid, citric acid, fumaric acid, maleic acid and benzoic acid.

The present invention also relates to medicaments comprising the compounds according to the invention together with at least one or more further active compounds, especially for prophylaxis and/or treatment of neoplastic disorders.

Solvates in the context of the invention are described as those forms of the compounds according to the invention which form a complex in the solid or liquid state by coordination with solvent molecules. Hydrates are a specific form of the solvates in which the coordination is with water. Solvates preferred in the context of the present invention are hydrates.

The present invention further provides all the possible crystalline and polymorphous forms of the compounds according to the invention, where the polymorphs may be present either as single polymorphs or as a mixture of a plurality of polymorphs in all concentration ranges.

The compounds according to the invention may, depending on their structure, exist in different stereoisomeric forms, i.e. in the form of configurational isomers or else optionally as conformational isomers. At position 4 of the benzazepine ring, which position denotes the ring carbon which is attached to $R^3$ via a methylene group, the compounds according to the invention have a uniformly configured centre of asymmetry. They may therefore take the form of pure diastereomers or mixtures thereof when one or more of the substituents described in the formula (I) contains a further element of asymmetry, for example a chiral carbon atom. The present invention therefore also encompasses diastereomers and the respective mixtures thereof. The pure diastereomers can be isolated in stereoisomeric form from such mixtures in a known manner; chromatography processes are preferably used for this, in particular HPLC chromatography on an achiral or chiral phase.

The present invention further provides enantiomer mixtures of the (4R)-configured compounds according to the invention with their (4S) enantiomers, especially the corresponding racemates and enantiomer mixtures in which the (4R) form predominates.

Where the compounds according to the invention can occur in tautomeric forms, the present invention encompasses all the tautomeric forms.

The present invention also encompasses all suitable isotopic variants of the compounds according to the invention. An isotopic variant of a compound according to the invention is understood here as meaning a compound in which at least one atom within the compound according to the invention has been exchanged for another atom of the same atomic number, but with a different atomic mass than the atomic mass which usually or predominantly occurs in nature. Examples of isotopes which can be incorporated into a compound according to the invention are those of hydrogen, carbon, nitrogen, oxygen, phosphorus, sulphur, fluorine, chlorine, bromine and iodine, such as $^2$H (deuterium), $^3$H (tritium), $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{129}$I and $^{131}$I.

Particular isotopic variants of a compound according to the invention, especially those in which one or more radioactive isotopes have been incorporated, may be beneficial, for example, for the examination of the mechanism of action or of the active compound distribution in the body; due to comparatively easy preparability and detectability, especially compounds labelled with $^3$H or $^{14}$C isotopes are suitable for this purpose. In addition, the incorporation of isotopes, for example of deuterium, can lead to particular therapeutic benefits as a consequence of greater metabolic stability of the compound, for example an extension of the half-life in the body or a reduction in the active dose required; such modifications of the compounds according to the invention may therefore in some cases also constitute a preferred embodiment of the present invention. Isotopic variants of the compounds according to the invention can be prepared by the processes known to those skilled in the art, for example by the methods described below and the procedures described in the working examples, by using corresponding isotopic modifications of the respective reagents and/or starting compounds.

In addition, the present invention also encompasses prodrugs of the compounds according to the invention. The term "prodrugs" includes compounds which may themselves be biologically active or inactive but are converted to compounds according to the invention while resident in the body (for example metabolically or hydrolytically).

The compounds according to the invention can act systemically and/or locally. For this purpose, they can be administered in a suitable manner, for example by the oral, parenteral, pulmonary, nasal, sublingual, lingual, buccal, rectal, dermal, transdermal, conjunctival or otic route, or as implant or stent.

The compounds according to the invention can be administered in suitable administration forms for these administration routes.

Suitable administration forms for oral administration are those which function according to the prior art and deliver the compounds according to the invention rapidly and/or in modified fashion, and which contain the compounds according to the invention in crystalline and/or amorphized and/or dissolved form, for example tablets (uncoated or coated tablets, for example having enteric coatings or coatings which are insoluble or dissolve with a delay and control the release of the compound according to the invention), tablets which disintegrate rapidly in the mouth, or films/wafers, films/lyophilizates, capsules (for example hard or soft gelatin capsules), sugar-coated tablets, granules, pellets, powders, emulsions, suspensions, aerosols or solutions.

Parenteral administration can be accomplished with avoidance of a resorption step (for example by an intravenous, intraarterial, intracardiac, intraspinal or intralumbar route) or with inclusion of a resorption (for example by an intramuscular, subcutaneous, intracutaneous, percutaneous or intraperitoneal route). Administration forms suitable for parenteral administration include preparations for injection and infusion in the form of solutions, suspensions, emulsions, lyophilizates or sterile powders.

For the other administration routes, suitable examples are inhalation medicaments (including powder inhalers, nebulizers), nasal drops, solutions or sprays; tablets for lingual, sublingual or buccal administration, films/wafers or capsules, suppositories, ear or eye preparations, vaginal capsules, aqueous suspensions (lotions, shaking mixtures), lipophilic suspensions, ointments, creams, transdermal therapeutic systems (for example patches), milk, pastes, foams, dusting powders, implants or stents.

The compounds according to the invention can be converted to the administration forms mentioned. This can be accomplished in a manner known per se by mixing with inert, non-toxic, pharmaceutically suitable excipients. These excipients include carriers (for example microcrystalline cellulose, lactose, mannitol), solvents (e.g. liquid polyethylene glycols), emulsifiers and dispersing or wetting agents (for example sodium dodecylsulphate, polyoxysorbitan oleate), binders (for example polyvinylpyrrolidone), synthetic and natural polymers (for example albumin), stabilizers (e.g. antioxidants, for example ascorbic acid), colourants (e.g. inorganic pigments, for example iron oxides) and flavour and/or odour correctants.

The present invention further provides medicaments comprising the compounds according to the invention, typically together with one or more inert, nontoxic, pharmaceutically suitable excipients, and for the use thereof for the aforementioned purposes.

The compounds according to the invention are formulated to give pharmaceutical preparations in a manner known per se, by converting the active compound(s) to the desired administration form with the excipients customary in pharmaceutical formulation.

The excipients used may, for example, be carrier substances, fillers, disintegrants, binders, humectants, glidants, absorbents and adsorbents, diluents, solvents, cosolvents, emulsifiers, solubilizers, taste correctors, colourants, preservatives, stabilizers, wetting agents, salts for modifying the osmotic pressure or buffers. Reference should be made to Remington's Pharmaceutical Science, 15th ed. Mack Publishing Company, East Pennsylvania (1980).

The pharmaceutical formulations may be in solid form, for example in the form of tablets, coated tablets, pills, suppositories, capsules, transdermal systems, or in semisolid form, for example in the form of ointments, creams, gels, suppositories, emulsions, or in liquid form, for example in the form of solutions, tinctures, suspensions or emulsions.

Excipients in the context of the invention may, for example, be salts, saccharides (mono-, di-, tri-, oligo- and/or polysaccharides), proteins, amino acids, peptides, fats, waxes, oils, hydrocarbons and derivatives thereof, and the excipients may be of natural origin or be obtained by synthetic or partially synthetic means.

Useful forms for oral or peroral administration are especially tablets, coated tablets, capsules, pills, powders, granules, pastilles, suspensions, emulsions or solutions.

Useful forms for parenteral administration are especially suspensions, emulsions, and particularly solutions.

The compounds according to the invention are suitable for prophylaxis and/or treatment of hyperproliferative disorders, for example psoriasis, keloids and other hyperplasias which affect the skin, benign prostate hyperplasias (BPH), solid tumours and haematological tumours.

Solid tumours that can be treated in accordance with the invention are, for example, tumours of the breast, the respiratory tract, the brain, the reproductive organs, the gastrointestinal tract, the urogenital tract, the eye, the liver, the skin, the head and the neck, the thyroid gland, the parathyroid gland, the bones, and the connective tissue and metastases of these tumours.

Haematological tumours that can be treated are, for example, multiple myeloma, lymphoma or leukaemia.

Breast tumours that can be treated are, for example, mammary carcinoma with positive hormone receptor status, mammary carcinoma with negative hormone receptor status, Her-2-positive mammary carcinoma, hormone receptor- and Her-2-negative mammary carcinoma, BRCA-associated mammary carcinoma and inflammatory mammary carcinoma.

Tumours of the respiratory tract that can be treated are, for example, non-small-cell bronchial carcinoma and small-cell bronchial carcinoma.

Brain tumours that can be treated are, for example, glioma, glioblastoma, astrocytoma, meningioma and medulloblastoma.

Tumours of the male reproductive organs that can be treated are, for example, prostate carcinoma, malignant epididymal tumours, malignant testicular tumours and penile carcinoma.

Tumours of the female reproductive organs that can be treated are, for example, endometrial carcinoma, cervical carcinoma, ovarian carcinoma, vaginal carcinoma and vulvar carcinoma.

Tumours of the gastrointestinal tract that can be treated are, for example, colorectal carcinoma, anal carcinoma, gastric carcinoma, pancreatic carcinoma, oesophageal carcinoma, gallbladder carcinoma, small-intestinal carcinoma, salivary gland carcinoma, neuroendocrine tumours and gastrointestinal stromal tumours.

Tumours of the urogenital tract that can be treated are, for example, urinary bladder carcinoma, renal cell carcinoma, and carcinoma of the renal pelvis and of the urinary tract.

Tumours of the eye that can be treated are, for example, retinoblastoma and intraocular melanoma.

Tumours of the liver that can be treated are, for example, hepatocellular carcinoma and cholangiocellular carcinoma.

Tumours of the skin that can be treated are, for example, malignant melanoma, basalioma, spinalioma, Kaposi's sarcoma and Merkel cell carcinoma.

Tumours of the head and neck that can be treated are, for example, laryngeal carcinoma and carcinoma of the pharynx and of the oral cavity.

Sarcomas that can be treated are, for example, soft tissue sarcoma and osteosarcoma.

Lymphomas that can be treated are, for example, non-Hodgkin's lymphoma, Hodgkin's lymphoma, cutaneous lymphoma, lymphoma of the central nervous system and AIDS-associated lymphoma.

Leukaemias that can be treated are, for example, acute myeloid leukaemia, chronic myeloid leukaemia, acute lymphatic leukaemia, chronic lymphatic leukaemia and hair cell leukaemia.

Advantageously, the compounds according to the invention can be used for prophylaxis and/or treatment of leukaemia, especially acute myeloid leukaemia, prostate carcinoma, especially androgen receptor-positive prostate carcinoma, cervical carcinoma, mammary carcinoma, especially hormone receptor-negative, hormone receptor-positive or BRCA-associated mammary carcinoma, pancreatic carcinoma, renal cell carcinoma, hepatocellular carcinoma, melanoma and other skin tumours, non-small-cell bronchial carcinoma, endometrial carcinoma and colorectal carcinoma.

Particularly advantageously, the compounds according to the invention can be used for prophylaxis and/or treatment of acute myeloid leukaemia, prostate carcinoma, especially androgen receptor-positive prostate carcinoma, cervical carcinoma, mammary carcinoma, especially oestrogen-alpha-positive and oestrogen-alpha-negative mammary carcinoma, prostate carcinoma or melanoma.

These disorders are well characterized in man, but also exist in other mammals.

The present application further provides the compounds according to the invention for use as medicaments, especially for prophylaxis and/or treatment of neoplastic disorders.

The present invention further provides for the use of the compounds according to the invention for prophylaxis and/or treatment of leukaemia, especially acute myeloid leukaemia, prostate carcinoma, especially androgen receptor-positive prostate carcinoma, cervical carcinoma, mammary carcinoma, especially hormone receptor-negative, hormone receptor-positive or BRCA-associated mammary carcinoma, pancreatic carcinoma, renal cell carcinoma, hepatocellular carcinoma, melanoma and other skin tumours, non-small-cell bronchial carcinoma, endometrial carcinoma and colorectal carcinoma.

The present invention further provides for the use of the compounds according to the invention for prophylaxis and/or treatment of acute myeloid leukaemia, prostate carcinoma, especially androgen receptor-positive prostate carcinoma, cervical carcinoma, mammary carcinoma, especially oestrogen-alpha-positive and oestrogen-alpha-negative mammary carcinoma, prostate carcinoma or melanoma.

The present invention further provides for the use of the compounds according to the invention for production of a medicament.

The present invention further provides for the use of the compounds according to the invention for production of a medicament for prophylaxis and/or treatment of neoplastic disorders.

The present invention further provides for the use of the compounds according to the invention for production of a medicament for prophylaxis and/or treatment of leukaemia, especially acute myeloid leukaemia, prostate carcinoma, especially androgen receptor-positive prostate carcinoma, cervical carcinoma, mammary carcinoma, especially hormone receptor-negative, hormone receptor-positive or BRCA-associated mammary carcinoma, pancreatic carcinoma, renal cell carcinoma, hepatocellular carcinoma, melanoma and other skin tumours, non-small-cell bronchial carcinoma, endometrial carcinoma and colorectal carcinoma.

The present invention further provides for the use of the compounds according to the invention for production of a medicament for prophylaxis and/or treatment of acute myeloid leukaemias, prostate carcinomas, especially androgen receptor-positive prostate carcinomas, cervical carcinomas, mammary carcinomas, especially oestrogen-alpha-positive and oestrogen-alpha-negative mammary carcinomas, prostate carcinomas or melanomas.

The present invention further provides for the use of the compound for prophylaxis and/or treatment of neoplastic disorders.

The present invention further provides for the use of the compounds according to the invention for prophylaxis and/or treatment of leukaemia, especially acute myeloid leukaemia, prostate carcinoma, especially androgen receptor-positive prostate carcinoma, cervical carcinoma, mammary carcinoma, especially hormone receptor-negative, hormone receptor-positive or BRCA-associated mammary carcinoma, pancreatic carcinoma, renal cell carcinoma, hepatocellular carcinoma, melanoma and other skin tumours, non-small-cell bronchial carcinoma, endometrial carcinoma and colorectal carcinoma.

The present invention further provides for the use of the compounds according to the invention for prophylaxis and/or treatment of acute myeloid leukaemia, prostate carcinoma, especially androgen receptor-positive prostate carcinoma, cervical carcinoma, mammary carcinoma, especially oestrogen-alpha-positive and oestrogen-alpha-negative mammary carcinoma, prostate carcinoma or melanoma.

The present invention further provides pharmaceutical formulations in the form of tablets comprising one of the compounds according to the invention for prophylaxis and/or treatment of leukaemia, especially acute myeloid leukaemia, prostate carcinoma, especially androgen receptor-positive prostate carcinoma, cervical carcinoma, mammary carcinoma, especially hormone receptor-negative, hormone receptor-positive or BRCA-associated mammary carcinoma, pancreatic carcinoma, renal cell carcinoma, hepatocellular carcinoma, melanoma and other skin tumours, non-small-cell bronchial carcinoma, endometrial carcinoma and colorectal carcinoma.

The present invention further provides pharmaceutical formulations in the form of tablets comprising one of the compounds according to the invention for prophylaxis and/or treatment of acute myeloid leukaemia, prostate carcinoma, especially androgen receptor-positive prostate carcinoma, cervical carcinoma, mammary carcinoma, especially oestrogen-alpha-positive and oestrogen-alpha-negative mammary carcinoma, prostate carcinoma or melanoma.

The invention thus also furthermore provides for the use of the compounds according to the invention for prophylaxis and treatment of hyperproliferative disorders, especially of tumours.

The compounds according to the invention are also suitable for prophylaxis and/or treatment of systemic inflammatory diseases, especially LPS-induced endotoxic shock and/or bacteria-induced sepsis.

The compounds according to the invention are also suitable for prophylaxis and/or treatment of inflammatory or autoimmune disorders, for example:

pulmonary disorders associated with inflammatory, allergic and/or proliferative processes: chronic obstructive pulmonary disorders of any origin, particularly bronchial asthma; bronchitis of different origin; all forms of restrictive pulmonary disorders, particularly allergic alveolitis; all forms of pulmonary oedema, particularly toxic pulmonary oedema; sarcoidoses and granulomatoses, particularly Boeck's disease, rheumatic disorders/autoimmune disorders/joint disorders associated with inflammatory, allergic and/or proliferative processes: all forms of rheumatic disorders, especially rheumatoid arthritis, acute rheumatic fever, polymyalgia rheumatica; reactive arthritis; inflammatory soft-tissue disorders of other origin; arthritic symptoms in the case of degenerative joint disorders (arthroses); traumatic arthritides; collagenoses of any origin, e.g. systemic lupus erythematosus, scleroderma, polymyositis, dermatomyositis, Sjögren's syndrome, Still's syndrome, Felty's syndrome allergies associated with inflammatory and/or proliferative processes: all forms of allergic reactions, e.g. angiooedema, hay fever, insect bites, allergic reactions to medicaments, blood derivatives, contrast agents, etc., anaphylactic shock, urticaria, contact dermatitis vascular inflammation (vasculitis): panarteritis nodosa, temporal arteritis, erythema nodosum dermatological disorders associated with inflammatory, allergic and/or proliferative processes: atopic dermatitis; psoriasis; *pityriasis rubra* pilaris; erythematous disorders triggered by different noxae, for example radiation, chemicals, burns, etc.; bullous dermatoses; lichenoid disorders; pruritus; seborrhoeic eczema; rosacea; *pemphigus vulgaris*; erythema exsudativum multiforme; balanitis; vulvitis; hair loss, such as alopecia areata; cutaneous T-cell lymphoma renal disorders associated with inflammatory, allergic and/or proliferative processes: nephrotic syndrome; all nephritides hepatic disorders associated with inflammatory, allergic and/or proliferative processes: acute hepatic disintegration; acute hepatitis of different origin, for example viral, toxic, medicament-induced; chronic aggressive and/or chronic intermittent hepatitis gastrointestinal disorders associated with inflammatory, allergic and/or proliferative processes: regional enteritis (Crohn's disease); ulcerative colitis; gastritis; reflux oesophagitis; gastroenteritides of other origin, e.g. indigenous sprue proctological disorders associated with inflammatory, allergic and/or proliferative processes: anal eczema; fissures; haemorrhoids; idiopathic proctitis, ocular disorders associated with inflammatory, allergic and/or proliferative processes: allergic keratitis, uveitis, iritis; conjunctivitis; blepharitis; optic neuritis; chlorioditis; sympathetic ophthalmia disorders of the ear-nose-throat region associated with inflammatory, allergic and/or proliferative processes: allergic rhinitis, hay fever; otitis externa, for example caused by contact eczema, infection, etc.; otitis media neurological disorders associated with inflammatory, allergic and/or proliferative processes: cerebral oedema, particularly tumour-related cerebral oedema;

multiple sclerosis; acute encephalomyelitis; meningitis; various forms of seizure, for example West's syndrome haematological disorders associated with inflammatory, allergic and/or proliferative processes: congenital haemolytic anaemia; idiopathic thrombocytopenia neoplastic disorders associated with inflammatory, allergic and/or proliferative processes: acute lymphatic leukaemia; malignant lymphoma; lymphogranulomatoses; lymphosarcoma; extensive metastases, particularly in the case of mammary, bronchial and prostate carcinoma endocrine disorders associated with inflammatory, allergic and/or proliferative processes: endocrine orbitopathy; thyrotoxic crisis; de Quervain's thyroiditis; Hashimoto's thyroiditis; Basedow's disease organ and tissue transplants, graft-versus-host disease severe states of shock, for example anaphylactic shock, systemic inflammatory response syndrome (SIRS)

substitution therapy in the case of: congenital primary adrenal insufficiency, for example congenital adrenogenital syndrome; acquired primary adrenal insufficiency, for example Addison's disease, autoimmune adrenalitis, postinfectious, tumours, metastases, etc; congenital secondary adrenal insufficiency, for example congenital hypopituitarism; acquired secondary adrenal insufficiency, for example postinfectious, tumours, etc.

emesis associated with inflammatory, allergic and/or proliferative processes, for example in combination with a 5-HT3 antagonist in the case of cytostatic-induced vomiting pain of inflammatory origin, for example lumbago The compounds according to the invention are also suitable for the treatment of viral disorders, for example infections caused by papilloma viruses, herpes viruses, Epstein-Barr viruses, hepatitis B or C viruses, and human immunodeficiency viruses.

The compounds according to the invention are also suitable for the treatment of atherosclerosis, dyslipidaemia, hypercholesterolaemia, hypertriglyceridaemia, peripheral vascular disorders, cardiovascular disorders, angina pectoris, ischaemia, stroke, myocardial infarction, angioplastic restenosis, hypertension, thrombosis, obesity, endotoxaemia.

The compounds according to the invention are also suitable for the treatment of neurodegenerative diseases, for example multiple sclerosis, Alzheimer's disease and Parkinson's disease.

The compounds according to the invention are also suitable for prophylaxis and/or treatment of benign hyperproliferative diseases, for example endometriosis, leiomyoma and benign prostate hyperplasia.

The present invention thus also relates to the use of the compounds according to the invention for prophylaxis and/or treatment of viral infections, neurodegenerative disorders, inflammatory disorders, atherosclerotic disorders and in male fertility control, and also to the use of the compounds according to the invention for production of a medicament for prophylaxis and/or treatment of viral infections, neurodegenerative disorders, inflammatory disorders, atherosclerotic disorders and in male fertility control.

The compounds according to the invention can be used alone or, if required, in combination with one or more further pharmacologically active substances, provided that this combination does not lead to undesirable and unacceptable side effects. The present invention therefore further provides medicaments comprising one of the compounds according to the invention and one or more further active ingredients, especially for prophylaxis and/or treatment of the aforementioned disorders.

For example, the compounds according to the invention can be combined with known antihyperproliferative, cytostatic or cytotoxic substances for treatment of cancer. The combination of the compounds according to the invention with other substances commonly used for cancer treatment, or else with radiotherapy, is particularly appropriate.

Examples of suitable combination active compounds include:

afinitor, aldesleukin, alendronic acid, alfaferone, alitretinoin, allopurinol, aloprim, aloxi, altretamine, aminoglutethimide, amifostine, amrubicin, amsacrine, anastrozole, anzmet, aranesp, arglabin, arsenic trioxide, aromasin, 5-azacytidine, azathioprine, BCG or tice-BCG, bestatin, betamethasone acetate, betamethasone sodium phosphate, bexarotene, bleomycin sulphate, broxuridine, bortezomib, busulfan, calcitonin, campath, capecitabine, carboplatin, casodex, cefesone, celmoleukin, cerubidin, chlorambucil, cisplatin, cladribin, clodronic acid, cyclophosphamide, cytarabine, dacarbazine, dactinomycin, daunoxome, decadron, decadron phosphate, delestrogen, denileukin diftitox, depomedrol, deslorelin, dexrazoxane, diethylstilbestrol, diflucan, docetaxel, doxifluridine, doxorubicin, dronabinol, DW-166HC, eligard, elitek, ellence, emend, epirubicin, epoetin-alfa, epogen, eptaplatin, ergamisol, estrace, estradiol, estramustine sodium phosphate, ethinylestradiol, ethyol, etidronic acid, etopophos, etoposide, fadrozole, farstone, filgrastim, finasteride, fligrastim, floxuridine, fluconazole, fludarabin, 5-fluorodeoxyuridine monophosphate, 5-fluorouracil (5-FU), fluoxymesterone, flutamide, formestane, fosteabine, fotemustine, fulvestrant, gammagard, gemcitabine, gemtuzumab, gleevec, gliadel, goserelin, granisetron hydrochloride, histrelin, hycamtin, hydrocortone, erythro-hydroxynonyladenine, hydroxyurea, ibritumomab tiuxetan, idarubicin, ifosfamide, interferon-alpha, interferon-alpha-2, interferon-alpha-2α, interferon-alpha-2β, interferon-alpha-n1, interferon-alpha-n3, interferon-beta, interferon-gamma-1α, interleukin-2, intron A, iressa, irinotecan, kytril, lapatinib, lentinan sulphate, letrozole, leucovorin, leuprolide, leuprolide acetate, levamisole, levofolic acid calcium salt, levothroid, levoxyl, lomustine, lonidamine, marinol, mechlorethamine, mecobalamin, medroxyprogesterone acetate, megestrol acetate, melphalan, menest, 6-mercaptopurine, mesna, methotrexate, metvix, miltefosine, minocycline, mitomycin C, mitotane, mitoxantrone, modrenal, myocet, nedaplatin, neulasta, neumega, neupogen, nilutamide, nolvadex, NSC-631570, OCT-43, octreotide, ondansetron hydrochloride, orapred, oxaliplatin, paclitaxel, pediapred, pegaspargase, pegasys, pentostatin, picibanil, pilocarpine hydrochloride, pirarubicin, plicamycin, porfimer sodium, prednimustine, prednisolone, prednisone, premarin, procarbazine, procrit, raltitrexed, RDEA119, rebif, regorafenib, rhenium-186 etidronate, rituximab, roferon-A, romurtide, salagen, sandostatin, sargramostim, semustine, sizofiran, sobuzoxane, solu-medrol, streptozocin, strontium-89 chloride, synthroid, tamoxifen, tamsulosin, tasonermin, tastolactone, taxoter, teceleukin, temozolomide, teniposide, testosterone propionate, testred, thioguanine, thiotepa, thyrotropin, tiludronic acid, topotecan, toremifen, tositumomab, tastuzumab, teosulfan, tretinoin, trexall, trimethylmelamine, trimetrexate, triptorelin acetate, triptorelin pamoate, UFT, uridine, valrubicin, vesnarinone, vinblastine, vincristine, vindesine, vinorelbine, virulizin, zinecard, zinostatin-stimalamer, zofran; ABI-007, acolbifen, actimmune, affinitak, aminopterin, arzoxifen, asoprisnil, atamestane, atrasentan, BAY 43-9006 (sorafenib), avastin, CCI-779, CDC-501, celebrex, cetuximab, crisnatol, cyproterone acetate, decitabine, DN-101, doxorubicin-MTC, dSLIM, dutasteride, edotecarin, eflornithine, exatecan, fenretinide, histamine dihydrochloride, histrelin hydrogel implant, holmium-166 DOTMP, ibandronic acid, interferon-gamma, intron-PEG, ixabepilone, keyhole limpet haemocyanin, L-651582, lanreotide, lasofoxifen, libra, lonafarnib, miproxifen, minodronate, MS-209, liposomal MTP-PE, MX-6, nafarelin, nemorubicin, neovastat, nolatrexed, oblimersen, onko-TCS, osidem, paclitaxel polyglutamate, pamidronate disodium, PN-401, QS-21, quazepam, R-1549, raloxifen, ranpirnas, 13-cis-retinoic acid, satraplatin, seocalcitol, T-138067, tarceva, taxoprexin, thymosin-alpha-1, tiazofurin, tipifarnib, tirapazamine, TLK-286, toremifen, trans-MID-107R, valspodar, vapreotide, vatalanib, verteporfin, vinflunin, Z-100, zoledronic acid, and combinations thereof.

In a preferred embodiment, the compounds according to the invention can be combined with antihyperproliferative agents, examples of which are given in the following non-exhaustive list:

aminoglutethimide, L-asparaginase, azathioprine, 5-azacytidine, bleomycin, busulfan, carboplatin, carmustine, chlorambucil, cisplatin, colaspase, cyclophosphamide, cytarabine, dacarbazine, dactinomycin, daunorubicin, diethylstilbestrol, 2',2'-difluorodeoxycytidine, docetaxel, doxorubicin (adriamycin), epirubicin, epothilone and its derivatives, erythro-hydroxynonyladenine, ethinylestradiol, etoposide, fludarabin phosphate, 5-fluorodeoxyuridine, 5-fluorodeoxyuridine monophosphate, 5-fluorouracil, fluoxymesterone, flutamide, hexamethylmelamine, hydroxyurea, hydroxyprogesterone caproate, idarubicin, ifosfamide, interferon, irinotecan, leucovorin, lomustine, mechlorethamine, medroxyprogesterone acetate, megestrol acetate, melphalan, 6-mercaptopurine, mesna, methotrexate, mitomycin C, mitotane, mitoxantrone, paclitaxel, pentostatin, N-phosphonoacetyl L-aspartate (PALA), plicamycin, prednisolone, prednisone, procarbazine, raloxifen, semustine, streptozocin, tamoxifen, teniposide, testosterone propionate, thioguanine, thiotepa, topotecan, trimethylmelamine, uridine, vinblastine, vincristine, vindesine and vinorelbine. In a very promising manner, the compounds according to the invention can also be combined with biological therapeutics such as antibodies (for example Avastin, Rituxan, Erbitux, Herceptin) and recombinant proteins.

The compounds according to the invention can also achieve positive effects in combination with other therapies directed against angiogenesis, for example with Avastin, axitinib, regorafenib, recentin, sorafenib or sunitinib. Combinations with inhibitors of the proteasome and of mTOR, and also antihormones and steroidal metabolic enzyme inhibitors, are particularly suitable because of their favourable profile of side effects.

The combination of the compounds according to the invention with a P-TEFb or CDK9 inhibitor is likewise particularly preferred.

In addition, the compounds according to the invention can also be used in conjunction with radiotherapy and/or surgical intervention.

IN THE PRESENT DESCRIPTION

ACN acetonitrile
CDCl$_3$ deuterochloroform

CHAPS 3-{dimethyl[3-(4-{5,9,16-trihydroxy-2,15-dimethyltetracyclo-[8.7.0.0$^{2,7}$0.0$^{11,15}$]heptadecan-14-yl}pentanamido)propyl]azaniumyl}propane-1-sulphonate
DEA diethylamine
DMF N,N-dimethylformamide
DMSO-d6 deuterated dimethyl sulphoxide
DMSO dimethyl sulphoxide
EA ethyl acetate
EtOH ethanol
sat. saturated
HATU (7-aza-1H-benzotriazol-1-yl)-1,1,3,3-tetramethyluronium hexafluorophosphate
HBTU O-benzotriazole-N,N,N',N'-tetramethyluronium hexafluorophosphate
HPLC high-pressure liquid chromatography
KHMDS potassium bis(trimethylsilyl)amide
KOtBu potassium tert-butoxide
LCMS liquid chromatography coupled with mass spectrometry
LDA lithium diisopropylamide
LiHMDS lithium bis(trimethylsilyl)amide
MeCl methylene chloride, dichloromethane
MTBE methyl tert-butyl ether
PyBOB (benzotriazol-1-yl)oxytripyrrolidinophosphonium hexafluorophosphate
RP-HPLC reverse-phase high-pressure liquid chromatography
RT room temperature
sept septet
T3P 2,4,6-tripropyl-1,3,5,2,4,6-trioxatriphosphorinane 2,4,6-trioxide
TFA trifluoroacetic acid
THF tetrahydrofuran Preparation of the Compounds of the General Formula I According to the Invention General Description of the Preparation of the Compounds of the General Formula I According to the Invention The compounds of the formulae (Ia), (Ib), (Ic), (Id), (Ie), (If), (Ig), (Ih) and (Ii) according to the invention shown in this section in Schemes 4, 5, 6, 7a and 7b can be prepared via synthesis routes described hereinafter. These formulae represent different subsets of the general formula (I) in which $R^1$, $R^2$, $R^3$ and $R^4$, unless described differently in the context of the schemes mentioned, are each as defined for the general formula (I).

In addition to the synthesis sequences discussed hereinafter, it is also possible, in accordance with the general knowledge of the person skilled in the art in organic chemistry, to take other synthesis routes for the synthesis of compounds of the general formula (I) according to the invention. The sequence of the synthesis steps shown in the schemes which follow is not binding, and synthesis steps from various of the schemes shown hereinafter may optionally be combined to form new sequences. In addition, interconversions of the substituents $R^1$, $R^2$, $R^3$ or $R^4$ can be performed before or after the synthesis stages shown. Examples of such conversions are the introduction or elimination of protective groups, reduction or oxidation of functional groups, halogenation, metallation, metal-catalysed coupling reactions, substitution reactions or further reactions known to the person skilled in the art. A specific example which may be mentioned here is the transformation of $R^1$ from bromine into dimethylisooxazolyl via Suzuki coupling as described in the Experimental Part for the synthesis of Example 48.

These reactions include conversions which introduce a functional group which enables the further conversion of substituents. Suitable protective groups and methods for their introduction and removal are known to the person skilled in the art (see, for example, T. W. Greene and P. G. M. Wuts in: *Protective Groups in Organic Synthesis*, 3rd Edition, Wiley 1999). In addition, it is possible to combine two or more reaction steps without intermediate workup in a manner known to the person skilled in the art (for example in what are called "one-pot" reactions).

Scheme 1 shows the synthesis of intermediates of the formula (IX) from benzazepinediones of the formula (II) in which $R^1$ is as defined for the general formula (I). Using a reagent suitable for converting the lactam into a thiolactam, for example Lawesson's reagent (2,4-bis(4-methoxyphenyl)-1,3-dithia-2,4-diphosphetane-2,4-disulphide, CAS#19172-47-5), these compounds are converted into compounds of the formula (III) (e.g. U.S. Pat. No. 5,696,111, 1997, Example 9.A, step A). These compounds are reacted with acylhydrazines of the formula (IV) in which $R^2$ is as defined for the general formula (I) and preferably represents methyl with formation of a triazole ring to give tricyclic intermediates of the formula (V) (Nature 2010, Vol 468, p 1067ff, SI, p 33-36; Filippakopoulos et al.). During this reaction, the carbonyl group is temporarily converted into an acylhydrazone which is decomposed by acidic hydrolysis, with restoration of the carbonyl group. The carbonyl group in (V) is then converted in a manner known to the person skilled in the art (see, for example, J. Org. Chem. 58, (1993), p. 600-10, W. Okamura; Org. Lett. 9, (2007), p. 517-20, A. de Meijere, Eur. J. Org. Chem. 8, (1998), p. 1521-34, K. Voigt et al.) by reaction with compounds of the formula (VI) in which LG represents a leaving group, preferably halogen, particularly preferably fluorine, and $R^F$ represents a perfluorinated $C_1$-$C_6$-alkyl radical, preferably trifluoromethyl, 1,1,2,2,2-pentafluoroethyl or 1,1,2,2,3,3,4,4,4-nonafluoro-n-butyl, and a suitable base such as lithium hexamethyldisilazide into an enol sulphonate, with formation of compounds of the formula (VII). This is reacted in a Suzuki coupling with boronic acid derivatives of the formula (VIII) in which $R^4$ is as defined for the general formula (I) and in which $R^B$ represents $C_1$-$C_4$-alkyl, or both radicals $R^B$ together with the oxygen atoms to which they are attached form a cyclic boronic ester, preferably a pinacolate. In this reaction, a palladium catalyst, for example Pd(0) catalysts such as tetrakis(triphenylphosphine)palladium(0) [Pd(PPh$_3$)$_4$], tris(dibenzylideneacetone)dipalladium(0) [Pd$_2$(dba)$_3$] or Pd(II) catalysts such as dichlorobis(triphenylphosphine)palladium(II) [Pd(PPh$_3$)$_2$Cl$_2$], palladium(II) acetate in combination with triphenylphosphine, or [1,1'-bis(diphenylphosphino)ferrocene]palladium dichloride [Pd(dppf)Cl$_2$], is employed, and the intermediates of the general formula (IX) are formed. Many boronic acid derivatives of the formula (VIII) are commercially available or can be prepared by methods known to the person skilled in the art (for a review, see D. G. Hall, Boronic Acids, 2005 WILEY-VCH Verlag GmbH & Co. KGaA, Weinheim, ISBN 3-527-30991-8, and the literature cited therein). Suzuki couplings are known to the person skilled in the art (for some examples see, for example, Eur. J. Chem 13, 2007, S. 2410-20, H.-U. Reissig et al., Tetrahedron 52, (1996), p. 1529-42, A. Cleve et al.). The reaction is preferably carried out at elevated temperature, for example at the boiling point of an appropriate solvent such as toluene.

Scheme 1: Preparation of intermediates of the formula (XI) from benzazepinediones of the formula (II).

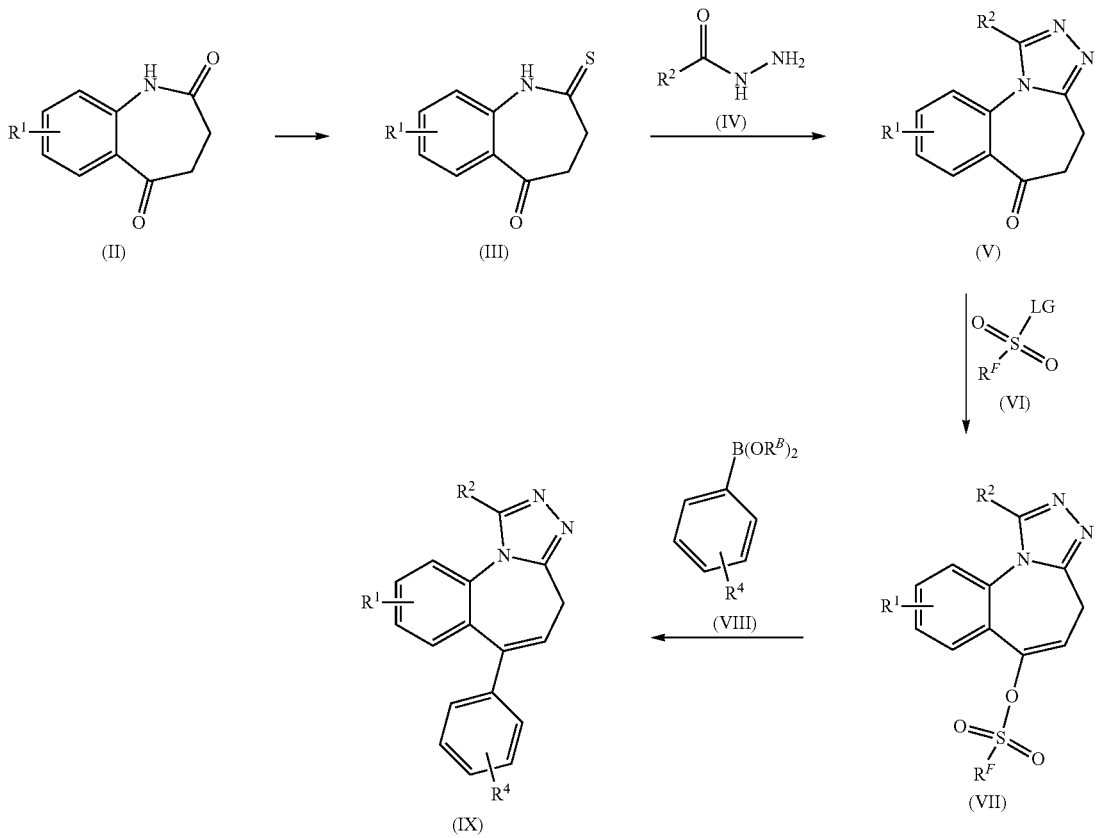

The benzazepinediones of the formula (II) used as starting materials are known from the literature (see, for example, Arch. Pharm. 324, (1991), pp. 579-81, C. Kunick; Arch. Pharm. 335, (2002), pp. 311-317, K. Wiekig et al.), or alternatively they can also be prepared from aminobenzoic esters of the formula (X) in which $R^1$ is as defined for the general formula (I) and in which $R^E$ represents $C_1$-$C_6$-alkyl or benzyl. Here, the compounds (X) are reacted with succinate reagents of the formula (XI) in which LG represents a leaving group, for example halogen and preferably chlorine, and in which $R^E$ represents $C_1$-$C_6$-alkyl or benzyl, in the presence of a suitable base such as, for example, pyridine, with formation of benzamides of the formula (XII). These can be transformed in a Dieckmann cyclization in the presence of DMSO and a suitable base, for example an alkali metal alkoxide such as potassium tert-butoxide, into enol esters of the formula (XIII); decarboxylation in DMSO at elevated temperature then leads to the benzazepinediones of the formula (II); see also Arch. Pharm. 324, (1991), p. 579-81, C. Kunick; Arch. Pharm. 335, (2002), p. 311-317, K. Wiekig et al.

The aminobenzoic esters of the formula (X) and the succinate reagents of the formula (XI) are known to the person skilled in the art and in many cases commercially available.

Alternatively, the intermediates of the formula (IX) can also, as shown in Scheme 3, be prepared from phenyl-1,3,4,5-tetrahydro-2H-1-benzazepin-2-ones of the formula (XIV) whose preparation is described, for example, in U.S. Pat. No. 5,484,917 and in J. Med. Chem. 37, (1994), p. 3789ff, J. Lowe et al., and in which $R^1$ and $R^4$ are defined as for the general formula (I), which are reacted with bromine in the presence of a light source, e.g. an incandescent lamp (U.S. Pat. No. 4,464,300A1, 1984, Example 5.f). During this reaction, with subsequent elimination of hydrogen bromide, the compounds of the formula (XV) are formed. These are, as shown in Scheme 1 for compounds of the formula (II), reacted with a sulphurizing agent, for example Lawesson's reagent, to give thiolactams of the formula (XVI). These are finally, in a manner analogous to that described in Scheme 1 for the conversion of compounds of the formula (III) into (V), converted with acylhydrazines of the formula (IV) with formation of the triazole ring into the intermediates of the formula (IX) (Nature 2010, Vol 468, p 1067ff, SI, p 33-36; Filippakopoulos et al.). However, in this case, owing to the lack of a carbonyl group in the substrate (XVI), an acidic hydrolysis of acylhydrazone intermediates as described above can be dispensed with.

Scheme 2: Preparation of benzazepinediones of the formula (II).

Scheme 3: Alternative preparation of intermediates of the formula (XI) from benzazepinones of the formula (XIV).

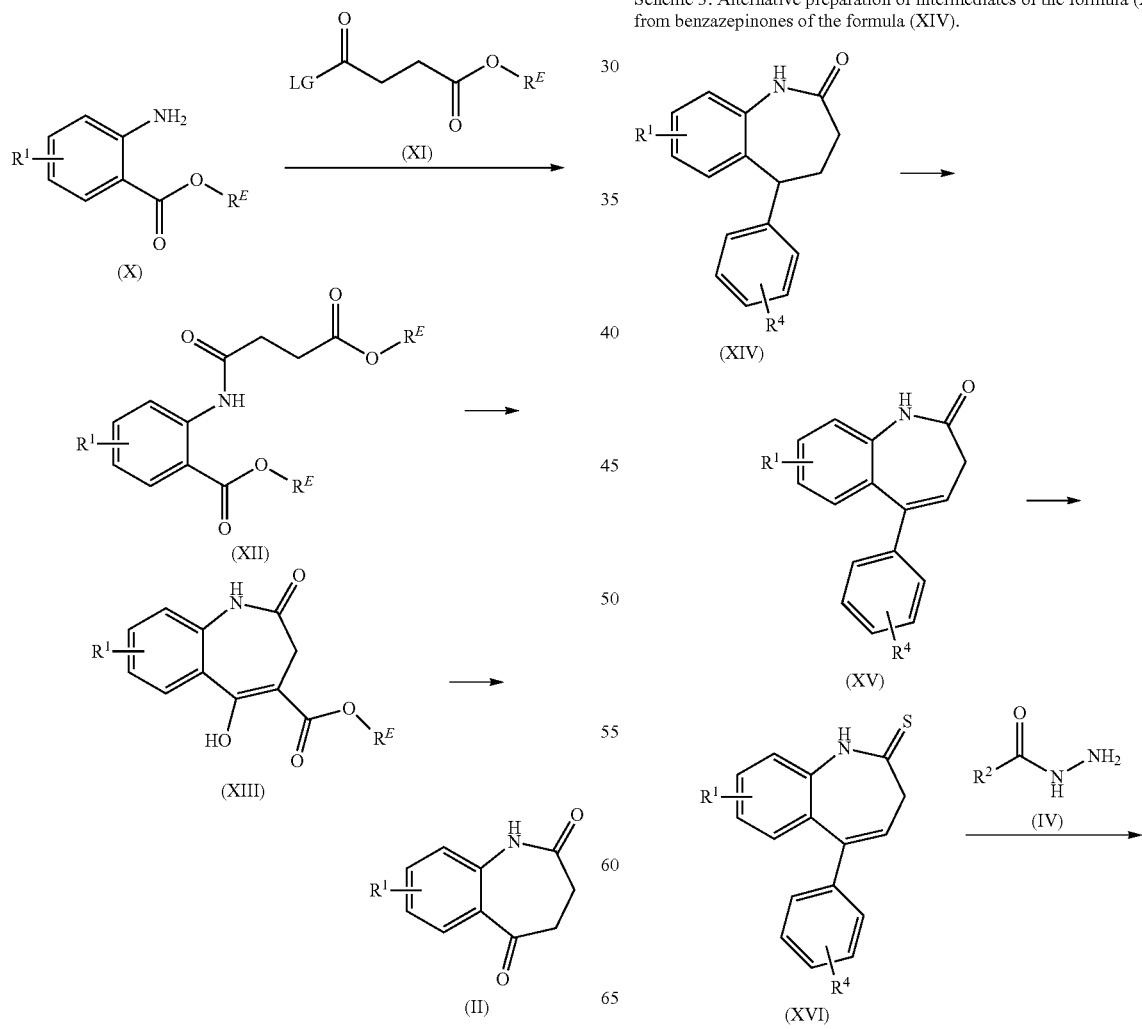

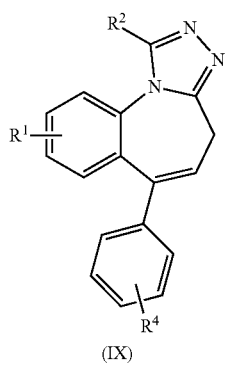

(IX)

As illustrated in Scheme 4, the intermediates of the formula (IX) in which $R^1$, $R^2$ and $R^4$ are as defined for the general formula (I) can be reacted further to give the compounds of the formulae (Ia), (Ib), (Ic) and (Id) according to the invention, all of which represent subgroups of the general formula (I). Here, the (R) enantiomer can be isolated at various stages using methods known to the person skilled in the art, for example chiral preparative HPLC. To this end, the intermediates of the formula (IX) are reacted with acetic acid derivatives of the formula (XVII) in which $R^8$ is as defined for the general formula (I), but different from hydrogen, and in which LG represents a leaving group, for example halogen, preferably chlorine or bromine, in the presence of a suitable base, for example lithium diisopropylamine, potassium tert-butoxide, lithium hexamethyldisilazide, sodium hexamethyldisilazide or sodium hydride, to give esters of the formula (Ia). In chemically similar systems, the introduction of a carbon-containing side chain in a similar way has been described, see, for example, H. Tabata et al., Org. Lett. (2008), 10, p. 4871ff. The esters mentioned of the formula (Ia) can be converted by methods familiar to the person skilled in the art, for example by basic hydrolysis with, for example, aqueous alkali metal hydroxides, or by acidic hydrolysis using, for example, hydrogen chloride in dioxane or trifluoroacetic acid, into the carboxylic acids (Ib). These can be converted by coupling with amines of the formula (XVIII) in which $R^6$ and $R^7$ are as defined for the general formula (I), or with cyclic amines of the formula (XIX) in which $R^9$ is as defined for the general formula (I), with the proviso that the coupling to the hydrogen atom shown in formula (XIX) is via a nitrogen atom, in the presence of a suitable coupling agent into the carboxamides of the formulae (Ic) and (Id) according to the invention. Coupling agents and methods for such syntheses of carboxamides from carboxylic acids and amines are known to the person skilled in the art. Examples which may be mentioned here include the use of HATU, HBTU, PyBOB or T3P with the addition of a suitable base. The conversion of the carboxylic acids to their amides is described in general terms in reference books such as "Compendium of Organic Synthetic Methods", volume I-VI (Wiley Interscience) or "The Practice of Peptide Synthesis", Bodansky (Springer Verlag).

Scheme 4: Synthesis of esters of the formula (Ia), carboxylic acids of the formula (Ib) and carboxamides of the formulae (Ic) and (Id) according to the invention from intermediates of the formula (IX).

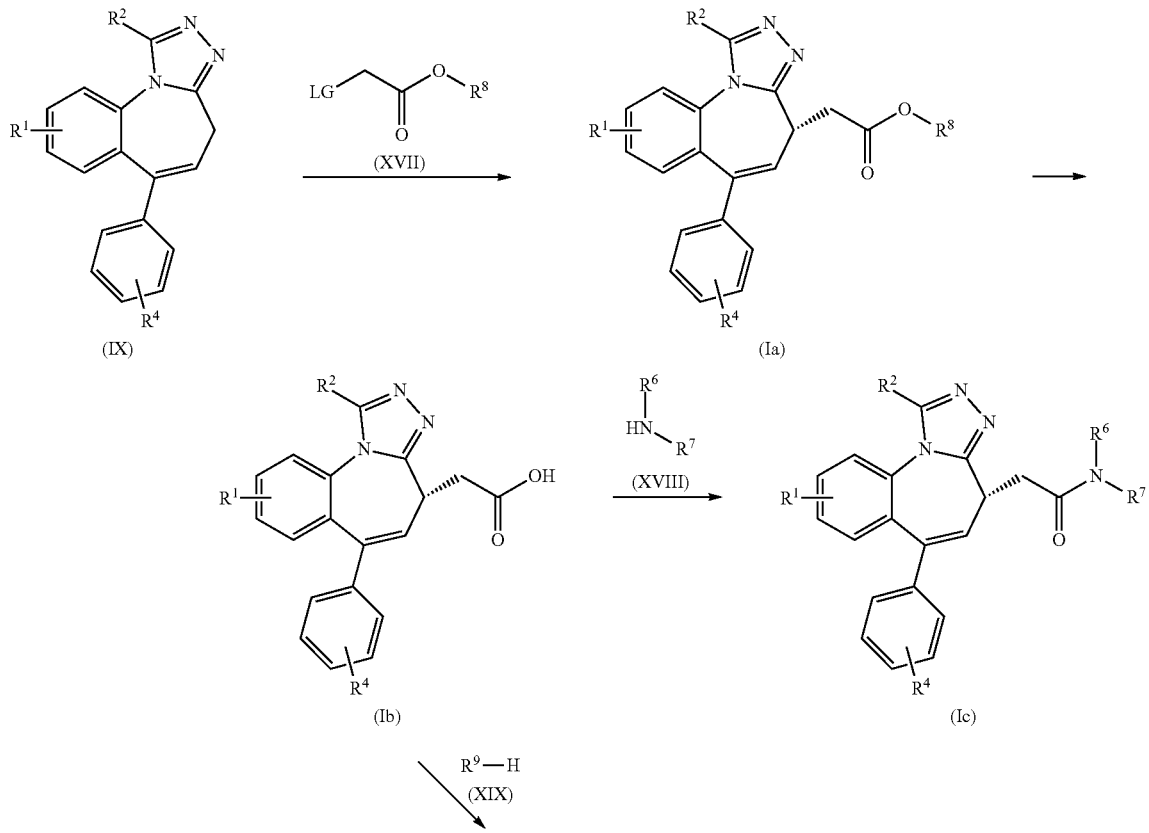

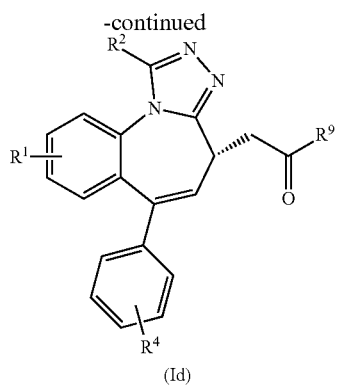

(Id)

As shown in Scheme 5, the intermediates of the formula (IX) in which $R^1$, $R^2$ and $R^4$ are as defined for the general formula (I) can be reacted further to give the compounds of the formula (Ie) according to the invention, all of which represent subgroups of the general formula (I). To this end, the compounds of the formula (IX) are reacted with compounds of the formula (XX) in which LG represents a leaving group, for example halogen, preferably chlorine or bromine, and in which "$R^3$ ring" represents a ring system as defined for $R^3$ in the general formula (I), in the presence of a suitable base, for example sec-butyllithium or lithium hexamethyldisilazide, and at temperatures below 0° C. (for this method, see also, for example, H. Tabata et al., Org. Lett. 2008, 10, p. 4871ff.). From the resulting racemic product, the (R) enantiomer (Ie) is obtained using a method known to the person skilled in the art, for example chiral preparative HPLC. Compounds of the formula (XX) are known to the person skilled in the art and in many cases commercially available. Optionally, the leaving group LG can be formed from suitable precursors (such as, for example, by halogenation of a hydroxymethyl group at the $R^3$ ring) using processes familiar to the person skilled in the art.

Scheme 5: Synthesis of compounds of the formula (Ie) according to the invention from intermediates of the formula (IX)

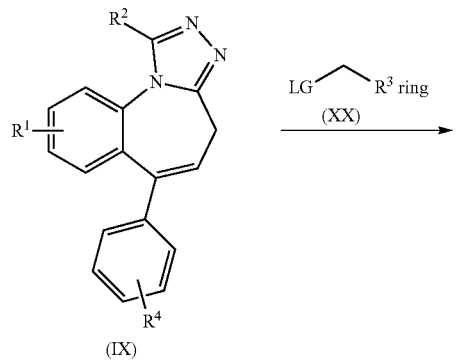

Scheme 6 illustrates a method for the synthesis of oxadiazole derivatives of the formula (If) according to the invention. To this end, the compounds of the formula (Ia) according to the invention in which $R^1$, $R^2$, $R^4$ and $R^8$ are as defined for the general formula (I), with the proviso that $R^8$ is different from hydrogen, are converted in the presence of an alkali metal alkoxide such as, for example, sodium methoxide, with imidoximes of the formula (XXI) in which $R^{5a}$ represents $C_1$-$C_6$-alkyl, $C_3$-$C_8$-cycloalkyl, $C_3$-$C_8$-heterocycloalkyl, aryl, heteroaryl, $C_1$-$C_3$-alkoxy-$C_1$-$C_3$-alkyl, aryloxy-$C_1$-$C_3$-alkyl or aryl-$C_1$-$C_3$-alkoxy-$C_1$-$C_3$-alkyl, directly into the compounds of the formula (If) according to the invention (Tetrahedon Lett. 47, (2006), p. 4271ff, W. Du et al.). The esters of the formula (Ia) can also be employed in racemic form, and from the resulting racemic product the (R) enantiomer (If) can then be obtained using a method known to the person skilled in the art, for example chiral preparative HPLC. The simple imidoximes are usually commercially available.

Scheme 6: Synthesis of compounds of the formula (If) according to the invention from compounds of the formula (Ia) according to the invention.

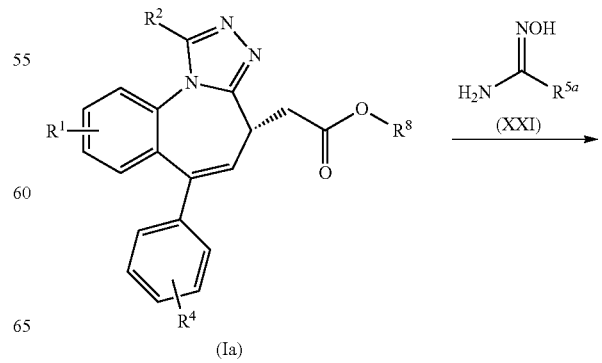

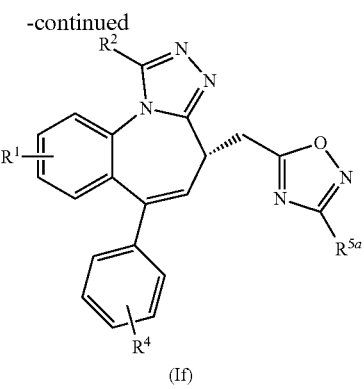

(If)

The synthesis of further compounds of the formulae (Ig), (Ih) and (Ii) according to the invention is shown in Schemes 7a and 7b. The starting materials used are carboxylic acids of the formula (Ib) according to the invention or else their racemates. In this case, the respective (R) enantiomers of the formulae (Ig), (Ih) and (Ii) can be obtained from the resulting racemic products using a method known to the person skilled in the art, for example chiral preparative HPLC.

For the synthesis of the compounds of the general formula (Ig) according to the invention, carboxylic acids of the formula (Ib) in which $R^1$, $R^2$ and $R^4$ are as defined for the general formula (I) are reacted with acylhydrazines of the formula (XXII) in which $R^{5b}$ represents $C_1$-$C_6$-alkyl, $C_3$-$C_8$-cycloalkyl, $C_3$-$C_8$-heterocycloalkyl, aryl, heteroaryl, $C_1$-$C_3$-alkoxy-$C_1$-$C_3$-alkyl, aryloxy-$C_1$-$C_3$-alkyl or aryl-$C_1$-$C_3$-alkoxy-$C_1$-$C_3$-alkyl, in the presence of a suitable amide coupling agent, for example T3P oder HATU, to give acylhydrazides of the formula (XXIII) which can subsequently be cyclized in the presence of a suitable reagent, for example an inorganic acid chjloride such as phosphoryl chloride $POCl_3$, to give the compounds according to the invention (Org. Lett. 7, (2005), p. 1039ff, J. Balsells et al.). The acylhydrazides of the formula (XXIII) can furthermore be cyclized in the presence of a suitable sulphurizing agent, for example Lawesson's reagent or $P_4S_{10}$, to give the thiadiazole derivatives of the formula (Ih) according to the invention (Bioorg. Med. Chem. Lett. 20, (2010), p. 5909ff, G. Le et al.).

Scheme 7a: Synthesis of compounds of the formulae (Ig) and (Ih) according to the invention from carboxylic acids of the formula (Ib).

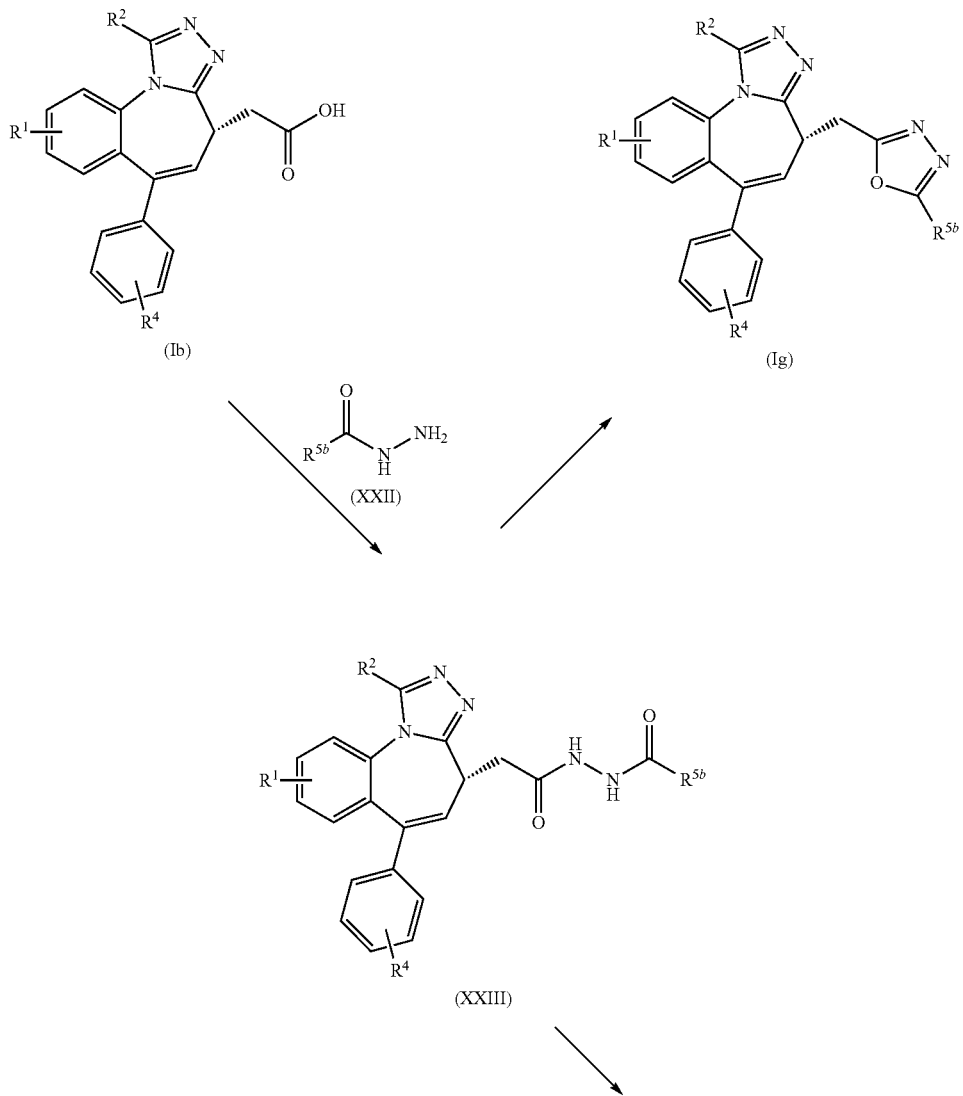

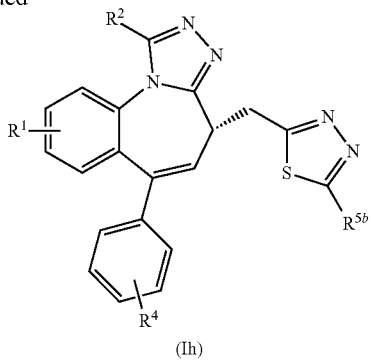

(Ih)

As shown in Scheme 7b, in an analogous manner it is also possible to convert the carboxylic acids (Ib) mentioned above, in which $R^1$, $R^2$ and $R^4$ are as defined for the general formula (I), with acylhydrazines of the formula (XXIV) in which $R^{15}$ is as defined for the general formula (I), with formation of acylhydrazide derivatives of the general formula (Ii) according to the invention.

Scheme 7b: Synthesis of acylhydrazide derivatives of the formula (Ii) according to the invention from carboxylic acids of the formula (Ib).

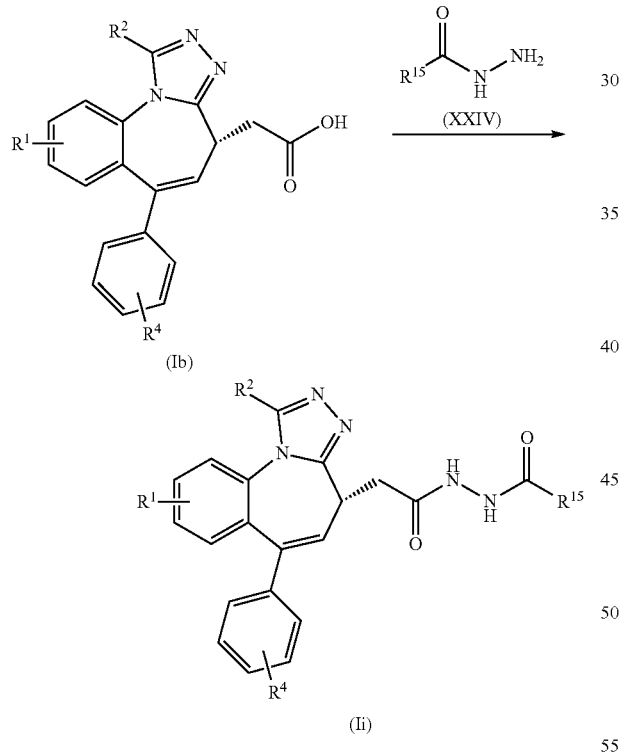

WORKING EXAMPLES

The examples which follow describe the preparation of the compounds according to the invention, without restricting the invention to these examples.

Optical rotation reported in the concentration g/l. Multiplicity of the NMR signals: s=singlet, d=doublet, t=triplet, q=quartet, qi=quintet, b=broad signal, m=multiplet. NMR signals: shift in ppm. The multiplicities are stated according to the signal form which appears in the spectrum, NMR-spectroscopic effects of a higher order were not taken into consideration.

IUPAC names were created with the aid of the nomenclature software ACD Name batch, Version 12.01, from Advanced Chemical Development, Inc., and adapted if required, for example to German-language nomenclature.

Example 1

Preparation of ethyl [6-(4-chlorophenyl)-1-methyl-4H-[1,2,4]triazolo[4,3-a][1]benzazepin-4-yl]acetate

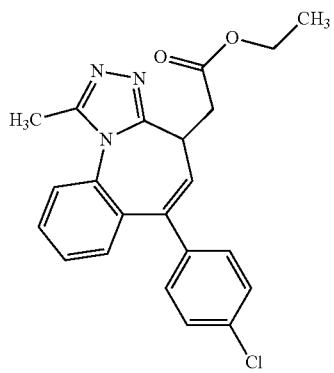 [SMILES: CCOC(=O)CC1C=C(c2ccc(Cl)cc2)c2ccccc2-n2c(C)nnc21]

Example 1A

Preparation of 5-(4-chlorophenyl)-1,3-dihydro-2H-1-benzazepin-2-one

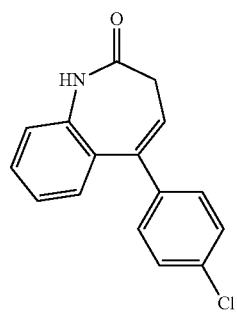 [SMILES: O=C1CC=C(c2ccc(Cl)cc2)c2ccccc2N1]

A solution of 8.1 g of 5-(4-chlorophenyl)-1,3,4,5-tetrahydro-2H-1-benzazepin-2-one (U.S. Pat. No. 5,484,917) in 1.77 l of carbon tetrachloride was admixed with 5.3 g of bromine and boiled under irradiation with a 500 W incandescent lamp. After 10 hours, the mixture was fully concentrated, taken up in ethyl acetate and stirred with saturated sodium hydrogencarbonate solution for 30 min. The organic phase was removed, washed with brine, dried over sodium sulphate and concentrated. The residue was purified by chromatography (silica gel, hexane/ethyl acetate gradient 0%-20%).

Yield: 5.6 g of 5-(4-chlorophenyl)-1,3-dihydro-2H-1-benzazepin-2-one.

$^1$H NMR (400 MHz, RT, CDCl$_3$): δ=3.01 (d, 2H); 6.18 (t, 1H); 7.10-7.18 (m, 3H), 7.20 (d, 2H); 7.33 (d, 2H); 7.38 (dt, 1H); 8.38 (bs, 1H).

Example 1B

Preparation of 5-(4-chlorophenyl)-1,3-dihydro-2H-1-benzazepine-2-thione

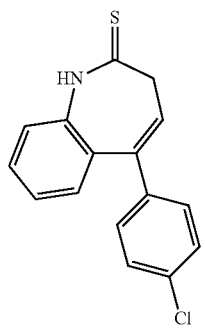 [SMILES: S=C1CC=C(c2ccc(Cl)cc2)c2ccccc2N1]

A solution of 1.1 g of 5-(4-chlorophenyl)-1,3-dihydro-2H-1-benzazepin-2-one (Example 1A) and 0.99 g of 2,4-bis[4-methoxyphenyl]-1,3-dithia-2,4-diphosphetane 2,4-disulphide (Lawesson's reagent) in 27 ml of tetrahydrofuran was heated at the boil for 2 hours. The solvent was then removed under reduced pressure and the residue was purified by chromatography (silica gel, hexane/ethyl acetate gradient 0%-20%).

Yield: 1.1 g of 5-(4-chlorophenyl)-1,3-dihydro-2H-1-benzazepine-2-thione.

$^1$H NMR (300 MHz, RT, CDCl$_3$): δ=3.45 (d, 2H); 6.19 (t, 1H); 7.13-7.22 (m, 5H); 7.28-7.41 (m, 3H); 9.74 (bs, 1H).

Example 1C

Preparation of 6-(4-chlorophenyl)-1-methyl-4H-[1,2,4]triazolo[4,3-a][1]benzazepine

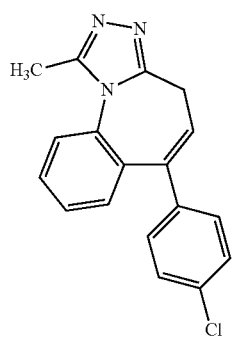 [SMILES: Cc1nnc2n1-c1ccccc1C(c1ccc(Cl)cc1)=CC2]

A solution of 1.1 g of 5-(4-chlorophenyl)-1,3-dihydro-2H-1-benzazepine-2-thione (Example 1B) and 342 mg of acetyl hydrazine in 22 ml of 1-butanol was stirred at boiling for 36 hours. Then the mixture was concentrated under reduced pressure and the residue was purified by chromatography (silica gel, dichloromethane/methanol gradient).

Yield: 620 mg of 6-(4-chlorophenyl)-1-methyl-4H-[1,2,4]triazolo[4,3-a][1]benzazepine.

$^1$H NMR (300 MHz, RT, CDCl$_3$): δ=2.61 (s, 3H); 3.02 (dd, 1H); 3.88 (dd, 1H); 6.35 (dd, 1H); 7.13 (d, 2H); 7.23-7.33 (m, 3H); 7.37 (dt, 1H); 7.40 (d, 1H); 7.50 (dt, 1H).

Example 1D

Alternative Access to Example 1C

2-Thioxo-1,2,3,4-tetrahydro-5H-1-benzazepin-5-one

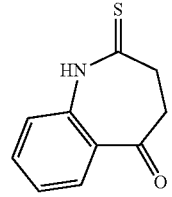 [SMILES: O=C1CCC(=S)Nc2ccccc21]

A solution of 40 g of 3,4-dihydro-1H-1-benzazepine-2,5-dione (Arch. Pharm. 324, (1991), p. 579-81, C. Kunick) and 61.4 g of Lawesson's reagent in 1.2 l of THF was stirred at 70° C. for 2 hours. The mixture was added to 2 l of 50% brine and extracted 3 times with ethyl acetate. The combined organic phases were washed with saturated sodium bicarbonate solution and brine and dried over sodium sulphate, and the solvent was removed under reduced pressure. The residue was taken up in about 400 ml of dichloromethane. Part of the substance did not go into solution. This part was filtered off, stirred once more with 100 ml of boiling MTBE and, after cooling, filtered off with suction. This gave a first residue of the target compound of 24 g. The dichloromethane mother liquor was purified by chromatography on silica gel (dichloromethane/methanol gradient). This gave a further 6 g of the title compound.

Yield: 30 g of 2-thioxo-1,2,3,4-tetrahydro-5H-1-benzazepin-5-one $^1$H NMR (300 MHz, RT, CDCl$_3$): δ=3.04-3.10 (m, 2H); 3.29-3.36 (m, 2H); 7.05 (d, 1H); 7.33 (dt, 1H); 7.58 (dt, 1H); 8.01 (dd, 1H); 9.65 (bs, 1H).

Example 1E

Alternative Access to Example 1C

1-Methyl-4,5-dihydro-6H-[1,2,4]triazolo[4,3-a][1]benzazepin-6-one

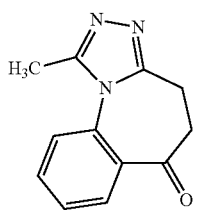 [SMILES: Cc1nnc2n1-c1ccccc1C(=O)CC2]

A solution of 24 g of 2-thioxo-1,2,3,4-tetrahydro-5H-1-benzazepin-5-one (Example 1D) and 27.9 g of acetylhydrazine in 670 ml of 1-butanol was initially stirred at 60° C. for 1 hour. The mixture was then heated to 150° C. and stirred for 16 hours. The solvent was removed under reduced pressure and the residue was taken up in 670 ml of dioxane. 32 ml of water were added, followed by the careful dropwise addition of 103.8 ml of concentrated hydrochloric acid. The reaction was stirred at RT for 16 hours. The precipitate formed was filtered off and the reaction was adjusted to a basic pH by addition of potassium carbonate. The reaction was filtered through again and the residue was washed with ethyl acetate. The combined phases were separated, the organic phase was dried over sodium sulphate and the solvent was removed under reduced pressure. The residue was purified by chromatography on silica gel (dichloromethane/methanol gradient).

Yield: 11.7 g of 1-methyl-4,5-dihydro-6H-[1,2,4]triazolo[4,3-a][1]benzazepin-6-one $^1$H NMR (300 MHz, RT, CDCl$_3$): δ=2.54 (s, 3H); 3.01-3.09 (m, 2H); 3.20-3.28 (m, 2H); 7.28 (dd, 1H); 7.54 (dt, 1H); 7.71 (dt, 1H); 7.82 (dd, 1H).

Example 1F

Alternative Access to Example 1C

1-Methyl-4H-[1,2,4]triazolo[4,3-a][1]benzazepin-6-yl 1,1,2,2,3,3,4,4,4-nonafluorobutane-1-sulphonate

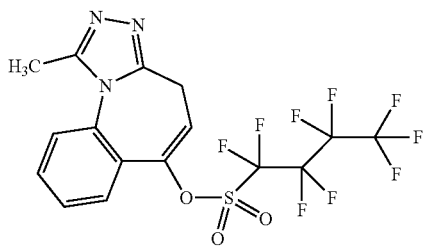 [SMILES: Cc1nnc2n1-c1ccccc1C(OS(=O)(=O)C(F)(F)C(F)(F)C(F)(F)C(F)(F)F)=CC2]

At −70° C., 78.1 ml of lithium hexamethyldisilazide solution (1M in toluene) were added over a period of 30 min to a solution of 11.7 g of 1-methyl-4,5-dihydro-6H-[1,2,4]triazolo[4,3-a][1]benzazepin-6-one (Example 1E) in 500 ml of THF. The mixture was stirred at −70° C. for a further 45 min. 23.6 g of nonafluorobutanesulphonyl fluoride (CAS 375-72-4) were added dropwise thereto, and the mixture was stirred for 16 hours with warming to RT. The mixture was added to semisaturated sodium bisulphate solution and extracted three times with ethyl acetate. The combined organic phases were washed with brine and dried over sodium sulphate, and the solvent was removed under reduced pressure. The residue was purified by chromatography on silica gel (dichloromethane/methanol gradient).

Yield: 26.5 g of 1-methyl-4H-[1,2,4]triazolo[4,3-a][1]benzazepin-6-yl 1,1,2,2,3,3,4,4,4-nonafluorobutane-1-sulphonate $^1$H NMR (300 MHz, RT, CDCl$_3$): δ=2.52 (s, 3H); 3.00-3.11 (m, 2H); 3.81-3.92 (m, 2H); 6.35 (dd, 1H); 7.43 (dd, 1H); 7.59 (dt, 1H); 7.65 (dt, 1H); 7.79 (dd, 1H).

Example 1C

Alternative Access 6-(4-Chlorophenyl)-1-methyl-4H-[1,2,4]triazolo[4,3-a][1]benzazepine

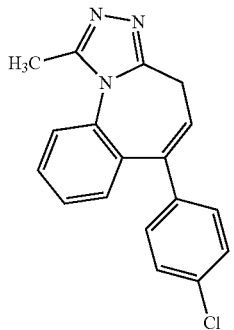

A solution of 26.5 g of 1-methyl-4H-[1,2,4]triazolo[4,3-a][1]benzazepin-6-yl 1,1,2,2,3,3,4,4,4-nonafluorobutane-1-sulphonate (Example 1F), 10.33 g of 4-chlorophenylboronic acid (CAS 1679-18-1), 4.31 g of lithium chloride, 10.77 g of sodium carbonate and 5.87 g of tetrakistriphenylphosphinepalladium in 830 ml of toluene and 207 ml of ethanol was stirred under an atmosphere of argon at 95° C. for 3 hours. The mixture was added to water and extracted four times with ethyl acetate. The combined organic phases were washed with brine and dried over sodium sulphate, and the solvent was removed under reduced pressure to a volume of about 200 ml. The mixture was allowed to stand overnight. The desired target compound separated off as a precipitate which was filtered off (8.0 g). The mother liquor was concentrated further and the residue was purified by chromatography on silica gel (dichloromethane/methanol gradient). This gave a further 3.5 g of the target compound.

Yield: 11.5 g of 6-(4-chlorophenyl)-1-methyl-4H-[1,2,4]triazolo[4,3-a][1]benzazepine $^1$H NMR (300 MHz, RT, CDCl$_3$): δ=2.62 (s, 3H); 3.03 (dd, 1H); 3.89 (dd, 1H); 6.36 (dd, 1H); 7.14 (d, 2H); 7.23-7.34 (m, 3H); 7.34-7.45 (m, 2H); 7.52 (dt, 1H).

Example 1G

Preparation of ethyl [6-(4-chlorophenyl)-1-methyl-4H-[1,2,4]triazolo[4,3-a][1]benzazepin-4-yl]acetate

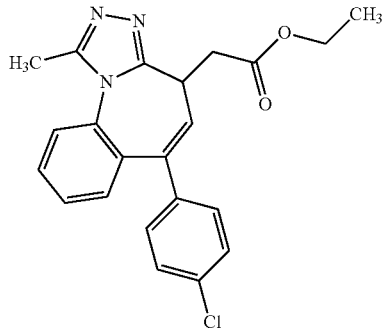 [SMILES: CCOC(=O)CC1C=C(c2ccc(Cl)cc2)c2ccccc2-n2c(C)nnc21]

At −78° C., 0.32 ml of a solution of lithium diisopropylamide (2M in THF/heptane/ethylbenzene) was added to 180 mg of 6-(4-chlorophenyl)-1-methyl-4H-[1,2,4]triazolo[4,3-a][1]benzazepine (Example 1C) in 5 ml of THF. After the addition had ended, the mixture was stirred at −78° C. for another 90 min. 0.065 ml of ethyl bromoacetate (CAS 105-36-2) was then added and the mixture was gradually warmed to room temperature overnight. The mixture was partitioned between dilute hydrochloric acid (0.1M) and ethyl acetate, the organic phase was removed, the aqueous phase was extracted with ethyl acetate, and the combined organic phases were washed with water and brine, dried over sodium sulphate and concentrated under reduced pressure. The residue was purified by chromatography (silica gel, dichloromethane/methanol gradient).

Yield: 100 mg of ethyl [6-(4-chlorophenyl)-1-methyl-4H-[1,2,4]triazolo[4,3-a][1]benzazepin-4-yl]acetate.

$^{1}$H NMR (300 MHz, RT, CDCl$_{3}$): δ=1.30 (t, (3H); 2.59 (s, 3H); 3.16 (dd, 1H); 3.46 (dd, 1H); 3.60-3.69 (m, 1H); 4.21 (q, 2H); 6.06 (dd, 1H); 7.04-7.18 (m, 2H); 7.23-7.33 (m, 3H); 7.34-7.44 (m, 2H); 7.51 (dt, 1H).

Example 2

Preparation of ethyl (−)-(4R)-[6-(4-chlorophenyl)-1-methyl-4H-[1,2,4]triazolo[4,3-a][1]benzazepin-4-yl]acetate

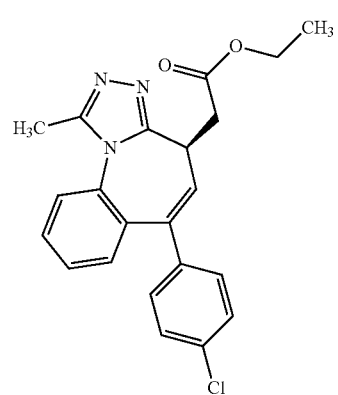 [SMILES: CCOC(=O)C[C@H]1C=C(c2ccc(Cl)cc2)c2ccccc2-n2c(C)nnc21]

190 mg of ethyl [6-(4-chlorophenyl)-1-methyl-4H-[1,2,4]triazolo[4,3-a][1]benzazepin-4-yl]acetate were separated into the enantiomers by chiral HPLC (Chiralpak IC 5 µm 250×30 mm, ethanol/methanol 50:50 (v/v), 30 ml/min).

Yield: 22 mg of ethyl (−)-(4R)-[6-(4-chlorophenyl)-1-methyl-4H-[1,2,4]triazolo[4,3-a][1]benzazepin-4-yl]acetate.

Optical rotation: [α]$_{D}^{20}$=−140.3°+/−0.12° (c=10.3, CHCl$_{3}$).

Example 3

Preparation of 2-[6-(4-chlorophenyl)-1-methyl-4H-[1,2,4]triazolo[4,3-a][1]benzazepin-4-yl]-1-(2-oxa-6-azaspiro[3.3]hept-6-yl)ethanone

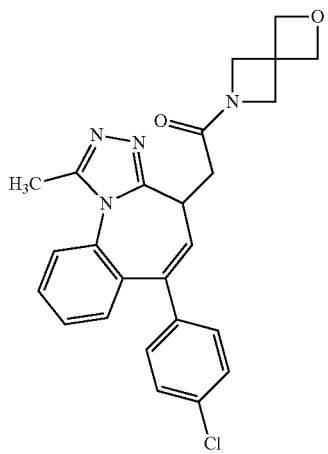 [SMILES: Cc1nnc2n1-c1ccccc1C(c1ccc(Cl)cc1)=CC2CC(=O)N1CC2(COC2)C1]

Example 3A

Preparation of [6-(4-chlorophenyl)-1-methyl-4H-[1,2,4]triazolo[4,3-a][1]benzazepin-4-yl]acetic acid

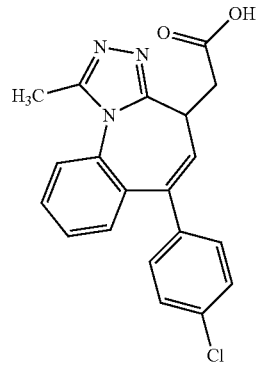 [SMILES: Cc1nnc2n1-c1ccccc1C(c1ccc(Cl)cc1)=CC2CC(=O)O]

A solution of 215 mg of ethyl [6-(4-chlorophenyl)-1-methyl-4H-[1,2,4]triazolo[4,3-a][1]benzazepin-4-yl]acetate and 0.6 ml of aqueous sodium hydroxide solution (1M) in 18 ml of methanol was stirred at room temperature for 18 hours. The solution was concentrated fully under reduced pressure and the residue was purified by RP-HPLC (column: X-Bridge C18 5 µm 100×30 mm, mobile phase: acetonitrile/water (0.1% by volume formic acid) gradient).

Yield: 200 mg of [6-(4-chlorophenyl)-1-methyl-4H-[1,2,4]triazolo[4,3-a][1]benzazepin-4-yl]acetic acid.

$^{1}$H NMR (400 MHz, RT, CDCl$_{3}$): δ=2.61 (s, 3H); 3.24 (dd, 1H); 3.48 (dd, 1H); 3.65-3.73 (m, 1H); 6.08 (d, 1H); 7.13 (d, 2H); 7.25-7.33 (m, 5H); 7.37-7.46 (m, 2H); 7.52 (dt, 1H).

Example 3B

Preparation of 2-[6-(4-chlorophenyl)-1-methyl-4H-[1,2,4]triazolo[4,3-a][1]benzazepin-4-yl]-1-(2-oxa-6-azaspiro[3.3]hept-6-yl)ethanone

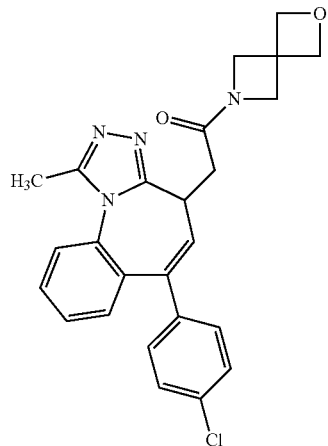 [SMILES: Cc1nnc2n1-c1ccccc1C(c1ccc(Cl)cc1)=CC2CC(=O)N1CC2(COC2)C1]

A solution of 200 mg of [6-(4-chlorophenyl)-1-methyl-4H-[1,2,4]triazolo[4,3-a][1]benzazepin-4-yl]acetic acid (Example 3A), 312 mg of HATU, 0.3 ml of triethylamine and 158 mg of 2-oxa-6-azaspiro[3.3]heptane oxalate (2:1) (CAS 174-78-7 for the free base) in 10 ml of DMF was stirred at room temperature for 3 hours. The mixture was partitioned between semiconcentrated brine and ethyl acetate, the organic phase was removed and the aqueous phase was extracted twice with ethyl acetate. The combined organic phases were washed with brine, dried over sodium sulphate and concentrated under reduced pressure. The residue was purified by chromatography (silica gel, dichloromethane/methanol gradient).

Yield: 200 mg of 2-[6-(4-chlorophenyl)-1-methyl-4H-[1,2,4]triazolo[4,3-a][1]benzazepin-4-yl]-1-(2-oxa-6-azaspiro[3.3]hept-6-yl)ethanone.

$^1$H NMR (400 MHz, RT, DMSO-d6): δ=2.50 (s, 3H); 2.82 (dd, 1H); 3.05 (dd, 1H); 3.44 (q, 1H); 4.01 (d, 1H); 4.05 (d, 1H); 4.43 (d, 1H); 4.49 (d, 1H); 4.65-4.75 (m, 4H); 6.19 (d, 1H); 7.13-7.29 (m, 3H); 7.41 (d, 2H); 7.47 (dt, 1H); 7.60 (dt, 1H); 7.74 (d, 1H).

Example 4

Preparation of (−)-2-[(4R)-6-(4-chlorophenyl)-1-methyl-4H-[1,2,4]triazolo[4,3-a][1]benzazepin-4-yl]-1-(2-oxa-6-azaspiro[3.3]hept-6-yl)ethanone

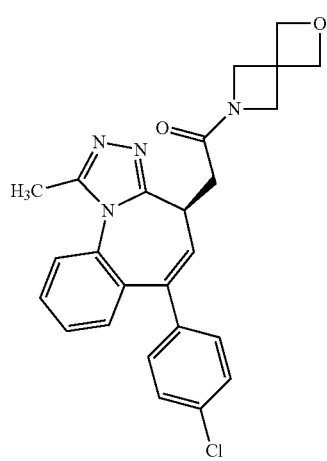 [SMILES: Cc1nnc2n1-c1ccccc1C(c1ccc(Cl)cc1)=C[C@@H]2CC(=O)N1CC2(COC2)C1]

200 mg of 2-[6-(4-chlorophenyl)-1-methyl-4H-[1,2,4]triazolo[4,3-a][1]benzazepin-4-yl]-1-(2-oxa-6-azaspiro[3.3]hept-6-yl)ethanone were separated into the enantiomers by chiral HPLC (Chiralpak IC 5 μm 250×30 mm, ethanol/methanol 50:50 (v/v), 30 ml/min).

Yield: 50 mg of (−)-2-[6-(4-chlorophenyl)-1-methyl-4H-[1,2,4]triazolo[4,3-a][1]benzazepin-4-yl]-1-(2-oxa-6-azaspiro[3.3]hept-6-yl)ethanone Optical rotation: $[\alpha]_D^{20}$=−151.2°+/−0.12° (c=10.6, CHCl$_3$)].

Example 5

Preparation of 1-(7-azabicyclo[2.2.1]hept-7-yl)-2-[6-(4-chlorophenyl)-1-methyl-4H-[1,2,4]triazolo[4,3-a][1]benzazepin-4-yl]ethanone

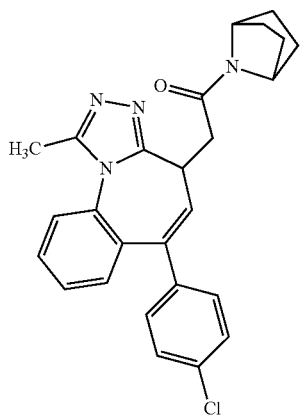 [SMILES: Cc1nnc2n1-c1ccccc1C(c1ccc(Cl)cc1)=CC2CC(=O)N1C2CCC1CC2]

A solution of 200 mg of [6-(4-chlorophenyl)-1-methyl-4H-[1,2,4]triazolo[4,3-a][1]benzazepin-4-yl]acetic acid (Example 3A), 312 mg of HATU, 0.3 ml of triethylamine and 53 mg of 7-azabicyclo[2.2.1]heptane hydrochloride (Zerenex ZX-IP016134) in 10 ml of DMF was stirred at room temperature for 3 hours. The mixture was partitioned between semiconcentrated brine and ethyl acetate, the organic phase was removed and the aqueous phase was extracted twice with ethyl acetate. The combined organic phases were washed with brine, dried over sodium sulphate and concentrated under reduced pressure. The residue was purified by chromatography (silica gel, dichloromethane/methanol gradient).

Yield: 210 mg of 1-(7-azabicyclo[2.2.1]hept-7-yl)-2-[6-(4-chlorophenyl)-1-methyl-4H-[1,2,4]triazolo[4,3-a][1]benzazepin-4-yl]ethanone.

$^1$H NMR (400 MHz, RT, CDCl$_3$): δ=1.40-1.63 (m, 1H); 1.70-2.02 (m, 3H); 2.59 (s, 3H); 3.12 (dd, 1H); 3.41 (dd, 1H); 3.76 (dt, 1H); 4.47 (t, 1H); 4.66 (t, 1H); 6.03 (d, 1H); 7.13 (d, 2H); 7.21-7.31 (m, 3H); 7.31-7.42 (m, 2H); 7.48 (dt, 1H).

Example 6

Preparation of (−)-1 (7-azabicyclo[2.2.1]hept-7-yl)-2-[(4R)-6-(4-chlorophenyl)-1-methyl-4H-[1,2,4]triazolo[4,3-a][1]benzazepin-4-yl]ethanone

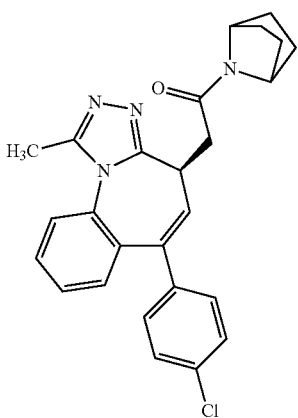 [SMILES: Cc1nnc2n1-c1ccccc1C(c1ccc(Cl)cc1)=C[C@@H]2CC(=O)N1C2CCC1CC2]

210 mg of 1-(7-azabicyclo[2.2.1]hept-7-yl)-2-[6-(4-chlorophenyl)-1-methyl-4H-[1,2,4]triazolo[4,3-a][1]benzazepin-4-yl]ethanone were separated into the enantiomers by chiral HPLC (Chiralpak IC 5 μm 250×30 mm, ethanol/methanol 50:50 (v/v), 30 ml/min).

Yield: 50 mg of (−)-1-(7-azabicyclo[2.2.1]hept-7-yl)-2-[(4R)-6-(4-chlorophenyl)-1-methyl-4H-[1,2,4]triazolo[4,3-a][1]benzazepin-4-yl]ethanone.

Optical rotation: $[\alpha]_D^{20} = -120.2° +/- 0.14°$ (c=9.8, CHCl$_3$).

Example 7

Preparation of ethyl [6-(3-chlorophenyl)-1-methyl-4H-[1,2,4]triazolo[4,3-a][1]benzazepin-4-yl]acetate

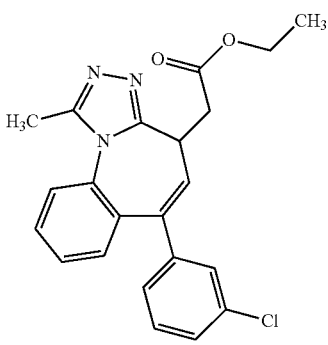 [SMILES: CCOC(=O)CC1C=C(c2cccc(Cl)c2)c2ccccc2-n2c(C)nnc21]

Example 7A 5-(3-Chlorophenyl)-1,3-dihydro-2H-1-benzazepin-2-one

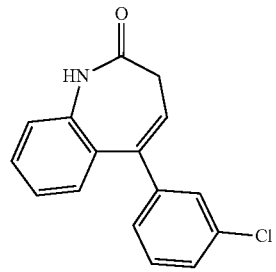

A solution of 8.1 g of 5-(3-chlorophenyl)-1,3,4,5-tetrahydro-2H-1-benzazepin-2-one (J. Med Chem. 37, (1994), p. 3789ff, J. A. Lowe et al.) in 1.77 l of carbon tetrachloride was admixed with 5.3 g of bromine and boiled under irradiation with a 500 W incandescent lamp. After 10 hours, the mixture was fully concentrated, taken up in ethyl acetate and stirred with saturated sodium bicarbonate solution for 30 min. The organic phase was removed, washed with brine, dried over sodium sulphate and concentrated. The residue was purified by chromatography (silica gel, hexane/ethyl acetate gradient 0%-20%).

Yield: This gave 5.6 g of 5-(4-chlorophenyl)-1,3-dihydro-2H-1-benzazepin-2-one.

$^1$H NMR (400 MHz, RT, CDCl$_3$): δ=3.01 (d, 2H); 6.20 (t, 1H); 7.12-7.24 (m, 4H), 7.27-7.28 (m, 1H); 7.30-7.44 m, 3H); 7.87 (bs, 1H).

Example 7B

Preparation of 5-(3-chlorophenyl)-1,3-dihydro-2H-1-benzazepine-2-thione

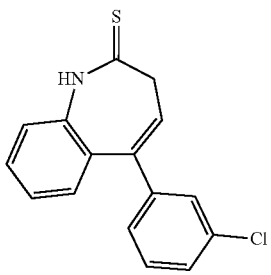 [SMILES: S=C1CC=C(c2cccc(Cl)c2)c2ccccc2N1]

A solution of 730 mg of 5-(3-chlorophenyl)-1,3-dihydro-2H-1-benzazepin-2-one (Example 7A) and 657 mg of 2,4-bis[4-methoxyphenyl]-1,3-dithia-2,4-diphosphetane 2,4-disulphide (Lawesson's reagent) in 18.1 ml of tetrahydrofuran was heated at the boil for 2 hours. Then the solvent was removed under reduced pressure and the residue was purified by chromatography (silica gel, hexane/ethyl acetate gradient 0%-20%).

Yield: 670 mg of 5-(3-chlorophenyl)-1,3-dihydro-2H-1-benzazepine-2-thione.

$^1$H NMR (300 MHz, RT, CDCl$_3$): δ=3.46 (d, 2H); 6.22 (t, 1H); 7.11 (dd, 1H); 7.16-7.26 (m, 4H); 7.28-7.42 (m, 3H); 9.64 (bs, 1H).

Example 7C

Preparation of 6-(3-chlorophenyl)-1-methyl-4H-[1,2,4]triazolo[4,3-a][1]benzazepine

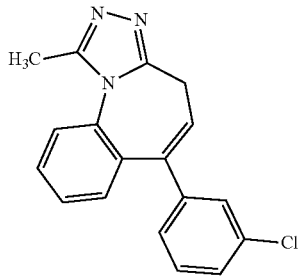 [SMILES: Cc1nnc2n1-c1ccccc1C(c1cccc(Cl)c1)=CC2]

A solution of 670 mg of 5-(3-chlorophenyl)-1,3-dihydro-2H-1-benzazepine-2-thione (Example 7B) and 208 mg of acetyl hydrazine in 13.4 ml of 1-butanol was stirred at the boil for 36 hours. Then the mixture was concentrated under reduced pressure and the residue was purified by chromatography (silica gel, dichloromethane/methanol gradient).

Yield: 440 mg of 6-(3-chlorophenyl)-1-methyl-4H-[1,2,4]triazolo[4,3-a][1]benzazepine.

$^1$H NMR (300 MHz, RT, CDCl$_3$): δ=2.61 (s, 3H); 3.03 (dd, 1H); 3.89 (dd, 1H); 6.37 (dd, 1H); 7.08 (dd, 1H); 7.18 (bs, 1H); 7.22-7.33 (m, 3H); 7.34-7.44 (m, 2H); 7.51 (dt, 1H).

Example 7D

Preparation of ethyl [6-(3-chlorophenyl)-1-methyl-4H-[1,2,4]triazolo[4,3-a][1]benzazepin-4-yl]acetate

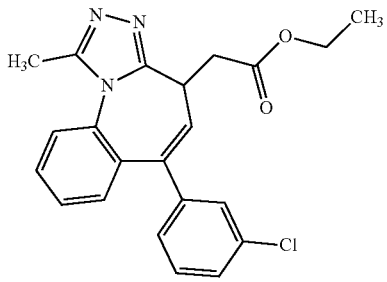 [SMILES: CCOC(=O)CC1C=C(c2cccc(Cl)c2)c2ccccc2-n2c(C)nnc21]

At −78° C., 0.79 ml of a solution of lithium diisopropylamide (2M in THF/heptane/ethylbenzene) was added to 440 mg of 6-(3-chlorophenyl)-1-methyl-4H-[1,2,4]triazolo[4,3-a][1]benzazepine (Example 7C) in 22 ml of THF. After the addition had ended, the mixture was stirred at −78° C. for another 90 min. 0.16 ml of ethyl bromoacetate was then added and the mixture was gradually warmed to room temperature overnight. The mixture was partitioned between saturated ammonium chloride solution and ethyl acetate, the organic phase was removed, the aqueous phase was extracted with ethyl acetate, and the combined organic phases were washed with water and brine, dried over sodium sulphate and concentrated under reduced pressure. The residue was purified by chromatography (silica gel, dichloromethane/methanol gradient).

Yield 220 mg of ethyl [6-(3-chlorophenyl)-1-methyl-4H-[1,2,4]triazolo[4,3-a][1]benzazepin-4-yl]acetate.

$^1$H NMR (300 MHz, RT, CDCl$_3$): δ=1.30 (t, 3H); 2.60 (s, 3H); 3.16 (dd, 1H); 3.46 (dd, 1H); 3.65 (dt, 1H); 4.21 (q, 2H); 6.07 (d, 1H); 7.06 (d, 1H); 7.21-7.32 (m, 3H); 7.35-7.44 (m, 2H); 7.52 (dt, 1H).

Example 8

Preparation of tert-butyl [6-(4-chlorophenyl)-1-methyl-4H-[1,2,4]triazolo[4,3-a][1]benzazepin-4-yl]acetate

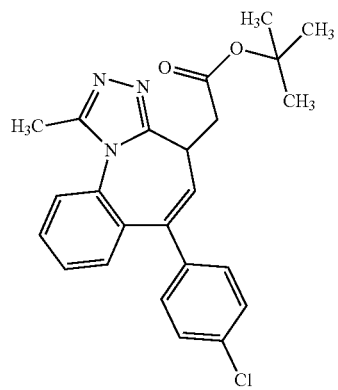 [SMILES: Cc1nnc2n1-c1ccccc1C(c1ccc(Cl)cc1)=CC2CC(=O)OC(C)(C)C]

At −78° C., 0.36 ml of a solution of lithium diisopropylamide (2M in THF/heptane/ethylbenzene) was added to 200 mg of 6-(4-chlorophenyl)-1-methyl-4H-[1,2,4]triazolo[4,3-a][1]benzazepine (Example 1C) in 10 ml of THF. After the addition had ended, the mixture was stirred at −78° C. for another 90 min. Then 0.095 ml of tert-butyl bromoacetate was added and the mixture was gradually warmed to room temperature overnight. The mixture was partitioned between saturated ammonium chloride solution and ethyl acetate, the organic phase was removed, the aqueous phase was extracted with ethyl acetate, and the combined organic phases were washed with water and brine, dried over sodium sulphate and concentrated under reduced pressure. The residue was purified by chromatography (silica gel, dichloromethane/methanol gradient).

Yield: 110 mg of tert-butyl [6-(4-chlorophenyl)-1-methyl-4H-[1,2,4]triazolo[4,3-a][1]benzazepin-4-yl]acetate.

$^1$H NMR (300 MHz, RT, CDCl$_3$): δ=1.48 (s, 9H); 2.59 (s, 3H); 3.09 (dd, 1H); 3.38 (dd, 1H); 3.59 (dt, 1H); 6.04 (d, 1H); 7.24-7.32 (m, 3H); 7.37 (dt, 1H); 7.40 (dd, 1H); 7.50 (dt, 1H).

Example 9

Preparation of tert-butyl (−)-[(4R)-6-(4-chlorophenyl)-1-methyl-4H-[1,2,4]triazolo[4,3-a][1]benzazepin-4-yl]acetate

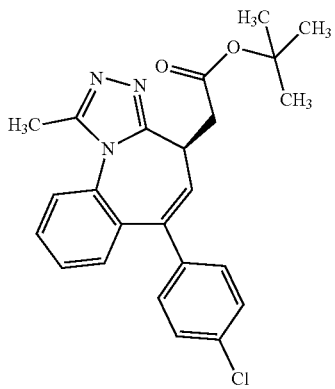 [SMILES: Cc1nnc2n1-c1ccccc1C(c1ccc(Cl)cc1)=C[C@@H]2CC(=O)OC(C)(C)C]

210 mg of tert-butyl [6-(4-chlorophenyl)-1-methyl-4H-[1,2,4]triazolo[4,3-a][1]benzazepin-4-yl]acetate were separated into the enantiomers by chiral HPLC (Chiralpak IC 5 µm 250×30 mm, ethanol/methanol 50:50 (v/v), 30 ml/min).

Yield: 33 mg of tert-butyl (+[(4R)-6-(4-chlorophenyl)-1-methyl-4H-[1,2,4]triazolo[4,3-a][1]benzazepin-4-yl]acetate.

Optical rotation: $[\alpha]_D^{20}=-109.1°+/-0.14°$ (c=10.0, CHCl$_3$).

Example 10

Preparation of 2-[6-(3-chlorophenyl)-1-methyl-4H-[1,2,4]triazolo[4,3-a][1]benzazepin-4-yl]-1-(2-oxa-6-azaspiro[3.3]hept-6-yl)ethanone

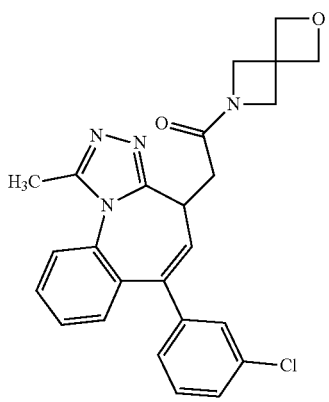 [SMILES: Cc1nnc2n1-c1ccccc1C(c1cccc(Cl)c1)=CC2CC(=O)N1CC2(COC2)C1]

A solution of 215 mg of ethyl [6-(3-chlorophenyl)-1-methyl-4H-[1,2,4]triazolo[4,3-a][1]benzazepin-4-yl]acetate (Example 7) and 0.6 ml of aqueous sodium hydroxide solution (1M) in 36 ml of THF was stirred at room temperature for 18 hours. The solution was concentrated fully under reduced pressure. This gave 199 mg of [6-(3-chlorophenyl)-1-methyl-4H-[1,2,4]triazolo[4,3-a][1]benzazepin-4-yl]acetic acid. This was dissolved in 10 ml of DMF and admixed with 310 mg of HATU, 0.3 ml of triethylamine and 157 mg of 2-oxa-6-azaspiro[3.3]heptane oxalate (2:1) and stirred at room temperature for 3 hours. The mixture was partitioned between semiconcentrated brine and ethyl acetate, the organic phase was removed and the aqueous phase was extracted twice with ethyl acetate. The combined organic phases were washed with brine, dried over sodium sulphate and concentrated under reduced pressure. The residue was purified by chromatography (silica gel, dichloromethane/methanol gradient).

Yield: 190 mg of 2-[6-(3-chlorophenyl)-1-methyl-4H-[1,2,4]triazolo[4,3-a][1]benzazepin-4-yl]-1-(2-oxa-6-azaspiro[3.3]hept-6-yl)ethanone.

$^1$H NMR (400 MHz, RT, CDCl$_3$): δ=2.59 (s, 3H); 2.78 (dd, 1H); 3.24 (dd, 1H); 3.75 (dt, 1H); 4.18 (bs, 2H); 4.42 (d, 1H); 4.74-4.89 (m, 5H); 6.01 (d, 1H); 7.06 (d, 1H); 7.18 (bs, 1H); 7.21-7.31 (m, 3H); 7.34-7.42 (m, 2H); 7.50 (dt, 1H).

Example 11

Preparation of (−)-2-[(4R)-6-(3-chlorophenyl)-1-methyl-4H-[1,2,4]triazolo[4,3-a][1]benzazepin-4-yl]-1-(2-oxa-6-azaspiro[3.3]hept-6-yl)ethanone

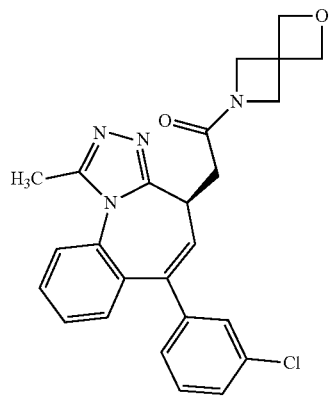 [SMILES: Cc1nnc2n1-c1ccccc1C(c1cccc(Cl)c1)=C[C@@H]2CC(=O)N1CC2(COC2)C1]

190 mg of 2-[6-(3-chlorophenyl)-1-methyl-4H-[1,2,4]triazolo[4,3-a][1]benzazepin-4-yl]-1-(2-oxa-6-azaspiro[3.3]hept-6-yl)ethanone were separated into the enantiomers by chiral HPLC (Chiralpak IA 5 µm 250×20 mm, methanol/ethanol 1:1 (v/v)+0.1% DEA, 15 ml/min).

Yield: 70 mg of (−)-2-[(4R)-6-(3-chlorophenyl)-1-methyl-4H-[1,2,4]triazolo[4,3-a][1]benzazepin-4-yl]-1-(2-oxa-6-azaspiro[3.3]hept-6-yl)ethanone.

Optical rotation: $[\alpha]_D^{20}=-129.9°+/-0.14°$ (c=9.8, CHCl$_3$).

Example 12

Preparation of 2-[6-(4-chlorophenyl)-1-methyl-4H-[1,2,4]triazolo[4,3-a][1]benzazepin-4-yl]-N-ethylacetamide

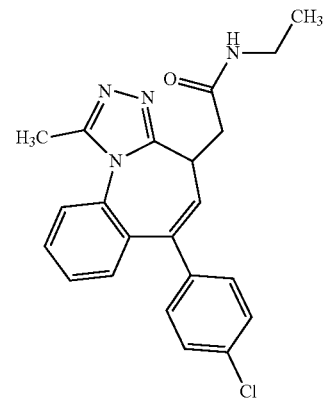 [SMILES: CCNC(=O)CC1C=C(c2ccc(Cl)cc2)c2ccccc2-n2c(C)nnc21]

A solution of 110 mg of [6-(4-chlorophenyl)-1-methyl-4H-[1,2,4]triazolo[4,3-a][1]benzazepin-4-yl]acetic acid (Example 3A), 171 mg of HATU, 0.17 ml of triethylamine and 0.165 ml of ethylamine in 3 ml of DMF was stirred at room temperature for 14 hours. The mixture was partitioned between semiconcentrated brine and ethyl acetate, the organic phase was removed and the aqueous phase was extracted twice with ethyl acetate. The combined organic phases were washed with brine, dried over sodium sulphate and concentrated under reduced pressure. The residue was purified by chromatography (silica gel, dichloromethane/methanol gradient).

Yield: 80 mg of 2-[6-(4-chlorophenyl)-1-methyl-4H-[1,2,4]triazolo[4,3-a][1]benzazepin-4-yl]-N-ethylacetamide.

$^1$H NMR (400 MHz, RT, CDCl$_3$): δ=1.18 (t, 3H); 2.65 (s, 3H); 2.98 (dd, 1H); 3.22-3.43 (m, 3H); 3.72 (dt, 1H); 6.07 (d, 1H); 6.84 (bs, 1H); 7.15 (d, 2H); 7.29-7.35 (m, 3H); 7.39-7.47 (m, 2H); 7.55 (dt, 1H).

Example 13

Preparation of (−)-2-[(4R)-6-(4-chlorophenyl)-1-methyl-4H-[1,2,4]triazolo[4,3-a][1]benzazepin-4-yl]-N-ethylacetamide

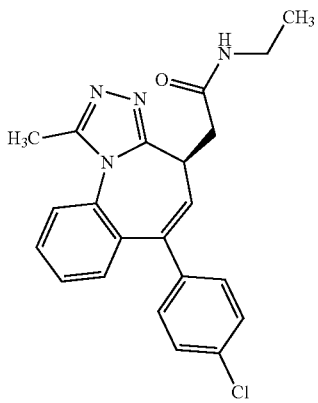 [SMILES: CCNC(=O)C[C@H]1C=C(c2ccc(Cl)cc2)c2ccccc2-n2c(C)nnc21]

80 mg of 2-[6-(4-chlorophenyl)-1-methyl-4H-[1,2,4]triazolo[4,3-a][1]benzazepin-4-yl]-N-ethylacetamide were separated into the enantiomers by chiral HPLC (Chiralpak IA 5 μm 250×20 mm, hexane/ethanol 75:25 (v/v)).

Yield: 31 mg of (−)-2-[(4R)-6-(4-chlorophenyl)-1-methyl-4H-[1,2,4]triazolo[4,3-a][1]benzazepin-4-yl]-N-ethylacetamide.

Optical rotation: $[α]_D^{20}$=−153.6°+/−0.13° (c=10.6, CHCl$_3$).

Example 14

Preparation of 2-[6-(4-chlorophenyl)-1-methyl-4H-[1,2,4]triazolo[4,3-a][1]-benzazepin-4-yl]-1-(morpholin-4-yl)ethanone

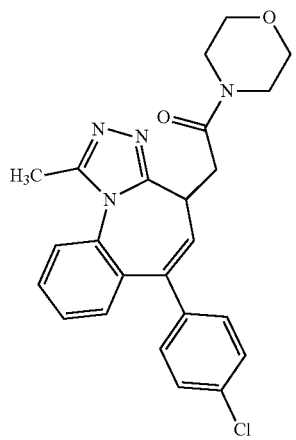 [SMILES: Cc1nnc2n1-c1ccccc1C(c1ccc(Cl)cc1)=CC2CC(=O)N1CCOCC1]

A solution of 110 mg of [6-(4-chlorophenyl)-1-methyl-4H-[1,2,4]triazolo[4,3-a][1]benzazepin-4-yl]acetic acid (Example 3A), 171 mg of HATU, 0.17 ml of triethylamine and 0.03 ml of morpholine in 3 ml of DMF was stirred at room temperature for 14 hours. The mixture was partitioned between semiconcentrated brine and ethyl acetate, the organic phase was removed and the aqueous phase was extracted twice with ethyl acetate. The combined organic phases were washed with brine, dried over sodium sulphate and concentrated under reduced pressure. The residue was purified by chromatography (silica gel, dichloromethane/methanol gradient).

Yield: 85 mg of 2-[6-(4-chlorophenyl)-1-methyl-4H-[1,2,4]triazolo[4,3-a][1]benzazepin-4-yl]-1-(morpholin-4-yl)ethanone.

$^1$H NMR (300 MHz, RT, CDCl$_3$): δ=2.59 (s, 3H); 3.11 (dd, 1H); 3.52 (dd, 1H); 3.58-3.84 (m, 9H); 6.02 (d, 1H); 7.13 (d, 2H); 2.25-7.31 (m, 3H (+CDCl$_3$)); 7.33-7.42 (m, 2H); 7.49 (dt, 1H).

Example 15

Preparation of (−)-2-[(4R)-6-(4-chlorophenyl)-1-methyl-4H-[1,2,4]triazolo[4,3-a][1]benzazepin-4-yl]-1-(morpholin-4-yl)ethanone

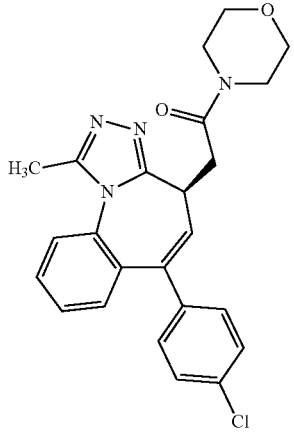 [SMILES: Cc1nnc2n1-c1ccccc1C(c1ccc(Cl)cc1)=C[C@@H]2CC(=O)N1CCOCC1]

85 mg of 2-[6-(4-chlorophenyl)-1-methyl-4H-[1,2,4]triazolo[4,3-a][1]benzazepin-4-yl]-1-(morpholin-4-yl)ethanone were separated into the enantiomers by chiral HPLC (Chiralpak ID 5 μm 250×20 mm, methanol/ethanol 1:1 (v/v)).

Yield: 35 mg of (−)-2-[(4R)-6-(4-chlorophenyl)-1-methyl-4H-[1,2,4]triazolo[4,3-a][1]benzazepin-4-yl]-1-(morpholin-4-yl)ethanone.

Optical rotation: $[α]_D^{20}$=−102.5°+/−0.13° (c=10.9, methanol).

Example 16

Preparation of 2-[6-(4-chlorophenyl)-1-methyl-4H-[1,2,4]triazolo[4,3-a][1]benzazepin-4-yl]-1-(3-fluoroazetidin-1-yl)ethanone

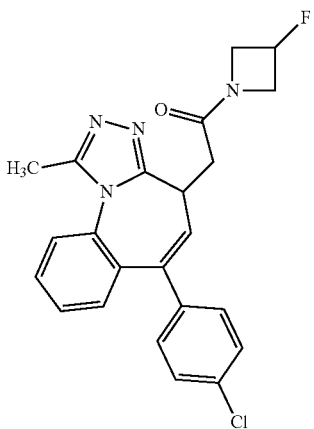 [SMILES: Cc1nnc2n1-c1ccccc1C(c1ccc(Cl)cc1)=CC2CC(=O)N1CC(F)C1]

A solution of 110 mg of [6-(4-chlorophenyl)-1-methyl-4H-[1,2,4]triazolo[4,3-a][1]benzazepin-4-yl]acetic acid (Example 3A), 171 mg of HATU, 0.17 ml of triethylamine and 37 mg of 3-fluoroazetidine hydrochloride (CAS 617718-46-4) in 3 ml of DMF was stirred at room temperature for 14 hours. The mixture was partitioned between semiconcentrated brine and ethyl acetate, the organic phase was removed and the aqueous phase was extracted twice with ethyl acetate. The combined organic phases were washed with brine, dried over sodium sulphate and concentrated under reduced pressure. The residue was purified by chromatography (silica gel, dichloromethane/methanol gradient).

Yield: 80 mg of 2-[6-(4-chlorophenyl)-1-methyl-4H-[1,2,4]triazolo[4,3-a][1]benzazepin-4-yl]-1-(3-fluoroazetidin-1-yl)ethanone.

$^1$H NMR (300 MHz, RT, CDCl$_3$, spectrum includes signals of diastereotopic protons): δ=2.59+2.59 (2s, 3H); 2.79+2.88 (2dd, 1H); 3.19-3.11 (m, 1H); 3.67-3.82 (m, 1H); 4.04-4.23 (m, 1H); 4.24-4.70 (2H); 4.89-5.05 (m, 1/2H); 5.35 (dm, 1H); 6.00+6.03 (2d, 1H); 7.12 (d, 2H); 7.22-7.32 (m+CDCl$_3$, 3H); 7.33-7.42 (m, 2H); 7.49 (dt, 1H).

Example 17

Preparation of (−)-2-[(4R)-6-(4-chlorophenyl)-1-methyl-4H-[1,2,4]triazolo[4,3-a][1]benzazepin-4-yl]-1-(3-fluoroazetidin-1-yl)ethanone

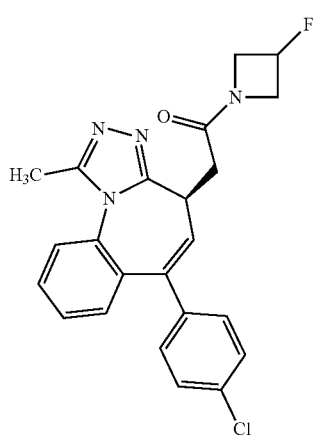 [SMILES: Cc1nnc2n1-c1ccccc1C(c1ccc(Cl)cc1)=C[C@@H]2CC(=O)N1CC(F)C1]

80 mg of 2-[6-(4-chlorophenyl)-1-methyl-4H-[1,2,4]triazolo[4,3-a][1]benzazepin-4-yl]-1-(3-fluoroazetidin-1-yl)ethanone were separated into the enantiomers by chiral HPLC (Chiralpak ID 5 μm 250×20 mm, methanol/ethanol 1:1 (v/v), 22 ml/min).

Yield: 25 mg of (−)-2-[(4R)-6-(4-chlorophenyl)-1-methyl-4H-[1,2,4]triazolo[4,3-a][1]benzazepin-4-yl]-1-(3-fluoroazetidin-1-yl)ethanone.

Optical rotation: $[α]_D^{20}$=−87.8°+/−0.21° (c=10.0, methanol).

Example 18

Preparation of 2-[6-(4-chlorophenyl)-1-methyl-4H-[1,2,4]triazolo[4,3-a][1]benzazepin-4-yl]-1-(1,1-dioxido-1-thia-6-azaspiro[3.3]hept-6-yl)ethanone

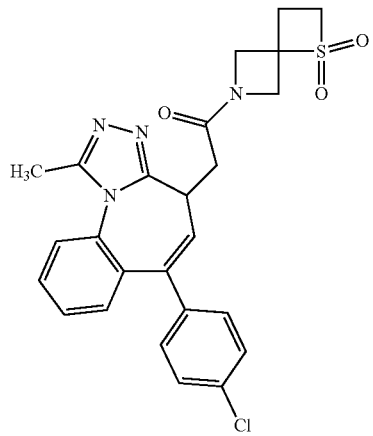 [SMILES: Cc1nnc2n1-c1ccccc1C(c1ccc(Cl)cc1)=CC2CC(=O)N1CC2(CCS2(=O)=O)C1]

A solution of 110 mg of [6-(4-chlorophenyl)-1-methyl-4H-[1,2,4]triazolo[4,3-a][1]benzazepin-4-yl]acetic acid (Example 3A), 171 mg of HATU, 0.17 ml of triethylamine and 48.7 mg of 1,1-dioxido-1-thia-6-azaspiro[3.3]heptane TFA salt (CAS 1352546-75-8 for the free base) in 3 ml of DMF was stirred at room temperature for 14 hours. The mixture was partitioned between semiconcentrated brine and ethyl acetate, the organic phase was removed and the aqueous phase was extracted twice with ethyl acetate. The combined organic phases were washed with brine, dried over sodium sulphate and concentrated under reduced pressure. The residue was purified by chromatography (silica gel, dichloromethane/methanol gradient).

Yield: 90 mg of 2-[6-(4-chlorophenyl)-1-methyl-4H-[1,2,4]triazolo[4,3-a][1]benzazepin-4-yl]-1-(1,1-dioxido-1-thia-6-azaspiro[3.3]hept-6-yl)ethanone.

$^1$H NMR (300 MHz, RT, DMSO-d6, characteristic signals): δ=2.83-2.99 (m, 1H); 3.04-3.18 (m, 1H); 3.46 (q, 1H); 4.08-4.19 (m, 3H); 4.24 (t, 1H); 4.60 (dd, 1H); 4.73 (t, 1H); 6.22 (d, 1H); 7.17-7.26 (m, 3H); 7.42 (d, 2H); 7.47 (t, 1H); 7.60 (dt, 1H); 7.75 (dd, 1H).

Example 19

Preparation of (−)-2-[(4R)-6-(4-chlorophenyl)-1-methyl-4H-[1,2,4]triazolo[4,3-a][1]benzazepin-4-yl]-1-(1,1-dioxido-1-thia-6-azaspiro[3.3]hept-6-yl)ethanone

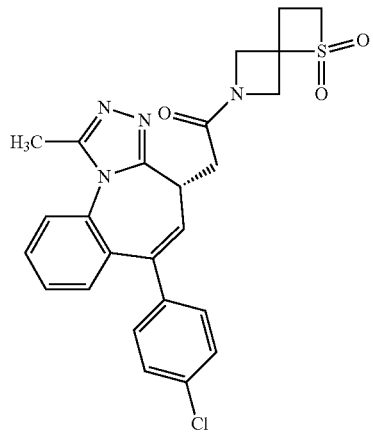 [SMILES: Cc1nnc2n1-c1ccccc1C(c1ccc(Cl)cc1)=C[C@H]2CC(=O)N1CC2(CCS2(=O)=O)C1]

90 mg of 2-[6-(4-chlorophenyl)-1-methyl-4H-[1,2,4]triazolo[4,3-a][1]benzazepin-4-yl]-1-(1,1-dioxido-1-thia-6-azaspiro[3.3]hept-6-yl)ethanone were separated into the enantiomers by chiral HPLC (Chiralpak IA 5 μm 250×20 mm, CO$_2$/2-propanol (v/v)+0.2% DEA 60:40, 80 ml/min, 150 bar, 40° C.).

Yield: 32 mg of (−)-2-[(4R)-6-(4-chlorophenyl)-1-methyl-4H-[1,2,4]triazolo[4,3-a][1]benzazepin-4-yl]-1-(1,1-dioxido-1-thia-6-azaspiro[3.3]hept-6-yl)ethanone.

Optical rotation: $[\alpha]_D^{20}$=−85.7°+/−0.13° (c=10.4, methanol).

Example 20

Preparation of 2-[6-(4-chlorophenyl)-1-methyl-4H-[1,2,4]triazolo[4,3-a][1]benzazepin-4-yl]-N-(2-oxo-2,3-dihydro-1H-indol-5-yl)acetamide

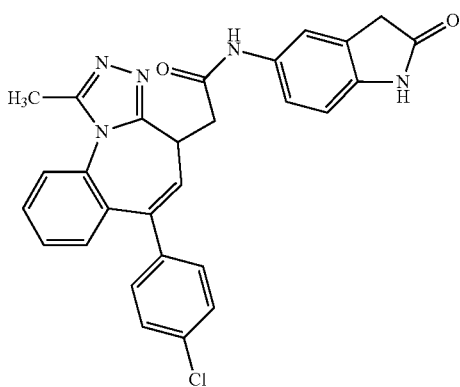 [SMILES: Cc1nnc2n1-c1ccccc1C(c1ccc(Cl)cc1)=CC2CC(=O)Nc1ccc2c(c1)CC(=O)N2]

A solution of 110 mg of [6-(4-chlorophenyl)-1-methyl-4H-[1,2,4]triazolo[4,3-a][1]benzazepin-4-yl]acetic acid (Example 3A), 171 mg of HATU, 0.17 ml of triethylamine and 49 mg of 5-aminoindol-2-one in 2 ml of DMF was stirred at room temperature for 14 hours. The mixture was partitioned between semiconcentrated brine and ethyl acetate, the organic phase was removed and the aqueous phase was extracted twice with ethyl acetate. The combined organic phases were washed with brine, dried over sodium sulphate and concentrated under reduced pressure. The residue was purified by chromatography (silica gel, dichloromethane/methanol gradient).

Yield: 95 mg of 2-[6-(4-chlorophenyl)-1-methyl-4H-[1,2,4]triazolo[4,3-a][1]benzazepin-4-yl]-N-(2-oxo-2,3-dihydro-1H-indol-5-yl)acetamide.

$^1$H NMR (300 MHz, CDCl$_3$): δ=2.62 (s, 3H); 3.16 (dd, 1H); 3.46 (s, 2H); 3.49 (dd, 1H); 3.67-3.77 (m, 1H); 6.08 (d, 1H); 6.74 (d, 1H); 7.12 (d, 2H); 7.23-7.39 (m, 4H+CDCD$_3$); 7.41 (d, 2H); 7.48-7.57 (m, 2H), 7.74 (bs, 1H); 9.63 (bs, 1H).

Example 21

Preparation of (−)-2-[(4R)-6-(4-chlorophenyl)-1-methyl-4H-[1,2,4]triazolo[4,3-a][1]benzazepin-4-yl]-N-(2-oxo-2,3-dihydro-1H-indol-5-yl)acetamide

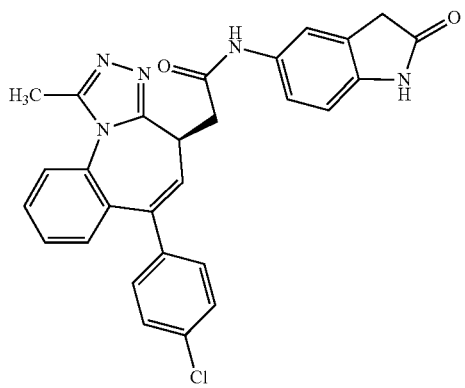 [SMILES: Cc1nnc2n1-c1ccccc1C(c1ccc(Cl)cc1)=C[C@@H]2CC(=O)Nc1ccc2c(c1)CC(=O)N2]

90 mg of 2-[6-(4-chlorophenyl)-1-methyl-4H-[1,2,4]triazolo[4,3-a][1]benzazepin-4-yl]-N-(2-oxo-2,3-dihydro-1H-indol-5-yl)acetamide were separated into the enantiomers by chiral HPLC (Chiralpak IA 5 μm 250×20 mm, CO$_2$/2-propanol (v/v)+0.2% DEA 60:40, 80 ml/min, 150 bar, 40° C.).

Yield: 30 mg of (−)-2-[(4R)-6-(4-chlorophenyl)-1-methyl-4H-[1,2,4]triazolo[4,3-a][1]benzazepin-4-yl]-N-(2-oxo-2,3-dihydro-1H-indol-5-yl)acetamide.

Optical rotation: $[\alpha]_D^{20}$=−128.3°+/−0.18° (c=10.0, methanol).

Example 22

Preparation of 3-{[(6-(4-chlorophenyl)-1-methyl-4H-[1,2,4]triazolo[4,3-a][1]benzazepin-4-yl]acetyl}-8-azabicyclo[3.2.1]octan-3-one

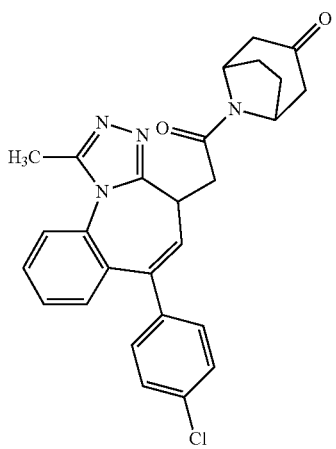 [SMILES: Cc1nnc2n1-c1ccccc1C(c1ccc(Cl)cc1)=C[C@H]2CC(=O)N1C2CCC1CC(=O)C2]

A solution of 110 mg of [6-(4-chlorophenyl)-1-methyl-4H-[1,2,4]triazolo[4,3-a][1]benzazepin-4-yl]acetic acid (Example 3A), 171 mg of HATU, 0.17 ml of triethylamine and 53 mg of nortropinone hydrochloride (CAS 25602-68-0) in 3 ml of DMF was stirred at room temperature for 14 hours. The mixture was partitioned between semiconcentrated brine and ethyl acetate, the organic phase was removed and the aqueous phase was extracted twice with ethyl acetate. The combined organic phases were washed with brine, dried over sodium sulphate and concentrated under reduced pressure. The residue was purified by chromatography (silica gel, dichloromethane/methanol gradient).

Yield: 95 mg of 3-{[(6-(4-chlorophenyl)-1-methyl-4H-[1,2,4]triazolo[4,3-a][1]benzazepin-4-yl]acetyl}-3-azabicyclo[3.2.1]octan-8-one.

$^1$H NMR (300 MHz, CDCl$_3$, includes signals of diastereotopic protons): δ=1.66-1.78 (m, 1H); 1.80-1.91 (m, 2H); 2.02-2.16 (m, 1H); 2.32-2.49 (m, 2H); 2.59-2.70 (m+s, 4H); 2.73-2.84 (m, 1H); 2.99+3.07 (2dd, 1H); 3.45+3.61 (2dd, 1H); 3.85 (q, 1H); 3.89-3.98 (m, 2H); 4.0-4.1 (m, 1H); 4.35-4.45 (m, 1H); 6.04+6.05 (2d, 1H); 7.13 (d, 2H); 7.25-7.33 (m, 3H+CDCl$_3$); 7.36-7.44 (m, 2H); 7.51 (dt, 1H).

Example 23

Preparation of (−)-3-{[(4R)-6-(4-chlorophenyl)-1-methyl-4H-[1,2,4]triazolo[4,3-a][1]benzazepin-4-yl]acetyl}-3-azabicyclo[3.2.1]octan-8-one

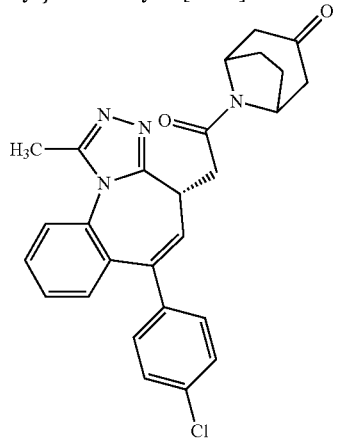

90 mg of 3-{[6-(4-chlorophenyl)-1-methyl-4H-[1,2,4]triazolo[4,3-a][1]benzazepin-4-yl]acetyl}-8-azabicyclo[3.2.1]octan-3-one were separated into the enantiomers by chiral HPLC (Chiralpak IA 5 µm 250×20 mm, ethanol/methanol (v/v) 50:50, 20 ml/min, RT° C.).

Yield: 38 mg of (−)-3-{[(4R)-6-(4-chlorophenyl)-1-methyl-4H-[1,2,4]triazolo[4,3-a][1]benzazepin-4-yl]acetyl}-3-azabicyclo[3.2.1]octan-8-one.

Optical rotation: $[\alpha]_D^{20}$=−98.7°+/−0.09° (c=10.0, methanol).

Example 24

Preparation of 2-[6-(4-chlorophenyl)-1-methyl-4H-[1,2,4]triazolo[4,3-a][1]benzazepin-4-yl]-1-(3-phenoxyazetidin-1-yl)ethanone

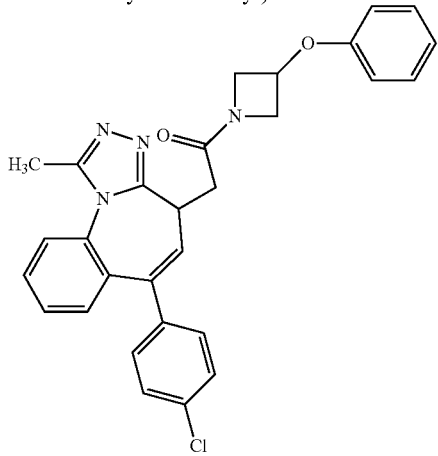

A solution of 110 mg of [6-(4-chlorophenyl)-1-methyl-4H-[1,2,4]triazolo[4,3-a][1]benzazepin-4-yl]acetic acid (Example 3A), 171 mg of HATU, 0.17 ml of triethylamine and 61.4 mg of 3-phenoxyazetidine hydrochloride in 3 ml of DMF was stirred at room temperature for 14 hours. The mixture was partitioned between semiconcentrated brine and ethyl acetate, the organic phase was removed and the aqueous phase was extracted twice with ethyl acetate. The combined organic phases were washed with brine, dried over sodium sulphate and concentrated under reduced pressure. The residue was purified by chromatography (silica gel, dichloromethane/methanol gradient).

Yield: 100 mg of 2-[6-(4-chlorophenyl)-1-methyl-4H-[1,2,4]triazolo[4,3-a][1]benzazepin-4-yl]-1-(3-phenoxyazetidin-1-yl)ethanone.

$^1$H NMR (300 MHz, DMSO-d6): δ=about 2.50 (s, 3H, signal obscured by DMSO); 2.90 (ddd, 1H); 3.14 (ddd, 1H); 3.48 (dq, 1H); 3.80 (dt, 1H); 4.23-4.33 (m, 2H); 4.77 (ddd, 1H); 5.04-5.13 (m, 1H); 6.21 (d, 1H); 6.88 (d, 2H); 7.0 (t, 1H); 7.17-7.24 (m, 3H); 7.33 (dd, 2H); 7.42 (dd, 2H); 7.47 (t, 1H); 7.60 (t, 1H); 7.75 (d, 1H).

Example 25

Preparation of (−)-2-[(4R)-6-(4-chlorophenyl)-1-methyl-4H-[1,2,4]triazolo[4,3-a][1]benzazepin-4-yl]-1-(3-phenoxyazetidin-1-yl)ethanone

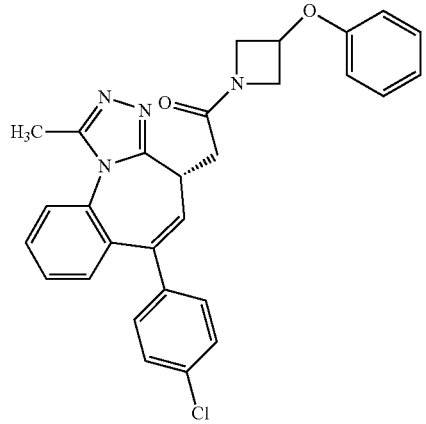 [SMILES: Cc1nnc2n1-c1ccccc1C(c1ccc(Cl)cc1)=C[C@H]2CC(=O)N1CC(Oc2ccccc2)C1]

95 mg of 2-[6-(4-chlorophenyl)-1-methyl-4H-[1,2,4]triazolo[4,3-a][1]benzazepin-4-yl]-1-(3-phenoxyazetidin-1-yl)ethanone were separated into the enantiomers by chiral HPLC (Chiralpak IB 5 µm 250×20 mm, CO$_2$/methanol (v/v) 70:30, 150 bar, 80 ml/min, 40° C.).

Yield: 39 mg of (−)-2-[(4R)-6-(4-chlorophenyl)-1-methyl-4H-[1,2,4]triazolo[4,3-a][1]benzazepin-4-yl]-1-(3-phenoxyazetidin-1-yl)ethanone.

Optical rotation: $[\alpha]_D^{20}$=−100.7°+/−0.14° (c=10.0, methanol).

Example 26

Preparation of 1-{[6-(4-chlorophenyl)-1-methyl-4H-[1,2,4]triazolo[4,3-a][1]benzazepin-4-yl]acetyl}pyrrolidin-3-one

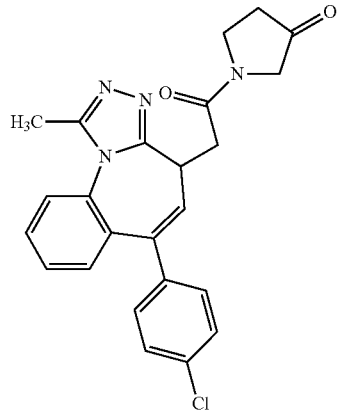 [SMILES: Cc1nnc2n1-c1ccccc1C(c1ccc(Cl)cc1)=CC2CC(=O)N1CCC(=O)C1]

A solution of 110 mg of [6-(4-chlorophenyl)-1-methyl-4H-[1,2,4]triazolo[4,3-a][1]benzazepin-4-yl]acetic acid (Example 3A), 171 mg of HATU, 0.17 ml of triethylamine and 40.2 mg of pyrrolidin-3-one hydrochloride in 3 ml of DMF was stirred at room temperature for 14 hours. The mixture was partitioned between semiconcentrated brine and ethyl acetate, the organic phase was removed and the aqueous phase was extracted twice with ethyl acetate. The combined organic phases were washed with brine, dried over sodium sulphate and concentrated under reduced pressure. The residue was purified by chromatography (silica gel, dichloromethane/methanol gradient).

Yield: 60 mg of 1-{[6-(4-chlorophenyl)-1-methyl-4H-[1,2,4]triazolo[4,3-a][1]benzazepin-4-yl]acetyl}pyrrolidin-3-one.

$^1$H NMR (300 MHz, CDCl$_3$, includes signals of diastereotopic protons): δ=2.61+2.62 (2s, 3H); 2.61-2.69 (m, 1H); 2.75-2.84 (m, 1H); 3.00+3.07 (2dd, 1H); 3.46+3.62 (2dd, 1H); 3.86 (q, 1H); 3.90-3.98 (m, 2H); 4.01-4.11 (m, 1H); 4.36-4.47 (m, 1H); 6.05+6.06 (2d, 1H); 7.14 (d, 2H); 7.26-7.33 (m, 3H); 7.37-7.45 (m, 2H); 7.52 (dt, 1H).

Example 27

Preparation of (−)-1-{[(4R)-6-(4-chlorophenyl)-1-methyl-4H-[1,2,4]triazolo[4,3-a][1]benzazepin-4-yl]acetyl}pyrrolidin-3-one

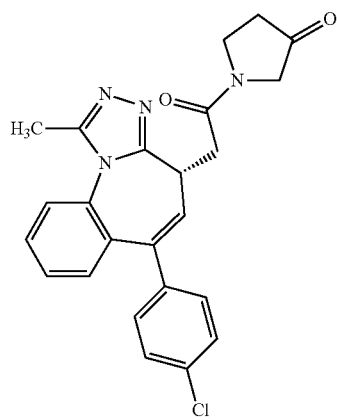 [SMILES: Cc1nnc2n1-c1ccccc1C(c1ccc(Cl)cc1)=C[C@H]2CC(=O)N1CCC(=O)C1]

60 mg of 1-{[6-(4-chlorophenyl)-1-methyl-4H-[1,2,4]triazolo[4,3-a][1]benzazepin-4-yl]acetyl}pyrrolidin-3-one were separated into the enantiomers by chiral HPLC (Chiralpak IB 5 μm 250×20 mm, CO$_2$/ethanol (v/v) 70:30, 150 bar, 60 ml/min, 40° C.).

Yield: 19 mg of (−)-1-{[(4R)-6-(4-chlorophenyl)-1-methyl-4H-[1,2,4]triazolo[4,3-a][1]benzazepin-4-yl]acetyl}pyrrolidin-3-one.

Optical rotation: $[α]_D^{20}$=−82.9°+/−0.29° (c=10.0, methanol).

Example 28

Preparation of 1-(8-azaspiro[4.5]dec-8-yl)-2-[6-(4-chlorophenyl)-1-methyl-4H-[1,2,4]triazolo[4,3-a][1]benzazepin-4-yl]ethanone

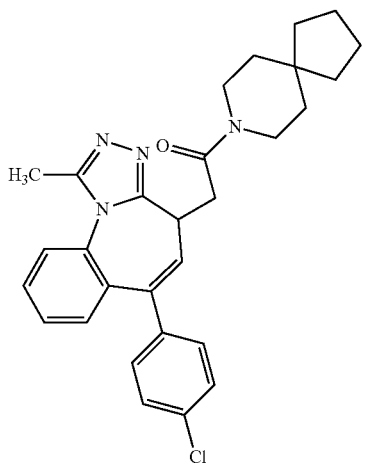 [SMILES: Cc1nnc2n1-c1ccccc1C(c1ccc(Cl)cc1)=CC2CC(=O)N1CCC2(CCCC2)CC1]

A solution of 110 mg of [6-(4-chlorophenyl)-1-methyl-4H-[1,2,4]triazolo[4,3-a][1]benzazepin-4-yl]acetic acid (Example 3A), 171 mg of HATU, 0.17 ml of triethylamine and 46.1 mg of 8-azaspiro[4.5]decane (CAS 176-64-7) in 3 ml of DMF was stirred at room temperature for 14 hours. The mixture was partitioned between semiconcentrated brine and ethyl acetate, the organic phase was removed and the aqueous phase was extracted twice with ethyl acetate. The combined organic phases were washed with brine, dried over sodium sulphate and concentrated under reduced pressure. The residue was purified by chromatography (silica gel, dichloromethane/methanol gradient).

Yield: 55 mg of 1-(8-azaspiro[4.5]dec-8-yl)-2-[6-(4-chlorophenyl)-1-methyl-4H-[1,2,4]triazolo[4,3-a][1]benzazepin-4-yl]ethanone.

$^1$H NMR (500 MHz, DMSO-d6): δ=1.33 (t, 2H); 1.42-1.47 (m, 4H); 1.49 (q, 2H); 1.58-1.62 (m, 4H); 3.08 (dd, 1H); 3.38-3.47 (m, 3H); 3.25-3.55 (m, 3H); 6.20 (d, 1H); 7.21 (dd, 1H); 7.22 (d, 2H); 7.41 (d, 2H); 7.47 (dt, 1H); 7.60 (dt, 1H); 7.75 (dd, 1H).

$^1$H NMR (300 MHz, CDCl$_3$): δ=1.43-1.56 (m, 6H); 1.61-1.72 (m, 6H); 2.61 (s, 3H); 3.20 (dd, 1H); 3.48 (dd, 1H); 3.56-3.65 (m, 4H); 3.76-3.83 (m, 1H); 6.04 (d, 1H); 7.15 (d, 2H); 7.25-7.33 (m, 3H+CHCl$_3$); 7.34-7.43 (m, 2H); 7.49 (dt, 1H).

Example 29

Preparation of (−)-1-(8-azaspiro[4.5]dec-8-yl)-2-[(4R)-6-(4-chlorophenyl)-1-methyl-4H-[1,2,4]triazolo[4,3-a][1]benzazepin-4-yl]ethanone

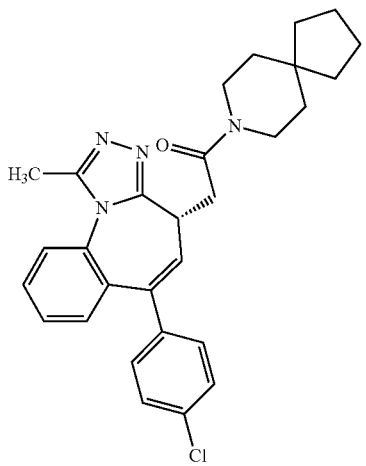 [SMILES: Cc1nnc2n1-c1ccccc1C(c1ccc(Cl)cc1)=C[C@H]2CC(=O)N1CCC2(CCCC2)CC1]

55 mg of 1-(8-azaspiro[4.5]dec-8-yl)-2-[6-(4-chlorophenyl)-1-methyl-4H-[1,2,4]triazolo[4,3-a][1]benzazepin-4-yl]ethanone were separated into the enantiomers by chiral HPLC (Chiralpak IA 5 μm 250×20 mm, $CO_2$/2-propanol (v/v) 60:40, 150 bar, 60 ml/min, 40° C.).

Yield: 32 mg of (−)-1-(8-azaspiro[4.5]dec-8-yl)-2-[(4R)-6-(4-chlorophenyl)-1-methyl-4H-[1,2,4]triazolo[4,3-a][1]benzazepin-4-yl]ethanone.

Optical rotation: $[\alpha]_D^{20}$=−97.3°+/−0.16° (c=10.0, methanol).

Example 30

Preparation of 2-[6-(4-chlorophenyl)-1-methyl-4H-[1,2,4]triazolo[4,3-a][1]benzazepin-4-yl]-1-(1,1-dioxido-1,3-thiazolidin-3-yl)ethanone

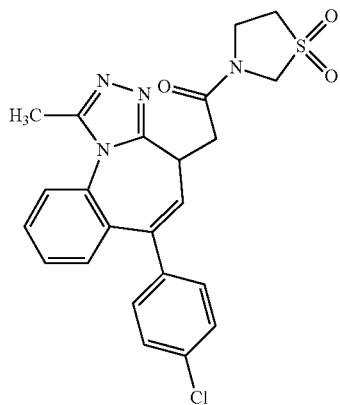

A solution of 110 mg of [6-(4-chlorophenyl)-1-methyl-4H-[1,2,4]triazolo[4,3-a][1]benzazepin-4-yl]acetic acid (Example 3A), 171 mg of HATU, 0.17 ml of triethylamine and 40.1 mg of 1,1-dioxido-1,3-thiazolidine in 3 ml of DMF was stirred at room temperature for 14 hours. The mixture was partitioned between semiconcentrated brine and ethyl acetate, the organic phase was removed and the aqueous phase was extracted twice with ethyl acetate. The combined organic phases were washed with brine, dried over sodium sulphate and concentrated under reduced pressure. The residue was purified by chromatography (silica gel, dichloromethane/methanol gradient).

Yield: 65 mg of 2-[6-(4-chlorophenyl)-1-methyl-4H-[1,2,4]triazolo[4,3-a][1]benzazepin-4-yl]-1-(1,1-dioxido-1,3-thiazolidin-3-yl)ethanone.

$^1$H NMR (300 MHz, DMSO-d6, includes signals of diastereotopic protons, selected signals): δ=about 2.50 (s, 3H, signal obscured by DMSO); 3.1-3.24 (m, 1H); 3.45 (t, 1H); 3.53 (dd, 1H); 3.60 (t, 1H); 3.75-3.95 (m, 1H); 4.16-4.25 (m, 1H); 4.43-4.55 (m, 1H); 4.89 (s, 1H); 6.18+6.22 (2d, 1H); 7.18-7.27 (m, 3H); 7.42 (d, 1H); 7.48 (dt, 1H); 7.61 (dt, 1H); 7.76 (dd, 1H).

Example 31

Preparation of (−)-2-[(4R)-6-(4-chlorophenyl)-1-methyl-4H-[1,2,4]triazolo[4,3-a][1]benzazepin-4-yl]-1-(1,1-dioxido-1,3-thiazolidin-3-yl)ethanone

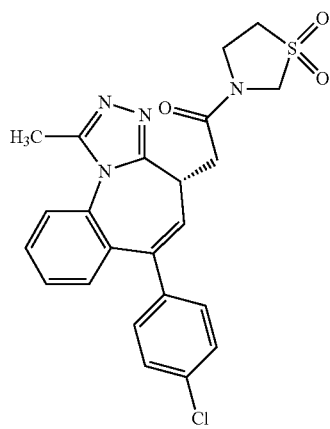 [SMILES: Cc1nnc2n1-c1ccccc1C(c1ccc(Cl)cc1)=C[C@H]2CC(=O)N1CCS(=O)(=O)C1]

65 mg of 2-[6-(4-chlorophenyl)-1-methyl-4H-[1,2,4]triazolo[4,3-a][1]benzazepin-4-yl]-1-(1,1-dioxido-1,3-thiazolidin-3-yl)ethanone were separated into the enantiomers by chiral HPLC (Chiralpak IA 5 μm 250×20 mm, $CO_2$/methanol (v/v) 60:40, 150 bar, 80 ml/min, 40° C.).

Yield: 23 mg of (−)-2-[(4R)-6-(4-chlorophenyl)-1-methyl-4H-[1,2,4]triazolo[4,3-a][1]benzazepin-4-yl]-1-(1,1-dioxido-1,3-thiazolidin-3-yl)ethanone.

Optical rotation: $[\alpha]_D^{20}$=−97.8°+/−0.20° (c=10.0, methanol).

Example 32

Preparation of 2-[6-(4-chlorophenyl)-1-methyl-4H-[1,2,4]triazolo[4,3-a][1]benzazepin-4-yl]-1-(8-oxa-3-azabicyclo[3.2.1]oct-3-yl)ethanone

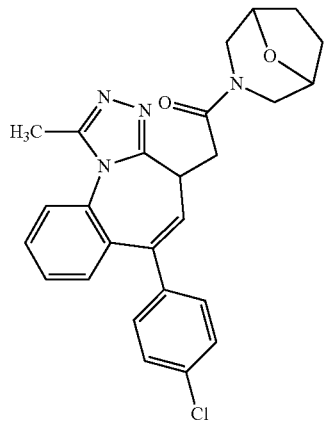 [SMILES: Cc1nnc2n1-c1ccccc1C(c1ccc(Cl)cc1)=CC2CC(=O)N1CC2CCC(C1)O2]

A solution of 110 mg of [6-(4-chlorophenyl)-1-methyl-4H-[1,2,4]triazolo[4,3-a][1]benzazepin-4-yl]acetic acid (Example 3A), 171 mg of HATU, 0.17 ml of triethylamine and 49.5 mg of 8-oxa-3-azabicyclo[3.2.1]octane hydrochloride (CAS 54745-74-3) in 3 ml of DMF was stirred at room temperature for 14 hours. The mixture was partitioned between semiconcentrated brine and ethyl acetate, the organic phase was removed and the aqueous phase was extracted twice with ethyl acetate. The combined organic phases were washed with brine, dried over sodium sulphate and concentrated under reduced pressure. The residue was purified by chromatography (silica gel, dichloromethane/methanol gradient).

Yield: 95 mg of 2-[6-(4-chlorophenyl)-1-methyl-4H-[1,2,4]triazolo[4,3-a][1]benzazepin-4-yl]-1-(8-oxa-3-azabicyclo[3.2.1]oct-3-yl)ethanone.

$^1$H NMR (300 MHz, DMSO-d6, selected signals): δ=1.46-1.60 (m, 1H); 1.73-2.03 2 m, 3H); about 2.50 (s, 3H, signal obscured by DMSO); 2.72-2.85 (m, 1H); 2.88-3.00 (m, 1/2H); 3.14-3.41 (m+water); 3.48 (t, 1/2H); 3.52-3.59 (m, 1H); 3.75 (dd, 1H); 3.95 (dd, 1H); 3.28-3.39 (m, 2H); 6.17-6.24 (m, 1H); 7.17-7.26 (m, 3H); 7.38-7.46 (m, 2H); 7.47 dt, 1H); 7.60 (dt, 1H); 7.75 (bd, 1H).

Example 33

Preparation of (−)-2-[(4R)-6-(4-chlorophenyl)-1-methyl-4H-[1,2,4]triazolo[4,3-a][1]benzazepin-4-yl]-1-(8-oxa-3-azabicyclo[3.2.1]oct-3-yl)ethanone

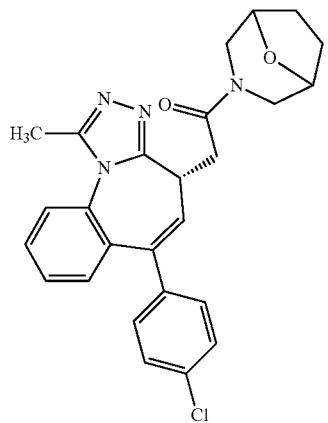

65 mg of 2-[6-(4-chlorophenyl)-1-methyl-4H-[1,2,4]triazolo[4,3-a][1]benzazepin-4-yl]-1-(8-oxa-3-azabicyclo[3.2.1]oct-3-yl)ethanone were separated into the enantiomers by chiral HPLC (Chiralpak ID 5 µm 250×20 mm, $CO_2$/ethanol (v/v) 60:40, 150 bar, 80 ml/min, 40° C.).

Yield: 33 mg of (−)-2-[(4R)-6-(4-chlorophenyl)-1-methyl-4H-[1,2,4]triazolo[4,3-a][1]benzazepin-4-yl]-1-(8-oxa-3-azabicyclo[3.2.1]oct-3-yl)ethanone.

Optical rotation: $[α]_D^{20}$=−93.9°+/−0.10° (c=10.0, methanol).

Example 34

Preparation of 6-(4-chlorophenyl)-1-methyl-4-[(3-methyl-1,2,4-oxadiazol-5-yl)methyl]-4H-[1,2,4]triazolo[4,3-a][1]benzazepine

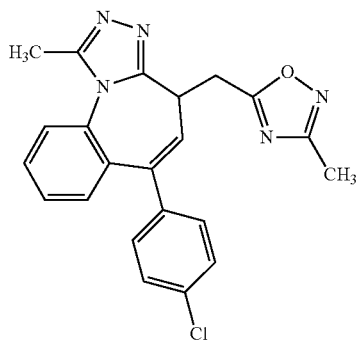 [SMILES: Cc1noc(CC2C=C(c3ccc(Cl)cc3)c3ccccc3-n3c(C)nnc32)n1]

108 mg of acetamide oxime (CAS 22059-22-9) in 0.46 ml of 1-methyl-2-pyrrolidone were stirred at room temperature until a homogeneous solution had formed. To this were added a solution of 130 mg of tert-butyl [6-(4-chlorophenyl)-1-methyl-4H-[1,2,4]triazolo[4,3-a][1]benzazepin-4-yl]acetate (Example 8) in 0.46 ml of 1-methyl-2-pyrrolidone and, gradually, 63 mg of sodium methoxide. The mixture was stirred at 70° C. for 3 hours. The mixture was added to water and extracted three times with ethyl acetate. The combined organic phases were washed with brine, dried over sodium sulphate and concentrated fully under reduced pressure. The residue was purified by chromatography on silica gel (dichloromethane/methanol gradient).

Yield: 36 mg of 6-(4-chlorophenyl)-1-methyl-4-[(3-methyl-1,2,4-oxadiazol-5-yl)methyl]-4H-[1,2,4]triazolo[4,3-a][1]benzazepine.

$^1$H NMR (400 MHz, DMSO-d6): δ=2.29 (s, 3H); about 2.50 (s, 3H, signal obscured by DMSO); 3.69-3.77 (m, 2H); 3.86 (dd, 1H); 6.35 (d, 1H); 7.20-7.28 (m, 3H); 7.43 (d, 2H); 7.49 (dt, 1H); 7.62 (dt, 1H); 7.79 (d, 1H).

Example 35

Preparation of (–)-6-[(4R)-4-chlorophenyl]-1-methyl-4-[(3-methyl-1,2,4-oxadiazol-5-yl)methyl]-4H-[1,2,4]triazolo[4,3-a][1]benzazepine

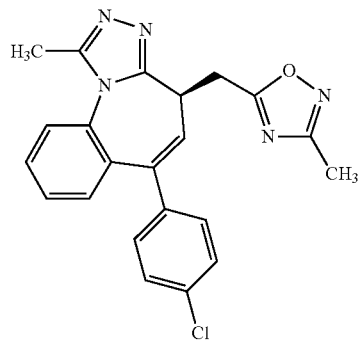 [SMILES: Cc1noc(C[C@H]2C=C(c3ccc(Cl)cc3)c3ccccc3-n3c(C)nnc32)n1]

27 mg of 6-(4-chlorophenyl)-1-methyl-4-[(3-methyl-1,2,4-oxadiazol-5-yl)methyl]-4H-[1,2,4]triazolo[4,3-a][1]benzazepine were separated into the enantiomers by chiral HPLC (Chiralpak IA 5 μm 250×20 mm, $CO_2$/2-propanol (v/v) 75:25, 150 bar, 80 ml/min, 40° C.).

Yield: 4 mg of (–)-6-[(4R)-4-chlorophenyl]-1-methyl-4-[(3-methyl-1,2,4-oxadiazol-5-yl)methyl]-4H-[1,2,4]triazolo[4,3-a][1]benzazepine.

Optical rotation: $[α]_D^{20}$=–141.7° (c=10.0, methanol).

Example 36

Preparation of (–)-(4R)-6-(4-chlorophenyl)-1-methyl-4-{[3-(propan-2-yl)-1,2,4-oxadiazol-5-yl]methyl}-4H-[1,2,4]triazolo[4,3-a][1]benzazepine

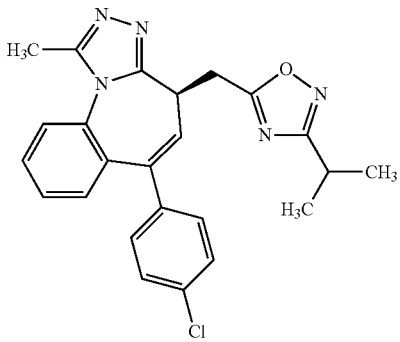 [SMILES: Cc1nnc2n1-c1ccccc1C(c1ccc(Cl)cc1)=C[C@@H]2Cc1nc(C(C)C)no1]

344 mg of 2-methylpropylimidoxim (CAS 35613-84-4) in 0.53 ml of 1-methyl-2-pyrrolidone were stirred at room temperature until a homogeneous solution formed. To this were added a solution of 150 mg of tert-butyl [6-(4-chlorophenyl)-1-methyl-4H-[1,2,4]triazolo[4,3-a][1]benzazepin-4-yl]acetate (Example 8) in 0.53 ml of 1-methyl-2-pyrrolidone and, gradually, 73 mg of sodium methoxide. The mixture was stirred at 70° C. for 3 hours. A further 73 mg of sodium methoxide were added and the mixture was stirred at 90° C. for 10 hours. The mixture was added to water and extracted three times with ethyl acetate. The combined organic phases were washed with brine, dried over sodium sulphate and concentrated fully under reduced pressure. The residue was purified by chromatography on silica gel (dichloromethane/methanol gradient). 74 mg of the racemate were obtained, which were separated into the enantiomers by chiral HPLC (Chiralpak IA 5 μm 250×20 mm, $CO_2$/2-propanol+0.4% diethylamine (v/v) 78:22, 150 bar, 80 ml/min, 40° C.).

Yield: 6 mg of (–)-(4R)-6-(4-chlorophenyl)-1-methyl-4-{[3-(propan-2-yl)-1,2,4-oxadiazol-5-yl]methyl}-4H-[1,2,4]triazolo[4,3-a][1]benzazepine.

$^1$H NMR (300 MHz, DMSO-d6, some sets of diastereotopic signals): δ=1.22 and 1.24 (2d, 6H); about 2.50 (s, 3H, signal obscured by DMSO); 3.02 (sept, 1H); 3.70-3.89 (m, 3H); 6.33 (d, 1H); 7.19-7.27 (m, 3H); 7.43 (d, 2H); 7.49 (dt, 1H); 7.62 (dt, 1H); 7.78 (d, 1H).

Optical rotation: $[α]_D^{20}$=–48.0° (c=10.0, methanol).

Example 37

Preparation of (–)-(4R)-6-(4-Chlorophenyl)-4-[(3-cyclopropyl-1,2,4-oxadiazol-5-yl)methyl]-1-methyl-4H-[1,2,4]triazolo[4,3-a][1]benzazepine

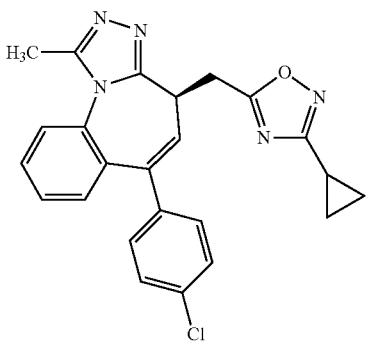 [SMILES: Cc1nnc2n1-c1ccccc1C(c1ccc(Cl)cc1)=C[C@@H]2Cc1nc(C2CC2)no1]

338 mg of N'-hydroxycyclopropanecarboximidamide (CAS 51285-13-3) in 0.53 ml of 1-methyl-2-pyrrolidone were stirred at room temperature until a homogeneous solution formed. To this were added a solution of 150 mg of tert-butyl [6-(4-chlorophenyl)-1-methyl-4H-[1,2,4]triazolo[4,3-a][1]benzazepin-4-yl]acetate (Example 8) in 0.53 ml of 1-methyl-2-pyrrolidone and, gradually, 73 mg of sodium methoxide. The mixture was stirred at 70° C. for 3 hours. A further 73 mg of sodium methoxide were added and the mixture was stirred at 90° C. for 3 hours. The mixture was added to water and extracted 3 times with ethyl acetate. The combined organic phases were washed with brine, dried over sodium sulphate and concentrated fully under reduced pressure. The residue was purified by chromatography on silica gel (dichloromethane/methanol gradient). 66 mg of the racemate were obtained, which were separated into the enantiomers by chiral HPLC (Chiralpak IA 5 μm 250×20 mm, $CO_2$/2-propanol+0.2% diethylamine (v/v) 75:25, 150 bar, 80 ml/min, 40° C.).

Yield: 11 mg of (–)-(4R)-6-(4-chlorophenyl)-4-[(3-cyclopropyl-1,2,4-oxadiazol-5-yl)methyl]-1-methyl-4H-[1,2,4]triazolo[4,3-a][1]benzazepine.

$^1$H NMR (300 MHz, DMSO-d6): δ=0.80-0.87 (m, 2H); 0.99-1.07 (m, 2H); 2.02-2.12 (m, 1H); about 2.50 (s, 3H, signal obscured by DMSO); 3.65-3.87 (m, 3H); 6.32 (d, 1H); 7.19-7.26 (m, 3H); 7.43 (d, 2H); 7.48 (dt, 1H); 7.62 (dt, 1H); 7.78 (d, 1H).

Optical rotation: $[α]_D^{20}$=–75.9° (c=10.0, methanol).

Example 38

Preparation of (−)-(4R)-6-(4-chlorophenyl)-1-methyl-4-[(5-methyl-1,3,4-oxadiazol-2-yl)methyl]-4H-[1,2,4]triazolo[4,3-a][1]benzazepine

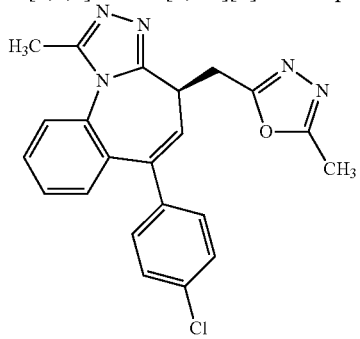

A solution of 150 mg of [6-(4-chlorophenyl)-1-methyl-4H-[1,2,4]triazolo[4,3-a][1]benzazepin-4-yl]acetic acid (Example 3A), 57 mg of acetylhydrazine, 0.27 ml of triethylamine and 1.24 g of 1-propylphosphonic anhydride (T3P, CAS 68957-94-8) in 1.2 ml of ethyl acetate was stirred at 90° C. for 4 hours. The mixture was added to brine and extracted three times with ethyl acetate. The combined organic phases were dried over sodium sulphate and concentrated fully under reduced pressure. The residue was dissolved in 1 ml of acetonitrile, and 0.06 ml of phosphorus oxychloride was added while cooling in an ice bath. The mixture was heated to 80° C. and stirred for 3 hours. The mixture was added to brine and extracted three times with ethyl acetate. The combined organic phases were dried over sodium sulphate and the solvent was removed under reduced pressure. The residue was purified by chromatography on silica gel (dichloromethane/methanol gradient). 32 mg of the racemate were obtained, which were separated into the enantiomers by chiral HPLC (Chiralpak IA 5 µm 250×20 mm, CO$_2$/2-propanol+0.2% diethylamine (v/v) 75:25, 150 bar, 80 ml/min, 40° C.).

Yield: 10 mg of (−)-(4R)-6-(4-chlorophenyl)-1-methyl-4-[(5-methyl-1,3,4-oxadiazol-2-yl)methyl]-4H-[1,2,4]triazolo[4,3-a][1]benzazepine.

$^1$H NMR (300 MHz, DMSO-d6): δ=2.47 (s, 3H); about 2.50 (s, 3H, signal obscured by DMSO); 3.65-3.80 (m, 3H); 6.32 (d, 1H); 7.19-7.27 (m, 3H); 7.42 (d, 2H); 7.49 (dt, 1H); 7.62 (dt, 1H); 7.77 (d, 1H).

Optical rotation: [α]$_D^{20}$=−95.7° (c=10.0, methanol).

The absolute stereochemistry of the carbon atom C4 was confirmed by X-ray structural analysis as the (R) configuration.

Example 39

Preparation of 6-(4-chlorophenyl)-1-methyl-4-[(5-methyl-1,3,4-oxadiazol-2-yl)methyl]-4H-[1,2,4]triazolo[4,3-a][1]benzazepine

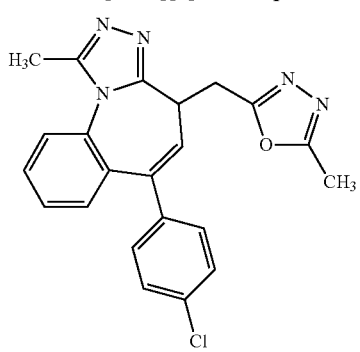

At −70° C., 36 ml of lithium hexamethyldisilazide solution (1M in toluene) were added slowly to a solution of 10.1 g of 6-(4-chlorophenyl)-1-methyl-4H-[1,2,4]triazolo[4,3-a][1]benzazepine (Example 1C) in 1 l of THF. The mixture was stirred for 90 min at −70° C., and a solution of 4.35 g of 2-(chloromethyl)-5-methyl-1,3,4-oxadiazole (CAS 3914-42-9) in 15 ml of THF was then added dropwise. With warming to RT, the mixture was stirred for 16 hours. The reaction was added to saturated ammonium chloride solution and extracted three times with dichloromethane. The combined organic phases were washed with 50% brine and dried over sodium sulphate, and the solvent was removed under reduced pressure. The residue was purified by chromatography on silica gel (dichloromethane/methanol gradient).

Yield: 9.2 g of 6-(4-chlorophenyl)-1-methyl-4-[(5-methyl-1,3,4-oxadiazol-2-yl)methyl]-4H-[1,2,4]triazolo[4,3-a][1]benzazepine.

$^1$H NMR (300 MHz, DMSO-d6): δ=2.47 (s, 3H); about 2.50 (s, 3H, signal obscured by DMSO); 3.65-3.80 (m, 3H); 6.32 (d, 1H); 7.19-7.27 (m, 3H); 7.42 (d, 2H); 7.49 (dt, 1H); 7.62 (dt, 1H); 7.77 (d, 1H).

Example 40

Preparation of N'-acetyl-2-[(4R)-6-(4-chlorophenyl)-1-methyl-4H-[1,2,4]triazolo[4,3-a][1]benzazepin-4-yl]acetohydrazide

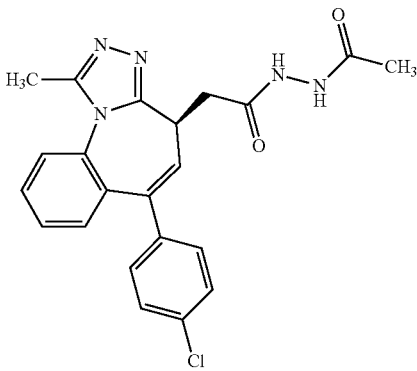 [SMILES: CC(=O)NNC(=O)C[C@H]1C=C(c2ccc(Cl)cc2)c2ccccc2-n2c(C)nnc21]

A solution of 1 g of [6-(4-chlorophenyl)-1-methyl-4H-[1,2,4]triazolo[4,3-a][1]benzazepin-4-yl]acetic acid (Example 3A), 148 mg of HATU, 1.5 ml of triethylamine and 212 mg of acetylhydrazine in 14 ml of DMF was stirred at room temperature for 14 hours. The reaction was added to sat. sodium bicarbonate solution and extracted 3 times with dichloromethane. The combined organic phases were washed with brine, dried over sodium sulphate and concentrated under reduced pressure. The residue was purified by chromatography (silica gel, dichloromethane/methanol gradient). The resulting racemate (210 mg) of the title compound was separated into the enantiomers by chiral HPLC (Chiralpak IA 5 µm 250×20 mm, CO$_2$/ethanol+0.4% diethylamine (v/v) 60:40, 150 bar, 80 ml/min, 40° C.).

Yield: 20 mg of N'-acetyl-2-[(4R)_6-(4-chlorophenyl)-1-methyl-4H-[1,2,4]triazolo[4,3-a][1]benzazepin-4-yl]acetohydrazide.

$^1$H NMR (300 MHz, DMSO-d6): δ=1.86 (s, 3H); about 2.50 (s, 3H, signal obscured by DMSO); 3.02 (d, 2H); 3.45 (q, 1H); 6.22 (d, 1H); 7.19 (dd, 1H); 7.28 (d, 2H); 7.40 (d, 2H); 7.46 (dt, 1H); 7.59 (dt, 1H); 7.73 (dd, 1H); 9.79 (bs, 1H); 10.03 (bs, 1H).

Example 41

Preparation of 6-(4-chlorophenyl)-1-methyl-4-[(5-methyl-1,3,4-thiadiazol-2-yl)methyl]-4H-[1,2,4]triazolo[4,3-a][1]benzazepine

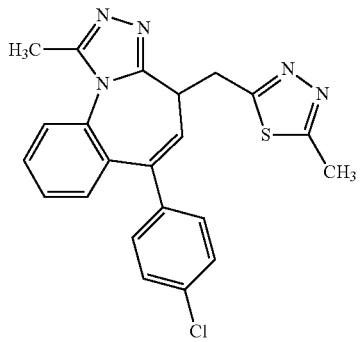 [SMILES: Cc1nnc(CC2C=C(c3ccc(Cl)cc3)c3ccccc3-n3c(C)nnc32)s1]

A solution of 50 mg of N'-acetyl-2-[6-(4-chlorophenyl)-1-methyl-4H-[1,2,4]triazolo[4,3-a][1]benzazepin-4-yl]acetohydrazide (Example 40, racemate) and 45 mg of Lawesson's reagent in 2 ml of THF was stirred at 65° C. for 2 hours. The mixture was added to aqueous sodium hydroxide solution (1N) and extracted three times with dichloromethane. The combined organic phases were washed with brine and dried over sodium sulphate, and the solvent was removed completely under reduced pressure. The residue was purified by chromatography on silica gel (dichloromethane/methanol gradient).

Yield: 40 mg of 6-(4-chlorophenyl)-1-methyl-4-[(5-methyl-1,3,4-thiadiazol-2-yl)methyl]-4H-[1,2,4]triazolo[4,3-a][1]benzazepine.

$^1$H NMR (300 MHz, DMSO-d6): δ=about 2.50 (s, 3H, signal obscured by DMSO); 2.67 (s, 3H); 3.65 (dd, 1H); 3.85 (dd, 1H); 3.99 (dd, 1H); 6.29 (d, 1H); 7.17-7.25 (m, 3H); 7.42 (d, 2H); 7.47 (dt, 1H); 7.61 (dt, 1H); 7.76 (dd, 1H).

Example 42

Preparation of (+)-(4R)-6-(4-chlorophenyl)-1-methyl-4-[(5-methyl-1,3,4-thiadiazol-2-yl)methyl]-4H-[1,2,4]triazolo[4,3-a][1]benzazepine

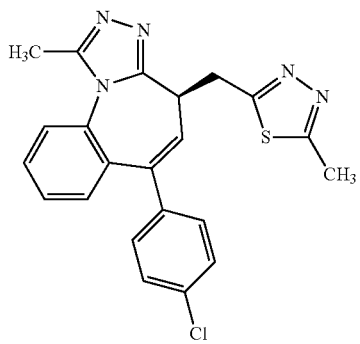

80 mg of 6-(4-chlorophenyl)-1-methyl-4-[(5-methyl-1,3,4-thiadiazol-2-yl)methyl]-4H-[1,2,4]triazolo[4,3-a][1]benzazepine were separated into the enantiomers by chiral HPLC (Chiralpak IC 5 μm 250×20 mm, acetonitrile/ethanol 90:10, 31 ml/min, RT).

Yield: 30 mg of (+)-(4R)-6-(4-chlorophenyl)-1-methyl-4-[(5-methyl-1,3,4-thiadiazol-2-yl)methyl]-4H-[1,2,4]triazolo[4,3-a][1]benzazepine.

$^1$H NMR (300 MHz, DMSO-d6): δ=about 2.50 (s, 3H, signal obscured by DMSO); 2.67 (s, 3H); 3.65 (dd, 1H); 3.85 (dd, 1H); 3.99 (dd, 1H); 6.29 (d, 1H); 7.17-7.25 (m, 3H); 7.42 (d, 2H); 7.47 (dt, 1H); 7.61 (dt, 1H); 7.76 (dd, 1H).

Optical rotation: $[α]_D^{20}$=+105.3° (c=10.0, methanol).

Example 43

Preparation of 6-(4-chlorophenyl)-4-[(5-cyclopropyl-1,3,4-oxadiazol-2-yl)methyl]-1-methyl-4H-[1,2,4]triazolo[4,3-a][1]benzazepine

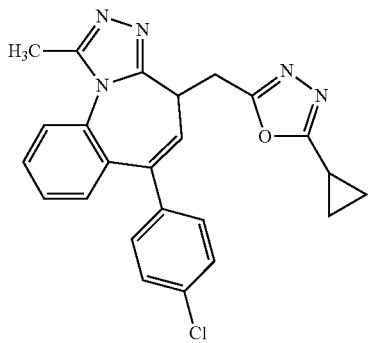 [SMILES: Cc1nnc2n1-c1ccccc1C(c1ccc(Cl)cc1)=CC2Cc1nnc(C2CC2)o1]

Example 43A

Preparation of N'-{2-[6-(4-chlorophenyl)-1-methyl-4H-[1,2,4]triazolo[4,3-a][1]benzazepin-4-yl]acetyl}cyclopropanecarbohydrazide

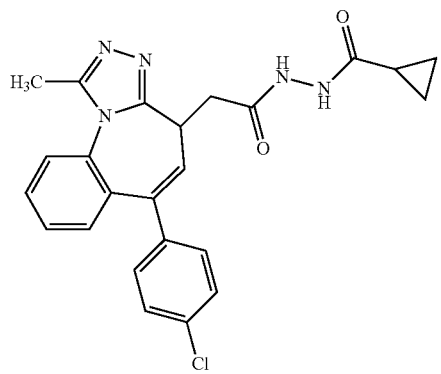 [SMILES: Cc1nnc2n1-c1ccccc1C(c1ccc(Cl)cc1)=CC2CC(=O)NNC(=O)C1CC1]

A solution of 50 mg of [6-(4-chlorophenyl)-1-methyl-4H-[1,2,4]triazolo[4,3-a][1]benzazepin-4-yl]acetic acid (Example 3A), 23 mg of 1-(3-dimethylaminopropyl)-3-ethylcarbodiimide hydrochloride, 18 mg of 1-hydroxy-1H-benzotriazole hydrate and 12 mg of cyclopropanecarboxylic acid hydrazide (CAS 6952-93-8) in 0.6 ml of THF was stirred at room temperature for 14 hours. The reaction was added to sat. sodium bicarbonate solution and extracted 3 times with dichloromethane. The combined organic phases were washed with brine, dried over sodium sulphate and concentrated under reduced pressure. The residue was purified by chromatography (silica gel, dichloromethane/methanol gradient). This gave 29 mg of N'-{2-[6-(4-chlorophenyl)-1-methyl-4H-[1,2,4]triazolo[4,3-a][1]benzazepin-4-yl]acetyl}cyclopropanecarbohydrazide.

$^1$H NMR (300 MHz, DMSO-d6): δ=0.67-0.79 (m, 4H); 1.56-1.68 (m, 1H); about 2.50 (s, 3H, signal obscured by DMSO); 2.97-3.06 (m, 2H); 3.40-3.52 (m, 1H); 6.22 (d, 1H); 7.19 (d, 1H); 7.26 (d, 2H); 7.40 (d, 2H); 7.46 (t, 1H); 7.60 (t, 1H); 7.73 (d, 1H); 10.02 (s, 1H); 10.04 (s, 1H).

Example 43B

Preparation of 6-(4-chlorophenyl)-4-[(5-cyclopropyl-1,3,4-oxadiazol-2-yl)methyl]-1-methyl-4H-[1,2,4]triazolo[4,3-a][1]benzazepine

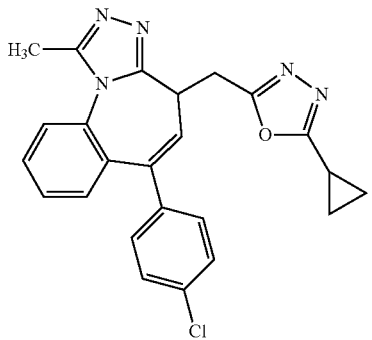 [SMILES: Cc1nnc2n1-c1ccccc1C(c1ccc(Cl)cc1)=CC2Cc1nnc(C2CC2)o1]

With ice-bath cooling, 0.028 ml of phosphorus oxychloride was added to a solution of 24 mg of N'-{2-[6-(4-chlorophenyl)-1-methyl-4H-[1,2,4]triazolo[4,3-a][1]benzazepin-4-yl]acetyl}cyclopropanecarbohydrazide (Example 43A) in 0.25 ml of acetonitrile. The mixture was heated to 95° C. and stirred for 3 hours. The mixture was added to brine and extracted three times with ethyl acetate. The combined organic phases were dried over sodium sulphate and the solvent was removed under reduced pressure. The residue was purified by chromatography on silica gel (dichloromethane/methanol gradient).

Yield: 13 mg of 6-(4-chlorophenyl)-4-[(5-cyclopropyl-1,3,4-oxadiazol-2-yl)methyl]-1-methyl-4H-[1,2,4]triazolo[4,3-a][1]benzazepine.

$^1$H NMR (300 MHz, DMSO-d6): δ=0.94-1.00 (m, 2H); 1.07-1.16 (m, 2H); 2.16-2.25 (m, 1H); about 2.50 (s, 3H, signal obscured by DMSO); 3.56-3.76 (m, 3H); 6.32 (d, 2H); 7.19-7.27 (m, 3H); 7.43 (d, 2H); 7.48 (dt, 1H); 7.62 (dt, 1H); 7.77 (dd, 1H).

Example 44

Preparation of 6-(4-chlorophenyl)-1-methyl-4-{[5-(pyridin-3-yl)-1,3,4-oxadiazol-2-yl]methyl}-4H-[1,2,4]triazolo[4,3-a][1]benzazepine

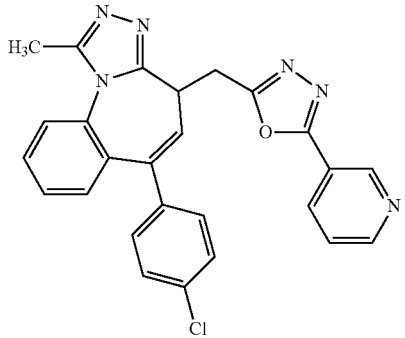 [SMILES: Cc1nnc2n1-c1ccccc1C(c1ccc(Cl)cc1)=CC2Cc1nnc(-c2cccnc2)o1]

Analogously to the preparation of Example 39, 280 mg of 6-(4-chlorophenyl)-1-methyl-4H-[1,2,4]triazolo[4,3-a][1]benzazepine (Example 1C) and 169 mg of 3-[5-(chloromethyl)-1,3,4-oxadiazol-2-yl]pyridine (CAS 677347-79-4) gave 145 mg of 6-(4-chlorophenyl)-1-methyl-4-{[5-(pyridin-3-yl)-1,3,4-oxadiazol-2-yl]methyl}-4H-[1,2,4]triazolo[4,3-a][1]benzazepine.

Yield: 145 mg of 6-(4-chlorophenyl)-1-methyl-4-{[5-(pyridin-3-yl)-1,3,4-oxadiazol-2-yl]methyl}-4H-[1,2,4]triazolo[4,3-a][1]benzazepine.

$^1$H NMR (300 MHz, DMSO-d6): δ=2.52 (s, 3H); 3.75-3.98 (m, 3H); 6.41 (d, 1H); 7.20-7.30 (m, 3H); 7.43 (d, 2H); 7.49 (dt, 1H); 7.57-7.69 (m, 2H); 7.79 (dd, 1H); 8.36 (dt, 1H); 8.80 (dd, 1H); 9.16 (dd, 1H).

Example 45

Preparation of (−)-(4R)-6-(4-chlorophenyl)-1-methyl-4-{[5-(pyridin-3-yl)-1,3,4-oxadiazol-2-yl]methyl}-4H-[1,2,4]triazolo[4,3-a][1]benzazepine

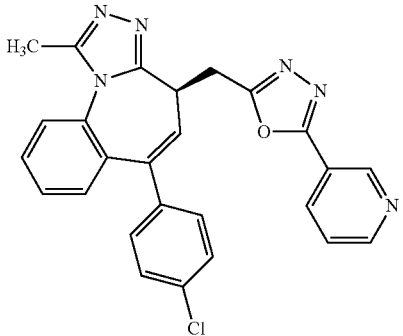 [SMILES: Cc1nnc2n1-c1ccccc1C(c1ccc(Cl)cc1)=C[C@@H]2Cc1nnc(-c2cccnc2)o1]

145 mg of 6-(4-chlorophenyl)-1-methyl-4-{[5-(pyridin-3-yl)-1,3,4-oxadiazol-2-yl]methyl}-4H-[1,2,4]triazolo[4,3-a][1]benzazepine were separated into the enantiomers by chiral HPLC (Chiralpak IC 5 µm 250×20 mm, acetonitrile/ethanol 90:10, 50 ml/min, RT).

Yield: 46 mg of (−)-(4R)-6-(4-chlorophenyl)-1-methyl-4-{[5-(pyridin-3-yl)-1,3,4-oxadiazol-2-yl]methyl}-4H-[1,2,4]triazolo[4,3-a][1]benzazepine.

$^1$H NMR (300 MHz, DMSO-d6): δ=2.52 (s, 3H); 3.75-3.98 (m, 3H); 6.41 (d, 1H); 7.20-7.30 (m, 3H); 7.43 (d, 2H); 7.49 (dt, 1H); 7.57-7.69 (m, 2H); 7.79 (dd, 1H); 8.36 (dt, 1H); 8.80 (dd, 1H); 9.16 (dd, 1H).

Optical rotation: $[α]_D^{20}$=−152.1° (c=8.0, methanol).

Example 46

Preparation of 6-(4-chlorophenyl)-1-methyl-4-[(5-methyl-1,2,4-oxadiazol-3-yl)methyl]-4H-[1,2,4]triazolo[4,3-a][1]benzazepine

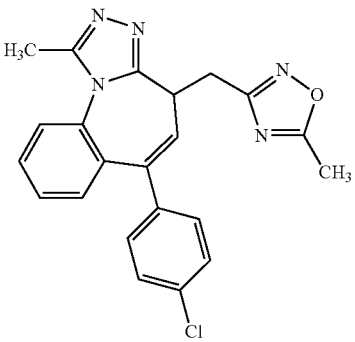 [SMILES: Cc1nc(CC2C=C(c3ccc(Cl)cc3)c3ccccc3-n3c(C)nnc32)no1]

Analogously to the preparation of Example 39, 150 mg of 6-(4-chlorophenyl)-1-methyl-4H-[1,2,4]triazolo[4,3-a][1]benzazepine (Example 1C) and 61 mg of 3-(chloromethyl)-5-methyl-1,2,4-oxadiazole (CAS 1192-80-9) gave 12 mg of 6-(4-chlorophenyl)-1-methyl-4-[(5-methyl-1,2,4-oxadiazol-3-yl)methyl]-4H-[1,2,4]triazolo[4,3-a][1]benzazepine.

Yield: 12 mg of 6-(4-chlorophenyl)-1-methyl-4-[(5-methyl-1,2,4-oxadiazol-3-yl)methyl]-4H-[1,2,4]triazolo[4,3-a][1]benzazepine.

$^1$H NMR (300 MHz, DMSO-d6): δ=about 2.50 (s, 3H, signal obscured by DMSO); 2.55 (s, 3H); 3.51 (dd, 1H); 3.57-3.69 (m, 2H); 6.27 (d, 1H); 7.18-7.25 (m, 3H); 7.42 (d, 2H); 7.47 (dt, 1H); 7.61 (dt, 1H); 7.77 (dd, 1H).

Example 47

Preparation of 6-(4-chlorophenyl)-8-methoxy-1-methyl-4-[(5-methyl-1,3,4-oxadiazol-2-yl)methyl]-4H-[1,2,4]triazolo[4,3-a][1]benzazepine

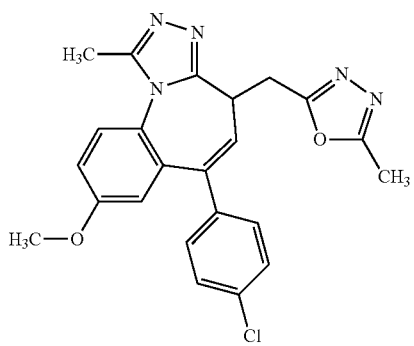

Example 47A

Preparation of 7-methoxy-2-thioxo-1,2,3,4-tetrahydro-5H-1-benzazepin-5-one

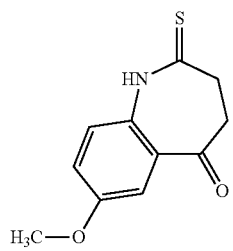

Analogously to the preparation of 2-thioxo-1,2,3,4-tetrahydro-5H-1-benzazepin-5-one (Example 1D), 50 g of 7-methoxy-3,4-dihydro-1H-1-benzazepine-2,5-dione (Arch. Pharm. 2002, 335, p. 311-17, K. Wieking et al.) and 72.9 g of Lawesson's reagent gave 40.9 g of 7-methoxy-2-thioxo-1,2,3,4-tetrahydro-5H-1-benzazepin-5-one.

Yield: 40.9 g of 7-methoxy-2-thioxo-1,2,3,4-tetrahydro-5H-1-benzazepin-5-one.

$^1$H NMR (300 MHz, DMSO-d6): δ=2.91-2.98 (m, 2H); 3.08-3.17 (m, 2H); 3.80 (s, 3H); 7.20-7.29 (m, 3H); 11.98 (bs, 1H).

Example 47B

Preparation of 8-methoxy-1-methyl-4,5-dihydro-6H-[1,2,4]triazolo[4,3-a][1]benzazepin-6-one

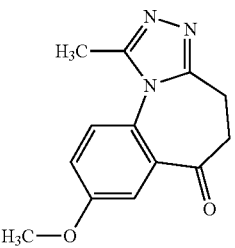 [SMILES: COc1ccc2c(c1)C(=O)CCc1nnc(C)n1-2]

Analogously to the preparation of 1-methyl-4,5-dihydro-6H-[1,2,4]triazolo[4,3-a][1]benzazepin-6-one (Example 1E), 20 g of 7-methoxy-2-thioxo-1,2,3,4-tetrahydro-5H-1-benzazepin-5-one and 20.1 g of acetylhydrazine gave 5.8 g of 8-methoxy-1-methyl-4,5-dihydro-6H-[1,2,4]triazolo[4,3-a][1]benzazepin-6-one.

Yield: 5.8 g of 8-methoxy-1-methyl-4,5-dihydro-6H-[1,2,4]triazolo[4,3-a][1]benzazepin-6-one.

$^1$H NMR (300 MHz, CDCl$_3$): δ=2.50 (s, 3H); 2.99-3.07 (m, 2H); 3.17-3.25 (m, 2H); 3.89 (s, 3H); 7.19 (bs, 2H); 7.26 (bs, 1H).

Example 47C

Preparation of 8-methoxy-1-methyl-4H-[1,2,4]triazolo[4,3-a][1]benzazepin-6-yl 1,1,2,2,3,3,4,4,4-nonafluorobutane-1-sulphonate

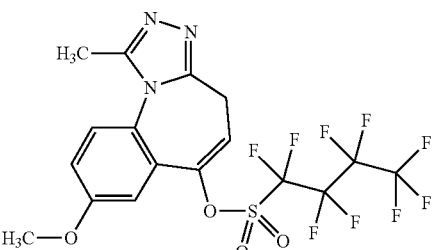

Analogously to the preparation of 1-methyl-4H-[1,2,4]triazolo[4,3-a][1]benzazepin-6-yl 1,1,2,2,3,3,4,4,4-nonafluorobutane-1-sulphonate (Example 1F), 2 g of 8-methoxy-1-methyl-4,5-dihydro-6H-[1,2,4]triazolo[4,3-a][1]benzazepin-6-one and 1.96 g of nonafluorobutanesulphonyl fluoride gave 140 mg of 8-methoxy-1-methyl-4H-[1,2,4]triazolo[4,3-a][1]benzazepin-6-yl 1,1,2,2,3,3,4,4,4-nonafluorobutane-1-sulphonate.

Yield: 140 mg of 8-methoxy-1-methyl-4H-[1,2,4]triazolo[4,3-a][1]benzazepin-6-yl 1,1,2,2,3,3,4,4,4-nonafluorobutane-1-sulphonate.

$^1$H NMR (300 MHz, CDCl$_3$): δ=2.63 (s, 3H); 3.04-3.13 (m, 1H); 3.85-3.96 (m+s, 4H); 6.32-6.39 (m, 1H); 7.16 (dd, 1H); 7.24 (d, 1H); 7.35 (d, 1H).

Example 47D

Preparation of 6-(4-chlorophenyl)-8-methoxy-1-methyl-4H-[1,2,4]triazolo[4,3-a][1]benzazepine

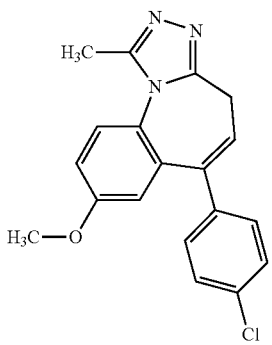 [SMILES: COc1ccc2c(c1)C(c1ccc(Cl)cc1)=CCc1nnc(C)n1-2]

Analogously to the preparation of 6-(4-chlorophenyl)-1-methyl-4H-[1,2,4]triazolo[4,3-a][1]benzazepine (Example 1C, alternative access), 125 mg of 8-methoxy-1-methyl-4H-[1,2,4]triazolo[4,3-a][1]benzazepin-6-yl 1,1,2,2,3,3,4,4,4-nonafluorobutane-1-sulphonate (Example 47C) and 46 mg of 4-chlorophenylboronic acid gave the title compound.

Yield: 60 mg of 6-(4-chlorophenyl)-8-methoxy-1-methyl-4H-[1,2,4]triazolo[4,3-a][1]benzazepine.

$^1$H-NMR (300 MHz, CDCl$_3$): δ=2.59 (s, 3H); 3.04 (dd, 1H); 3.76 (s, 3H); 3.87 (dd, 1H); 6.34 (dd, 1H); 6.70 (d, 1H); 7.04 (dd, 1H); 7.16 (d, 2H); 7.30 (d, 2H); 7.33 (d, 1H).

Example 47E

Preparation of 6-(4-chlorophenyl)-8-methoxy-1-methyl-4-[(5-methyl-1,3,4-oxadiazol-2-yl)methyl]-4H-[1,2,4]triazolo[4,3-a][1]benzazepine

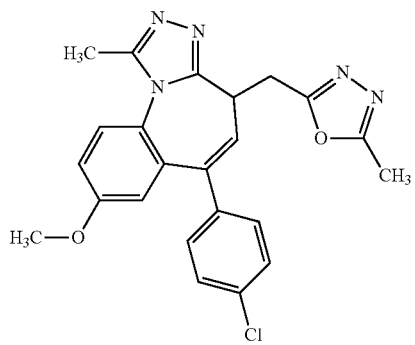

Analogously to the preparation of Example 39, 50 mg of 6-(4-chlorophenyl)-8-methoxy-1-methyl-4H-[1,2,4]triazolo[4,3-a][1]benzazepine (Example 47D) and 19 mg of 3-(chloromethyl)-5-methyl-1,3,4-oxadiazole (CAS 3914-42-9) gave 6 mg of 6-(4-chlorophenyl)-8-methoxy-1-methyl-4-[(5-methyl-1,3,4-oxadiazol-2-yl)methyl]-4H-[1,2,4]triazolo[4,3-a][1]benzazepine.

Yield: 6 mg of 6-(4-chlorophenyl)-8-methoxy-1-methyl-4-[(5-methyl-1,3,4-oxadiazol-2-yl)methyl]-4H-[1,2,4]triazolo[4,3-a][1]benzazepine.

$^1$H NMR (300 MHz, DMSO-d6): δ=about 2.50 (2s, 6H, signal obscured by DMSO); 3.61-3.80 (m+s, 6H); 6.31 (d, 1H); 6.64 (d, 1H); 7.20 (dd, 1H); 7.24 (d, 2H); 7.42 (d, 2H); 7.72 (d, 1H).

Example 48

Preparation of 6-(4-chlorophenyl)-8-(3,5-dimethyl-1,2-oxazol-4-yl)-1-methyl-4-[(5-methyl-1,3,4-oxadiazol-2-yl)methyl]-4H-[1,2,4]triazolo[4,3-a][1]benzazepine

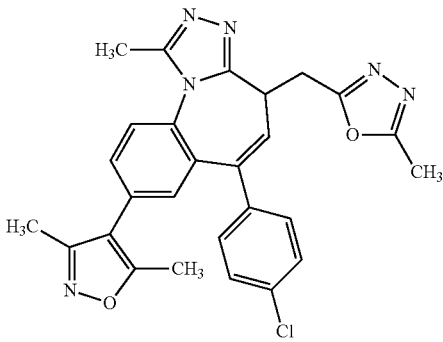

Example 48A

Preparation of 7-bromo-2-thioxo-1,2,3,4-tetrahydro-5H-1-benzazepin-5-one

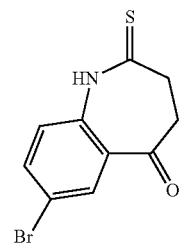 [SMILES: O=C1CCC(=S)Nc2ccc(Br)cc21]

23.1 g of 7-bromo-3,4-dihydro-1H-1-benzazepine-2,5-dione (CAS 137046-58-3) and 27.2 g of Lawesson's reagent (CAS 19172-47-5) were stirred together in 471 ml of tetrahydrofuran at 60° C. for 1 h. The mixture was concentrated, the residue was triturated with methanol and the product was filtered off with suction. Drying under reduced pressure at 40° C. gave 18.7 g.

$^1$H NMR (600 MHz, DMSO-d6): δ=2.93-2.98 (m, 2H), 3.16-3.21 (m, 2H), 7.27 (d, 1H), 7.80 (dd, 1H), 7.86 (d, 1H).

Example 48B

Preparation of N'-(8-bromo-1-methyl-4,5-dihydro-6H-[1,2,4]triazolo[4,3-a][1]benzazepin-6-ylidene)acetohydrazide

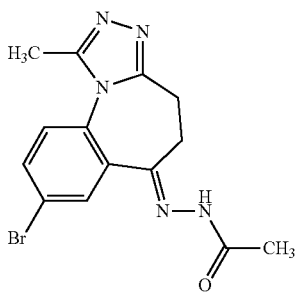 [SMILES: CC(=O)N/N=C1\CCc2nnc(C)n2-c2ccc(Br)cc21]

15.3 g of 7-bromo-2-thioxo-1,2,3,4-tetrahydro-5H-1-benzazepin-5-one and 12.6 g of acetylhydrazine (CAS#1068-57-1) were stirred in 1-butanol at 60° C. for 1 h and at 125° C. for 16 h. The mixture was concentrated and directly reacted further. This gave 30.2 g of crude product.

Example 48C

Preparation of 8-bromo-1-methyl-4,5-dihydro-6H-[1,2,4]triazolo[4,3-a][1]benzazepin-6-one

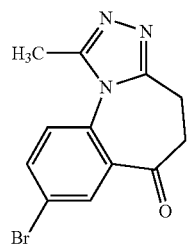 [SMILES: Cc1nnc2n1-c1ccc(Br)cc1C(=O)CC2]

6.04 g of crude N'-(8-bromo-1-methyl-4,5-dihydro-6H-[1,2,4]triazolo[4,3-a][1]benzazepin-6-ylidene)acetohydrazide were stirred with 14.4 ml of conc. hydrochloric acid in 93 ml of dioxane and 4 ml of water at room temperature overnight. The solid was filtered off with suction and washed with ethyl acetate. The filtrate was adjusted to pH 8 with sodium bicarbonate solution. The aqueous phase was extracted with ethyl acetate and ethyl acetate/ethanol 99/1. The extract was dried over sodium sulphate and concentrated. The product was purified by column chromatography on 50 g of silica gel using MeCl/EtOH 100/0-90/10. This gave 2.82 g of product.

$^1$H NMR (300 MHz, DMSO-d6): δ=2.42 (s, 3H), 2.92-2.99 (m, 2H), 3.08-3.16 (m, 2H), 7.59 (d, 1H), 7.80 (d, 1H), 7.96 (dd, 1H).

Example 48D

Preparation of 8-(3,5-dimethyl-1,2-oxazol-4-yl)-1-methyl-4,5-dihydro-6H-[1,2,4]triazolo[4,3-a][1]benzazepin-6-one

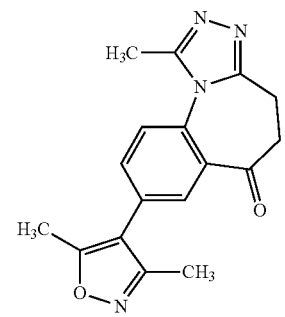 [SMILES: Cc1noc(C)c1-c1ccc2c(c1)C(=O)CCc1nnc(C)n1-2]

73 ml of water and 300 ml of dioxane were added to 7.5 g of 8-bromo-1-methyl-4,5-dihydro-6H-[1,2,4]triazolo[4,3-a][1]benzazepin-6-one, 5.0 g of 3,5-dimethylisoxazole-4-boronic acid (CAS 16114-47-9), 2.1 g of [1,1'-bis(diphenylphosphino)ferrocene]dichloropalladium(II), complex with dichloromethane (CAS 95464-05-4) and 5.0 g of sodium bicarbonate. The mixture was degassed with ultrasound, stirred under argon at 80° C. for 1 h and then concentrated. 100 ml of saturated sodium bicarbonate solution were added to the residue, and the mixture was extracted with dichloromethane. The extract was dried over sodium sulphate and concentrated. This gave 10 g of crude product which were purified by column chromatography on 340 g of silica gel using MeCl/EtOH 100/0-90/10. This gave 7.85 g of product.

$^1$H NMR (300 MHz, CDCl$_3$): δ=2.34 (s, 3H), 2.49 (s, 3H), 2.59 (s, 3H), 3.07-3.14 (m, 2H), 3.26-3.35 (m, 2H), 7.38 (d, 1H), 7.61 (dd, 1H), 7.72 (d, 1H).

Example 48E

Preparation of 6-(4-chlorophenyl)-8-(3,5-dimethyl-1,2-oxazol-4-yl)-1-methyl-4H-[1,2,4]triazolo[4,3-a][1]benzazepine

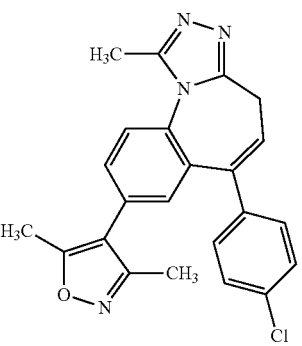 [SMILES: Cc1noc(C)c1-c1ccc2c(c1)C(c1ccc(Cl)cc1)=CCc1nnc(C)n1-2]

1) 1.16 g of 8-(3,5-dimethyl-1,2-oxazol-4-yl)-1-methyl-4,5-dihydro-6H-[1,2,4]triazolo[4,3-a][1]benzazepin-6-one were suspended in 145 ml of THF, and 18.8 ml of 1.0 M 4-chlorophenylmagnesium bromide solution were added. The mixture was stirred under nitrogen at 60° C. for 17 h and at 70° C. for 18 h and then concentrated to about 50% of its volume. Ice and 1N HCl (pH 1.5) were added to the residue, and the mixture was extracted with 250 ml of dichloromethane/isopropanol (4:1). The extract was washed with 30 ml of water and concentrated. This gave 2.97 g.

2) 134 ml of toluene and 1.94 g of p-toluenesulphonic acid were added to 1.58 g of the residue, and the mixture was stirred at 110° C. for 2 h. The solution was washed with sodium bicarbonate solution and the aqueous phase was extracted with ethyl acetate. The organic phases were combined, dried over sodium sulphate and concentrated. The residue was chromatographed on 100 g of silica gel using MeCl/EtOH 100/0-95/5. This gave 190 mg of product.

$^1$H NMR (300 MHz, CDCl$_3$): δ=2.20 (s, 3H), 2.34 (s, 3H), 2.66 (s, 3H), 3.10 (dd, 1H), 3.94 (dd, 1H), 6.42 (dd, 1H), 7.12 (d, 1H), 7.17 (d, 2H), 7.32 (d, 2H), 7.40 (dd, 1H), 7.50 (d, 1H).

Example 48F

Preparation of 6-(4-chlorophenyl)-8-(3,5-dimethyl-1,2-oxazol-4-yl)-1-methyl-4-[(5-methyl-1,3,4-oxadiazol-2-yl)methyl]-4H-[1,2,4]triazolo[4,3-a][1]benzazepine

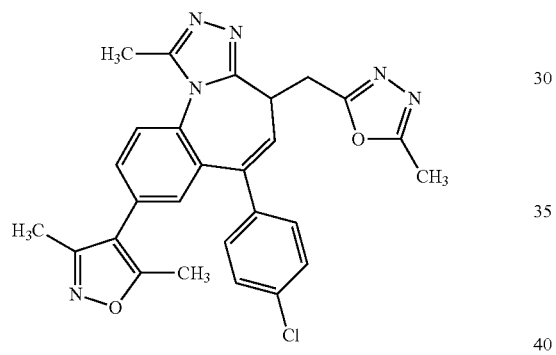

75 mg of 6-(4-chlorophenyl)-8-(3,5-dimethyl-1,2-oxazol-4-yl)-1-methyl-4H-[1,2,4]triazolo[4,3-a][1]benzazepine were initially charged in 5.7 ml of THF. The solution was cooled to −60° C., and 0.40 ml of 1.4 M sec-butyllithium solution was added slowly under argon (time for the dropwise addition 1 min) The solution was stirred in the dark and at −67--60° C. for 1 h. 74 mg of 2-(chloromethyl)-5-methyl-1,3,4-oxadiazole (CAS 3914-42-9) in 1.3 ml of THF were added dropwise at −65° C. The cooling bath was removed, the mixture was stirred was at room temperature overnight and 3 ml of ammonium chloride solution were added. The mixture was extracted three times with ethyl acetate. The extract was dried over sodium sulphate and concentrated. This gave 110 mg of crude product which were purified by column chromatography on 10 g of silica gel using MeCl/EtOH 100/0-95/5. This gave 16 mg of product which were purified by RP-HPLC (column: X-Bridge C18 5 μm 100×30 mm, mobile phase: acetonitrile/water (0.1% by volume of formic acid) gradient, flow rate 50 ml/min, RT). This gave 2.4 mg of 6-(4-chlorophenyl)-8-(3,5-dimethyl-1,2-oxazol-4-yl)-1-methyl-4-[(5-methyl-1,3,4-oxadiazol-2-yl)methyl]-4H-[1,2,4]triazolo[4,3-a][1]benzazepine.

$^1$H NMR (400 MHz, CDCl$_3$): δ=2.21 (s, 3H), 2.36 (s, 3H), 2.56 (s, 3H), 2.66 (s, 3H), 3.64-3.77 (m, 1H), 3.86-3.99 (m, 2H), 6.19 (d, 1H), 7.13-7.17 (m, 3H), 7.31 (d, 2H), 7.43 (dd, 1H), 7.52 (d, 1H).

Example 49

Preparation of tert-butyl [6-(4-chlorophenyl)-1-methyl-8-(trifluoromethoxy)-4H-[1,2,4]triazolo[4,3-a][1]benzazepin-4-yl]acetate

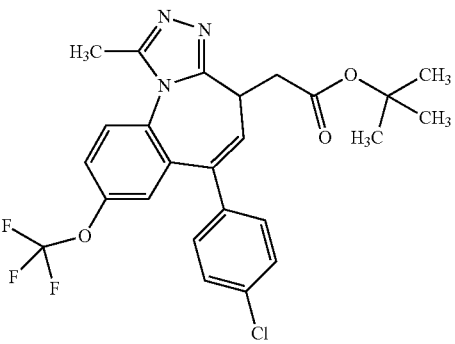 [SMILES: Cc1nnc2n1-c1ccc(OC(F)(F)F)cc1C(c1ccc(Cl)cc1)=CC2CC(=O)OC(C)(C)C]

Example 49A

Preparation of ethyl 2-[(4-ethoxy-4-oxobutanoyl)amino]-5-(trifluoromethoxy)benzoate

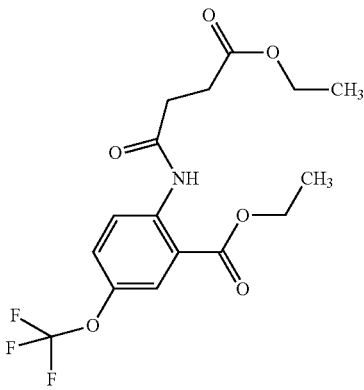 [SMILES: CCOC(=O)CCC(=O)Nc1ccc(OC(F)(F)F)cc1C(=O)OCC]

At RT, 25.8 g of ethyl succinyl chloride were slowly added dropwise to a solution of 23.6 g of ethyl 2-amino-5-(trifluoromethoxy)benzoate (CAS 220107-20-0) in 7.6 ml of pyridine and 450 ml of THF. The mixture was left stirring at RT for 16 hours. The mixture was added to water and extracted with ethyl acetate. The organic phase was washed with 2M hydrochloric acid, saturated sodium bicarbonate solution and brine and dried over sodium sulphate, and the solvent was removed under reduced pressure.

Yield: 25.7 g of ethyl 2-[(4-ethoxy-4-oxobutanoyl)amino]-5-(trifluoromethoxy)benzoate.

$^1$H NMR (400 MHz, CDCl$_3$): δ=1.27 (t, 3H); 1.44 (t, 3H); 2.71-2.81 (m, 4H); 4.17 (q, 2H); 4.42 (q, 2H); 7.39 (dd, 1H); 7.88 (d, 1H); 8.77 (d, 1H); 11.15 (bs, 1H).

Example 49B

Preparation of ethyl 5-hydroxy-2-oxo-7-(trifluoromethoxy)-2,3-dihydro-1H-1-benzazepine-4-carboxylate

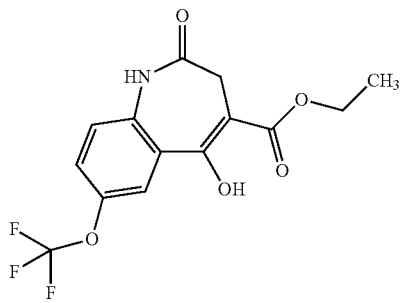 [SMILES: CCOC(=O)C1=C(O)c2cc(OC(F)(F)F)ccc2NC(=O)C1]

At RT, 35.8 g of ethyl 2-[(4-ethoxy-4-oxobutanoyl)amino]-5-(trifluoromethoxy)benzoate (Example 49A) were added to a solution of 40.5 g of potassium tert-butoxide in 477 ml of DMF. A few minutes later, 176 ml of DMSO were added and the mixture was stirred at RT for 90 min. The mixture was added to 2 l of ice-water and the pH was adjusted to less than 4 using hydrochloric acid (1N). This resulted in the precipitation of a solid. The suspension was stirred for one hour and the solid was then filtered off with suction. The solid was dried in a drying cabinet under reduced pressure at 50° C.

Yield: 31.6 g of ethyl 5-hydroxy-2-oxo-7-(trifluoromethoxy)-2,3-dihydro-1H-1-benzazepine-4-carboxylate.

$^1$H NMR (400 MHz, CDCl$_3$): δ=1.40 (t, 3H); 3.14 (s, 2H); 4.36 (q, 2H); 7.13 (d, 1H); 7.35 (dd, 1H); 7.78 (d, 1H); 8.65 (bs, 1H); 12.74 (bs, 1H).

Example 49C

Preparation of 7-(trifluoromethoxy)-3,4-dihydro-1H-1-benzazepine-2,5-dione

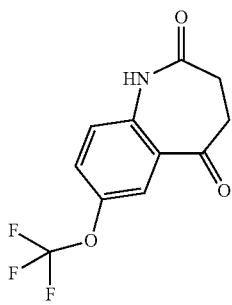 [SMILES: O=C1CCC(=O)c2cc(OC(F)(F)F)ccc2N1]

A solution of 31.6 g of ethyl 5-hydroxy-2-oxo-7-(trifluoromethoxy)-2,3-dihydro-1H-1-benzazepine-4-carboxylate (Example 49B) in 125 ml of DMSO was stirred at 150° C. for 9 hours. After cooling, the mixture was added to 1.2 l of ice-water and stirred. The mixture was extracted with ethyl acetate, the organic phase was washed with water and brine and dried over sodium sulphate and the solvent was removed under reduced pressure. The residue was purified by chromatography on silica gel (hexane/ethyl acetate gradient).

Yield: 11.1 g of 7-(trifluoromethoxy)-3,4-dihydro-1H-1-benzazepine-2,5-dione.

$^1$H NMR (400 MHz, DMSO-d6): δ=2.66-2.75 (m, 2H); 2.90-2.99 (m, 2H); 7.28 (d, 1H); 7.61 (dd, 1H); 7.69 (d, 1H); 10.28 (bs, 1H).

Example 49D

Preparation of 2-thioxo-7-(trifluoromethoxy)-1,2,3,4-tetrahydro-5H-1-benzazepin-5-one

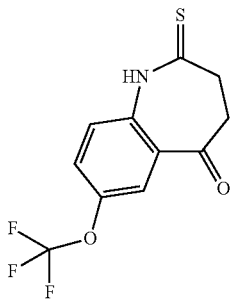 [SMILES: O=C1CCC(=S)Nc2ccc(OC(F)(F)F)cc21]

Analogously to the preparation of 2-thioxo-1,2,3,4-tetrahydro-5H-1-benzazepin-5-one (Example 1D), 11.1 g of 7-(trifluoromethoxy)-3,4-dihydro-1H-1-benzazepine-2,5-dione (Example 49C) and 11.5 g of Lawesson's reagent gave 8.5 g of 2-thioxo-7-(trifluoromethoxy)-1,2,3,4-tetrahydro-5H-1-benzazepin-5-one.

Yield: 8.5 g of 2-thioxo-7-(trifluoromethoxy)-1,2,3,4-tetrahydro-5H-1-benzazepin-5-one.

$^1$H NMR (400 MHz, CDCl$_3$): δ=3.04-3.14 (m, 2H); 3.29-3.40 (m, 2H); 7.09 (d, 1H); 7.43 (dd, 1H); 7.87 (d, 1H); 9.55 (bs, 1H).

Example 49E

Preparation of 1-methyl-8-(trifluoromethoxy)-4,5-dihydro-6H-[1,2,4]triazolo[4,3-a][1]benzazepin-6-one

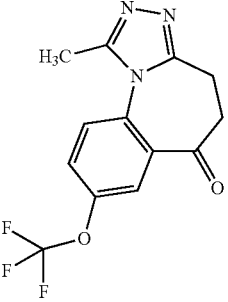 [SMILES: Cc1nnc2n1-c1ccc(OC(F)(F)F)cc1C(=O)CC2]

Analogously to the preparation of 1-methyl-4,5-dihydro-6H-[1,2,4]triazolo[4,3-a][1]benzazepin-6-one (Example 1E), 8.5 g of 2-thioxo-7-(trifluoromethoxy)-1,2,3,4-tetrahydro-5H-1-benzazepin-5-one (Example 49D) and 6.8 g of acetylhydrazine gave 3.6 g of 1-methyl-8-(trifluoromethoxy)-4,5-dihydro-6H-[1,2,4]triazolo[4,3-a][1]benzazepin-6-one.

Yield: 3.6 g of 1-methyl-8-(trifluoromethoxy)-4,5-dihydro-6H-[1,2,4]triazolo[4,3-a][1]benzazepin-6-one.

¹H NMR (400 MHz, CDCl₃): δ=2.56 (s, 3H); 3.05-3.12 (m, 2H); 3.23-3.31 (m, 2H); 7.35 (d, 1H); 7.55 (dd, 1H); 7.68 (d, 1H).

Example 49F

Preparation of 1-methyl-8-(trifluoromethoxy)-4H-[1,2,4]triazolo[4,3-a][1]benzazepin-6-yl 1,1,2,2,3,3,4,4,4-nonafluorobutane-1-sulphonate

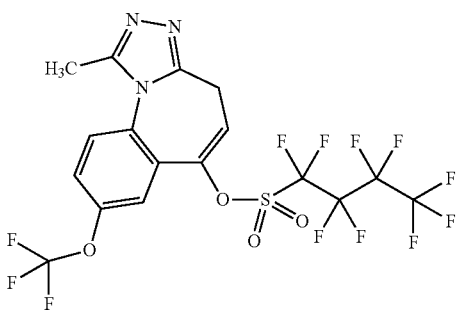 [SMILES: Cc1nnc2n1-c1ccc(OC(F)(F)F)cc1C(OS(=O)(=O)C(F)(F)C(F)(F)C(F)(F)C(F)(F)F)=CC2]

Analogously to the preparation of 1-methyl-4H-[1,2,4]triazolo[4,3-a][1]benzazepin-6-yl 1,1,2,2,3,3,4,4,4-nonafluorobutane-1-sulphonate (Example 1F), 3.6 g of 1-methyl-8-(trifluoromethoxy)-4,5-dihydro-6H-[1,2,4]triazolo[4,3-a][1]benzazepin-6-one (Example 49E) and 5.21 g of nonafluorobutanesulfonyl fluoride gave 4.5 mg of 1-methyl-8-(trifluoromethoxy)-4H-[1,2,4]triazolo[4,3-a][1]benzazepin-6-yl 1,1,2,2,3,3,4,4,4-nonafluorobutane-1-sulphonate.

Yield: 4.5 g of 1-methyl-8-(trifluoromethoxy)-4H-[1,2,4]triazolo[4,3-a][1]benzazepin-6-yl 1,1,2,2,3,3,4,4,4-nonafluorobutane-1-sulphonate.

¹H NMR (400 MHz, CDCl₃): δ=2.56 (s, 3H); 3.05-3.19 (m, 1H); 3.88-4.03 (m, 1H); 6.46 (dd, 1H); 7.50 (bs, 2H); 7.64 (bs, 1H).

Example 49G

Preparation of 6-(4-chlorophenyl)-1-methyl-8-(trifluoromethoxy)-4H-[1,2,4]triazolo[4,3-a][1]benzazepine

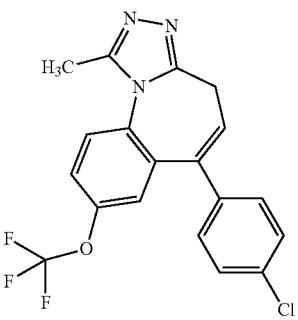 [SMILES: Cc1nnc2n1-c1ccc(OC(F)(F)F)cc1C(c1ccc(Cl)cc1)=CC2]

Analogously to the preparation of 6-(4-chlorophenyl)-1-methyl-4H-[1,2,4]triazolo[4,3-a][1]benzazepine (Example 1C, alternative access), 4.5 g of 1-methyl-8-(trifluoromethoxy)-4H-[1,2,4]triazolo[4,3-a][1]benzazepin-6-yl 1,1,2,2,3,3,4,4,4-nonafluorobutane-1-sulphonate (Example 49F) and 1.18 g of 4-chlorophenylboronic acid gave the title compound.

Yield: 1.5 g of 6-(4-chlorophenyl)-1-methyl-8-(trifluoromethoxy)-4H-[1,2,4]triazolo[4,3-a][1]benzazepine.

¹H NMR (400 MHz, CDCl₃): δ=2.62 (s, 3H); 3.05 (dd, 1H); 3.93 (dd, 1H); 6.42 (dd, 1H); 7.09-7.17 (m, 3H); 7.33 (d, 2H); 7.38 (dd, 1H); 7.46 (d, 1H).

Example 49H

Preparation of tert-butyl [6-(4-chlorophenyl)-1-methyl-8-(trifluoromethoxy)-4H-[1,2,4]triazolo[4,3-a][1]benzazepin-4-yl]acetate

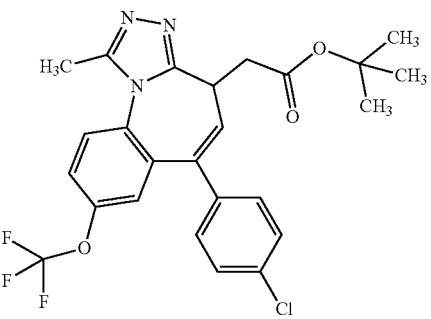 [SMILES: Cc1nnc2n1-c1ccc(OC(F)(F)F)cc1C(c1ccc(Cl)cc1)=CC2CC(=O)OC(C)(C)C]

Analogously to the preparation of Example 39, 1 g of 6-(4-chlorophenyl)-1-methyl-8-(trifluoromethoxy)-4H-[1,2,4]triazolo[4,3-a][1]benzazepine (Example 49G) and 483 mg of tert-butyl bromoacetate gave 690 mg of tert-butyl [6-(4-chlorophenyl)-1-methyl-8-(trifluoromethoxy)-4H-[1,2,4]triazolo[4,3-a][1]benzazepin-4-yl]acetate.

Yield: 690 mg of tert-butyl [6-(4-chlorophenyl)-1-methyl-8-(trifluoromethoxy)-4H-[1,2,4]triazolo[4,3-a][1]benzazepin-4-yl]acetate.

¹H NMR (400 MHz, CDCl₃): δ=1.50 (s, 9H); 2.60 (s, 3H); 3.10 (dd, 1H); 3.41 (dd, 1H); 3.57-3.66 (m, 1H); 6.11 (d, 1H); 7.08-7.15 (m, 3H); 7.32 (d, 2H); 7.37 (dd, 1H); 7.46 (d, 1H).

Example 50

Preparation of tert-butyl (−)-[(4R)-6-(4-chlorophenyl)-1-methyl-8-(trifluoromethoxy)-4H-[1,2,4]triazolo[4,3-a][1]benzazepin-4-yl]acetate

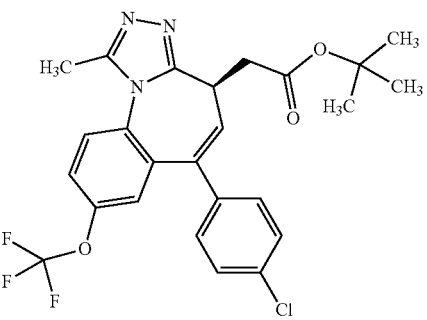 [SMILES: Cc1nnc2n1-c1ccc(OC(F)(F)F)cc1C(c1ccc(Cl)cc1)=C[C@@H]2CC(=O)OC(C)(C)C]

680 mg of tert-butyl [6-(4-chlorophenyl)-1-methyl-8-(trifluoromethoxy)-4H-[1,2,4]triazolo[4,3-a][1]benzazepin-4- yl]acetate (Example 49H) were separated into the enantiomers by chiral HPLC (Chiralpak IC 5 μm 250×20 mm, acetonitrile/ethanol 90:10, 20 ml/min, RT).

Yield: 280 mg of tert-butyl (+[(4R)-6-(4-chlorophenyl)-1-methyl-8-(trifluoromethoxy)-4H-[1,2,4]triazolo[4,3-a][1]benzazepin-4-yl]acetate.

$^1$H NMR (400 MHz, CDCl$_3$): δ=1.50 (s, 9H); 2.60 (s, 3H); 3.10 (dd, 1H); 3.41 (dd, 1H); 3.57-3.66 (m, 1H); 6.11 (d, 1H); 7.08-7.15 (m, 3H); 7.32 (d, 2H); 7.37 (dd, 1H); 7.46 (d, 1H).

Optical rotation: $[α]_D^{20}$=-87.7° (c=10.7, methanol).

Example 51

Preparation of 2-[(4R)-6-(4-chlorophenyl)-1-methyl-8-(trifluoromethoxy)-4H-[1,2,4]triazolo[4,3-a][1,4]benzodiazepin-4-yl]-1-(2-oxa-6-azaspiro[3.3]hept-6-yl)ethanone

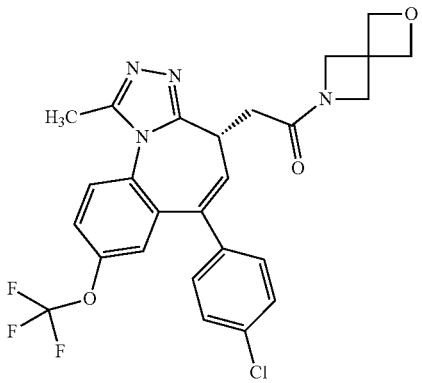 [SMILES: Cc1nnc2n1-c1ccc(OC(F)(F)F)cc1C(c1ccc(Cl)cc1)=C[C@H]2CC(=O)N1CC2(COC2)C1]

Example 51A

Preparation of [(4R)-6-(4-chlorophenyl)-1-methyl-8-(trifluoromethoxy)-4H-[1,2,4]triazolo[4,3-a][1]benzazepin-4-yl]acetic acid

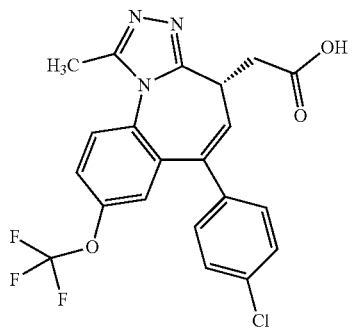 [SMILES: Cc1nnc2n1-c1ccc(OC(F)(F)F)cc1C(c1ccc(Cl)cc1)=C[C@H]2CC(=O)O]

A solution of 240 mg of tert-butyl [(4R)-6-(4-chlorophenyl)-1-methyl-8-(trifluoromethoxy)-4H-[1,2,4]triazolo[4,3-a][1]benzazepin-4-yl]acetate (Example 50) in 2.25 ml of HCl in dioxane (4M) was stirred at RT for 4 hours. The solvent was then removed under reduced pressure.

Yield: 240 mg of [(4R)-6-(4-chlorophenyl)-1-methyl-8-(trifluoromethoxy)-4H-[1,2,4]triazolo[4,3-a][1]benzazepin-4-yl]acetic acid.

Analysis: UPLC-MS: Waters Acquity UPLC-MS SQD; column: Acquity UPLC BEH C18 1.7 50×2.1 mm; mobile phase A: water+0.1% by volume formic acid (99%), mobile phase B: acetonitrile; gradient: 0-1.6 min 1-99% B, 1.6-2.0 min 99% B; flow rate 0.8 ml/min; temperature: 60° C.; injection: 2 μl; DAD scan: 210-400 nm Rt=1.23 min.

Example 51B

Preparation of 2-[(4R)-6-(4-chlorophenyl)-1-methyl-8-(trifluoromethoxy)-4H-[1,2,4]triazolo[4,3-a][1,4]benzazepin-4-yl]-1-(2-oxa-6-azaspiro[3.3]hept-6-yl)ethanone

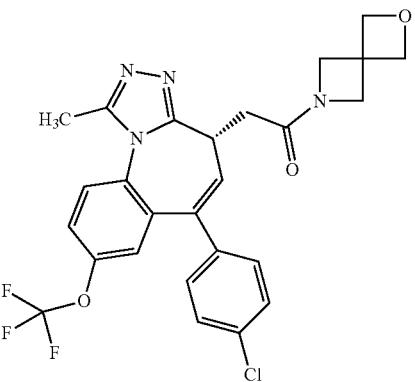 [SMILES: Cc1nnc2n1-c1ccc(OC(F)(F)F)cc1C(c1ccc(Cl)cc1)=C[C@H]2CC(=O)N1CC2(COC2)C1]

Analogously to the preparation of Example 3B, 50 mg of [(4R)-6-(4-chlorophenyl)-1-methyl-8-(trifluoromethoxy)-4H-[1,2,4]triazolo[4,3-a][1]benzazepin-4-yl]acetic acid (Example 51A) and 32 mg of 2-oxa-6-azaspiro[3.3]heptane oxalate (2:1) gave the title compound.

Yield: 35 mg of 2-[(4R)-6-(4-chlorophenyl)-1-methyl-8-(trifluoromethoxy)-4H-[1,2,4]triazolo[4,3-a][1.4]benzazepin-4-yl]-1-(2-oxa-6-azaspiro[3.3]hept-6-yl)ethanone.

$^1$H NMR (400 MHz, CDCl$_3$): δ=2.60 (s, 3H); 2.80 (dd, 1H); 3.26 (dd, 1H); 3.71-3.80 (m, 1H); 4.19 (bs, 2H); 4.43 (d, 1H); 4.73-4.91 (m, 5H); 6.09 (d, 1H); 7.08-7.17 (m, 3H); 7.27-7.35 (m, 2H); 7.35-7.42 (m, 1H); 7.45 (d, 1H).

Example 52

Preparation of 2-[(4R)-6-(4-chlorophenyl)-1-methyl-8-(trifluoromethoxy)-4H-[1,2,4]triazolo[4,3-a][1]benzazepin-4-yl]-N-ethylacetamide

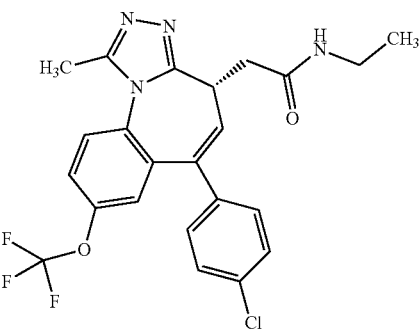 [SMILES: CCNC(=O)C[C@@H]1C=C(c2ccc(Cl)cc2)c2cc(OC(F)(F)F)ccc2-n2c(C)nnc21]

Analogously to the preparation of Example 3B, 50 mg of [(4R)-6-(4-chlorophenyl)-1-methyl-8-(trifluoromethoxy)-4H-[1,2,4]triazolo[4,3-a][1]benzazepin-4-yl]acetic acid (Example 51A) and 6 mg of ethylamine gave the title compound.

Yield: 40 mg of 2-[(4R)-6-(4-chlorophenyl)-1-methyl-8-(trifluoromethoxy)-4H-[1,2,4]triazolo[4,3-a][1]benzazepin-4-yl]-N-ethylacetamide.

¹H NMR (400 MHz, CDCl₃): δ=1.18 (t, 3H); 2.61 (s, 3H); 3.06 (dd, 1H); 3.22-3.44 (m, 3H); 3.73 (q, 1H); 6.13 (d, 1H); 7.08-7.18 (m, 4H); 7.26-7.35 (m, 2H); 7.38 (bd, 1H); 7.47 (d, 1H).

Example 53

Preparation of 2-[(4R)-6-(4-chlorophenyl)-1-methyl-8-(trifluoromethoxy)-4H-[1,2,4]triazolo[4,3-a][1]benzazepin-4-yl]-N-[2-(morpholin-4-yl)ethyl]acetamide

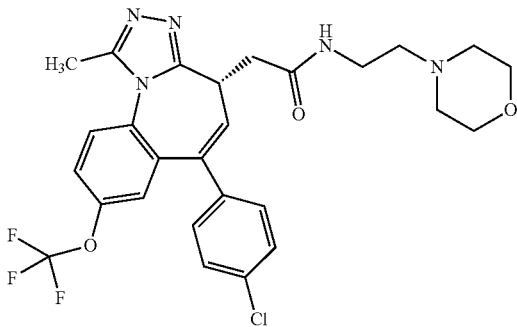 [SMILES: Cc1nnc2n1-c1ccc(OC(F)(F)F)cc1C(c1ccc(Cl)cc1)=C[C@H]2CC(=O)NCCN1CCOCC1]

Analogously to the preparation of Example 3B, 50 mg of [(4R)-6-(4-chlorophenyl)-1-methyl-8-(trifluoromethoxy)-4H-[1,2,4]triazolo[4,3-a][1]benzazepin-4-yl]acetic acid (Example 51A) and 16 mg of 4-(2-aminoethyl)morpholine gave the title compound.

Yield: 50 mg of 2-[(4R)-6-(4-chlorophenyl)-1-methyl-8-(trifluoromethoxy)-4H-[1,2,4]triazolo[4,3-a][1]benzazepin-4-yl]-N-[2-(morpholin-4-yl)ethyl]acetamide.
¹H NMR (400 MHz, CDCl₃): δ=2.42-2.56 (m, 6H); 2.61 (s, 3H); 3.04 (dd, 1H); 3.30-3.45 (m, 3H); 3.67-3.79 (m, 5H); 6.14 (d, 1H); 6.90 (bs, 1H); 7.10-7.19 (m, 3H); 7.32 (d, 2H); 7.38 (bd, 1H); 7.47 (d, 1H).

Example 54

Preparation of 6-(4-chlorophenyl)-1-methyl-4-[(5-methyl-1,3,4-oxadiazol-2-yl)methyl]-8-(trifluoromethoxy)-4H-[1,2,4]triazolo[4,3-a][1]benzazepine

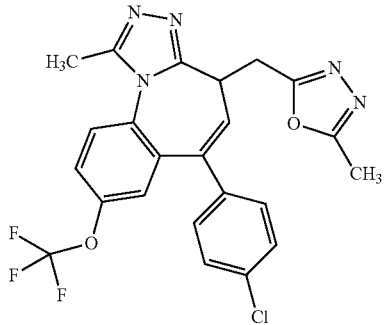 [SMILES: Cc1nnc(CC2C=C(c3ccc(Cl)cc3)c3cc(OC(F)(F)F)ccc3-n3c(C)nnc32)o1]

Analogously to the preparation of Example 39, 100 mg of 6-(4-chlorophenyl)-1-methyl-8-(trifluoromethoxy)-4H-[1,2,4]triazolo[4,3-a][1]benzazepine (Example 49G) and 33.8 mg of 3-(chloromethyl)-5-methyl-1,3,4-oxadiazole (CAS 3914-42-9) gave 30 mg of 6-(4-chlorophenyl)-1-methyl-4-[(5-methyl-1,3,4-oxadiazol-2-yl)methyl]-8-(trifluoromethoxy)-4H-[1,2,4]triazolo[4,3-a][1]benzazepine.

Yield: 30 mg of 6-(4-chlorophenyl)-1-methyl-4-[(5-methyl-1,3,4-oxadiazol-2-yl)methyl]-8-(trifluoromethoxy)-4H-[1,2,4]triazolo[4,3-a][1]benzazepine.
¹H NMR (400 MHz, CDCl₃): δ=2.56 (s, 3H); 2.62 (s, 3H); 3.71 (dd, 1H); 3.79-3.87 (m, 1H); 3.91 (dd, 1H); 6.21 (d, 1H); 7.08-7.15 (m, 3H); 7.32 (d, 2H); 7.40 (dd, 1H); 7.49 (d, 1H).

Example 55

Preparation of (4R)-6-(4-chlorophenyl)-1-methyl-4-[(5-methyl-1,3,4-oxadiazol-2-yl)methyl]-8-(trifluoromethoxy)-4H-[1,2,4]triazolo[4,3-a][1]benzazepine

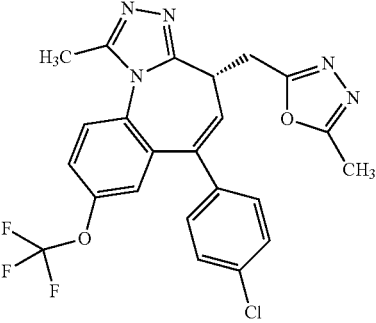 [SMILES: Cc1nnc(C[C@@H]2C=C(c3ccc(Cl)cc3)c3cc(OC(F)(F)F)ccc3-n3c(C)nnc32)o1]

30 mg of 6-(4-chlorophenyl)-1-methyl-4-[(5-methyl-1,3,4-oxadiazol-2-yl)methyl]-8-(trifluoromethoxy)-4H-[1,2,4]triazolo[4,3-a][1]benzazepine (Example 54) were separated into the enantiomers by chiral HPLC (Chiralpak IB 5 μm 250×20 mm, hexane/ethanol/diethylamine 70:30:0.1, 20 ml/min, RT).

Yield: 8 mg of (4R)-6-(4-chlorophenyl)-1-methyl-4-[(5-methyl-1,3,4-oxadiazol-2-yl)methyl]-8-(trifluoromethoxy)-4H-[1,2,4]triazolo[4,3-a][1]benzazepine.
¹H NMR (400 MHz, CDCl₃): δ=2.56 (s, 3H); 2.62 (s, 3H); 3.71 (dd, 1H); 3.79-3.87 (m, 1H); 3.91 (dd, 1H); 6.21 (d, 1H); 7.08-7.15 (m, 3H); 7.32 (d, 2H); 7.40 (dd, 1H); 7.49 (d, 1H).

Example 56

Preparation of 2-{[(4R)-6-(4-chlorophenyl)-1-methyl-8-(trifluoromethoxy)-4H-[1,2,4]triazolo[4,3-a][1]benzazepin-4-yl]acetyl}hexahydropyrrolo[1,2-a]pyrazin-6(2H)-one

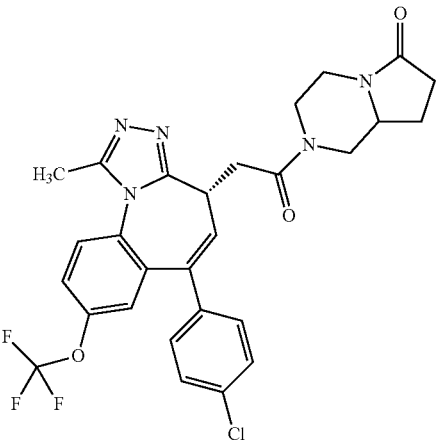 [SMILES: Cc1nnc2n1-c1ccc(OC(F)(F)F)cc1C(c1ccc(Cl)cc1)=C[C@H]2CC(=O)N1CCN2C(=O)CCC2C1]

Analogously to the preparation of Example 3B, 50 mg of [(4R)-6-(4-chlorophenyl)-1-methyl-8-(trifluoromethoxy)-4H-[1,2,4]triazolo[4,3-a][1]benzazepin-4-yl]acetic acid (Example 51A) and 17 mg of (rac)-hexahydropyrrolo[1,2-a]pyrazin-6-one (CAS 117810-52-3) gave the title compound.

Yield: 50 mg of 2-{[(4R)-6-(4-chlorophenyl)-1-methyl-8-(trifluoromethoxy)-4H-[1,2,4]triazolo[4,3-a][1]benzazepin-4-yl]acetyl}hexahydropyrrolo[1,2-a]pyrazin-6(2H)-one.

¹H NMR (400 MHz, CDCl₃, selected signals): δ=1.57-1.80 (m); 2.15-2.54 (m, 4H); 2.61 (s, 3H); 3.02-3.30 (m, 2H); 3.48-3.73 (m, 2H); 4.76 (dd, 1H); 6.02-6.18 (m, 1H); 7.07-7.20 (m, 3H); 7.32 (d, 2H); 7.38 (bd, 1H); 7.47 (d, 1H).

Example 57

Preparation of (4R)-4-({5-[(benzyloxy)methyl]-1,3,4-oxadiazol-2-yl}methyl)-6-(4-chlorophenyl)-1-methyl-4H-[1,2,4]triazolo[4,3-a][1]benzazepine

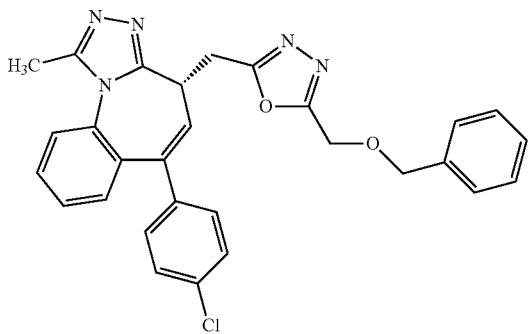 [SMILES: Cc1nnc2n1-c1ccccc1C(c1ccc(Cl)cc1)=C[C@H]2Cc1nnc(COCc2ccccc2)o1]

Example 57A

Preparation of (4R)-[6-(4-chlorophenyl)-1-methyl-4H-[1,2,4]triazolo[4,3-a][1]benzazepin-4-yl]acetic acid

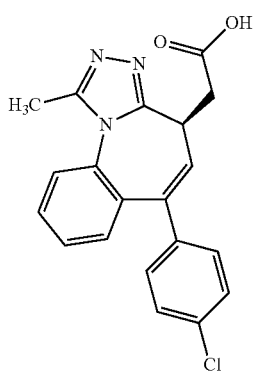 [SMILES: Cc1nnc2n1-c1ccccc1C(c1ccc(Cl)cc1)=C[C@@H]2CC(=O)O]

A solution of 500 mg of tert-butyl (−)-[(4R)-6-(4-chlorophenyl)-1-methyl-4H-[1,2,4]triazolo[4,3-a][1]benzazepin-4-yl]acetate (Example 9) in 6 ml of hydrochloric acid in dioxane solution (4M) was stirred at room temperature for 3 hours. The solution was concentrated fully under reduced pressure.

Yield: 420 mg of (4R)-[6-(4-chlorophenyl)-1-methyl-4H-[1,2,4]triazolo[4,3-a][1]benzazepin-4-yl]acetic acid.

¹H NMR (400 MHz, RT, DMSO-d6): δ=2.67 (s, 3H); 3.14 (dd, 1H); 3.23 (dd, 1H); 3.52 (dd, 1H); 6.26 (d, 1H); 7.22-7.31 (n, 3H); 7.44 (d, 2H); 7.56 (dt, 1H); 7.67 (dt, 1H); 7.87 (dd, 1H).

Example 57B

Preparation of 2-(benzyloxy)-N'-{[(4R)-6-(4-chlorophenyl)-1-methyl-4H-[1,2,4]triazolo[4,3-a][1]benzazepin-4-yl]acetyl}acetohydrazide

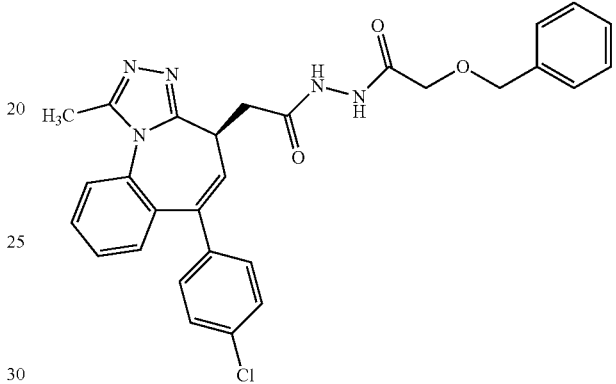

Analogously to the preparation of Example 3B, 420 mg of (4R)-[6-(4-chlorophenyl)-1-methyl-4H-[1,2,4]triazolo[4,3-a][1]benzazepin-4-yl]acetic acid (Example 57A) and 228 mg of 2-(benzyloxy)acetohydrazide (CAS 39256-35-4) gave the title compound.

Yield: 520 mg of 2-(benzyloxy)-N'-{[(4R)-6-(4-chlorophenyl)-1-methyl-4H-[1,2,4]triazolo[4,3-a][1]benzazepin-4-yl]acetyl}acetohydrazide.

¹H NMR (300 MHz, CDCl₃): δ=2.56 (s, 3H); 3.14 (dd, 1H); 3.43 (dd, 1H); 3.66-3.77 (m, 1H); 4.08 (s, 2H); 4.56 (s, 2H); 6.08 (d, 1H); 7.13 (d, 2H); 7.22-7.37 (m, 8H); 7.39 (d, 2H); 7.50 (dt, 1H); 8.67 (s, 1H); 9.78 (bs, 1H).

Example 57C

Preparation of (4R)-4-({5-[(benzyloxy)methyl]-1,3,4-oxadiazol-2-yl}methyl)-6-(4-chlorophenyl)-1-methyl-4H-[1,2,4]triazolo[4,3-a][1]benzazepine

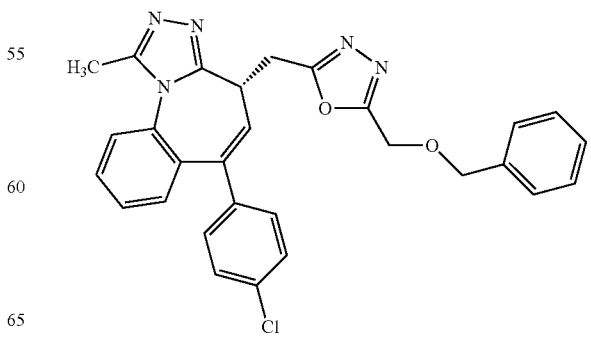

Analogously to the preparation of Example 43B, 380 mg of 2-(benzyloxy)-N'-{[(4R)-6-(4-chlorophenyl)-1-methyl-4H-[1,2,4]triazolo[4,3-a][1]benzazepin-4-yl]acetyl}acetohydrazide and 1.05 g of phosphoryl chloride gave the title compound.

Yield: 140 mg of (4R)-4-({5-[(benzyloxy)methyl]-1,3,4-oxadiazol-2-yl}methyl)-6-(4-chlorophenyl)-1-methyl-4H-[1,2,4]triazolo[4,3-a][1]benzazepine.

$^1$H NMR (300 MHz, CDCl$_3$): δ=2.62 (s, 3H); 3.70-3.85 (m, 2H); 3.86-4.01 (m, 1H); 4.66 (s, 2H); 4.73 (s, 2H); 6.14 (d, 1H); 7.10 (d, 2H); 7.23-7.46 (m, 10H); 7.54 (dt, 1H).

Biological Efficacy of the Compounds According to the Invention

1. BRD4 Binding Strength

To assess the BRD4 binding strength of the compounds according to the invention, the ability thereof to inhibit the interaction between BRD4 and acetylated histone H4 in a dose-dependent manner was quantified.

For this purpose, a time-resolved fluorescence resonance energy transfer (TR-FRET) assay was used, which measures the binding between N-terminally His6-tagged BRD4(1) (amino acids 44-168) and a synthetic acetylated histone H4 (Ac-H4) peptide with sequence GRGK(Ac)GGK(Ac)GLGK(Ac)GGAK(Ac)RHGSGSK-biotin. The recombinant BRD4 protein produced in-house according to Filippakopoulos et al., Cell, 2012, 149:214-231 was expressed in *E. coli* and purified by means of (Ni-NTA) affinity and (Sephadex G-75) size exclusion chromatography. The Ac-H4 peptide can be purchased, for example, from Biosyntan (Berlin, Germany).

In the assay, typically 11 different concentrations of each substance (0.1 nM, 0.33 nM, 1.1 nM, 3.8 nM, 13 nM, 44 nM, 0.15 μM, 0.51 μM, 1.7 μM, 5.9 μM and 20 μM) were analysed as duplicates on the same microtitre plate. For this purpose, 100-fold concentrated solutions in DMSO were prepared by serial dilutions (1:3.4) of a 2 mM stock solution into a clear, 384-well microtitre plate (Greiner Bio-One, Frickenhausen, Germany). From this, 50 nl were transferred into a black test plate (Greiner Bio-One, Frickenhausen, Germany). The test was started by the addition of 2 μl of a BRD4 solution of 2.5 times the concentration (final concentration typically 10 to 50 nM in the 5 μl of reaction volume) in aqueous assay buffer [50 mM HEPES pH 7.5, 50 mM sodium chloride (NaCl), 0.25 mM CHAPS and 0.05% bovine serum albumin (BSA)] to the substances in the test plate. This was followed by a 10-minute incubation step at 22° C. for the pre-equilibration of putative complexes between BRD4 and the substances. Subsequently, 3 μl of a solution of 1.67 times the concentration (in assay buffer) consisting of Ac-H4 peptide (83.5 nM) and TR-FRET detection reagents [16.7 nM anti-6His-XL665 and 3.34 nM streptavidin cryptate (both from Cisbio Bioassays, Codolet, France), and 668 mM potassium fluoride (KF)] were added.

The mixture was then incubated in the dark at 22° C. for one hour and then at 4° C. overnight. The formation of BRD4/Ac-H4 complexes was determined by the measurement of the resonance energy transfer from the streptavidin-Eu cryptate to the anti-6His-XL665 antibody present in the reaction. For this purpose, the fluorescence emission was measured at 620 nm and 665 nm after excitation at 330-350 nm in a TR-FRET measuring instrument, for example a Rubystar or Pherastar (both from BMG Lab Technologies, Offenburg, Germany) or a Viewlux (Perkin-Elmer). The ratio of the emissions at 665 nm and at 622 nm was taken as an indicator of the amount of BRD4/Ac-H4 complexes formed.

The data (ratios) obtained were normalized, with 0% inhibition corresponding to the mean from the measurements for a set of controls (typically 32 data points) in which all the reagents were present. In these, in place of test substances, 50 nl of DMSO (100%) were used Inhibition of 100% corresponded to the mean from the measurements for a set of controls (typically 32 data points) in which all the reagents except BRD4 were present. The IC$_{50}$ was determined by regression analysis based on a 4-parameter equation (minimum, maximum, IC$_{50}$, Hill; Y=max+(min−max)/(1+(X/IC50)$^{Hill}$)) with the aid of a suitable analysis software.

The results are listed in Table 1.

TABLE 1

| Compound Example No. | HTRF IC$_{50}$ (nmol/l) |
|---|---|
| 1 | 180 |
| 2 | 30 |
| 3 | 220 |
| 4 | 130 |
| 5 | 1400 |
| 6 | 600 |
| 7 | 230 |
| 8 | 350 |
| 9 | 200 |
| 10 | 730 |
| 11 | 300 |
| 12 | 130 |
| 13 | 30 |
| 14 | 310 |
| 15 | 40 |
| 16 | 220 |
| 17 | 90 |
| 18 | 200 |
| 19 | 50 |
| 20 | 240 |
| 21 | 80 |
| 22 | 340 |
| 23 | 450 |
| 24 | 220 |
| 25 | 1400 |
| 26 | 40 |
| 27 | 110 |
| 28 | 1400 |
| 29 | 1800 |
| 30 | 80 |
| 31 | 180 |
| 32 | 390 |
| 33 | 450 |
| 34 | 90 |
| 35 | 30 |
| 36 | 90 |
| 37 | 50 |
| 38 | 20 |
| 39 | 40 |
| 40 | 40 |
| 41 | 100 |
| 42 | 50 |
| 43 | 130 |
| 44 | 90 |
| 45 | 50 |
| 46 | 80 |
| 47 | 50 |
| 48 | 340 |
| 50 | 790 |
| 51 | 220 |
| 52 | 190 |
| 53 | 80 |
| 54 | 130 |
| 55 | 90 |
| 56 | 180 |
| 57 | 270 |

2. Cell Proliferation

The ability of the compounds according to the invention to inhibit the proliferation of various cell lines was determined.

Cell viability was determined by means of the alamarBlue® reagent (Invitrogen). The cells were sown at different densities (MOLM-13, LAPC-4, MOLP-8 and MDA-MB-231: 4000 cells/well; B16F10: 400 cells/well) in 100 µl of growth medium on 96-well microtitre plates. After overnight incubation at 37° C., the fluorescence values (CI values) were determined. The plates were then treated with various substance dilutions and incubated at 37° C. for 96 hours (MOLM-13, MDA-MB-231 and B16F10 cells), 120 hours (MOLP-8 cells) or 168 hours (LAPC-4 cells). Subsequently, the fluorescence values were determined (CO values). For the data analysis, the CI values were subtracted from the CO values and the results were compared between cells which had been treated with various dilutions of the substance or only with buffer solution. The $IC_{50}$ values (substance concentration needed for 50% inhibition of cell proliferation) were calculated therefrom.

The compounds according to the invention were tested in the cell lines in Table 2, which represent the indications specified by way of example:

TABLE 2

| Cell line | Source | Indication |
|---|---|---|
| MOLM-13 | ATCC | acute myeloid leukaemia |
| LAPC-4 | ATCC | prostate carcinoma (androgen receptor-positive) |
| MOLP-8 | ATCC | multiple myeloma |
| MDA-MB-231 | ATCC | mammary carcinoma |
| B16F10 | ATCC | melanoma |

The results of the tests for inhibition of cell proliferation are listed in Tables 3a and 3b below. The indications corresponding to the different cell lines can be found in Table 2.

TABLE 3a

| Compound Example No. | MOLM-13 $IC_{50}$ (nmol/l) | LAPC-4 $IC_{50}$ (nmol/l) | B16F10 $IC_{50}$ (nmol/l) | MOLP-8 $IC_{50}$ (nmol/l) |
|---|---|---|---|---|
| 1 | 330 | 260 | 300 | |
| 2 | 120 | 80 | 100 | |
| 3 | 630 | 470 | 740 | |
| 4 | 360 | 660 | 550 | 740 |
| 5 | 1120 | 620 | 870 | |
| 6 | 670 | 1060 | 1020 | |
| 7 | 720 | 750 | 780 | |
| 8 | 3910 | 820 | 1000 | 4800 |
| 9 | 430 | 310 | 430 | 350 |
| 10 | 2630 | 1610 | 3030 | 1290 |
| 11 | 4190 | 7890 | 9470 | |
| 12 | 270 | 80 | 230 | |
| 13 | 310 | 60 | 150 | |
| 14 | 460 | 210 | 410 | |
| 15 | 230 | 60 | 130 | |
| 16 | 530 | 260 | 460 | |
| 17 | 340 | 140 | 280 | |
| 18 | 330 | 200 | 360 | |
| 19 | 150 | 170 | 160 | 190 |
| 20 | 540 | 140 | 350 | |
| 21 | 170 | 80 | 190 | |
| 22 | 1730 | 210 | 840 | |
| 23 | 360 | 170 | 440 | |
| 24 | 2940 | 550 | 1050 | |
| 25 | 1130 | 170 | 490 | 590 |
| 26 | 830 | 310 | 610 | 380 |
| 27 | 250 | 180 | 340 | |
| 28 | >10000 | 1200 | 7050 | 6300 |
| 29 | 2960 | 670 | 2120 | 1670 |
| 30 | 850 | 190 | 490 | |
| 31 | 190 | 80 | 220 | |
| 32 | 1810 | 250 | 800 | |
| 33 | 330 | 150 | 400 | |
| 34 | 360 | | | |
| 35 | 160 | 80 | 150 | 130 |
| 36 | 400 | 160 | 240 | |
| 37 | 330 | 310 | 220 | |
| 38 | 120 | 40 | 60 | 45 |
| 39 | 320 | | | |
| 40 | 170 | | | 80 |
| 41 | 720 | | | 410 |
| 42 | 170 | | 140 | 110 |
| 43 | 370 | | | 210 |
| 44 | 420 | | | 220 |
| 45 | 100 | | 60 | |
| 46 | 270 | | | 140 |
| 47 | 150 | | | 90 |
| 48 | 1380 | | | 1620 |
| 49 | 1690 | | 2200 | 1890 |
| 50 | 880 | | 1170 | 1050 |
| 51 | 390 | | 580 | 360 |
| 52 | 310 | | 420 | 260 |
| 53 | 150 | | 220 | 110 |
| 54 | 300 | | 500 | 360 |
| 55 | 180 | | 270 | 170 |
| 56 | 150 | | 220 | 120 |
| 57 | 410 | | 570 | 420 |

TABLE 3b

| Compound Example No. | MDA-MB-231 $IC_{50}$ (nmol/l) |
|---|---|
| 4 | 2370 |
| 12 | 480 |
| 13 | 320 |
| 14 | 1010 |
| 15 | 350 |
| 16 | 1040 |
| 17 | 570 |
| 18 | 800 |
| 19 | 380 |
| 20 | 980 |
| 21 | 480 |
| 22 | 2900 |
| 23 | 1350 |
| 24 | 2530 |
| 25 | 1330 |
| 26 | 1360 |
| 27 | 710 |
| 28 | >10000 |
| 29 | 4730 |
| 30 | 1130 |
| 31 | 560 |
| 32 | 2040 |
| 33 | 1290 |
| 35 | 210 |
| 36 | 410 |
| 37 | 380 |
| 38 | 110 |

The invention claimed is:
1. Compounds of formula (I)

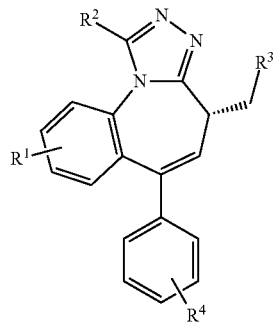

in which
represents hydrogen, hydroxy, $C_1$-$C_6$-alkyl, halo-$C_1$-$C_6$-alkyl, $C_1$-$C_6$-alkoxy, halo-$C_1$-$C_6$-alkoxy, halogen or cyano,
or
represents $C_3$-$C_8$-cycloalkyl, $C_3$-$C_8$-cycloalkoxy, $C_3$-$C_8$-heterocycloalkyl, aryl or heteroaryl having 5 or 6 ring atoms which may optionally be mono- or polysubstituted by identical or different substituents from the group consisting of $C_1$-$C_6$-alkyl, halo-$C_1$-$C_6$-alkyl, $C_1$-$C_6$-alkoxy, halo-$C_1$-$C_6$-alkoxy, hydroxy, oxo, halogen, cyano, heteroaryl and aryl, or represents —C(=O)—OR$^8$, —C(=O)—NR$_{12}$R$_{13}$, —C(=O)—R$^{14}$, —S(=O)$_2$—$C_1$-$C_6$-alkyl, —S(=O)$_2$—OR$^8$ or —S(=O)$_2$—NR$^{12}$R$^{13}$, $R^2$ represents hydrogen, $C_1$-$C_6$-alkyl or —NR$^6$R$^7$,
$R^3$ represents cyano, —C(=O)—OR$^8$, —C(=O)—R$^9$ or —C(=O)—NR$^6$R$^7$,
or
represents a 5- or 6-membered ring system which contains 0, 1, 2, 3 or 4 heteroatoms independently of one another selected from the group consisting of O, N and S, which may optionally be aromatic or else non-aromatic and which may optionally be mono- or polysubstituted by identical or different radicals $R^5$, $R^4$ represents hydrogen, fluorine, chlorine, bromine or cyano, $R^5$ represents hydrogen, $C_1$-$C_6$-alkyl, $C_3$-$C_8$-cycloalkyl, $C_3$-$C_8$-heterocycloalkyl, halo-$C_1$-$C_6$-alkyl, aryl, heteroaryl, hydroxy, $C_1$-$C_6$-alkoxy, $C_1$-$C_3$-alkoxy-$C_1$-$C_3$-alkyl, aryloxy-$C_1$-$C_3$-alkyl, aryl-$C_1$-$C_3$-alkoxy-$C_1$-$C_3$-alkyl, halo-$C_1$-$C_6$-alkoxy, halogen, cyano or oxo, $R^6$ and $R^7$ independently of one another
represent hydrogen or —NH—C(=O)—R$^{15}$,
or
represent $C_1$-$C_6$-alkyl, $C_1$-$C_6$-alkoxy, $C_3$-$C_8$-heterocycloalkyl, aryl, heteroaryl, $C_3$-$C_8$-cycloalkyl, $C_6$-$C_{12}$-bicycloalkyl, $C_5$-$C_{11}$-spirocycloalkyl, $C_6$-$C_{12}$-heterobicycloalkyl or $C_5$-$C_{11}$-heterospirocycloalkyl which may optionally be mono- or polysubstituted by identical or different substituents from the group consisting of $C_1$-$C_6$-alkyl, halo-$C_1$-$C_6$-alkyl, $C_1$-$C_6$-alkoxy, halo-$C_1$-$C_6$-alkoxy, phenoxy, hydroxy, oxo, halogen, cyano, $C_3$-$C_8$-cycloalkyl, $C_3$-$C_8$-heterocycloalkyl, heteroaryl and aryl,
or represent the group

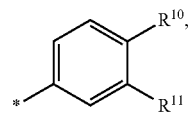

in which
$R^{10}$ and $R^{11}$ together represent $C_3$-$C_6$-alkylene or $C_3$-$C_6$-heteroalkylene which may optionally be mono- or polysubstituted by identical or different substituents from the group consisting of halogen, oxo, hydroxy, cyano, nitro, $C_1$-$C_3$-alkyl, halo-$C_1$-$C_6$-alkyl, $C_1$-$C_6$-alkoxy, halo-$C_1$-$C_6$-alkoxy, $C_1$-$C_6$-alkoxy-$C_1$-$C_6$-alkyl, $C_1$-$C_6$-alkylcarbonyl,
and in which "*" denotes the point of attachment to the remainder of the molecule, $R^8$ represents hydrogen, $C_1$-$C_6$-alkyl, $C_3$-$C_8$-cycloalkyl, $C_3$-$C_8$-heterocycloalkyl, aryl or heteroaryl which may optionally be mono- or polysubstituted by identical or different substituents from the group consisting of $C_1$-$C_6$-alkyl, halo-$C_1$-$C_6$-alkyl, $C_1$-$C_6$-alkoxy, halo-$C_1$-$C_6$-alkoxy, hydroxy, oxo, halogen, cyano, nitro, heteroaryl and aryl, $R^9$ represents $C_3$-$C_8$-heterocycloalkyl, $C_5$-$C_{11}$-spiroheterocycloalkyl, $C_6$-$C_{12}$-heterobicycloalkyl or represents a bridged heterocycle consisting of 7 to 15 ring atoms which may optionally be mono- or polysubstituted by identical or different substituents from the group consisting of $C_1$-$C_4$-alkyl, $C_3$-$C_8$-cycloalkyl, $C_3$-$C_8$-heterocycloalkyl, halo-$C_1$-$C_6$-alkyl, aryl, aryloxy, aryl-$C_1$-$C_2$-alkyl, —C(=O)—O—$C_1$-$C_6$-alkyl, heteroaryl, hydroxy, $C_1$-$C_6$-alkoxy, halo-$C_1$-$C_6$-alkoxy, halogen, cyano and oxo, $R^{12}$ and $R^{13}$ independently of one another represent hydrogen, $C_1$-$C_6$-alkyl, $R^{14}$ represents hydrogen, $C_1$-$C_6$-alkyl, amino, $C_1$-$C_6$-alkoxy, $C_3$-$C_8$-cycloalkyl, $C_3$-$C_8$-heterocycloalkyl, aryl or heteroaryl which may optionally be mono- or polysubstituted by identical or different substituents from the group consisting of $C_1$-$C_6$-alkyl, halo-$C_1$-$C_6$-alkyl, $C_1$-$C_6$-alkoxy, halo-$C_1$-$C_6$-alkoxy, hydroxy, oxo, halogen, cyano, nitro, heteroaryl and aryl, and $R^{15}$ represents hydrogen, $C_1$-$C_6$-alkyl, halo-$C_1$-$C_6$-alkyl, aryl or aryl-$C_1$-$C_2$-alkyl,
where the aryl and the aryl present in aryl-$C_1$-$C_2$-alkyl for their part may optionally be mono- or polysubstituted by identical or different substituents from the group consisting of halogen, cyano, $C_1$-$C_3$-alkyl, $C_1$-$C_3$-alkoxy and trifluoromethyl, and the diastereomers, racemates, tautomers, and physiologically acceptable salts thereof.

2. Compounds of formula (I) according to claim 1 in which $R^1$ represents hydrogen, hydroxy, $C_1$-$C_6$-alkyl, fluoro-$C_1$-$C_6$-alkyl, $C_1$-$C_6$-alkoxy, fluoro-$C_1$-$C_6$-alkoxy, halogen or cyano,
or
represents $C_3$-$C_8$-cycloalkyl, $C_3$-$C_8$-cycloalkoxy, $C_3$-$C_8$-heterocycloalkyl, aryl or heteroaryl having 5 or 6 ring atoms which may optionally be mono- or polysubstituted by identical or different substituents from the group consisting of $C_1$-$C_6$-alkyl, fluoro-$C_1$-$C_6$-alkyl, $C_1$-$C_6$-alkoxy, fluoro-$C_1$-$C_6$-alkoxy, hydroxy, oxo, halogen, cyano, heteroaryl and aryl, $R^2$ represents methyl or methylamino, $R^3$ represents cyano, —C(=O)—OR$^8$, —C(=O)—R$^9$ or —C(=O)—NR$^6$R$^7$, or represents a 5- or 6-membered ring system which contains 0, 1, 2 or 3 heteroatoms independently of one another selected from the group consisting of O, N and S, which may optionally be aromatic or else non-aromatic and which may optionally be mono- or polysubstituted by identical or different radicals R$^5$, $R^4$ represents hydrogen, fluorine, chlorine, bromine or cyano, $R^5$ represents hydrogen, $C_1$-$C_6$-alkyl, $C_3$-$C_8$-cycloalkyl, $C_3$-$C_8$-heterocycloalkyl, fluoro-$C_1$-$C_6$-alkyl, aryl, heteroaryl, hydroxy, $C_1$-$C_6$-alkoxy, $C_1$-$C_3$-alkoxy-$C_1$-$C_3$-alkyl, aryloxy-$C_1$-$C_3$-alkyl, aryl-$C_1$-$C_3$-alkoxy-$C_1$-$C_3$-alkyl, fluoro-$C_1$-$C_6$-alkoxy, halogen, cyano or oxo, $R^6$ and $R^7$ independently of one another represent hydrogen or —NH—C(=O)—R$^{15}$, or represent $C_1$-$C_6$-alkyl, $C_1$-$C_6$-alkoxy, $C_3$-$C_8$-heterocycloalkyl, aryl, heteroaryl, $C_3$-$C_8$-cycloalkyl, $C_6$-$C_{12}$-bicycloalkyl, $C_5$-$C_{11}$-spirocycloalkyl, $C_6$-$C_{12}$-heterobicycloalkyl or $C_5$-$C_{11}$-heterospirocycloalkyl which may optionally be mono- or polysubstituted by identical or different substituents from the group consisting of $C_1$-$C_3$-alkyl, fluoro-$C_1$-$C_3$-alkyl, $C_1$-$C_3$-alkoxy, fluoro-$C_1$-$C_3$-alkoxy, phenoxy, hydroxy, oxo, halogen, cyano, $C_3$-$C_8$-cycloalkyl, $C_3$-$C_8$-heterocycloalkyl, heteroaryl and aryl, or represent the group

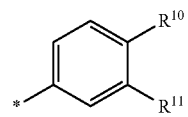

in which $R^{10}$ and $R^{11}$ together represent $C_3$-$C_6$-alkylene or $C_3$-$C_6$-heteroalkylene which may optionally be mono- or polysubstituted by identical or different substituents from the group consisting of halogen, oxo, hydroxy, cyano, nitro, $C_1$-$C_3$-alkyl, fluoro-$C_1$-$C_3$-alkyl, $C_1$-$C_3$-alkoxy, fluoro-$C_1$-$C_3$-alkoxy, $C_1$-$C_3$-alkoxy-$C_1$-$C_3$-alkyl, $C_1$-$C_3$-alkylcarbonyl, and in which "*" denotes the point of attachment to the remainder of the molecule, $R^8$ represents hydrogen, $C_1$-$C_6$-alkyl, $C_3$-$C_8$-cycloalkyl, aryl or heteroaryl which may optionally be mono- or polysubstituted by identical or different substituents from the group consisting of $C_1$-$C_6$-alkyl, fluoro-$C_1$-$C_6$-alkyl, $C_1$-$C_6$-alkoxy, fluoro-$C_1$-$C_6$-alkoxy, hydroxy, oxo, halogen, cyano, nitro, heteroaryl and aryl, $R^9$ represents $C_3$-$C_8$-heterocycloalkyl, $C_5$-$C_{11}$-spiroheterocycloalkyl, $C_6$-$C_{12}$-heterobicycloalkyl or represents a bridged heterocycle consisting of 7 to 15 ring atoms which may optionally be mono- or polysubstituted by identical or different substituents from the group consisting of $C_1$-$C_4$-alkyl, $C_3$-$C_8$-cycloalkyl, $C_3$-$C_8$-heterocycloalkyl, fluoro-$C_1$-$C_6$-alkyl, aryl, aryloxy, aryl-$C_1$-$C_2$-alkyl, —C(=O)—O—$C_1$-$C_6$-alkyl, heteroaryl, hydroxy, $C_1$-$C_6$-alkoxy, fluoro-$C_1$-$C_6$-alkoxy, halogen, cyano and oxo, and $R^{15}$ represents $C_1$-$C_6$-alkyl, fluoro-$C_1$-$C_3$-alkyl, phenyl or phenyl-$C_1$-$C_2$-alkyl, where the phenyl and the phenyl present in phenyl-$C_1$-$C_2$-alkyl for their part may optionally be mono- or polysubstituted by identical or different substituents from the group consisting of halogen, cyano, $C_1$-$C_3$-alkyl, $C_1$-$C_3$-alkoxy and trifluoromethyl, and the diastereomers, racemates, tautomers, and physiologically acceptable salts thereof.

3. Compounds of formula (I) according to claim 1 in which $R^1$ represents hydrogen, hydroxy, $C_1$-$C_3$-alkyl, fluoro-$C_1$-$C_3$-alkyl, $C_1$-$C_3$-alkoxy or fluoro-$C_1$-$C_3$-alkoxy, or represents heteroaryl having 5 or 6 ring atoms which may optionally be mono- or polysubstituted by identical or different substituents from the group consisting of $C_1$-$C_3$-alkyl, fluoro-$C_1$-$C_3$-alkyl, $C_1$-$C_3$-alkoxy, fluoro-$C_1$-$C_3$-alkoxy, halogen and cyano, $R^2$ represents methyl, $R^3$ represents —C(=O)—OR$^8$, —C(=O)—R$^9$ or —C(=O)—NR$^6$R$^7$, or represents a 5-membered aromatic ring system which contains 1, 2 or 3 heteroatoms independently of one another selected from the group consisting of O, N and S, which may optionally be mono- or polysubstituted by identical or different radicals R$^5$, $R^4$ represents chlorine, $R^5$ represents hydrogen, $C_1$-$C_3$-alkyl, $C_3$-$C_6$-cycloalkyl, $C_3$-$C_6$-heterocycloalkyl, fluoro-$C_1$-$C_3$-alkyl, aryl, heteroaryl, hydroxy, $C_1$-$C_3$-alkoxy, $C_1$-$C_3$-alkoxy-$C_1$-$C_3$-alkyl, aryloxy-$C_1$-$C_3$-alkyl, aryl-$C_1$-$C_3$-alkoxy-$C_1$-$C_3$-alkyl, fluoro-$C_1$-$C_3$-alkoxy, halogen or cyano, $R^6$ and $R^7$ independently of one another represent hydrogen or NH—C(=O)—R$^{15}$, or represent $C_1$-$C_6$-alkyl, $C_1$-$C_6$-alkoxy, $C_3$-$C_8$-heterocycloalkyl, aryl, heteroaryl, $C_3$-$C_8$-cycloalkyl, $C_6$-$C_{12}$-bicycloalkyl, $C_5$-$C_{11}$-spirocycloalkyl, $C_6$-$C_{12}$-heterobicycloalkyl or $C_5$-$C_{11}$-heterospirocycloalkyl which may optionally be mono- or polysubstituted by identical or different substituents from the group consisting of $C_1$-$C_3$-alkyl, fluoro-$C_1$-$C_3$-alkyl, $C_1$-$C_3$-alkoxy, fluoro-$C_1$-$C_3$-alkoxy, phenoxy, hydroxy, oxo, halogen, cyano, $C_3$-$C_8$-cycloalkyl, $C_3$-$C_8$-heterocycloalkyl, heteroaryl and aryl, or represent the group

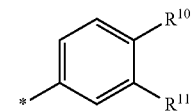

in which $R^{10}$ and $R^{11}$ together represent $C_3$-$C_6$-alkylene or $C_3$-$C_6$-heteroalkylene which may optionally be mono- or polysubstituted by identical or different substituents from the group consisting of halogen, oxo, hydroxy, cyano, nitro, $C_1$-$C_3$-alkyl, fluoro-$C_1$-$C_3$-alkyl, $C_1$-$C_3$-alkoxy, fluoro-$C_1$-$C_3$-alkoxy, $C_1$-$C_3$-alkoxy-$C_1$-$C_3$-alkyl, $C_1$-$C_3$-alkylcarbonyl, and in which "*" denotes the point of attachment to the remainder of the molecule, $R^8$ represents $C_1$-$C_6$-alkyl, $R^9$ represents one of the groups below

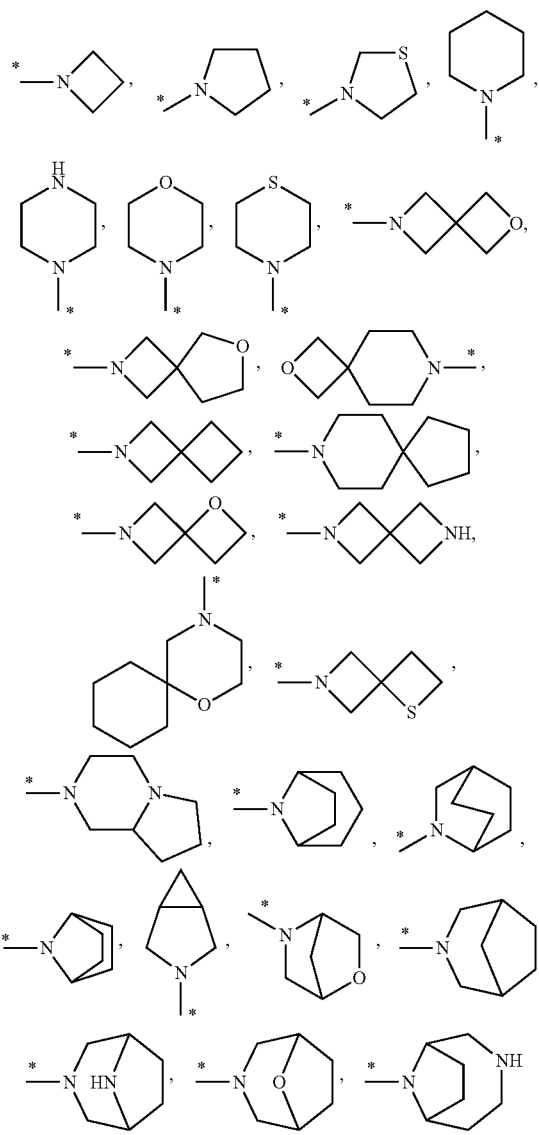

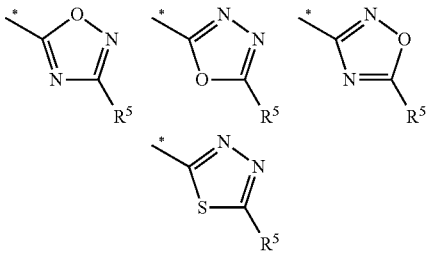

which may optionally be mono- or polysubstituted by identical or different substituents from the group consisting of $C_1$-$C_4$-alkyl, $C_3$-$C_8$-cycloalkyl, $C_3$-$C_8$-heterocycloalkyl, fluoro-$C_1$-$C_6$-alkyl, aryl, aryloxy, aryl-$C_1$-$C_2$-alkyl, —C(=O)—O—$C_1$-$C_6$-alkyl, heteroaryl, hydroxy, $C_1$-$C_6$-alkoxy, fluoro-$C_1$-$C_6$-alkoxy, halogen, cyano and oxo, and in which "*" denotes the point of attachment to the remainder of the molecule, and $R^{15}$ represents $C_1$-$C_3$-alkyl, trifluoromethyl, phenyl or benzyl, in which the phenyl and the phenyl present in benzyl for their part may optionally be mono- or polysubstituted by identical or different substituents from the group consisting of fluorine, chlorine, bromine, methyl and methoxy, and the diastereomers, racemates, tautomers, and physiologically acceptable salts thereof.

4. Compounds of formula (I) according to claim 1 in which $R^1$ represents hydrogen, hydroxy, $C_1$-$C_3$-alkyl, fluoro-$C_1$-$C_3$-alkyl, $C_1$-$C_3$-alkoxy or fluoro-$C_1$-$C_3$-alkoxy, or represents heteroaryl having 5 ring atoms which may optionally be mono- or polysubstituted by identical or different substituents from the group consisting of $C_1$-$C_3$-alkyl and $C_1$-$C_3$-alkoxy, $R^2$ represents methyl, $R^3$ represents —C(=O)—$OR^8$, —C(=O)—$R^9$ or —C(=O)—$NR^6R^7$, or represents one of the ring systems below

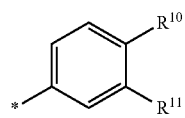

in which "*" denotes the point of attachment to the remainder of the molecule, $R^4$ represents chlorine, $R^5$ represents hydrogen, $C_1$-$C_3$-alkyl, $C_3$-$C_6$-cycloalkyl, $C_3$-$C_6$-heterocycloalkyl, phenyl, 5- or 6-membered heteroaryl, $C_1$-$C_3$-alkoxy-$C_1$-$C_3$-alkyl, phenoxy-$C_1$-$C_3$-alkyl or benzyloxy-$C_1$-$C_3$-alkyl, $R^6$ and $R^7$ independently of one another represent hydrogen or —NH—C(=O)—$R^{15}$, or represent $C_1$-$C_6$-alkyl, $C_3$-$C_8$-heterocycloalkyl, phenyl, heteroaryl having 5 or 6 ring atoms or $C_3$-$C_8$-cycloalkyl which may optionally be mono- or polysubstituted by identical or different substituents from the group consisting of $C_1$-$C_3$-alkyl, fluoro-$C_1$-$C_3$-alkyl, $C_1$-$C_3$-alkoxy, phenoxy, hydroxy, oxo, halogen, cyano, $C_3$-$C_8$-cycloalkyl, $C_3$-$C_8$-heterocycloalkyl, 5- or 6-membered heteroaryl and phenyl, or represent the group ![structure with $R^{10}$ and $R^{11}$ on phenyl ring]

in which $R^{10}$ and $R^{11}$ together represent $C_3$-$C_4$-alkylene or $C_3$-$C_4$-heteroalkylene which may optionally be mono- or polysubstituted by identical or different substituents from the group consisting of halogen, oxo, hydroxy, $C_1$-$C_3$-alkyl, $C_1$-$C_3$-alkoxy, $C_1$-$C_3$-alkylcarbonyl, and in which "*" denotes the point of attachment to the remainder of the molecule, $R^8$ represents $C_1$-$C_4$-alkyl, $R^9$ represents one of the groups below

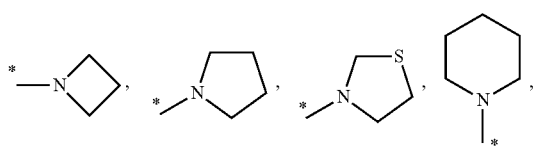

-continued

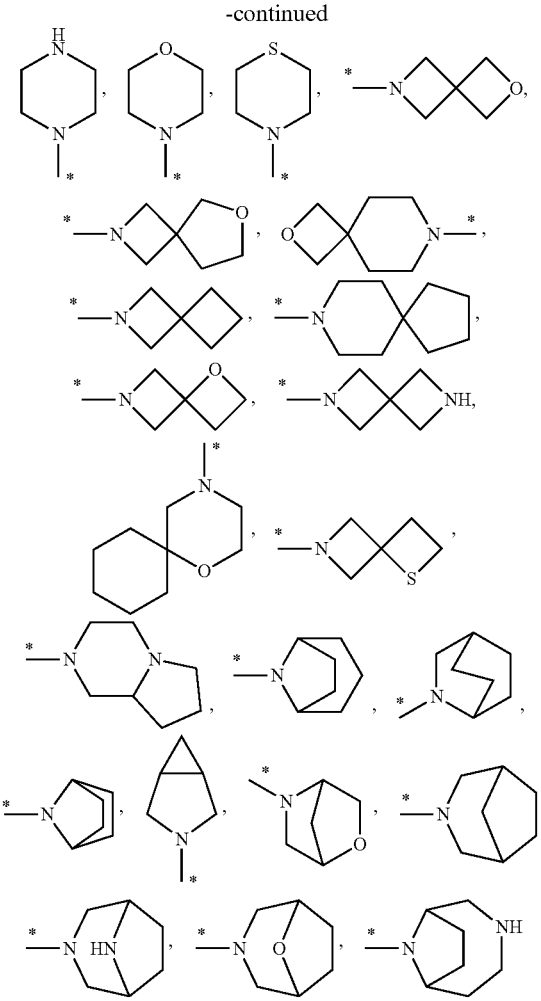

which may optionally be mono- or polysubstituted by identical or different substituents from the group consisting of $C_1$-$C_4$-alkyl, phenyl, phenoxy, benzyl, —C(=O)—O—$C_1$-$C_4$-alkyl, 5- or 6-membered heteroaryl, hydroxy, $C_1$-$C_4$-alkoxy, fluorine, cyano and oxo, and in which "*" denotes the point of attachment to the remainder of the molecule, and $R^{15}$ represents $C_1$-$C_3$-alkyl, and the diastereomers, racemates, tautomers, and physiologically acceptable salts thereof.

5. Compounds of formula (I) according to claim 1 in which $R^1$ represents hydrogen, $C_1$-$C_3$-alkoxy or fluoro-$C_1$-$C_3$-alkoxy, or represents oxazolyl or isoxazolyl which may optionally be mono- or polysubstituted by identical or different substituents from the group consisting of $C_1$-$C_3$-alkyl and $C_1$-$C_3$-alkoxy, $R^2$ represents methyl, $R^3$ represents —C(=O)—$OR^8$, —C(=O)—$R^9$ or —C(=O)—$NR^6R^7$, or represents one of the ring systems below

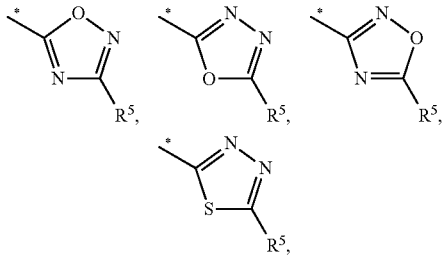

in which "*" denotes the point of attachment to the remainder of the molecule, $R^4$ represents chlorine, $R^5$ represents hydrogen, $C_1$-$C_3$-alkyl-, $C_3$-$C_6$-cycloalkyl, pyridinyl or benzyloxy-$C_1$-$C_3$-alkyl, $R^6$ and $R^7$ independently of one another represent hydrogen or NH—C(=O)—$R^{15}$, or represent $C_1$-$C_6$-alkyl which may optionally be mono- or polysubstituted by identical or different substituents from the group consisting of $C_3$-$C_8$-heterocycloalkyl, or represent the group

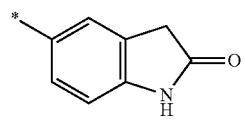

in which "*" denotes the point of attachment to the remainder of the molecule, $R^8$ represents ethyl or tert-butyl, $R^9$ represents one of the groups below

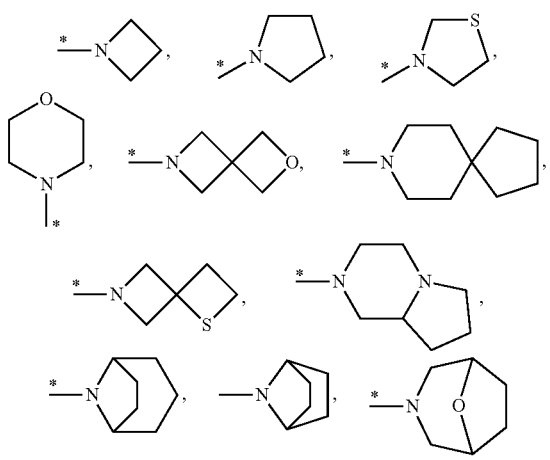

which may optionally be mono- or polysubstituted by identical or different substituents from the group consisting of $C_1$-$C_4$-alkyl, phenoxy, benzyl, —C(=O)—O—$C_1$-$C_4$-alkyl, fluorine and oxo, and in which "*" denotes the point of attachment to the remainder of the molecule, and $R^{15}$ represents $C_1$-$C_3$-alkyl, and the diastereomers, racemates, tautomers, and physiologically acceptable salts thereof.

6. Compounds of formula (I) according to claim 1 in which
R¹ represents hydrogen, methoxy, trifluoromethoxy or represents 3,5-dimethylisoxazol-4-yl,
R² represents methyl,
R³ represents —C(=O)—OR⁸, —C(=O)—R⁹ or —C(=O)—NR⁶R⁷,
or
represents one of the ring systems below

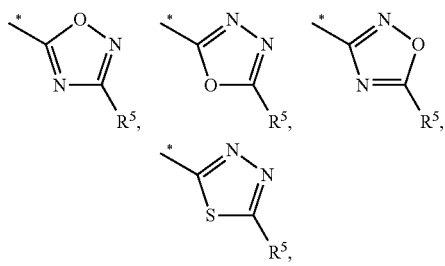

in which "*" denotes the point of attachment to the remainder of the molecule,
R⁴ represents chlorine,
R⁵ represents methyl, isopropyl, cyclopropyl, pyridin-3-yl or benzyloxymethyl,
R⁶ and R⁷ independently of one another
represent hydrogen or —NH—C(=O)—R¹⁵,
or
represent ethyl which may optionally be monosubstituted by morpholinyl,
or represent the group

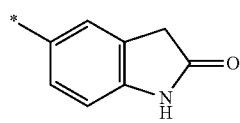

in which "*" denotes the point of attachment to the remainder of the molecule,
R⁸ represents ethyl or tert-butyl,
R⁹ represents one of the groups below

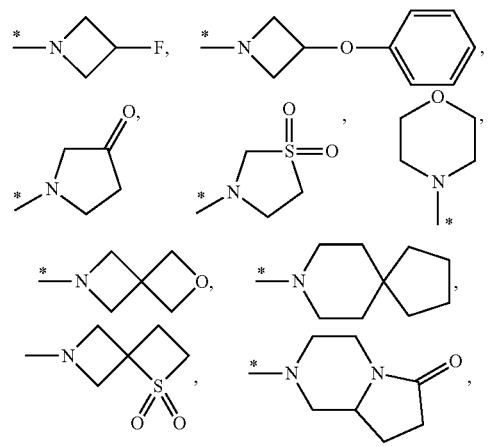

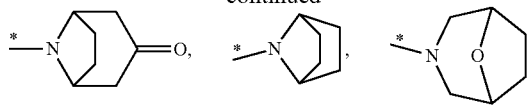

in which "*" denotes the point of attachment to the remainder of the molecule, and
R¹⁵ represents methyl,
and the diastereomers, racemates, tautomers, and physiologically acceptable salts thereof.

7. A compound of formula (I) according to claim 1 selected from the group consisting of:
ethyl [6-(4-chlorophenyl)-1-methyl-4H-[1,2,4]triazolo[4,3-a][1]benzazepin-4-yl]acetate;
ethyl (−)-(4R)-[6-(4-chlorophenyl)-1-methyl-4H-[1,2,4]triazolo[4,3-a][1]benzazepin-4-yl]acetate;
2-[6-(4-chlorophenyl)-1-methyl-4H-[1,2,4]triazolo[4,3-a][1]benzazepin-4-yl]-1-(2-oxa-6-azaspiro[3.3]hept-6-yl)ethanone;
(−)-2-[(4R)-6-(4-chlorophenyl)-1-methyl-4H-[1,2,4]triazolo[4,3-a][1]benzazepin-4-yl]-1-(2-oxa-6-azaspiro[3.3]hept-6-yl)ethanone;
1-(7-azabicyclo[2.2.1]hept-7-yl)-2-[6-(4-chlorophenyl)-1-methyl-4H-[1,2,4]triazolo[4,3-a][1]benzazepin-4-yl]ethanone;
(−)-1-(7-azabicyclo[2.2.1]hept-7-yl)-2-[(4R)-6-(4-chlorophenyl)-1-methyl-4H-[1,2,4]triazolo[4,3-a][1]benzazepin-4-yl]ethanone;
ethyl [6-(3-chlorophenyl)-1-methyl-4H-[1,2,4]triazolo[4,3-a][1]benzazepin-4-yl]acetate;
tert-butyl [6-(4-chlorophenyl)-1-methyl-4H-[1,2,4]triazolo[4,3-a][1]benzazepin-4-yl]acetate;
tert-butyl (−)-[(4R)-6-(4-chlorophenyl)-1-methyl-4H-[1,2,4]triazolo[4,3-a][1]benzazepin-4-yl]acetate;
2-[6-(3-chlorophenyl)-1-methyl-4H-[1,2,4]triazolo[4,3-a][1]benzazepin-4-yl]-1-(2-oxa-6-azaspiro[3.3]hept-6-yl)ethanone;
(−)-2-[(4R)-6-(3-chlorophenyl)-1-methyl-4H-[1,2,4]triazolo[4,3-a][1]benzazepin-4-yl]-1-(2-oxa-6-azaspiro[3.3]hept-6-yl)ethanone;
2-[6-(4-chlorophenyl)-1-methyl-4H-[1,2,4]triazolo[4,3-a][1]benzazepin-4-yl]-N-ethylacetamide;
(−)-2-[(4R)-6-(4-chlorophenyl)-1-methyl-4H-[1,2,4]triazolo[4,3-a][1]benzazepin-4-yl]-N-ethylacetamide;
2-[6-(4-chlorophenyl)-1-methyl-4H-[1,2,4]triazolo[4,3-a][1]benzazepin-4-yl]-1-(morpholin-4-yl)ethanone;
(−)-2-[(4R)-6-(4-chlorophenyl)-1-methyl-4H-[1,2,4]triazolo[4,3-a][1]benzazepin-4-yl]-1-(morpholin-4-yl)ethanone;
2-[6-(4-chlorophenyl)-1-methyl-4H-[1,2,4]triazolo[4,3-a][1]benzazepin-4-yl]-1-(3-fluoroazetidin-1-yl)ethanone;
(−)-2-[(4R)-6-(4-chlorophenyl)-1-methyl-4H-[1,2,4]triazolo[4,3-a][1]benzazepin-4-yl]-1-(3-fluoroazetidin-1-yl)ethanone;
2-[6-(4-chlorophenyl)-1-methyl-4H-[1,2,4]triazolo[4,3-a][1]benzazepin-4-yl]-1-(1,1-dioxido-1-thia-6-azaspiro[3.3]hept-6-yl)ethanone;
(−)-2-[(4R)-6-(4-chlorophenyl)-1-methyl-4H-[1,2,4]triazolo[4,3-a][1]benzazepin-4-yl]-1-(1,1-dioxido-1-thia-6-azaspiro[3.3]hept-6-yl)ethanone;
2-[6-(4-chlorophenyl)-1-methyl-4H-[1,2,4]triazolo[4,3-a][1]benzazepin-4-yl]-N-(2-oxo-2,3-dihydro-1H-indol-5-yl)acetamide;

(−)-2-[(4R)-6-(4-chlorophenyl)-1-methyl-4H-[1,2,4]triazolo[4,3-a][1]benzazepin-4-yl]-N-(2-oxo-2,3-dihydro-1H-indol-5-yl)acetamide;
3-{[(6-(4-chlorophenyl)-1-methyl-4H-[1,2,4]triazolo[4,3-a][1]benzazepin-4-yl]acetyl}-8-azabicyclo[3.2.1]octan-3-one;
(−)-3-{[(4R)-6-(4-chlorophenyl)-1-methyl-4H-[1,2,4]triazolo[4,3-a][1]benzazepin-4-yl]acetyl}-8-azabicyclo[3.2.1]octan-3-one;
2-[6-(4-chlorophenyl)-1-methyl-4H-[1,2,4]triazolo[4,3-a][1]benzazepin-4-yl]-1-(3-phenoxyazetidin-1-yl)ethanone;
(−)-2-[(4R)-6-(4-chlorophenyl)-1-methyl-4H-[1,2,4]triazolo[4,3-a][1]benzazepin-4-yl]-1-(3-phenoxyazetidin-1-yl)ethanone;
1-{[6-(4-chlorophenyl)-1-methyl-4H-[1,2,4]triazolo[4,3-a][1]benzazepin-4-yl]acetyl}pyrrolidin-3-one;
(−)-1-{[(4R)-6-(4-chlorophenyl)-1-methyl-4H-[1,2,4]triazolo[4,3-a][1]benzazepin-4-yl]acetyl}pyrrolidin-3-one;
1-(8-azaspiro[4.5]dec-8-yl)-2-[6-(4-chlorophenyl)-1-methyl-4H-[1,2,4]triazolo[4,3-a][1]benzazepin-4-yl]ethanone;
(−)-1-(8-azaspiro[4.5]dec-8-yl)-2-[(4R)-6-(4-chlorophenyl)-1-methyl-4H-[1,2,4]triazolo[4,3-a][1]benzazepin-4-yl]ethanone;
2-[6-(4-chlorophenyl)-1-methyl-4H-[1,2,4]triazolo[4,3-a][1]benzazepin-4-yl]-1-(1,1-dioxido-1,3-thiazolidin-3-yl)ethanone;
(−)-2-[(4R)-6-(4-chlorophenyl)-1-methyl-4H-[1,2,4]triazolo[4,3-a][1]benzazepin-4-yl]-1-(1,1-dioxido-1,3-thiazolidin-3-yl)ethanone;
2-[6-(4-chlorophenyl)-1-methyl-4H-[1,2,4]triazolo[4,3-a][1]benzazepin-4-yl]-1-(8-oxa-3-azabicyclo[3.2.1]oct-3-yl)ethanone;
(−)-2-[(4R)-6-(4-chlorophenyl)-1-methyl-4H-[1,2,4]triazolo[4,3-a][1]benzazepin-4-yl]-1-(8-oxa-3-azabicyclo[3.2.1]oct-3-yl)ethanone;
6-(4-chlorophenyl)-1-methyl-4-[(3-methyl-1,2,4-oxadiazol-5-yl)methyl]-4H-[1,2,4]triazolo[4,3-a][1]benzazepine;
(−)-6-[(4R)-4-chlorophenyl]-1-methyl-4-[(3-methyl-1,2,4-oxadiazol-5-yl)methyl]-4H-[1,2,4]triazolo[4,3-a][1]benzazepine;
(−)-(4R)-6-(4-chlorophenyl)-1-methyl-4-{[3-(propan-2-yl)-1,2,4-oxadiazol-5-yl]methyl}-4H-[1,2,4]triazolo[4,3-a][1]benzazepine;
(−)6-(4R)-(4-chlorophenyl)-4-[(3-cyclopropyl-1,2,4-oxadiazol-5-yl)methyl]-1-methyl-4H-[1,2,4]triazolo[4,3-a][1]benzazepine;
(−)-(4R)-6-(4-chlorophenyl)-1-methyl-4-[(5-methyl-1,3,4-oxadiazol-2-yl)methyl]-4H-[1,2,4]triazolo[4,3-a][1]benzazepine;
6-(4-chlorophenyl)-1-methyl-4-[(5-methyl-1,3,4-oxadiazol-2-yl)methyl]-4H-[1,2,4]triazolo[4,3-a][1]benzazepine;
N'-acetyl-2-[(4R)-6-(4-chlorophenyl)-1-methyl-4H-[1,2,4]triazolo[4,3-a][1]benzazepin-4-yl]acetohydrazide;
6-(4-chlorophenyl)-1-methyl-4-[(5-methyl-1,3,4-thiadiazol-2-yl)methyl]-4H-[1,2,4]triazolo[4,3-a][1]benzazepine;
(+)-(4R)-6-(4-chlorophenyl)-1-methyl-4-[(5-methyl-1,3,4-thiadiazol-2-yl)methyl]-4H-[1,2,4]triazolo[4,3-a][1]benzazepine;
6-(4-chlorophenyl)-4-[(5-cyclopropyl-1,3,4-oxadiazol-2-yl)methyl]-1-methyl-4H-[1,2,4]triazolo[4,3-a][1]benzazepine;
6-(4-chlorophenyl)-1-methyl-4-{[5-(pyridin-3-yl)-1,3,4-oxadiazol-2-yl]methyl}-4H-[1,2,4]triazolo[4,3-a][1]benzazepine;
(−)-(4R)-6-(4-chlorophenyl)-1-methyl-4-{[5-(pyridin-3-yl)-1,3,4-oxadiazol-2-yl]methyl}-4H-[1,2,4]triazolo[4,3-a][1]benzazepine;
6-(4-chlorophenyl)-1-methyl-4-[(5-methyl-1,2,4-oxadiazol-3-yl)methyl]-4H-[1,2,4]triazolo[4,3-a][1]benzazepine;
6-(4-chlorophenyl)-8-methoxy-1-methyl-4-[(5-methyl-1,3,4-oxadiazol-2-yl)methyl]-4H-[1,2,4]triazolo[4,3-a][1]benzazepine;
6-(4-chlorophenyl)-8-(3,5-dimethyl-1,2-oxazol-4-yl)-1-methyl-4-[(5-methyl-1,3,4-oxadiazol-2-yl)methyl]-4H-[1,2,4]triazolo[4,3-a][1]benzazepine;
tert-butyl [6-(4-chlorophenyl)-1-methyl-8-(trifluoromethoxy)-4H-[1,2,4]triazolo[4,3-a][1]benzazepin-4-yl]acetate;
tert-butyl (−)-[(4R)-6-(4-chlorophenyl)-1-methyl-8-(trifluormethoxy)-4H-[1,2,4]triazolo[4,3-a][1]benzazepin-4-yl]acetate;
2-[(4R)-6-(4-chlorophenyl)-1-methyl-8-(trifluoromethoxy)-4H-[1,2,4]triazolo[4,3-a][1,4]benzazepin-4-yl]-1-(2-oxa-6-azaspiro[3.3]hept-6-yl)ethanone;
2-[(4R)-6-(4-chlorophenyl)-1-methyl-8-(trifluoromethoxy)-4H-[1,2,4]triazolo[4,3-a][1]benzazepin-4-yl]-N-ethylacetamide;
2-[(4R)-6-(4-chlorophenyl)-1-methyl-8-(trifluoromethoxy)-4H-[1,2,4]triazolo[4,3-a][1]benzazepin-4-yl]-N-[2-(morpholin-4-yl)ethyl]acetamide;
6-(4-chlorophenyl)-1-methyl-4-[(5-methyl-1,3,4-oxadiazol-2-yl)methyl]-8-(trifluoromethoxy)-4H-[1,2,4]triazolo[4,3-a][1]benzazepine;
(4R)-6-(4-chlorophenyl)-1-methyl-4-[(5-methyl-1,3,4-oxadiazol-2-yl)methyl]-8-(trifluoromethoxy)-4H-[1,2,4]triazolo[4,3-a][1]benzazepine;
2-{[(4R)-6-(4-chlorophenyl)-1-methyl-8-(trifluoromethoxy)-4H-[1,2,4]triazolo[4,3-a][1]benzazepin-4-yl]acetyl}hexahydropyrrolo[1,2-a]pyrazin-6(2H)one; and
(4R)-4-({5-[(benzyloxy)methyl]-1,3,4-oxadiazol-2-yl}methyl)-6-(4-chlorophenyl)-1-methyl-4H-[1,2,4]triazolo[4,3-a][1]benzazepine,
and the diastereomers, racemates, tautomers, and physiologically acceptable salts thereof.

8. A method for the treatment of acute myeloid leukaemia, prostate carcinoma, multiple myeloma, mammary carcinoma, or melanoma comprising administering to a patient in need thereof a therapeutically effective amount of a compound according to claim 1.

9. A pharmaceutical composition comprising a compound according to claim 1 in combination with a pharmacologically active substance selected from the group consisting of: aminoglutethimide, L-asparaginase, azathioprine, 5-azacytidine, bleomycin, busulfan, carboplatin, carmustine, chlorambucil, cisplatin, colaspase, cyclophosphamide, cytarabine, dacarbazine, dactinomycin, daunorubicin, diethylstilbestrol, 2',2'-difluorodeoxycytidine, docetaxel, doxorubicin (adriamycin), epirubicin, epothilone and its derivatives, erythro-hydroxynonyladenine, ethinylestradiol, etoposide, fludarabin phosphate, 5-fluorodeoxyuridine, 5-fluorodeoxyuridine monophosphate, 5-fluorouracil, fluoxymesterone, flutamide, hexamethylmelamine, hydroxyurea, hydroxyprogesterone caproate, idarubicin, ifosfamide, interferon, irinotecan, leucovorin, lomustine, mechlorethamine, medroxyprogesterone acetate, megestrol acetate, melphalan, 6-mercaptopurine, mesna, methotrexate, mitomycin C, mitotane, mitoxantrone, paclitaxel, pentostatin, N-phosphonoacetyl L-aspartate (PALA), plicamycin, prednisolone, prednisone, procarbazine, raloxifen, semustine, streptozocin, tamoxifen, teniposide, testosterone propionate, thioguanine, thiotepa, topotecan, trimethylmelamine, uridine, vinblastine, vincristine, vindesine, vinorelbine, bevacizumab, rituximab, cetuximab, trastuzumab, axitinib, regorafenib, recentin, sorafenib, and sunitinib.

10. A method for the treatment of acute myeloid leukaemia, prostate carcinoma, multiple myeloma, mammary carcinoma, or melanoma comprising administering to a patient in need thereof a therapeutically effective amount of a pharmaceutical combination according to claim 9.

\* \* \* \* \*

UNITED STATES PATENT AND TRADEMARK OFFICE
CERTIFICATE OF CORRECTION

PATENT NO. : 9,663,523 B2
APPLICATION NO. : 14/432158
DATED : May 30, 2017
INVENTOR(S) : Schmees et al.

Page 1 of 7

It is certified that error appears in the above-identified patent and that said Letters Patent is hereby corrected as shown below:

On the Title Page

Page 2, left column, Line 15 (item [56] in the OTHER PUBLICATION section) replace Greenwall et al., Blood, 2005, 103:1475 - 1484 with -- Greenwald et al., Blood, 2004, 103:1475 - 1478 --.

In the Specification

Column 2, Line 15, replace Greenwall et al., Blood, 2005, 103:1475 - 1484 with -- Greenwald et al., Blood, 2004, 103:1475 - 1478 --.

Column 33, Line 60, replace (-)6-[(4*R*)-4-chlorophenyl]-1-methyl-4-[(3-methyl-1,2,4-oxadiazol-5-yl)methyl]-4H-[1,2,4]triazolo[4,3-a][1]benzazepine; with -- (-)-6-[(4*R*)-4-chlorophenyl]-1-methyl-4-[(3-methyl-1,2,4-oxadiazol-5-yl)methyl]-4H-[1,2,4]triazolo[4,3-a][1]benzazepine; --.

Column 60, Line 24, replace required, for example to German-language nomenclature with -- required --.

Column 65, Line 40, replace with -- 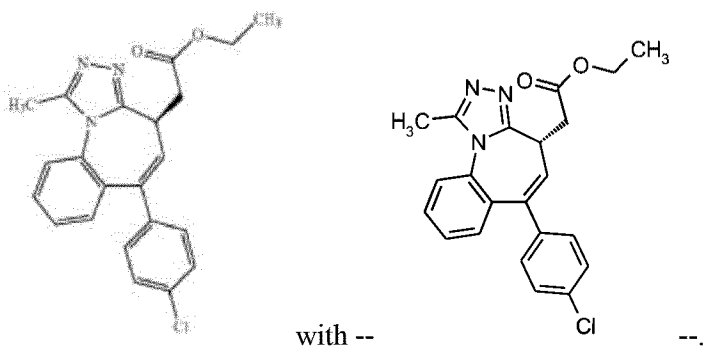 --.

Signed and Sealed this
Fourth Day of December, 2018

Andrei Iancu
*Director of the United States Patent and Trademark Office*

CERTIFICATE OF CORRECTION (continued)
U.S. Pat. No. 9,663,523 B2

Column 67, Line 55, replace 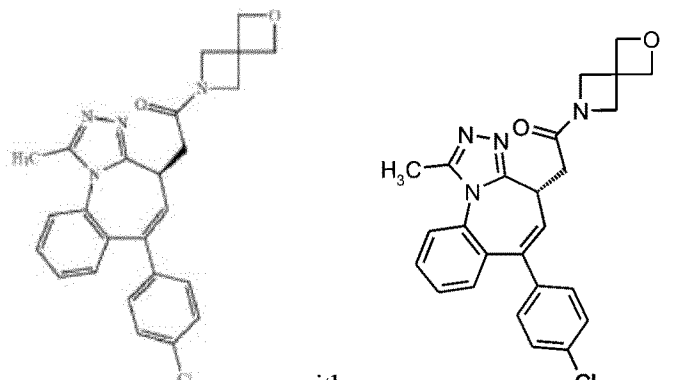 with -- --.

Column 69, Line 10, replace 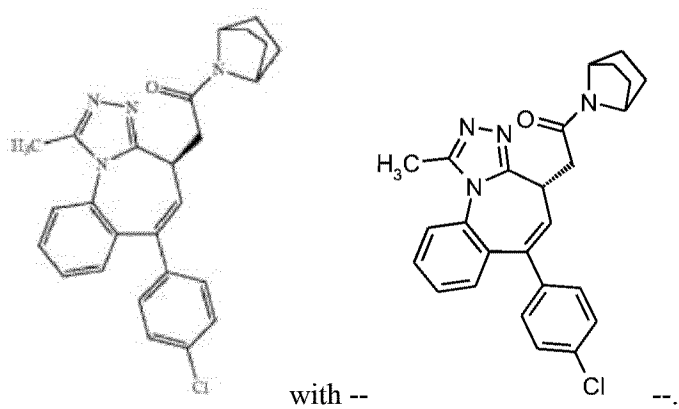 with -- --.

Column 72, Line 55, replace 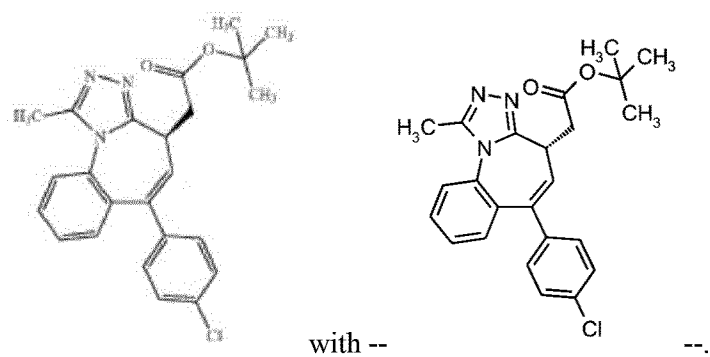 with -- --.

Column 73, Line 5, replace *tert*-butyl (+[(4*R*)-6-(4-chlorophenyl)-1-methyl-4H-[1,2,4]triazolo[4,3-a][1]benzazepin-4-yl]acetate with -- *tert*-butyl (-)-[(4*R*)-6-(4-chlorophenyl)-1-methyl-4H-[1,2,4]triazolo[4,3-a][1]benzazepin-4-yl]acetate --.

CERTIFICATE OF CORRECTION (continued)
U.S. Pat. No. 9,663,523 B2

Page 3 of 7

Column 74, Line 10, replace 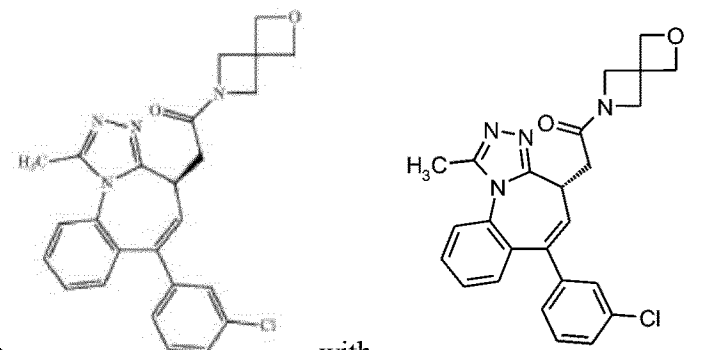 with -- --.

Column 75, Line 15, replace 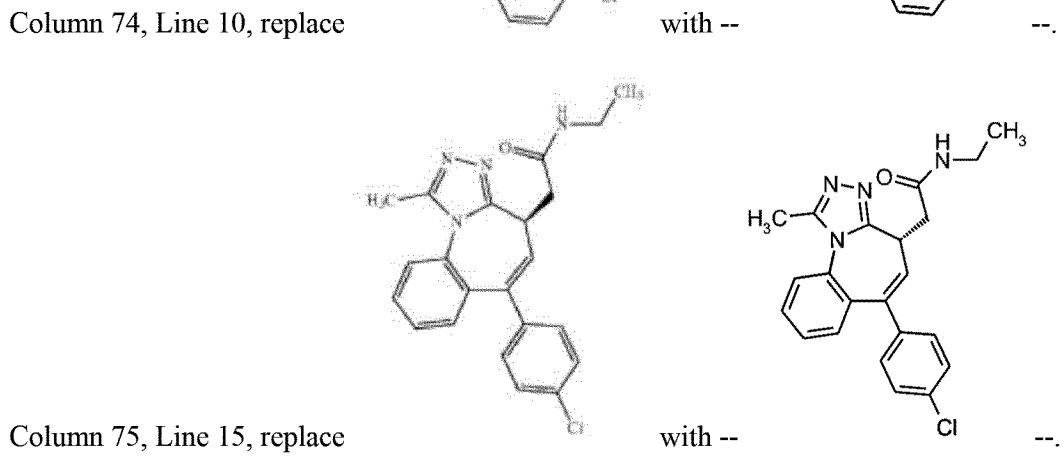 with -- --.

Column 76, Line 20, replace 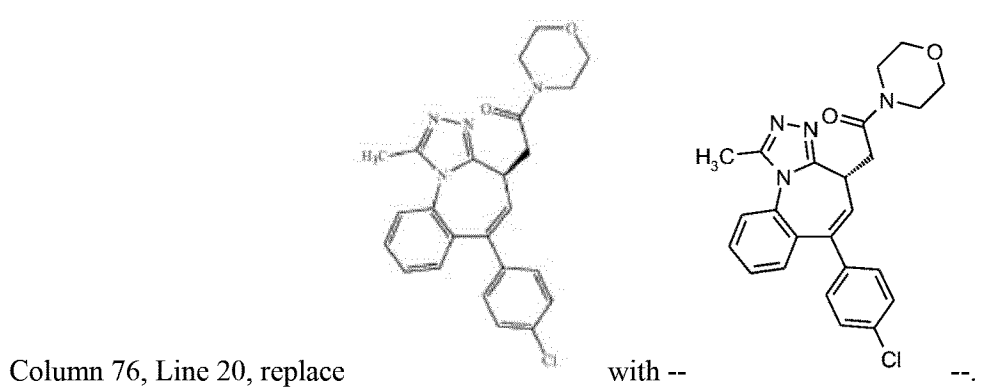 with -- --.

Column 77, Line 40, replace 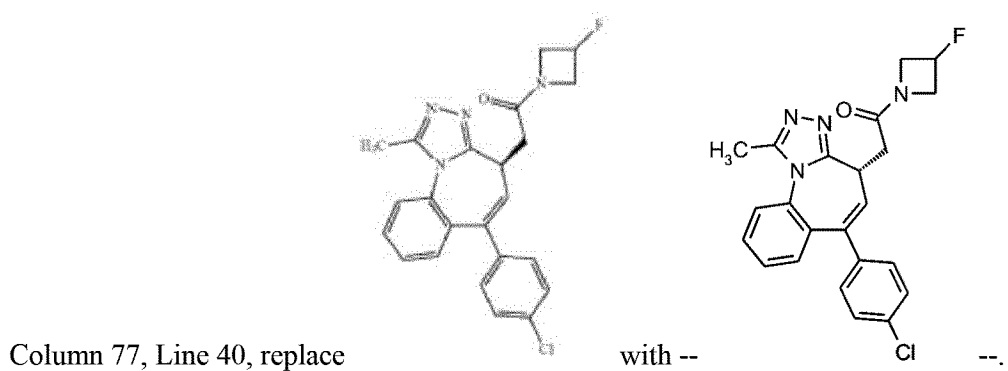 with -- --.

Column 80, Line 10, replace
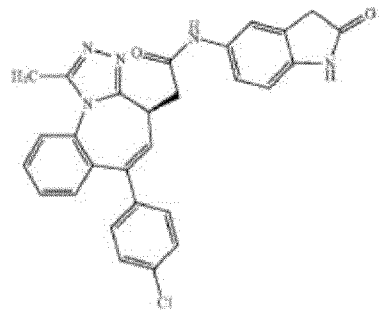 with -- 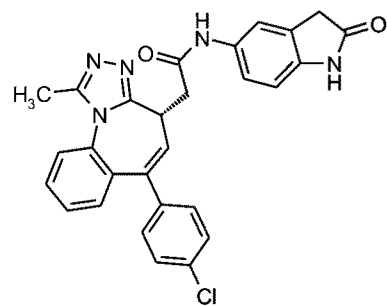 --.
Column 83, Line 1, replace 1Example 26 with -- Example 26 --.
Column 89, Line 10, replace 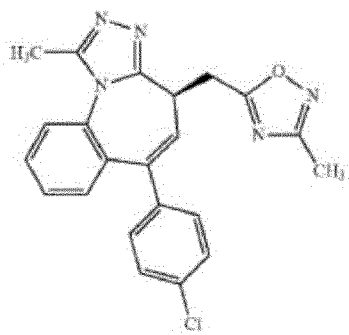 with -- 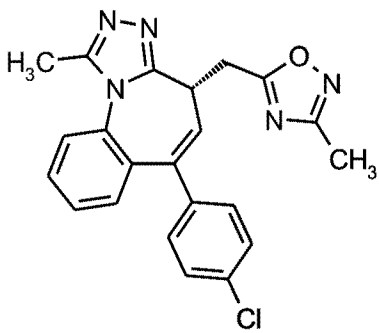 --.
Column 89, Line 40, replace
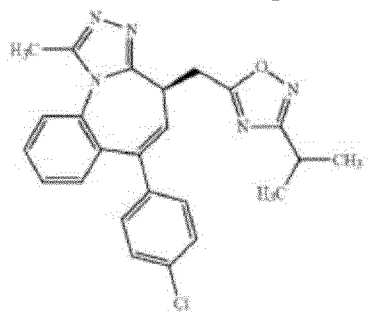 with -- 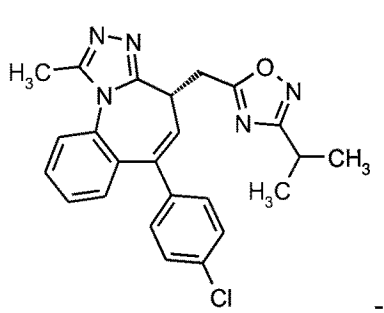 --.
Column 90, Line 25, replace 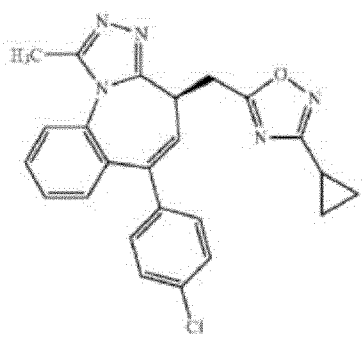 with -- 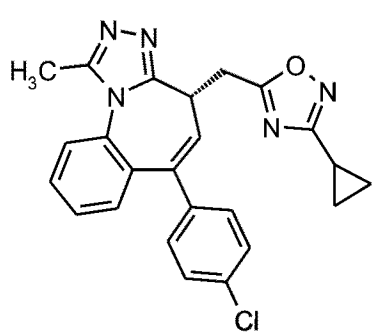 --.

CERTIFICATE OF CORRECTION (continued)
U.S. Pat. No. 9,663,523 B2

Column 91, Line 10, replace

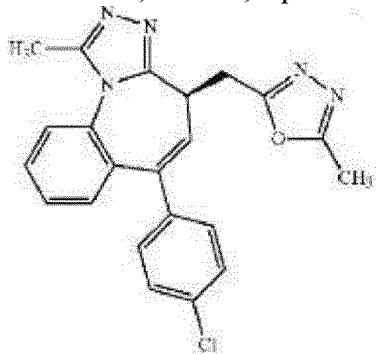

with --

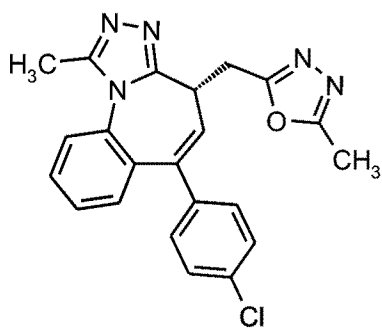

--.

Column 92, Line 30, replace

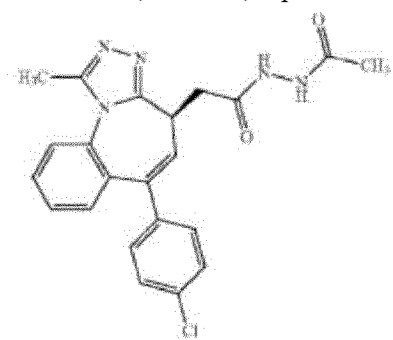

with --

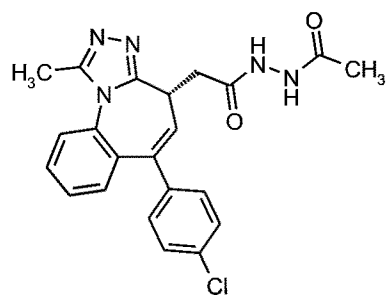

--.

Column 92, Line 60, replace N'-acetyl-2-[(4R)_6-(4-chlorophenyl)-1-methyl-4H-[1,2,4]triazolo[4,3-a][1]benzazepin-4-yl]acetohydrazide with -- N'-acetyl-2-[(4R)-6-(4-chlorophenyl)-1-methyl-4H-[1,2,4]triazolo[4,3-a][1]benzazepin-4-yl]acetohydrazide --.

Column 93, Line 50, replace

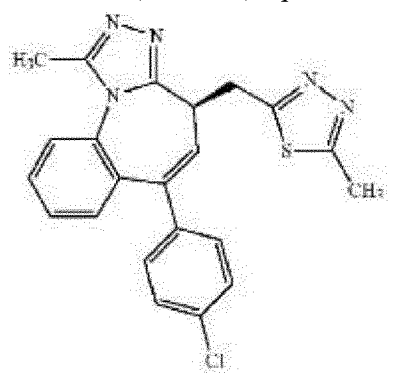

with --

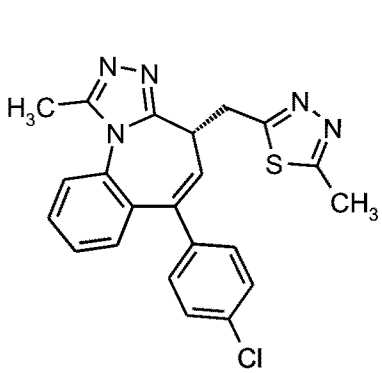

--.

CERTIFICATE OF CORRECTION (continued)
U.S. Pat. No. 9,663,523 B2

Page 6 of 7

Column 96, Line 20, replace

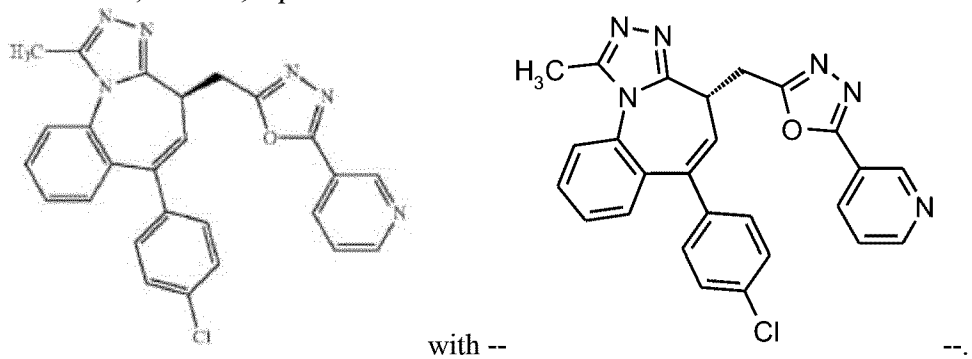

with --        --.

Column 108, Line 55, replace

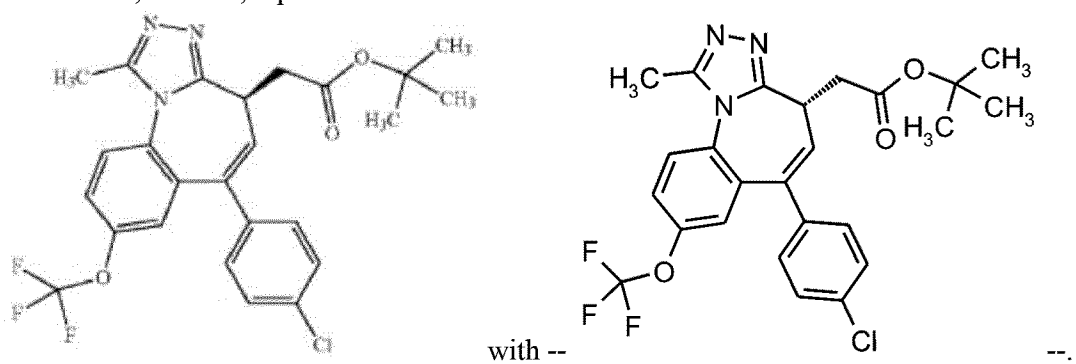

with --        --.

Column 109, Line 4, replace *tert*-butyl (+[(4*R*)-6-(4-chlorophenyl)-1-methyl-8-(trifluoromethoxy)-4H-[1,2,4]triazolo[4,3-a][1]benzazepin-4-yl]acetate with -- *tert*-butyl (-)-[(4*R*)-6-(4-chlorophenyl)-1-methyl-8-(trifluoromethoxy)-4H-[1,2,4]triazolo[4,3-a][1]benzazepin-4-yl]acetate --.

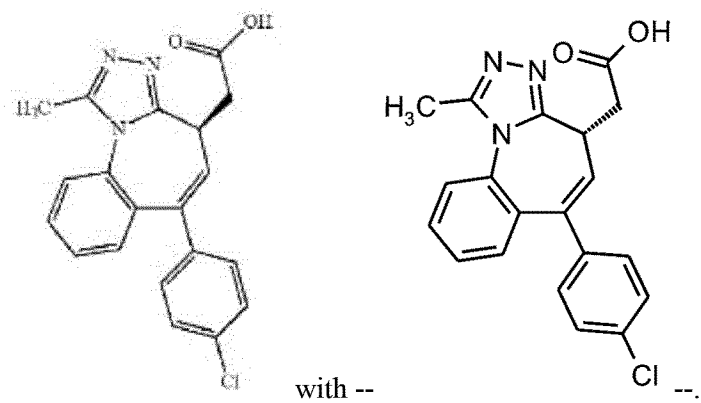

Column 113, Line 50, replace        with --        --.

Column 114, Line 20, replace
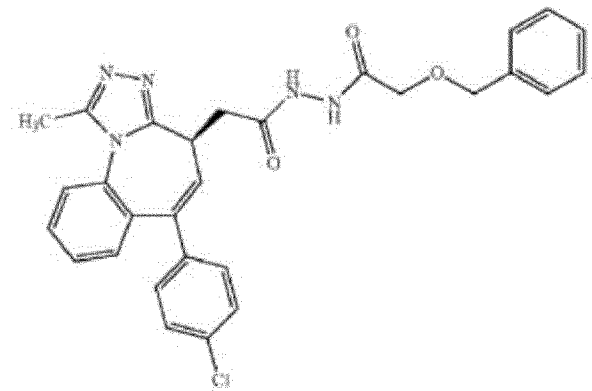 [SMILES: Cc1nnc2n1-c1ccccc1C(c1ccc(Cl)cc1)=C[C@@H]2CC(=O)NNC(=O)COCc1ccccc1] with
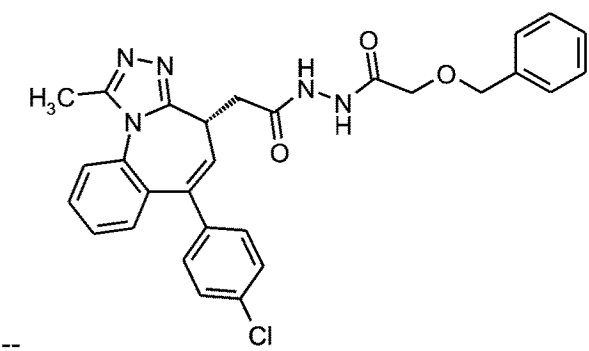 --.
In the Claims
Claim 1, Column 119, Line 21, change represents to -- $R^1$ represents --.
Claim 1, Column 119, Line 32, change -C(=O)-NR₁₂R₁₃ to -- -C(=O)-NR$^{12}$R$^{13}$ --.
Claim 7, Column 129, Line 48, change (-)6-(4R)-(4-chlorophenyl)-4-[(3-cyclopropyl-1,2,4-oxadiazol-5-yl)methyl]-1-methyl-4H-[1,2,4]triazolo[4,3-a][1]benzazepine to -- (-)-6-(4R)-(4-chlorophenyl)-4-[(3-cyclopropyl-1,2,4-oxadiazol-5-yl)methyl]-1-methyl-4H-[1,2,4]triazolo[4,3-a][1]benzazepine --.